(12) United States Patent
Rose et al.

(10) Patent No.: US 8,404,664 B2
(45) Date of Patent: Mar. 26, 2013

(54) PHOSPHONATED RIFAMYCINS AND USES THEREOF FOR THE PREVENTION AND TREATMENT OF BONE AND JOINT INFECTIONS

(75) Inventors: Yannick Stephane Rose, Montréal (CA); Stephane Ciblat, Montréal (CA); Ting Kang, Kirkland (CA); Adel Rafai Far, Ville Mont-Royal (CA); Evelyne Dietrich, Laval (CA); Yanick Lafontaine, Montreal (CA); Ranga Reddy, Hyderabad (IN)

(73) Assignee: Targanta Therapeutics, Inc., St. Laurent, Quebec (CA)

( * ) Notice: Subject to any disclaimer, the term of this patent is extended or adjusted under 35 U.S.C. 154(b) by 774 days.

(21) Appl. No.: 12/063,300

(22) PCT Filed: Aug. 11, 2006

(86) PCT No.: PCT/IB2006/004128
§ 371 (c)(1),
(2), (4) Date: Oct. 13, 2010

(87) PCT Pub. No.: WO2007/096703
PCT Pub. Date: Aug. 30, 2007

(65) Prior Publication Data
US 2011/0263534 A1    Oct. 27, 2011

Related U.S. Application Data

(60) Provisional application No. 60/707,145, filed on Aug. 11, 2005.

(51) Int. Cl.
*A01N 57/00* (2006.01)
*A61K 31/66* (2006.01)
*C07D 225/04* (2006.01)

(52) U.S. Cl. ............ 514/102; 514/80; 514/81; 540/453; 540/457; 540/458

(58) Field of Classification Search .................. None
See application file for complete search history.

(56) References Cited

U.S. PATENT DOCUMENTS

| 5,854,227 | A | 12/1998 | Hartmann et al. |
| 5,880,111 | A | 3/1999 | Farcasiu et al. |
| 6,333,424 | B1 | 12/2001 | Herczegh et al. |
| 6,605,609 | B2 | 8/2003 | Barbachyn et al. |

FOREIGN PATENT DOCUMENTS
WO    WO 2004/096285    11/2004

OTHER PUBLICATIONS

T. Yamane et al., "Synthesis and Biological Activity of 3'-Hydroxy-5'-aminobenzoxazinorifamycin Derivatives," Chem. Pharma. Bull., Japan, 1993, vol. 41(1), pp. 148-155.
International Search Report and Written Opinion for International Application No. PCT/IB06/004128, mail date Oct. 25, 2007.
Morisaki, N. et al., Structures of ADP-ribosylated rifampicin and its metabolite: intermediates of rifampicin-ribosylation by *Mycobacterium smegmatis* DSM43756, Journal of Antibiotics, 2000, vol. 53, No. 3, pp. 269-275.
Extended European Search Report dated Jul. 29, 2011, from the European Patent Office in corresponding European Application No. 06849478.0.

*Primary Examiner* — Jeffrey S. Lundgren
*Assistant Examiner* — Michael Schmitt
(74) *Attorney, Agent, or Firm* — Roylance, Abrams, Berdo & Goodman, L.L.P.

(57) ABSTRACT

The present invention relates to phosphonated Rifamycins, and methods of making and using such compounds. These compounds are useful as antibiotics for prophylaxis and/or the treatment of bone and joint infections, especially for the prophylaxis and/or treatment of osteomyelitis.

28 Claims, 5 Drawing Sheets

PHOSPHONATED RIFAMYCINS AND USES THEREOF FOR THE PREVENTION AND TREATMENT OF BONE AND JOINT INFECTIONS

CROSS-REFERENCE TO RELATED APPLICATIONS

The present application claims benefit of U.S. provisional application No. 60/707,145, filed Aug. 11, 2005, which is incorporated herein in its entirety.

BACKGROUND OF THE INVENTION

A) Field of the Invention

The invention relates to phosphonated Rifamycins. These compounds are useful as antibiotics for prophylaxis and/or treatment of bone and joint infections, especially for the prophylaxis and/or treatment of osteomyelitis.

B) Brief Description of the Prior Art

Osteomyelitis is an inflammation of bone caused by a variety of microorganisms, mainly *Staphylococcus aureus* (Carek et al., American Family Physician (2001), Vol 12, 12:2413-2420). This painful and debilitating disease occurs more commonly in children. Within the adult population, diabetics and kidney dialysis patients are also vulnerable. The acute form of the disease is treatable with antibiotics, but requires a lengthy period of daily therapy. It can, however, revert to a recurrent or chronic form requiring repeated hospital stays and heavy treatment regimens.

The Rifamycins are a class of semisynthetic antibacterial ansamycins, several members of which are currently used clinically or are under clinical evaluation (Burman et al, Clin. Pharmacokinet. (2001), 40:327-341). Rifamycins target the bacterial DNA-dependent RNA polymerase with 2-4 orders of magnitude greater affinity than for the equivalent eukaryotic enzymes (Floss and Yu, Chem. Rev. (2005), 105:621-632). Rifamycins act by binding a well defined site on the β subunit of the RNA polymerase holoenzyme, and as a result, interfere with and inhibit the initial phase of RNA synthesis. The common structural scaffold of these inhibitors presents a well defined position which allows for the modulation of their pharmacokinetic and pharmacodynamic properties without substantially altering their mode of binding. This has resulted in a number of well investigated compounds within the class, including Rifampicin (U.S. Pat. No. 3,342,810), Rifapentin (U.S. Pat. No. 4,002,752), Rifandin (U.S. Pat. No. 4,353,826), Rifabutin (U.S. Pat. No. 4,219,478), Rifalazil (U.S. Pat. No. 4,983,602) and Rifaximin (U.S. Pat. No. 4,341,785). Recently, a number of 25-deacetyl analogs have also been demonstrated to be attractive antibacterials (US patent application 2005/043298). Rifamycins are extremely potent against Gram positive pathogens, less so against the Gram negative ones, and display side effects generally only at high dose or in the presence of Cytochrome P3A inhibitors. Their unique ability to affect bacteria in a quiescent state, which may stem from their need for short bursts of RNA synthesis even in the absence of growth, makes them prime candidates for chronic infections, often in combination so as to avoid a relatively high frequency of resistance. In this respect, Rifampicin, generally in combination with other antibacterials, has resulted in attractive outcomes in the treatment of bone and joint infections (Darley and McGowan, J. Antimicrob. Chemother. (2004) 53, 928-935; Widmer et al, Clin. Infect. Dis. (1992) 14, 1251-1253)

Bisphosphonates are well-characterized bone-seeking agents. These compounds are recognized for having a high affinity to the bones due to their ability to bind the $Ca^{2+}$ ions found in the hydroxyapatite forming the bone tissues (Hirabayashi and Fujisaki, Clin. Pharmacokinet. (2003) 42(15): 1319-1330). Therefore, many different types of bisphosphonate-conjugated compounds have been made for targeting drugs selectively to the bone, including proteins (Uludag et al., Biotechnol Prog. (2000) 16:1115-1118), vitamins (U.S. Pat. No. 6,214,812, US 2003/0129194 and WO 02/083150), tyrosine kinase inhibitors (WO 01/44258 and WO 01/44259), hormones (U.S. Pat. No. 5,183,815 and US 2004/0116673) and bone scanning agents (U.S. Pat. No. 4,810,486). These and other bisphosphonate derivatives have been used as therapeutic agents for bone diseases such as arthritis (U.S. Pat. No. 4,746,654), osteoporosis (U.S. Pat. Nos. 5,428,181 and 6,420,384), hypercalcemia (U.S. Pat. No. 4,973,576), and bone cancers (U.S. Pat. No. 6,548,042).

Several strategies have also been investigated for targeted delivery of antibiotics (U.S. Pat. No. 5,900,410, US 2002/0142994; US 2004/0033969, US 2005/026864). For bone-targeted delivery of antibiotics, some have suggested the use of bisphosphonated-antibiotics. However, only a few of such compounds have actually being synthesized, including tetracyclines, β-lactams and fluoroquinolones (U.S. Pat. Nos. 5,854,227; 5,880,111; DE 195 32 235; Pieper and Keppler, Phosphorus, Sulfur and Silicon (2001) 170:5-14; and Herczegh et al. J. Med. Chem. (2002) 45:2338-41). Furthermore, none of these compounds has been administered in vivo or shown to have any bone-targeting activity.

Despite the progress which has been made in the past years, bone-specific delivery is still limited by the unique anatomical features of the bones. Although bisphosphonate modification might be a promising method, there is no certainty of success because several decades of progress demonstrate that therapeutically optimized bisphosphonate derivatives have to be designed and optimized on a compound-to-compound basis (Hirabasashi and Fujisaki, Clin Pharmacokinet (2003), 42(15):1319-1330).

In view of the above, there is a need for better administrable drugs for the prevention and treatment of bone and joint infections. More particularly, there is a need for highly active phosphonated derivatives of Rifamycins capable of achieving both time-controlled (or sustained) and spatially controlled (or targeted) drug delivery to the bones.

The present invention fulfills these needs and also other needs as will be apparent to those skilled in the art upon reading the following specification.

SUMMARY OF THE INVENTION

The present invention is directed to antimicrobial compounds which have an affinity for binding bones. More particularly, the invention is directed to phosphonated Rifamycins. These compounds are useful as antibiotics for the prophylaxis and/or treatment of bone and joint infections, especially for the prophylaxis and/or treatment of osteomyelitis.

In one embodiment, the compounds of the invention are represented by Formula (I) or a pharmaceutically acceptable salt or prodrug thereof:

  (I)

wherein:
B is a phosphonated group;
L is a cleavable linker for coupling B to A;
n is 1, 2, 3, 4, 5, 6 or 7, preferably 1, 2 or 3; and
A is a Rifamycin.

In a preferred embodiment, B is a phosphonated group having a high affinity to osseous tissues. Preferably B is a bisphosphonate. More preferably, B is a bisphosphonate selected from the group consisting of:

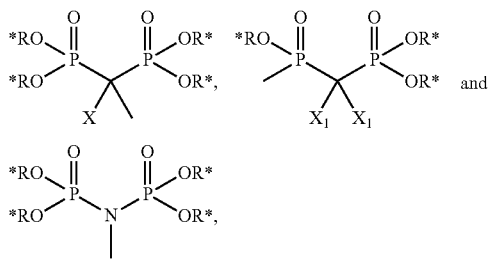

wherein:
  each R* is independently selected from the group consisting of H, lower alkyl, cycloalkyl, aryl and heteroaryl, with the proviso that at least two R* are H;
  X is H, OH, $NH_2$, or a halo group; and
  $X_1$ are both H, or each is independently selected from the group consisting of H, OH, $NH_2$, and a halo group.

In another preferred embodiment, L is a cleavable linker for covaltently and reversibly coupling B to A.

Preferably, L couples B to A through one or more hydroxyl groups on A, through one or more nitrogen atoms on A, or through one or more hydroxyl groups and one or more nitrogen atoms on A. When L couples B to A through a hydroxyl group on A, preferably L is one of the following linkers:

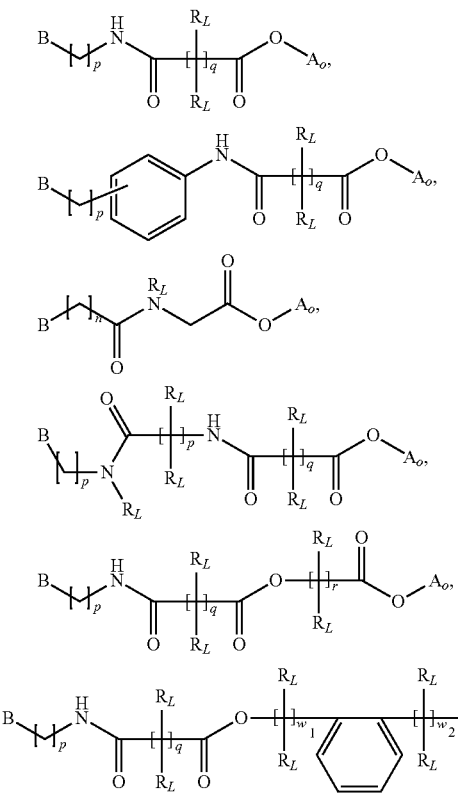

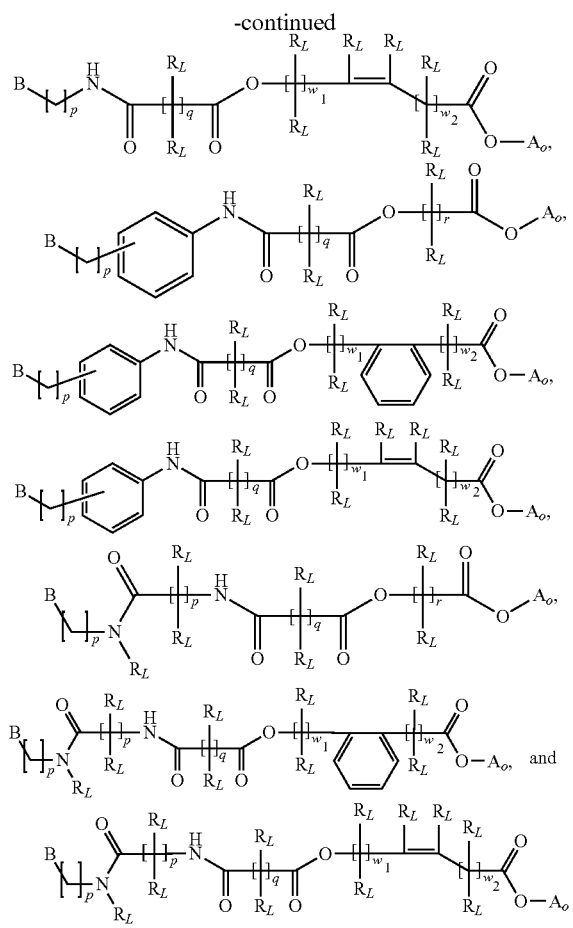

wherein:
  n is an integer $\leq 10$, preferably 1, 2, 3 or 4, more preferably 1 or 2;
  each p is independently 0 or an integer $\leq 10$, preferably 0, 1, 2, 3 or 4, more preferably 0 or 1;
  q is 2 or 3
  r is 1, 2, 3, 4 or 5
  $w_1$ and $w_2$ are integers $\geq 0$ such that their sum $(w_1+w_2)$ is 1, 2 or 3
  each $R_L$ is independently selected from the group consisting of H, ethyl and methyl, preferably H;
  B represents the phosphonated group;
  and the substructure

of the linker represents the hydroxyl moiety of A.

When L couples B to A through a nitrogen atom on A, preferably L is one of the following linkers:

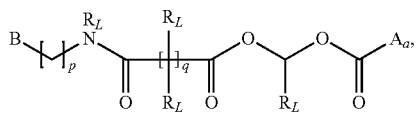

-continued

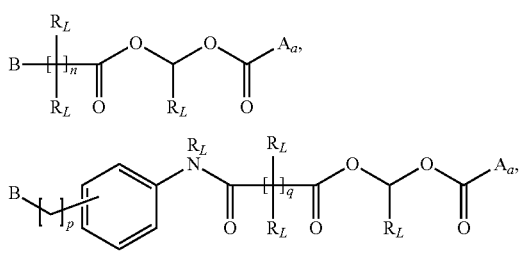
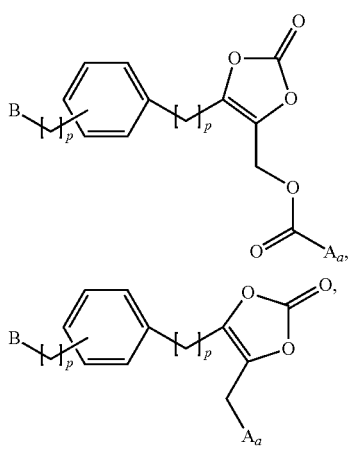
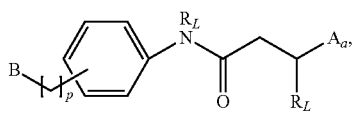
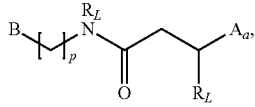
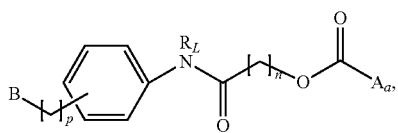
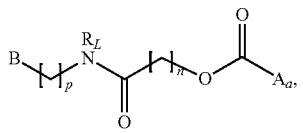
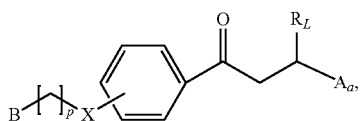
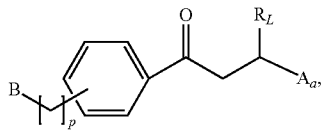
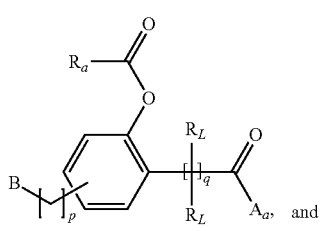

and

-continued

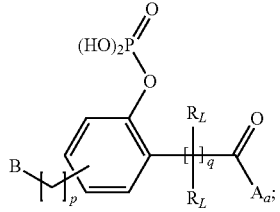

wherein:
n is an integer $\leq 10$, preferably 1, 2, 3 or 4, more preferably 1 or 2;
each p is independently 0 or an integer $\leq 10$, preferably 0, 1, 2, 3 or 4, more preferably 0 or 1;
q is 2 or 3;
each $R_L$ is independently selected from the group consisting of H, ethyl and methyl, preferably H;
$R_a$ is $C_xH_y$ where x is an integer of 0 to 20 and y is an integer of 1 to 2x+1;
X is $CH_2$, —$CONR_L$—, —CO—O—$CH_2$—, or —CO—O—;
B represents the phosphonated group; and
$A_a$ represents the nitrogen atom on A.

In further preferred embodiment, at least one of B-L- is coupled to a hydroxyl functionality on the RifamycinA. Preferably, when B-L- is coupled to a hydroxyl functionality B-L- is one of the following:

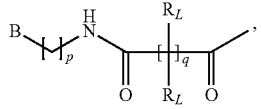
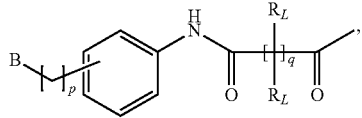
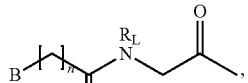
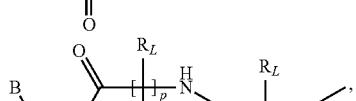
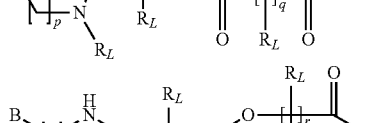
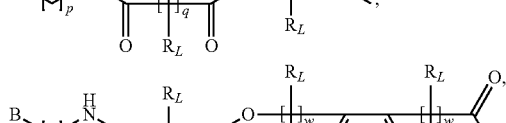
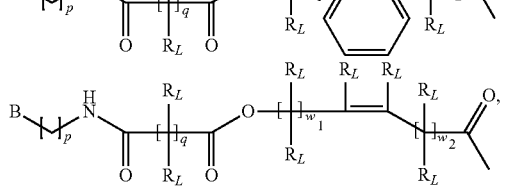

-continued

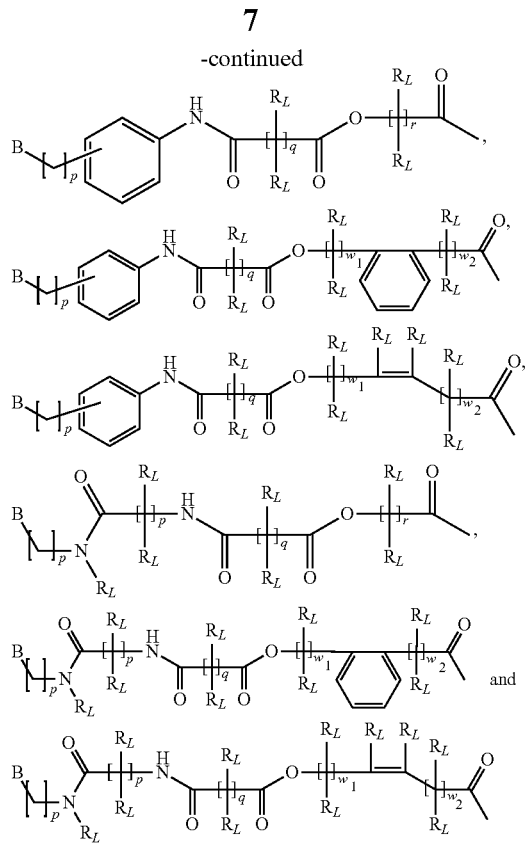

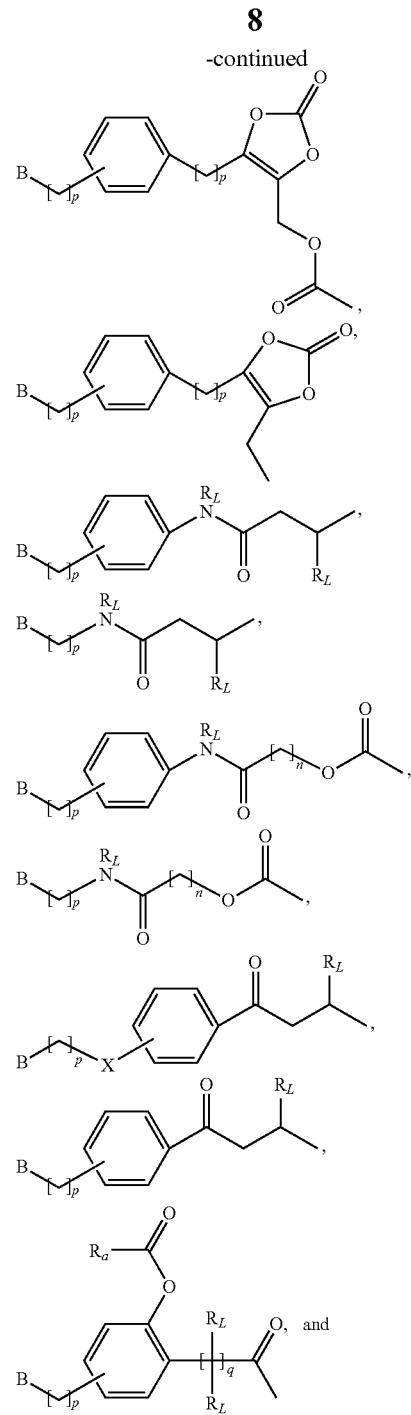

wherein:
B represents a phosphonated group;
each p is independently 0 or an integer $\leq 10$, preferably 0, 1, 2, 3, or 4, more preferably 0 or 1;
each $R_L$ is independently selected from the group consisting of H, ethyl and methyl, preferably H;
q is 2 or 3;
n is an integer $\leq 10$, preferably 1, 2, 3, or 4, more preferably 1 or 2;
r is 1, 2, 3, 4 or 5; and
$w_1$ and $w_2$ are each integers $\geq 0$ such that their sum ($w_1$+$w_2$) is 1, 2 or 3.

In further preferred embodiment, at least one of B-L- is coupled to a nitrogen atom on the RifamycinA. Preferably, when B-L- is coupled to a nitrogen atom B-L- is one of the following:

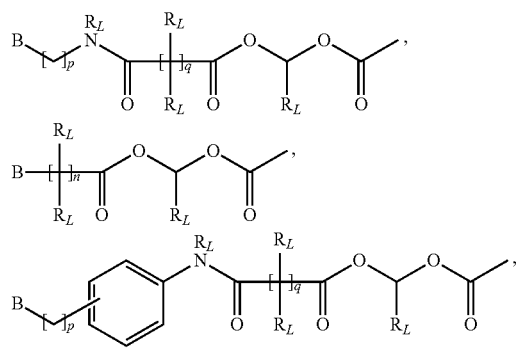

wherein:
B represents said phosphonated group;
n is an integer $\leq 10$, preferably 1, 2, 3, or 4, more preferably 1 or 2;
each p is independently 0 or an integer $\leq 10$, preferably 0, 1, 2, 3, or 4, more preferably 0 or 1;

each $R_L$ is independently selected from the group consisting of H, ethyl and methyl, preferably H;

q is 2 or 3;

X is $CH_2$, $-CONR_L-$, $-CO-O-CH_2-$, or $-CO-O-$; and $R_a$ is $C_xH_y$, where x is an integer of 0 to 20 and y is an integer of 1 to 2x+1.

In an additional preferred embodiment, n is an integer of 2 to 7, at least one of B-L- is coupled to a hydroxyl functionality on the Rifamycin A, and at least one of B-L- is coupled to a nitrogen atom on the Rifamycin A. Preferably, when B-L- is coupled to a hydroxyl functionality B-L- is one of the following:

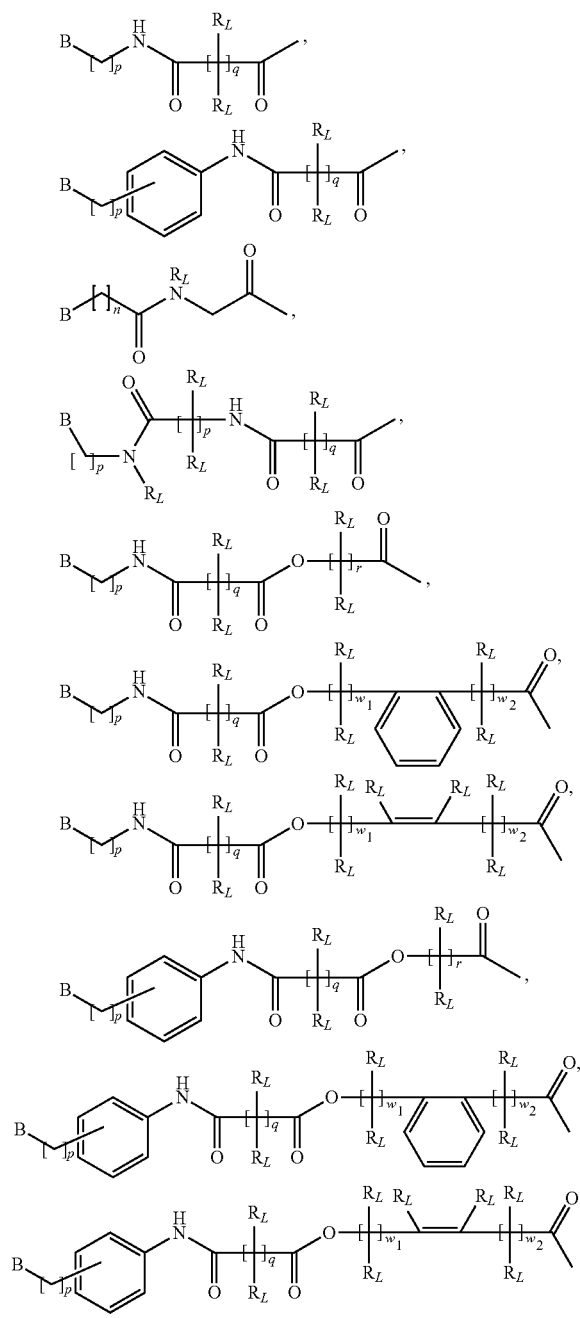

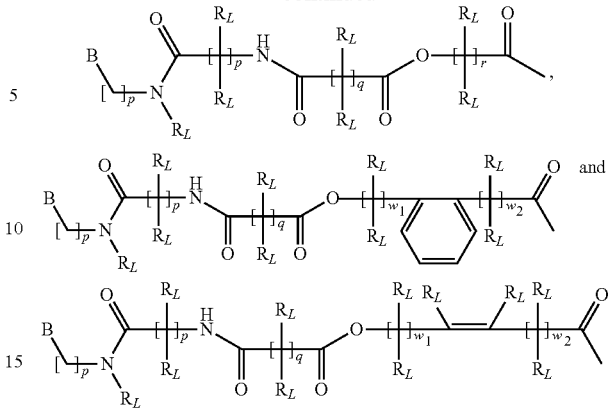

wherein:

B represents a phosphonated group;

each p is independently 0 or an integer $\leq 10$, preferably 0, 1, 2, 3, or 4, more preferably 0 or 1;

each $R_L$ is independently selected from the group consisting of H, ethyl and methyl, preferably H;

q is 2 or 3;

n is an integer $\leq 10$, preferably 1, 2, 3, or 4, more preferably 1 or 2;

r is 1, 2, 3, 4 or 5; and $w_1$ and $w_2$ are each integers $\geq 0$ such that their sum $(w_1+w_2)$ is 1, 2 or 3. Preferably, when B-L- is coupled to a nitrogen atom B-L- is one of the following:

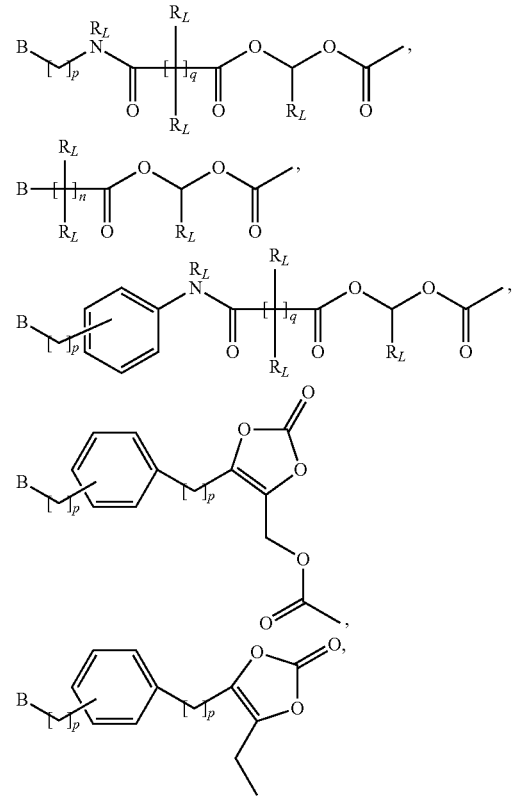

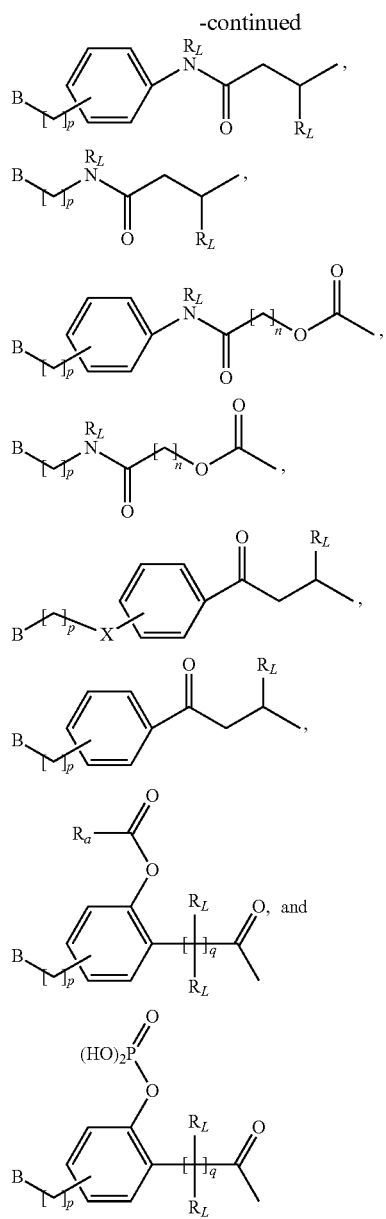

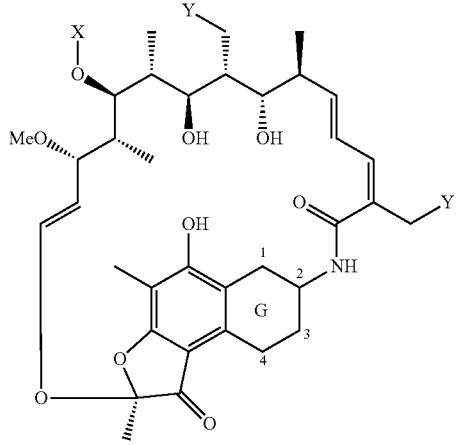

wherein:
B represents said phosphonated group;
n is an integer ≦10, preferably 1, 2, 3, or 4, more preferably 1 or 2;
each p is independently 0 or an integer ≦10, preferably 0, 1, 2, 3, or 4, more preferably 0 or 1;
each $R_L$ is independently selected from the group consisting of H, ethyl and methyl, preferably H;
q is 2 or 3;
X is $CH_2$, —$CONR_L$—, —CO—O—$CH_2$—, or —CO—O—; and
$R_a$ is $C_xH_y$, where x is an integer of 0 to 20 and y is an integer of 1 to 2x+1.

In a further preferred embodiment, n is 1, 2 or 3.

Preferably, the Rifamycin A has a structure represented by the following Formula A1:

wherein:
X is H— or $R_1CO$—, wherein $R_1$ is a substituted or unsubstituted alkyl chain of 1-6 carbons;
each Y is independently selected from the group consisting of H— and RO—, wherein R is H—, $R_1$—, or $R_1CO$—, with $R_1$ defined as above;

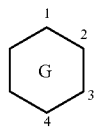

is selected from the group consisting of formulae A2-A10:

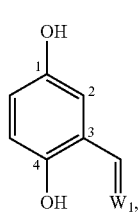

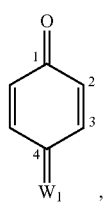

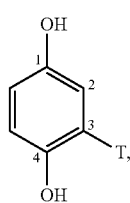

-continued

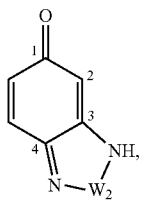
A5

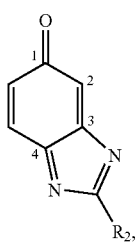
A6

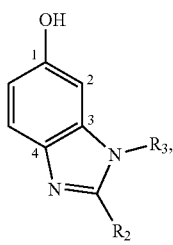
A7

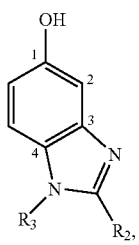
A8

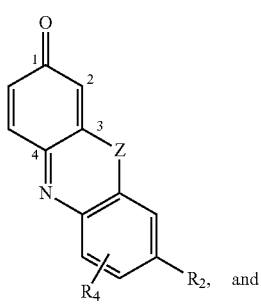
A9

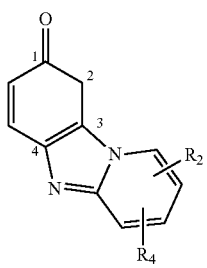
A10 wherein:
R$_2$ is H—, a substituted or unsubstituted alkyl chain of 1-10 carbons, or a dialkyl amino group, preferably said dialkyl amino group is a substituted piperidine, a substituted morpholine or a substituted piperazine;

R$_3$ is H— or a substituted or unsubstituted alkyl chain of 1-7 carbons;

R$_4$ is a hydroxyl group, a sulfhydryl group or a substituted or unsubstituted alkyl chain of 1-3 carbons;

W$_1$ is oxygen or —NR$_2$ with R$_2$ defined as above;

W$_2$ is a substituted or unsubstituted methylene, including:

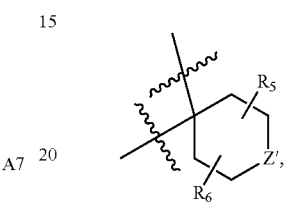

wherein R$_5$ and R$_6$ are independently H— or a substituted or unsubstituted alkyl chain of 1-5 carbons, and Z' is an oxygen atom, a sulfur atom, a substituted methylene, a carbonyl, —NR$_1$ or —N(O)R$_1$ where R$_1$ is defined as above;

T is a halogen or R$_2$, where R$_2$ is defined as above; and

Z is O, S or NR$_3$, where R$_3$ is defined as above.

More preferably, the Rifamycin A has a structure represented by one of the following formulas or an antimicrobial derivative thereof:

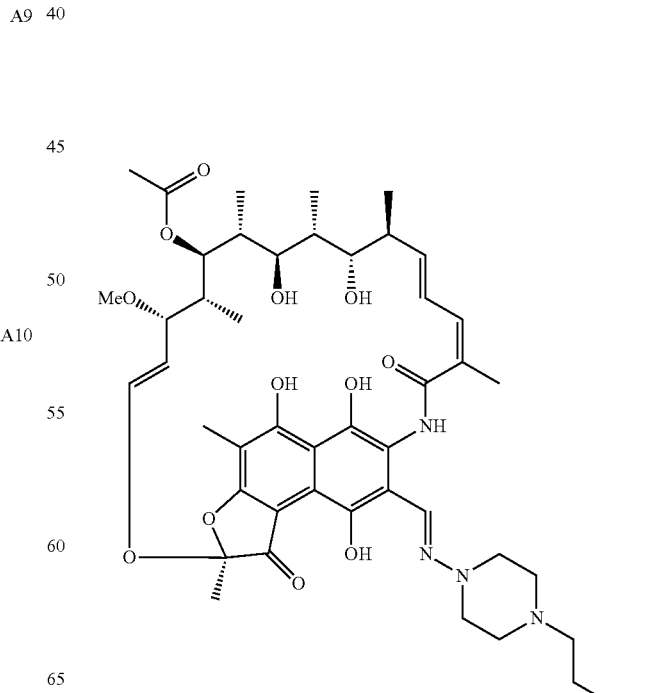

-continued

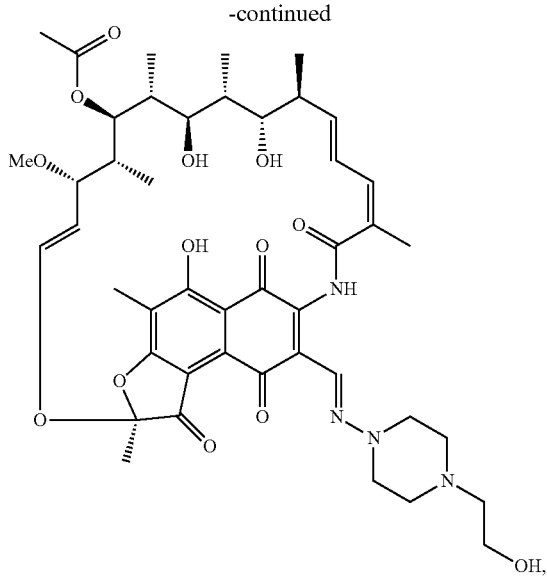

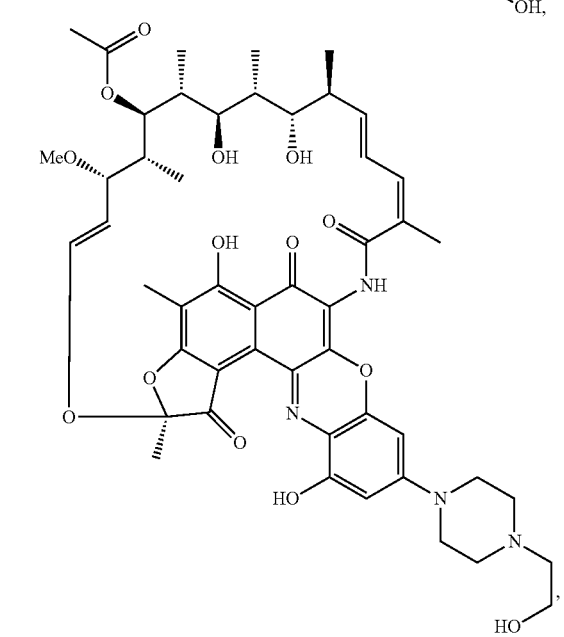

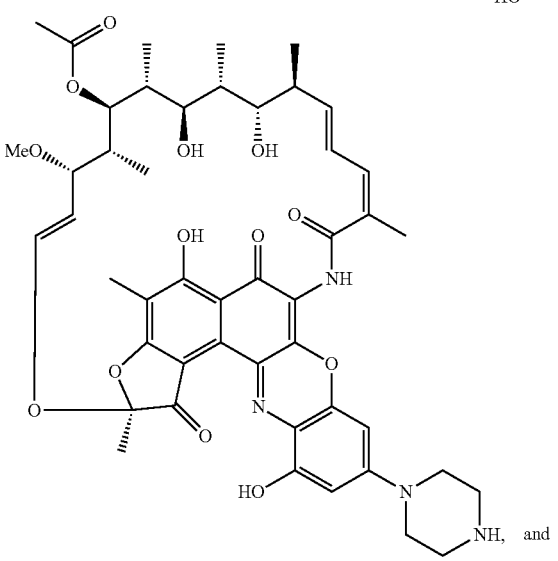

-continued

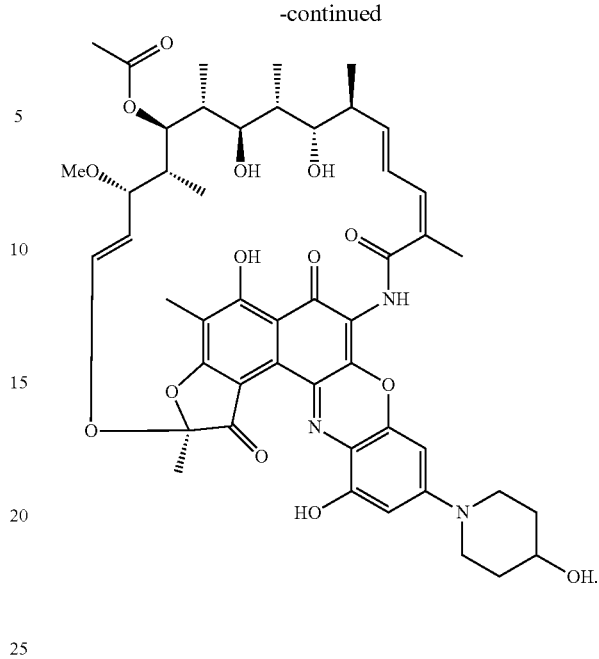

Also preferably, the Rifamycin A is Rifampicin, Rifapentin, Rifabutin, Rifalazil, Rifaximin, Rifandin, or an antimicrobial derivative of one of these compounds.

In another embodiment, the compounds of the invention are represented by Formula (II) or a pharmaceutically acceptable salt or prodrug thereof:

(II)

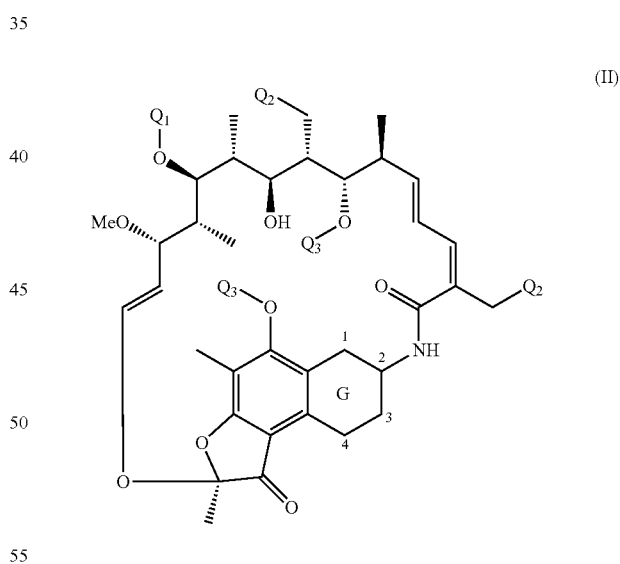

wherein:
Q1 is H—, $R_1$CO— or $L_1$-, wherein $R_1$ is a substituted or unsubstituted alkyl chain of 1-6 carbons;
each $Q_2$ is independently selected from the group consisting of H—, RO— and $L_2$O—, wherein R is H—, $R_1$— or $R_1$CO—, with $R_1$ defined as above;
each $Q_3$ is independently selected from the group consisting of H— and $L_3$-;

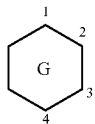

is selected from the group consisting of formulae A2-A10:

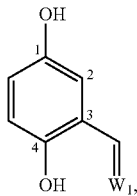
A2

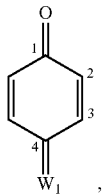
A3

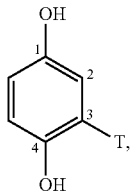
A4

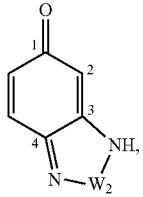
A5

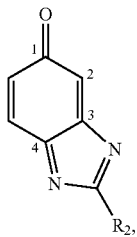
A6

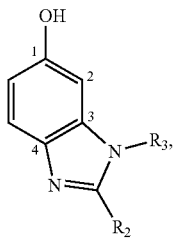
A7

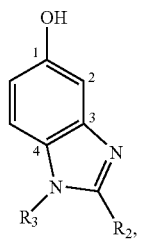
A8

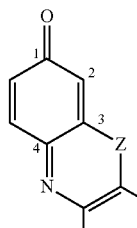
A9 and

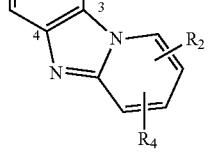
A10 wherein
$R_2$ is H—, a substituted or unsubstituted alkyl chain of 1-10 carbons or a dialkyl amino group, preferably said dialkyl amino group is a substituted piperidine, a substituted morpholine or a substituted piperazine, wherein when $R_2$ is a substituted alkyl chain of 1-10 carbons, a substituted piperidine, a substituted morpholine or a substituted piperazine, the substituent is one member selected from the group consisting of $L_4O$—, $L_5S$— and $L_6NR_7$—, wherein $R_7$ is a substituted or unsubstituted alkyl chain of 1-7 carbons;
$R_3$ is H—, a substituted or unsubstituted alkyl chain of 1-7 carbons or $L_7$-;
$R_4$ is a hydroxyl group, a sulfhydryl group or a substituted or unsubstituted alkyl chain of 1-3 carbons, $L_5O$— or $L_9S$—;
$W_1$ is oxygen or —$NR_2$, with $R_2$ defined as above;
$W_2$ is a substituted or unsubstituted methylene, including wherein

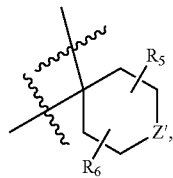

$R_5$ and $R_6$ are independently H— or a substituted or unsubstituted alkyl chain of 1-5 carbons, and $Z'$ is an oxygen atom, a sulfur atom, a substituted methylene, a carbonyl, —$NR_1$ or —$N(O)R_1$ where $R_1$ is defined as above;

T is a halogen or $R_2$, where $R_2$ is defined as above;

Z is O, S or $NR_3$, where $R_3$ is defined as above;

each $L_1$, $L_2$, $L_3$, $L_4$, $L_5$, $L_8$ and $L_9$ is a cleavable linker independently selected from the group consisting of:

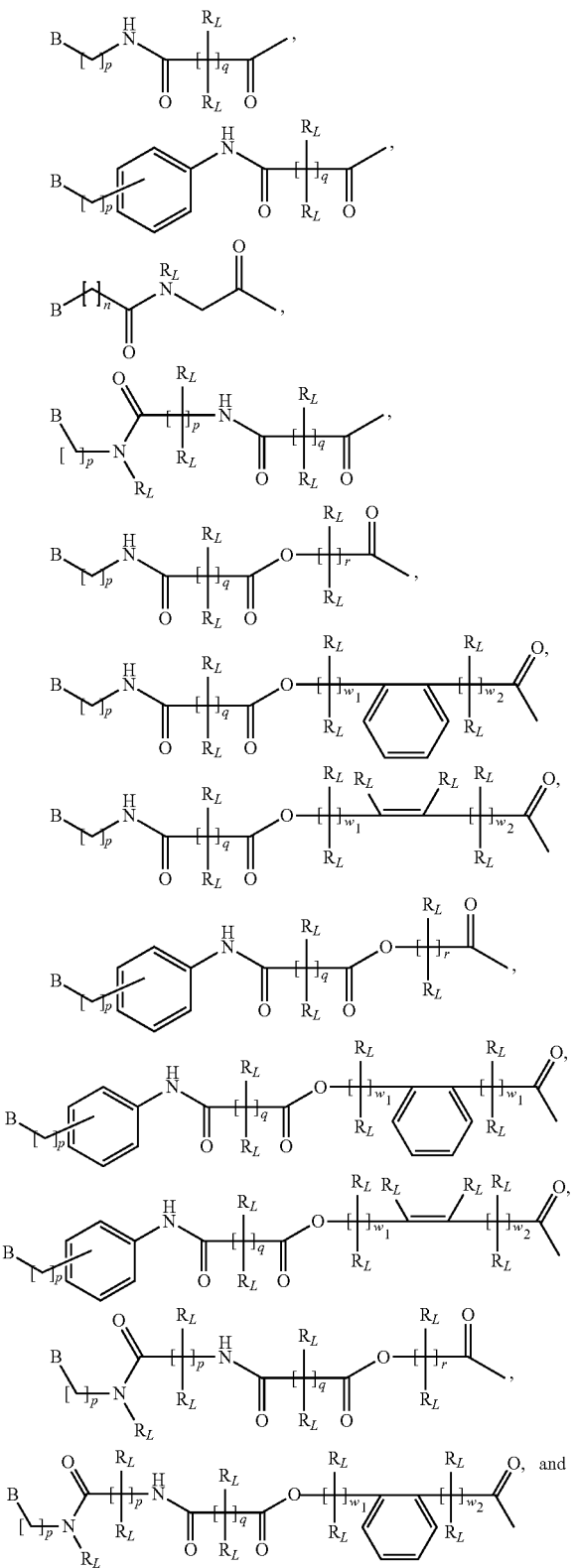

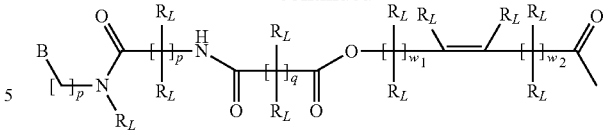

wherein:
- n is an integer $\leq 10$, preferably 1, 2, 3 or 4, more preferably 1 or 2;
- each p is independently 0 or an integer $\leq 10$, preferably 0, 1, 2, 3 or 4, more preferably 0 or 1;
- q is 2 or 3;
- r is 1, 2, 3, 4 or 5;
- $w_1$ and $w_2$ are integers $\geq 0$ such that their sum ($w_1+w_2$) is 1, 2 or 3;
- each $R_L$ is independently selected from the group consisting of H, ethyl and methyl, preferably H;
- each $L_6$ and $L_7$ is a cleavable linker independently selected from the group consisting of:

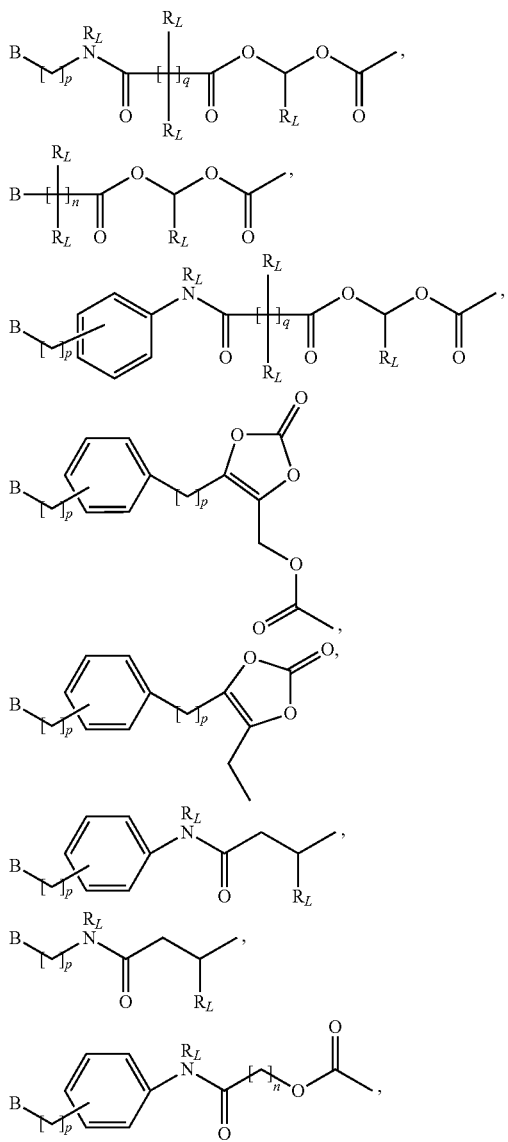

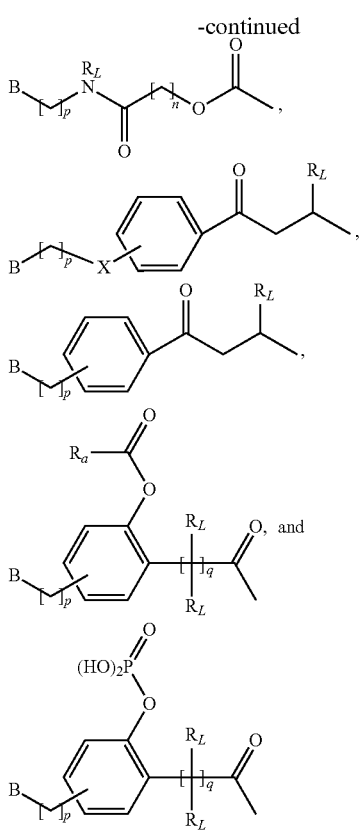

wherein:
- n is an integer $\leq 10$, preferably 1, 2, 3 or 4, more preferably 1 or 2;
- each p is independently 0 or an integer $\leq 10$, preferably 0, 1, 2, 3 or 4, more preferably 0 or 1;
- q is 2 or 3;
- each $R_L$ is independently selected from the group consisting of H, ethyl and methyl, preferably H;
- $R_a$ is $C_xH_y$, where x is an integer of 0 to 20 and y is an integer of 1 to 2x+1; and
- X is $CH_2$, —$CONR_L$—, —CO—O—$CH_2$—, or —CO—O—;
- B is a phosphonated group selected from the group consisting of:

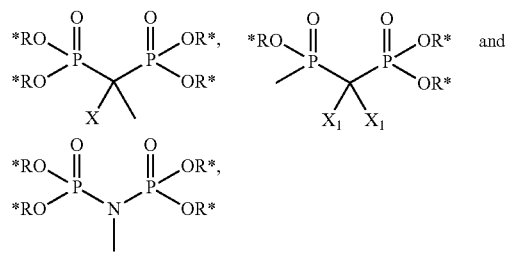

wherein:
- each R* is independently selected from the group consisting of H, lower alkyl, cycloalkyl, aryl and heteroaryl, with the proviso that at least two R* are H;
- X is H, OH, $NH_2$, or a halo group;
- each $X_1$ is independently selected from the group consisting of H, OH, $NH_2$, and a halo group;
- with the proviso that at least one of $L_1$, $L_2$, $L_3$, $L_4$, $L_5$, $L_6$, $L_7$, $L_8$ and $L_9$ is present.

In further preferred embodiments, the compounds of the invention have a structure selected among the structures illustrated below, as well as pharmaceutically acceptable salts and prodrugs thereof:

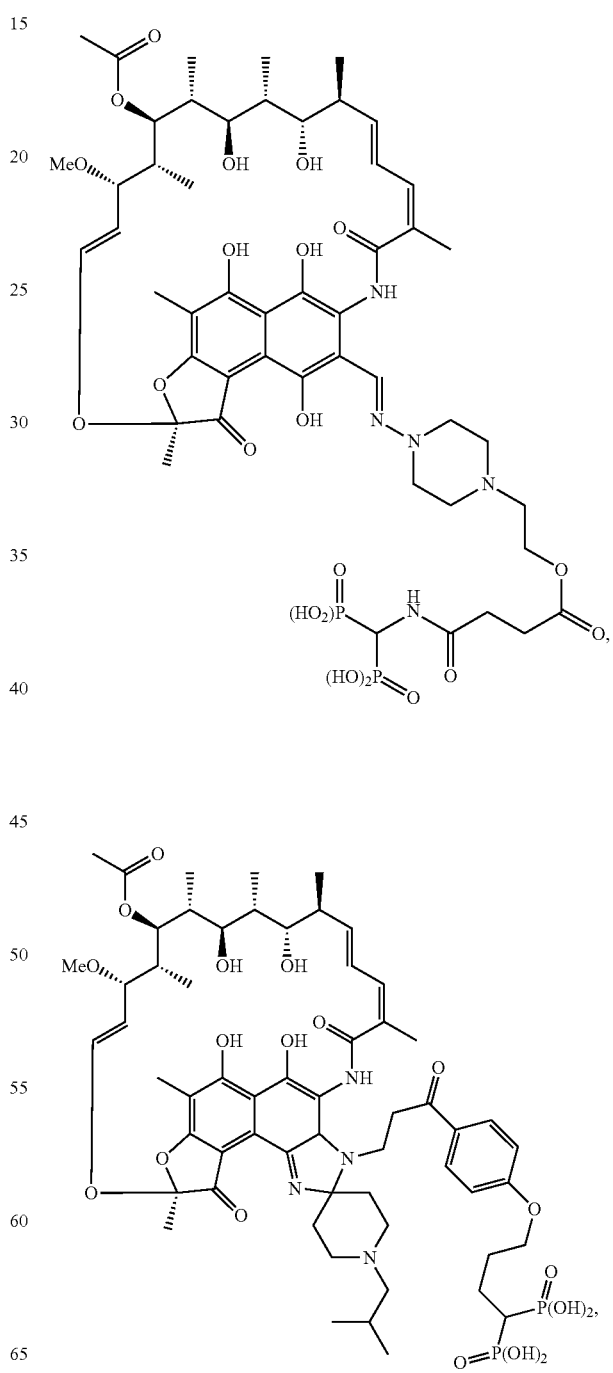

23
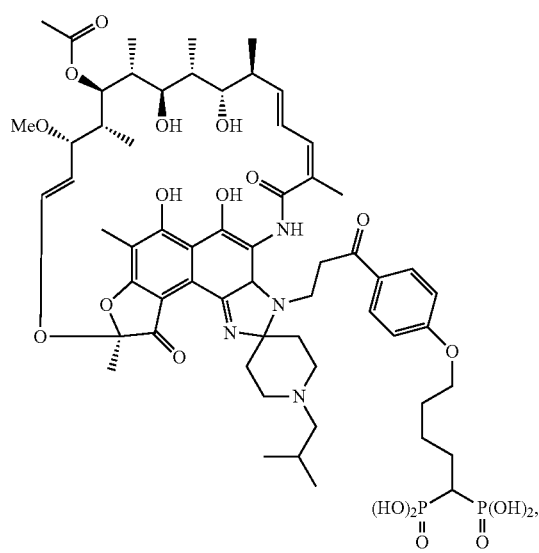
24
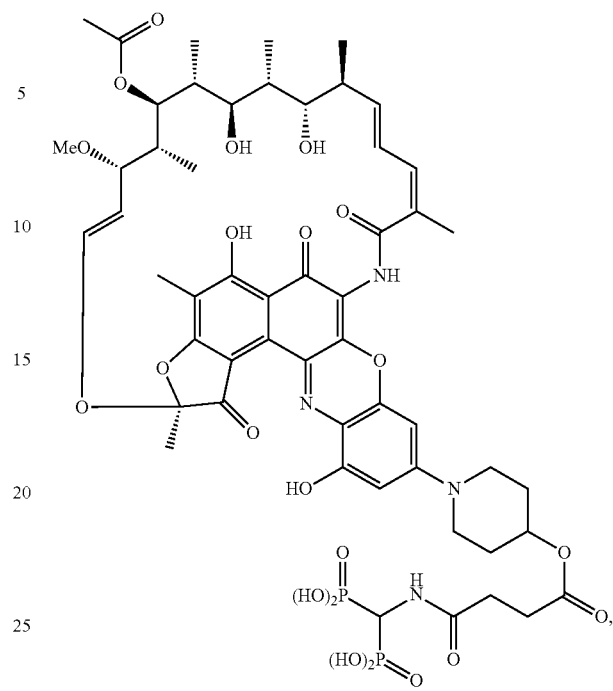
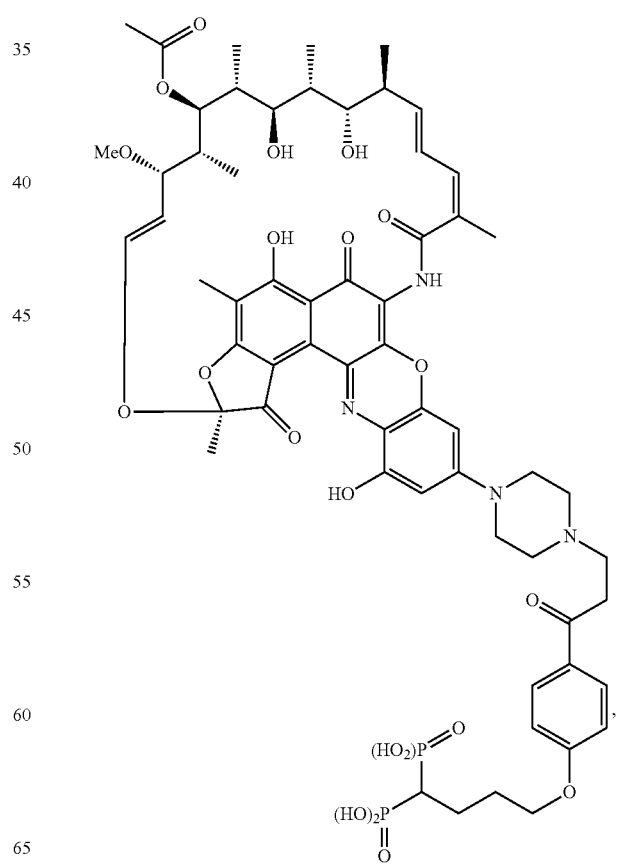

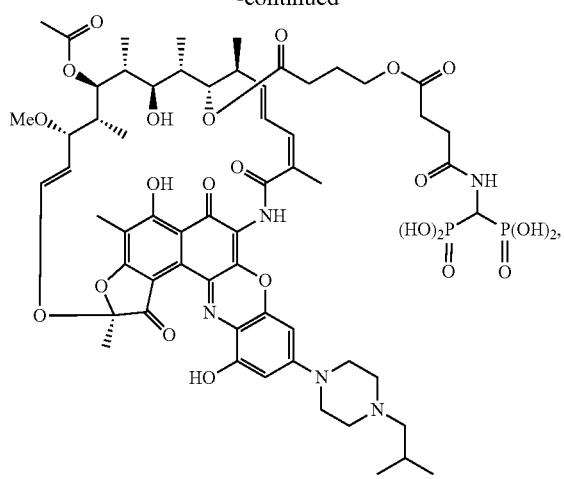
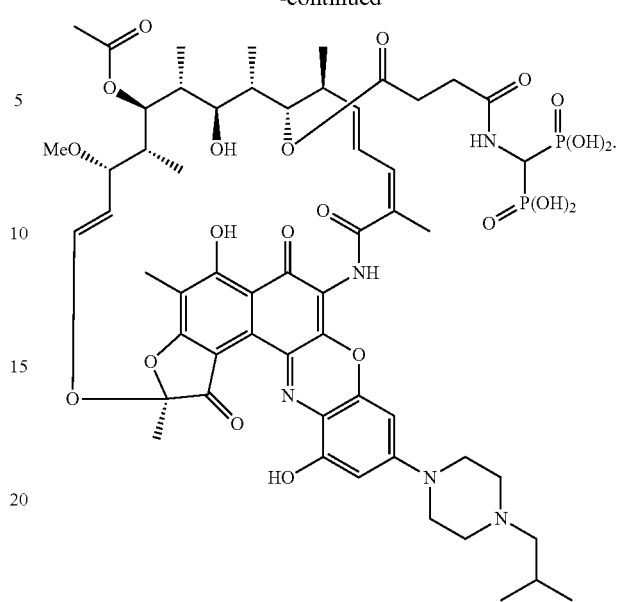
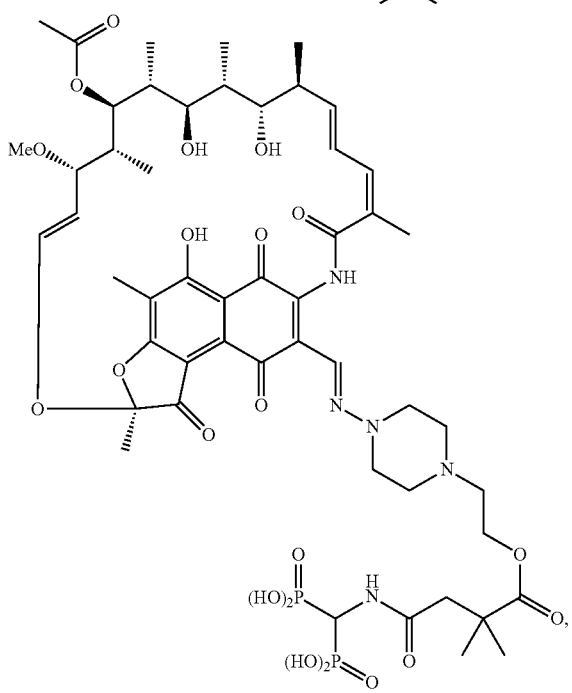
Particularly preferred compounds of the present invention have a structure selected among the structures illustrated below, as well as pharmaceutically acceptable salts and prodrugs thereof:
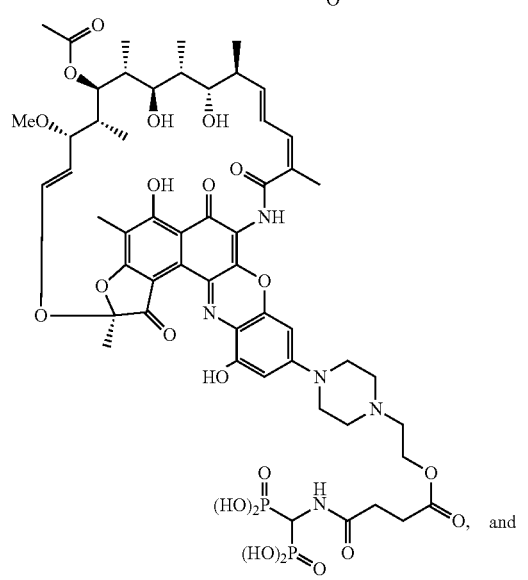
, and
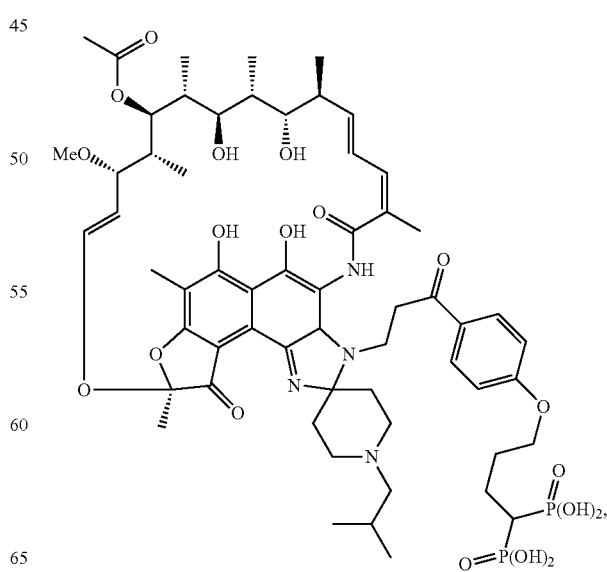

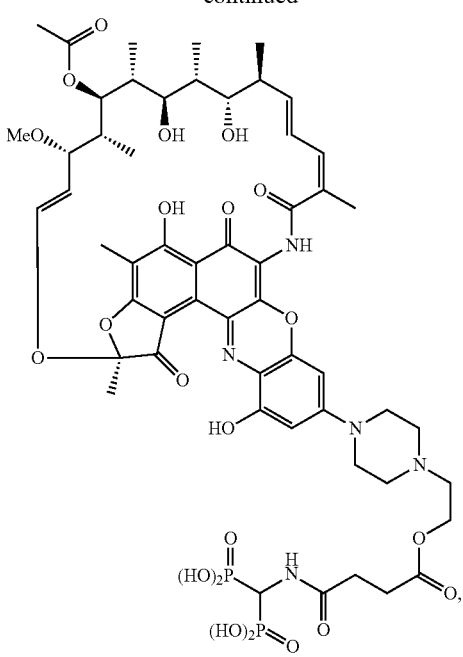

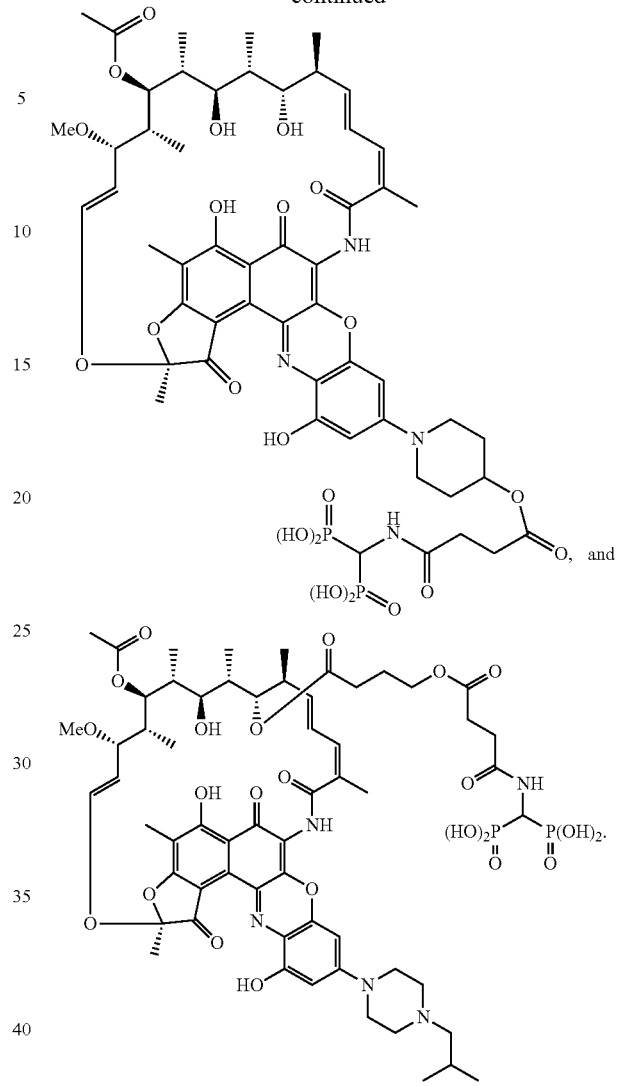

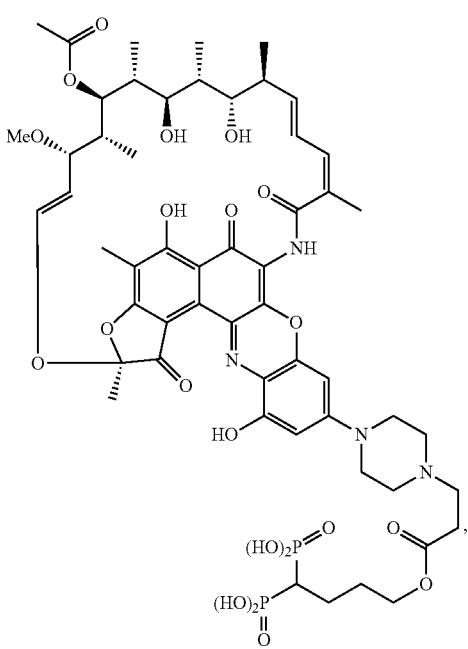

In another aspect of the present invention there are disclosed pharmaceutical compositions comprising one or more of the compounds as defined herein and a pharmaceutically acceptable carrier or excipient.

The present invention also encompasses methods for treating a bacterial infection in a subject, comprising administering to a subject having a bacterial infection or otherwise in need of such treatment a pharmaceutically effective amount of one or more of the compounds as defined herein, or a pharmaceutical composition as defined herein. The subject may be an animal, preferably a mammal, more preferably a human.

The present invention further encompasses methods for prophylaxis for a bacterial infection in a subject, comprising administering to a subject a prophylactically effective amount of one or more of the compounds as defined herein, or a pharmaceutical composition as defined herein. The prophylactically effective amount of the compounds or pharmaceutical composition may be administered to a subject prior to, during, or after an invasive medical treatment. The subject may be an animal, preferably a mammal, more preferably a human.

The present invention also encompasses methods for treating a bacterial infection in a subject, comprising administering to a subject having a bacterial infection or otherwise in need of such treatment a pharmaceutically effective amount of one or more of the compounds as defined herein, or a pharmaceutical composition as defined herein, and concurrently administering a second therapeutic agent. Preferably the second therapeutic agent is an antibiotic. More preferably the second therapeutic agent is an antibiotic selected from the group consisting of tetracycline, a tetracycline derived antibacterial agent, glycylcycline, a glycylcycline derived antibacterial agent, minocycline, aminocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, daptomycin, and a daptomycin derived antibacterial agent.

The invention also provides a method for accumulating a Rifamycin in a bone of a subject, comprising administering to a subject one or more of the compounds as defined herein, or a pharmaceutical composition as defined herein. Such method for accumulating a Rifamycin in a bone of a subject may also be used to prolong the presence of a Rifamycin in a bone of a subject. In each instance, the subject may be an animal, preferably a mammal, more preferably a human.

In a further aspect of the present invention there are provided processes for the preparation of a phosphonated Rifamycin, preferably a phosphonated Rifamycin of Formula (I) and/or Formula (II) as defined herein.

An advantage of the invention is that it provides antimicrobial compounds having an increased binding affinity for bone. The invention also provides methods for the unmet medical need of prevention and treatment of bone and joint infections.

Additional objects, advantages and features of the present invention will become more apparent upon reading of the following non-restrictive description of preferred embodiments with reference to the accompanying drawings which are exemplary and should not be interpreted as limiting the scope of the present invention.

DETAILED DESCRIPTION OF THE INVENTION

A) General Overview of the Invention

Figure 1:
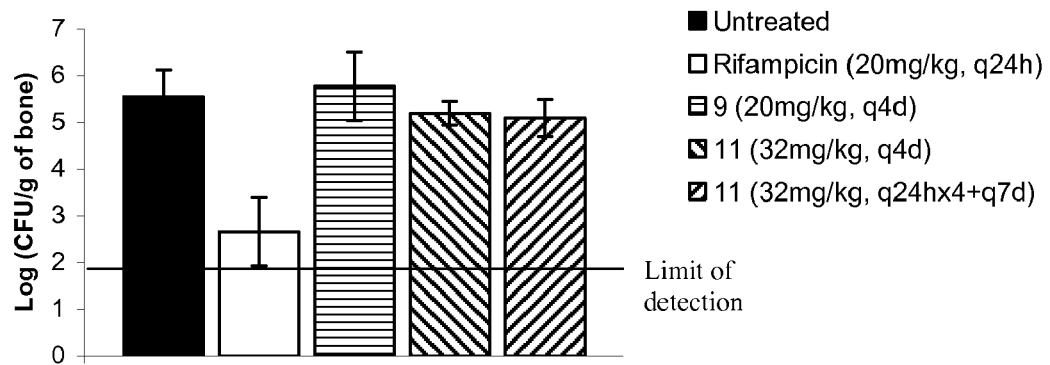
FIG. 1 is a bar graph showing the testing of 20 mg/kg of Rifamycin derivative 9 and the small but not statistically significant effect (versus the untreated control) of 32 mg/kg of its parent bisphosphonated prodrug 11 on bacterial titer in bone infection when used either every four days or on four consecutive days and then every week for 4 weeks post-infection.

The present invention discloses phosphonated Rifamycins, in particular, those phosphonated compounds defined in Formula (I) and Formula (II) as defined above and hereinafter. These compounds are useful antimicrobial agents effective against a number of human and veterinary pathogens. A phosphonated group is reversibly coupled to a Rifamycin via a cleavable linker.

Phosphonated Rifamycins have been synthesized and demonstrated to have an increased affinity for osseous materials. In vivo, these phosphonated compounds accumulate in bones in amounts greater than amounts of non-phosphonated equivalents. The presence of Rifamycins in the bones can be prolonged by administering phosphonated Rifamycins according to the invention. In addition, significant in vivo protection against bone infection has been demonstrated for at least three days prior to infection for animals injected with phosphonated Rifamycins according to the invention. Accordingly, the compounds of the invention are particularly useful for the prophylaxis and/or treatment of bone and joint-related infections and bone-related diseases such as osteomyelitis.

B) Definitions

In order to provide an even clearer and more consistent understanding of the invention, including the scope given herein to particular terms, the following general definitions are provided:

The term "alkyl" refers to saturated aliphatic groups including straight-chain, branched-chain, cyclic groups, and combinations thereof, having the number of carbon atoms specified, or if no number is specified, having 1 to 12 carbon atoms (preferably 1 to 6). Examples of alkyl groups include, but are not limited to groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, cyclobutylmethyl, cyclobutylethyl, cyclopentylmethyl, cyclopentylethyl, and adamantyl. Cyclic alkyl groups (e.g. cycloalkyl or heterocycloalkyl) can consist of one ring, including, but not limited to, groups such as cycloheptyl, or multiple fused rings, including, but not limited to, groups such as adamantyl or norbornyl.

The term "alkylaryl" refers to an alkyl group having the number of carbon atoms designated, appended to one, two, or three aryl groups.

The term "N-alkylaminocarbonyl" refers to the radical —C(O)NHR where R is an alkyl group.

The term "N,N-dialkylaminocarbonyl" refers to the radical —C(O)NR$_a$R$_b$ where R$_a$ and R$_b$ are each independently an alkyl group.

The term "alkylthio" refers to the radical —SR where R is an alkyl group.

The term "alkoxy" as used herein refers to an alkyl, alkenyl, or alkynyl linked to an oxygen atom and having the number of carbon atoms specified, or if no number is specified, having 1 to 12 carbon atoms (preferably 1 to 6). Examples of alkoxy groups include, but are not limited to, groups such as methoxy, ethoxy, tert-butoxy, and allyloxy. The term "alkoxycarbonyl" refers to the radical —C(O)OR where R is an alkyl. The term "alkylsulfonyl" refers to the radical —SO$_2$R where R is an alkyl group.

The term "alkylene" means a saturated divalent aliphatic group including straight-chain, branched-chain, cyclic groups, and combinations thereof, having the number of carbon atoms specified, or if no number is specified, having 1 to 12 carbon atoms (preferably 1 to 6), e.g., methylene, ethylene, 2,2-dimethylethylene, propylene, 2-methyl-propylene, butylene, pentylene, cyclopentylmethylene, and the like.

The term "substituted alkyl" means an alkyl group as defined above that is substituted with one or more substituents, preferably one to three substituents, wherein the substituents are preferably selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents, wherein the substituents are preferably selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl, methoxycarbonylmethyl, 1- or 2-methoxycarbonyl ethyl, benzyl, pyrdinylmethyl, thiophenylmethyl, imidazolinylmethyl, dimethylaminoethyl and the like.

The term "substituted alkylene" means an alkylene group as defined above that is substituted with one or more substituents, preferably one to three substituents, wherein the substituents are preferably selected from the group consisting of halogen, alkyl, aryl, alkoxy, acyloxy, amino, mono or dialkylamino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. The phenyl group may optionally be substituted with one to three substituents, wherein the substituents are preferably selected from the group consisting of halogen, alkyl, aryl, alkoxy, acyloxy, amino, mono or dialkylamino, hydroxyl, mercapto, carboxy, benzyloxy, benzyl, cyano, nitro, thioalkoxy, carboxaldehyde, carboalkoxy and carboxamide. Examples of substituted alkyl groups include, but are not limited to —CF$_2$—, —CF$_2$—CF$_2$—, hydroxymethylene, 1- or 2-hydroxyethylene, methoxymethylene, 1- or 2-ethoxyethylene, carboxymethylene, 1- or 2-carboxyethylene, and the like.

The term "alkenyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenyl groups include, but are not limited to allyl vinyl, —CH$_2$—CH=CH—CH$_3$, —CH$_2$—CH$_2$-cyclopentenyl and —CH$_2$—CH$_2$-cyclohexenyl where the ethyl group can be attached to the cyclopentenyl, cyclohexenyl moiety at any available carbon valence.

The term "alkenylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one double bond (—C=C—). Examples of alkenylene groups include, but are not limited to —CH=CH—, —CH$_2$—CH=CH—CH$_2$—, —CH$_2$—CH(cyclopentenyl)- and the like.

The term "alkynyl" refers to unsaturated aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynyl groups include, but are not limited to acetylene, 2-butynyl, and the like.

The term "alkynylene" refers to unsaturated divalent aliphatic groups including straight-chain, branched-chain, cyclic groups, and combinations thereof, having the number of carbon atoms specified, or if no number is specified, having 1 to 12 carbon atoms (preferably 1 to 6), which contain at least one triple bond (—C≡C—). Examples of alkynylene groups include, but are not limited to —C≡C—, —C≡C—CH$_2$—, and the like.

The term "substituted alkenyl" or "substituted alkynyl" refers to the alkenyl and alkynyl groups as defined above that are substituted with one or more substituents, wherein the substituents are preferably selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkenyl and alkynyl groups include, but are not limited to —CH=CF$_2$, methoxyethenyl, methoxypropenyl, bromopropynyl, and the like.

The term "substituted alkenylene" or "substituted alkynylene" refers to the alkenylene and alkynylene groups as defined above that are substituted with one or more substituents, wherein the substituents are preferably selected from the group consisting of halogen, alkyl, aryl, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

The term "aryl" or "Ar" refers to an aromatic carbocyclic group of 6 to 14 carbon atoms having a single ring (including but not limited to groups such as phenyl) or multiple condensed rings (including but not limited to groups such as naphthyl or anthryl), and includes both unsubstituted and substituted aryl groups. Substituted aryl is an aryl group that is substituted with one or more substituents, preferably one to three substituents, wherein the substituents are preferably selected from the group consisting of alkyl, aryl, alkenyl, alkynyl, halogen, alkoxy, acyloxy, amino, mono or dialkylamino, hydroxyl, mercapto, carboxy, benzyloxy, phenyl, aryloxy, benzyl, cyano, nitro, thioalkoxy, carboxaldehyde, carboalkoxy and carboxamide, or a functionality that can be suitably blocked, if necessary for purposes of the invention, with a protecting group. Representative examples include, but are not limited to naphthyl, phenyl, chlorophenyl, iodophenyl, methoxyphenyl, carboxyphenyl, and the like. The term "aryloxy" refers to an aryl group linked to an oxygen atom at one of the ring carbons. Examples of alkoxy groups include, but are not limited to, groups such as phenoxy, 2-, 3-, or 4-methylphenoxy, and the like. The term "arylthio group" refers to the radical —$SR_c$ where $R_c$ is an aryl group. The term "heteroarylthio group" refers to the radical —$SR_d$ where $R_d$ is a heteroaryl.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —$NH_2$.

The term "N-alkylamino" and "N,N-dialkylamino" means a radical —NHR and —NRR' respectively where R and R' independently represent an alkyl group as defined herein. Representative examples include, but are not limited to N,N-dimethylamino, N-ethyl-N-methylamino, N,N-di(1-methylethyl)amino, N-cyclohexyl-N-methylamino, N-cyclohexyl-N-ethylamino, N-cyclohexyl-N-propylamino, N-cyclohexylmethyl-N-methylamino, N-cyclohexylmethyl-N-ethylamino, and the like.

The term "thioalkoxy" means a radical —SR where R is an alkyl as defined above e.g., methylthio, ethylthio, propylthio, butylthio, and the like.

The term "acyl group" means a radical —C(O)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "thioacyl group" means a radical —C(S)R, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "sulfonyl group" means a radical —$SO_2R$, where R is hydrogen, halogen, alkyl, aryl, heteroaryl, alkoxy, aryloxy, N-alkylamino, N,N-dialkylamino, N-arylamino, thioalkoxy, thioaryloxy or substituted alkyl wherein alkyl, aryl, heteroaryl, and substituted alkyl are as defined herein.

The term "acyloxy" means a radical —OC(=O)R, where R is hydrogen, alkyl, aryl, heteroaryl or substituted alkyl wherein alkyl, aryl, heteroaryl, and substituted alkyl are as defined herein. Representative examples include, but are not limited to formyloxy, acetyloxy, cylcohexylcarbonyloxy, cyclohexylmethylcarbonyloxy, benzoyloxy, benzylcarbonyloxy, and the like.

The term "heteroalkyl," "heteroalkenyl," and "heteroalkynyl" refers to alkyl, alkenyl, and alkynyl groups respectively as defined above, that contain the number of carbon atoms specified (or if no number is specified, having 1 to 12 carbon atoms, preferably 1 to 6) which contain one or more heteroatoms, preferably one to three heteroatoms, as part of the main, branched, or cyclic chains in the group. Heteroatoms are independently selected from the group consisting of —NR—, —NRR, —S—, —S(O)—, —$S(O)_2$—, —O—, —SR, —S(O)R, —$S(O)_2R$, —OR—, —PR—, —PRR, —P(O)R— and —P(O)RR; (where each R is hydrogen, alkyl or aryl) preferably —NR where R is hydrogen or alkyl and/or O. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—CH($CH_3$)—S—$CH_3$, —$CH_2$—$CH_2$—NH—$CH_2$—$CH_3$, 1-ethyl-6-propylpiperidino, 2-ethylthiophenyl, piperazino, pyrrolidino, piperidino, morpholino, and the like. Examples of heteroalkenyl groups include, but are not limited to groups such as —CH=CH—$CH_2$—N($CH_3)_2$, and the like.

The term "heteroaryl" or "HetAr" refers to an aromatic monovalent monocyclic, bicyclic, or tricyclic radical containing 4, 5, 6, 7, 8, 9, 10, 11, 12, 13, 14, 15, 16, 17, or 18-member ring atoms, including 1, 2, 3, 4, or 5 heteroatoms, preferably one to three heteroatoms including, but not limited to, heteroatoms such as N, O, P, or S, within the ring. Representative examples include, but are not limited to, single ring such as imidazolyl, pyrazolyl, pyrazinyl, pyridazinyl, pyrimidinyl, pyrrolyl, pyridyl, thiophene, and the like, or multiple condensed rings such as indolyl, quinoline, quinazoline, benzimidazolyl, indolizinyl, benzothienyl, and the like.

The heteroalkyl, heteroalkenyl, heteroalkynyl and heteroaryl groups can be unsubstituted or substituted with one or more substituents, preferably one to three substituents, wherein the substituents are preferably selected from the group consisting of alkyl, alkenyl, alkynyl, benzyl, halogen, alkoxy, acyloxy, amino, mono or dialkylamino, hydroxyl, mercapto, carboxy, benzyloxy, phenyl, aryloxy, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, pyrrolidine, morpholine, or piperidine, substituted at a nitrogen or carbon by a phenyl or benzyl group, and attached to the remainder of the molecule by any available valence on a carbon or nitrogen, —NH—S(=O)$_2$-phenyl, —NH—(C=O)O-alkyl, —NH—C(=O)O-alkyl-aryl, and the like. The heteroatom(s) as well as the carbon atoms of the group can be substituted. The heteroatom(s) can also be in oxidized form.

The term "heteroarylene" refers to the diradical group derived from heteroaryl (including substituted heteroaryl), as defined above, and is exemplified by the groups 2,6-pyridinylene, 2,4-pyridinylene, 1,2-quinolinylene, 1,8-quinolinylene, 1,4-benzofuranylene, 2,5-pyridinylene, 2,5-indolenylene, and the like.

The term "heteroalkylene", "heteroalkenylene", and "heteroalkynylene" refers to the diradical group derived from heteroalkyl, heteroalkenyl, and heteroalkynyl (including substituted heteroalkyl, heteroalkenyl, and heteroalkynyl) as defined above.

The term "carboxaldehyde" means —CHO.

The term "carboalkoxy" means —C(=O)OR where R is alkyl as defined above and include groups such as methoxycarbonyl, ethoxycarbonyl, and the like.

The term "carboxamide" means —C(=O)NHR or —C(=O)NRR' where R and R' are independently hydrogen, aryl or alkyl as defined above. Representative examples include groups such as aminocarbonyl, N-methylaminocarbonyl, N,N-dimethylaminocarbonyl, and the like.

The term "carboxy" refers to the radical —C(O)OH.

The term "carbamoyl" refers to the radical —C(O)$NH_2$.

The term "halogen" or "halo" as used herein refer to Cl, Br, F or I substituents, preferably fluoro or chloro.

The term "hydroxy" refers to a —OH radical.

"Isomers": Compounds that have the same molecular formula (or elemental composition) but differ in the nature or sequence of bonding of their atoms or the arrangement of their atoms in space are termed "isomers". Isomers in which the connectivity between atoms is the same but which differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example which is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing equal proportions of the enantiomers is called a "racemic mixture".

The compounds of this invention may possess one or more asymmetric centers. Such compounds can therefore be produced as individual (R)- or (S)-stereoisomers or as mixtures thereof. For example, the carbons numbered 20, 22 and 24 in compounds 9, 11 and 21 as described in the Exemplification section are each linked to a hydrogen atom, a methyl group, and two different methylene groups, and therefore these carbons are asymmetric centers. The compounds 9, 11 and 21 can exist as stereoisomers. Unless indicated otherwise, the description or naming of a particular compound in the specification and claims is intended to include both individual enantiomers and mixtures, racemic or otherwise, thereof. The description is also intended to include all possible diastereomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

"Optically pure": As generally understood by those skilled in the art, an optically pure compound is one that is enantiomerically pure. As used herein, the term "optically pure" is intended to mean a compound which comprises at least a sufficient amount of a single enantiomer to yield a compound having the desired pharmacological activity. Preferably, "optically pure" is intended to mean a compound that comprises at least 90% of a single isomer (80% enantiomeric excess), preferably at least 95% (90% e.e.), more preferably at least 97.5% (95% e.e.), and most preferably at least 99% (98% e.e.). Preferably, the compounds of the invention are optically pure.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDMS), 9-fluorenylmethyl-oxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxyl protecting groups include acetyl (Ac), benzoyl (Bz), benzyl (Bn), Tetrahydropyranyl (THP), TBDMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxy-methyloxycarbonyl).

"Prodrug": refers to a compound that can undergo processing to release an active drug molecule. Compounds of Formula (I) and Formula (II) according to the invention are prodrugs as the linker L may be cleaved to release a Rifamycin. In particular, prodrugs of the present invention include compounds which release, in vivo, an active parent drug (i.e., compounds of Formula A1 as defined herein) when such prodrug is administered to a subject.

"Prodrugs" also include complex prodrug compounds that undergo two or more events in prodrug processing. According to this embodiment, complex prodrugs would release, upon processing, a prodrug of Formula (I) or Formula (II) that in turn undergoes cleavage to release a desired Rifamycin.

Complex prodrug compounds according to the present invention may be prepared by modifying functional groups present in phosphonated Rifamycins, such as hydroxy and amino groups. Examples of complex prodrugs include, but are not limited to, esters (e.g., acetate, formate, and benzoate derivatives) and carbamates (e.g., N,N-dimethylaminocarbonyl) of hydroxy functional groups of phosphonated Rifamycins.

A "pharmaceutically acceptable prodrug" is intended to mean prodrug of a phosphonated Rifamycin, such as a prodrug of a compound of Formula (I) and/or Formula (II), in a formulation that may be administered to a subject, such as a mammal, preferably a human. For example, the prodrug may be in a formulation comprising a pharmaceutically acceptable carrier or excipient.

A "pharmaceutically acceptable active metabolite" is intended to mean a pharmacologically active product produced through metabolism in the body of a compound of Formula (I) or Formulae (II) as defined herein.

A "pharmaceutically acceptable solvate" is intended to mean a solvate that retains the biological effectiveness and properties of the biologically active components of compounds of Formula I and/or Formula II. Examples of pharmaceutically acceptable solvates include, but are not limited to water, isopropanol, ethanol, methanol, DMSO, ethyl acetate, acetic acid, and ethanolamine.

A "pharmaceutically acceptable carrier or excipient" means any compound, solution, substance or material that can be used in a formulation of the compounds of the present invention that may be administered to a subject. In particular, carriers and excipients of the present invention are those useful in preparing a pharmaceutical composition that is generally safe, non-toxic and neither biologically nor otherwise undesirable, and that may present pharmacologically favorable profiles and that includes carriers and excipient that are acceptable for veterinary use as well as human pharmaceutical use. Suitable pharmaceutically acceptable carriers and excipients are well known in art and can be determined by those of skill in the art as the clinical situation warrants. The skilled artisan will understand that diluents are includes within the scope of the terms carriers and excipients. Examples of suitable carriers and excipients include saline, buffered saline, dextrose, water, glycerol, ethanol, more particularly: (1) Dulbecco's phosphate buffered saline, pH about 7.4, containing about 1 mg/ml to 25 mg/ml human serum albumin, (2) 0.9% saline (0.9% w/v NaCl), (3) 5% (w/v) dextrose, and (4) water.

A "pharmaceutically acceptable salt" is intended to mean a salt of a phosphonated Rifamycin, such as a salt of a compound of Formula (I) and/or Formula (II), in a formulation that may be administered to a subject, such as a mammal, preferably a human. For example, the salt may be in a formulation comprising a pharmaceutically acceptable carrier or excipient.

"Salt": Phosphonated Rifamycins of the present invention may be in the form of a salt. Salts of phosphonated Rifamycins of the present invention means a salt that retains or improves the biological effectiveness and properties of the free acids and bases of the parent compound as defined herein or that takes advantage of an intrinsically charged functionality on the molecule and that is not biologically or otherwise undesirable. Such salts include the following:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-napthalenesulfonic acid, 4-toluenesulfonic acid, camphorsulfonic acid, 3-phenyl propionic acid, trimethylacetic acid, tertiary butylacetic acid, lauryl sulfuric acid, gluconic acid, glutamic acid, hydroxynapthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like; or (3) salts formed when a charged functionality is present on the molecule and a suitable counterion is present, such as a tetraalkyl(aryl)ammonium functionality and an alkali metal ion, a tetraalkyl(aryl)phosphonium functionality and an alkali metal ion, an imidazolium functionality and an alkali metal ion, and the like.

As used herein, the terms "bone", "bone tissues" or "osseous tissues" refer to the dense, semi rigid, porous, calcified connective tissue forming the major portion of the skeleton of most vertebrates. It also encompasses teeth, osteoarticular tissues and calcifications that are frequently seen in the walls of atherosclerotic vessels.

As used herein, the terms "Rifamycin" and "Rifamycins" mean both the compound identified as Rifamycin itself, as well as all derivative compounds having antimicrobial activity understood by the skilled artisan to fall within the Rifamycin class of compounds. These derivative compounds may be variously described herein as "Rifamycin derived antimicrobial molecules", "Rifamycin derived molecules", "Rifamycin derived antibacterial agents" and "Rifamycin derivatives." Such related terms have the same meaning and refer to antimicrobial agents which are part of the well known class of "Rifamycins" as described in more detail herein. Such derivative compounds are chemical analogs of Rifamycin that have antimicrobial (e.g., antibacterial) activity. These derivatives will be understood by the skilled artisan to be similar in structure to Rifamycin, but also include those chemical compounds not traditionally defined as a Rifamycin. Rifamycin derivatives include, but are not limited to, those compounds of formula (IA) of the present invention. Specific examples include Rifampicin (U.S. Pat. No. 3,342,810), Rifapentin (U.S. Pat. No. 4,002,752), Rifandin (U.S. Pat. No. 4,353,826), Rifabutin (U.S. Pat. No. 4,219,478), Rifalazil (U.S. Pat. No. 4,983,602) and Rifaximin (U.S. Pat. No. 4,341,785).

The term "phosphonated group" is intended to mean any compound non-toxic to humans having at least one phosphorus atom bonded to at least three oxygen atoms and having a measurable affinity to osseous tissues as described hereinafter.

The term "antibacterial" includes those compounds that inhibit, halt or reverse growth of bacteria, those compounds that inhibit, halt, or reverse the activity of bacterial enzymes or biochemical pathways, those compounds that kill or injure bacteria, and those compounds that block or slow the development of a bacterial infection.

The terms "treating" and "treatment" are intended to mean at least the mitigation of a disease condition associated with a bacterial infection in a subject, including mammals such as a human, that is alleviated by a reduction of growth, replication, and/or propagation of any bacterium such as Gram-positive or Gram-negative organisms, and includes curing, healing, inhibiting, relieving from, improving and/or alleviating, in whole or in part, the disease condition.

The term "prophylaxis" is intended to mean at least a reduction in the likelihood that a disease condition associated with a bacterial infection will develop in a subject, such as a mammal, preferably a human. The terms "prevent" and "prevention" are intended to mean blocking or stopping a disease condition associated with a bacterial infection from developing in a subject, such as a mammal, preferably a human. In particular, the terms are related to the treatment of a subject to reduce the likelihood ("prophylaxis") or prevent the occurrence of a bacterial infection, such as bacterial infection that may occur during or following a surgery involving bone reparation or replacement. The terms also include reducing the likelihood ("prophylaxis") of or preventing a bacterial infection when the mammal is found to be predisposed to having a disease condition but not yet diagnosed as having it. For example, one can reduce the likelihood or prevent a bacterial infection in a subject by administering a compound of Formula (I) and/or Formula (II), or a pharmaceutically acceptable prodrug, salt, active metabolite, or solvate thereof, before occurrence of such infection.

The term "subject" is intended to mean an animal, such birds or mammals, including humans and animals of veterinary or agricultural importance, such as dogs, cats, horses, sheep, goats, and cattle.

C) Compounds of the Invention

As will be described hereinafter in the Exemplification section, the inventors have prepared phosphonated Rifamycins having a high binding affinity to osseous tissues.

In one embodiment, the compounds of the invention are represented by Formula (I) or a pharmaceutically acceptable salt or prodrug thereof:

wherein:
B is a phosphonated group;
L is a cleavable linker for coupling B to A;
n is 1, 2, 3, 4, 5, 6 or 7, preferably 1, 2 or 3; and
A is a Rifamycin.

As mentioned previously, the essence of the invention lies in the presence of a phosphonated group reversibly coupled to a Rifamycin via a cleavable linker for the purpose of increasing the affinity, binding, accumulation and/or retention time of the Rifamycin to or within the bones, while permitting its gradual release through the cleavage of the cleavable linker or release of the compound from the bone.

Phosphonates

All non-toxic phosphonated groups having a high affinity to bone due to their ability to bind the $Ca^{2+}$ ions found in the hydroxyapatite forming the bone tissues are suitable according to the present invention. Suitable examples of phosphonated groups can be found in WO 04/026315 (Ilex Oncology Research), U.S. Pat. No. 6,214,812 (MBC Research), U.S. Pat. No. 5,359,060 (Pfizer), U.S. Pat. Nos. 5,854,227 and 6,333,424 (Elizanor Pharm.), U.S. Pat. No. 6,548,042 (Arstad and Skattelbol) and WO 2004/089925 (Semaphore Pharmaceuticals).

Examples of bisphosphonate and trisphosphonate groups suitable for the present invention include but are not limited to those having the formula:

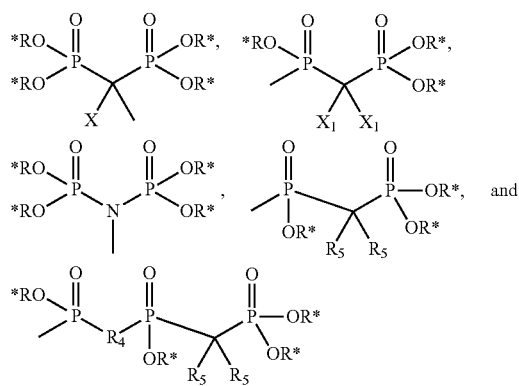

wherein:
- each R* is independently selected from the group consisting of H, lower alkyl, cycloalkyl, aryl and heteroaryl, with the proviso that at least two, preferably three, R* are H;
- $R_4$ is $CH_2$, O, S, or NH;
- each $R_5$ is independently selected from the group consisting of H, $R_6$, $OR_6$, $NR_6$, and $SR_6$, wherein $R_6$ is H, lower alkyl, cycloalkyl, aryl, heteroaryl or $NH_2$;
- X is H, OH, $NH_2$, or a halo group; and
- $X_1$ are both H, or each is independently selected from the group consisting of H, OH, $NH_2$, and a halo group.

Although monophosphonates, bisphosphonates, and tris- or tetraphosphonates could potentially be used, bisphosphonates are preferred. More preferably, the bisphosphonate group is the bisphosphonate $—CH(P(O)(OH)_2)_2$. As shown in Example 3 hereinafter, Rifamycins possessing such a bisphosphonate group have a strong binding affinity for bone powder. Of course, other types of phosphonated group could be selected and synthesized by those skilled in the art. For instance the phosphonated group may be an esterase-activated bisphosphonate radical (Vepsäläinen J., Current Medicinal Chemistry, 9, 1201-1208, 2002) or be any other suitable prodrug thereof. These and other suitable phosphonated groups are encompassed by the present invention.

Rifamycins

Rifamycins are a well known class of semisynthetic antimicrobial agents. Rifampin (also commonly spelled as Rifampicin) (U.S. Pat. No. 3,342,810), Rifapentin (U.S. Pat. No. 4,002,752), Rifabutin (U.S. Pat. No. 4,219,478), and Rifalazil (U.S. Pat. No. 4,983,602) are among the best known compounds in this class. These drugs have proven to be very successful both economically and clinically. The present invention is not restricted to a specific Rifamycin, but encompasses Rifamycin derived antimicrobial molecules having a suitable antimicrobial activity including, but not limited to, Rifandin (U.S. Pat. No. 4,353,826) and Rifaximin (U.S. Pat. No. 4,341,785), as well as other Rifamycin derivatives and hybrids, such as those described in United states patent applications 2003/0105086, 2005/0043298, 2005/0143374, 2005/0203076, 2005/0203085, 2005/0209210, 2005/0256096, 2005/0261262, 2005/0277633, 2006/0019985, and 2006/0019986 or those described in International Patent Application Publications WO03/045319, WO03/051299, WO04/034961 and WO05/062882. Those skilled in the art will readily prepare the Rifamycin derived antimicrobial molecules according to the invention. If necessary, the skilled artisan may refer to the numerous literatures found in the art, including the US patents, PCT patent applications and scientific publications listed hereinbefore, and incorporated herein by reference.

According to one embodiment, the Rifamycins for use according to the invention are selected from compounds falling within the following generic formula (A1) illustrated below:

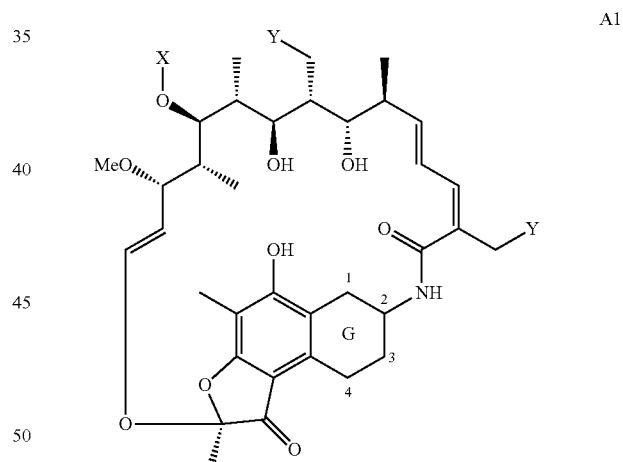

A1 wherein:
- X is H— or $R_1CO$—, wherein $R_1$ is a substituted or unsubstituted alkyl chain of 1-6 carbons;
- each Y is independently selected from the group consisting of H— and RO—, wherein R is H—, $R_1$—, or $R_1CO$—, with $R_1$ defined as above;

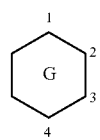

is selected from the group consisting of formulae A2-A10:

A2 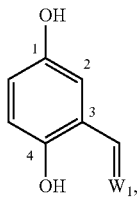

A3 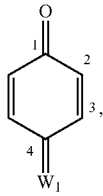

A4 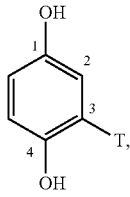

A5 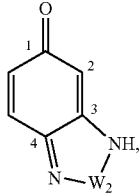

A6 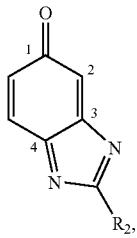

A7 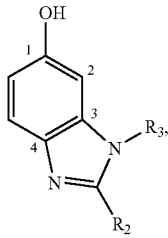

A8 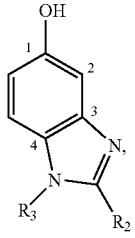

A9 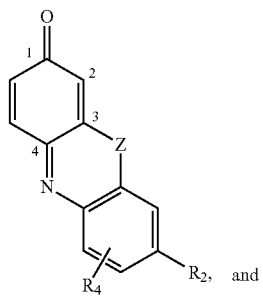

A10 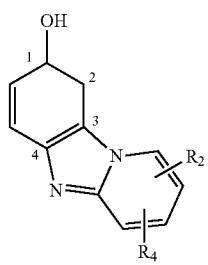

wherein:

$R_2$ is H—, a substituted or unsubstituted alkyl chain of 1-10 carbons, or a dialkyl amino group, preferably said dialkyl amino group is a substituted piperidine, a substituted morpholine or a substituted piperazine;

$R_3$ is H— or a substituted or unsubstituted alkyl chain of 1-7 carbons;

$R_4$ is a hydroxyl group, a sulfhydryl group or a substituted or unsubstituted alkyl chain of 1-3 carbons;

$W_1$ is oxygen or —$NR_2$ with $R_2$ defined as above;

$W_2$ is a substituted or unsubstituted methylene, including:

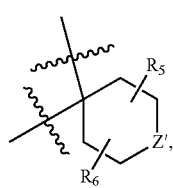

wherein $R_5$ and $R_6$ are independently H— or a substituted or unsubstituted alkyl chain of 1-5 carbons, and Z' is an oxygen atom, a sulfur atom, a substituted methylene, a carbonyl, —$NR_1$ or —$N(O)R_1$ where $R_1$ is defined as above;

T is a halogen or $R_2$, where $R_2$ is defined as above; and

Z is O, S or $NR_3$, where $R_3$ is defined as above.

According to one particular embodiment, the Rifamycin is Rifampicin, its quinone form, its deacetylated form or the deacetylated form of its quinone form. According to another particular embodiment, the Rifamycin is the hydrazone of 1-amino-4-(2-hydroxyethyl)piperazine and 3-formyl Rifamycin S (compound 9 in Example 1), its quinone form, its deacetylated form or the deacetylated form of its quinone form. According to another particular embodiment, the Rifamycin is Rifabutin or its deacetylated form. According to another particular embodiment, the Rifamycin is Rifapentin, its quinone form, its deacetylated form or the deacetylated form of its quinone form. According to another particular embodiment, the Rifamycin is Rifalazil or its deacetylated form. According to another particular embodiment, the Rifamycin is Rifamixin or its deacetylated form. According to another particular embodiment, the Rifamycin is Rifandin, its quinone form, its deacetylated form or the deacetylated form of its quinone form. According to another particular embodiment, the Rifamycin is compound 56 in example 1 or its deacetylated form. According to another particular embodiment, the Rifamycin is compound 63 in example 1 or its deacetylated form. According to another particular embodiment, the Rifamycin is compound 69 in example 1 or its deacetylated form. The chemical structures of these molecules are illustrated hereinafter. Arrows indicate preferred sites for attachment of the phosphonated group.

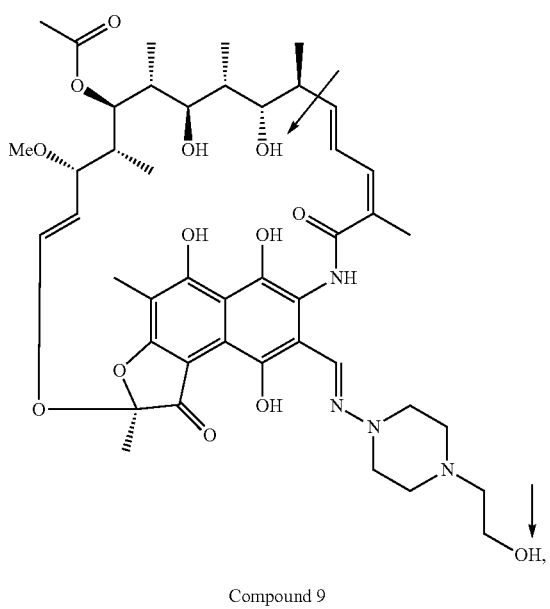

Compound 9

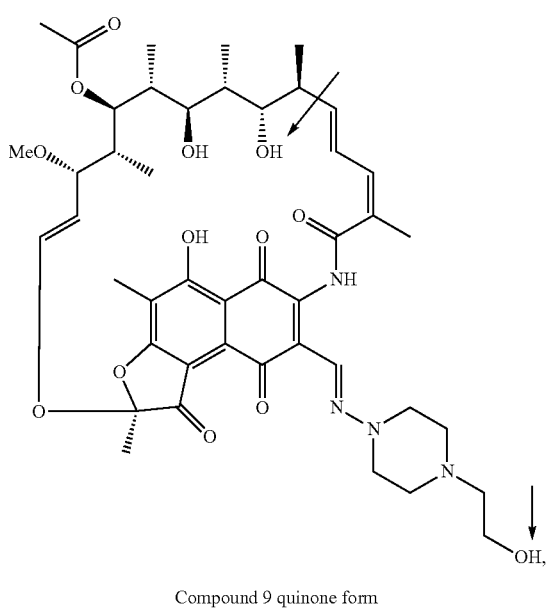

Compound 9 quinone form

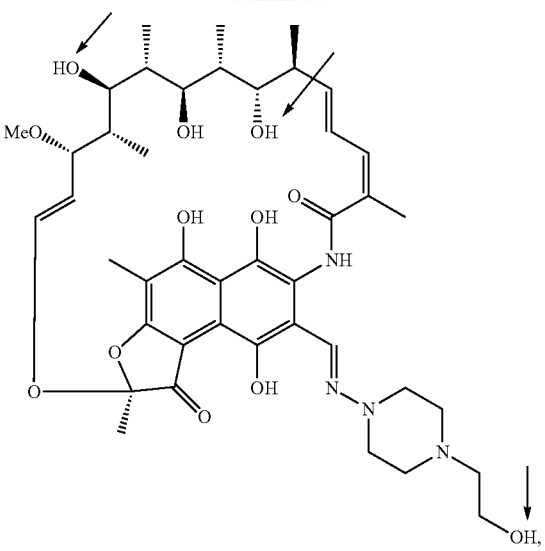

Deacetylated compound 9

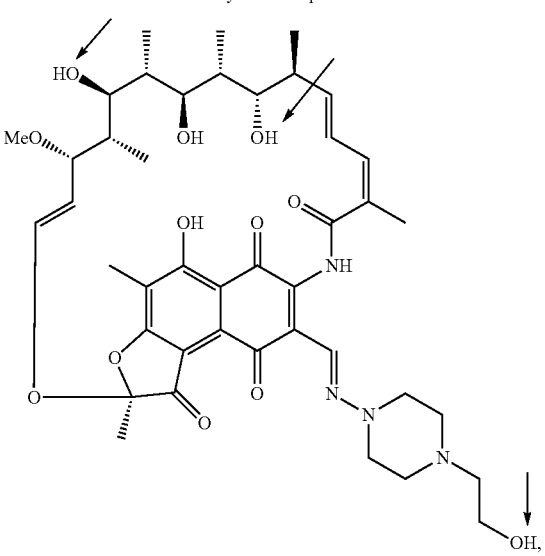

Deacetylated quinone form of compound 9

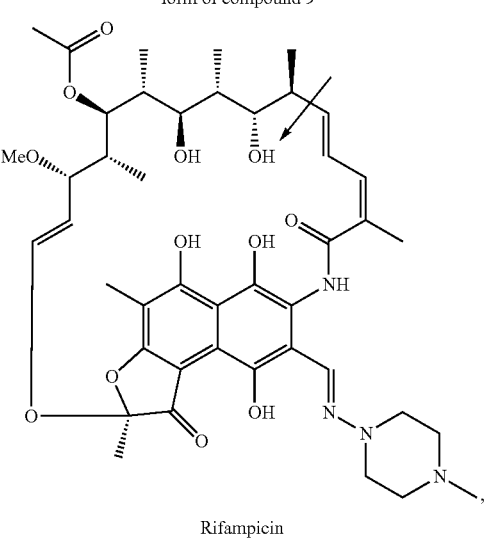

Rifampicin

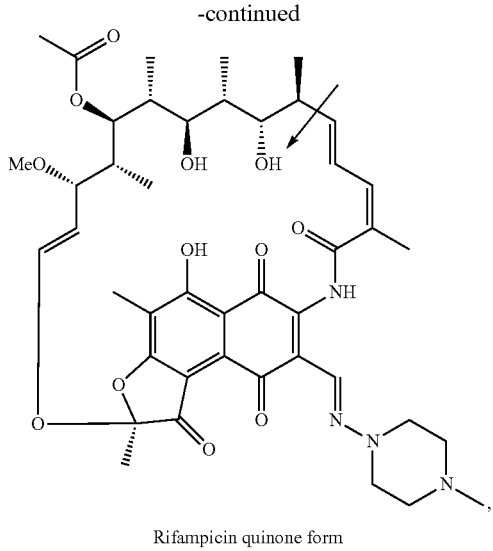
Rifampicin quinone form
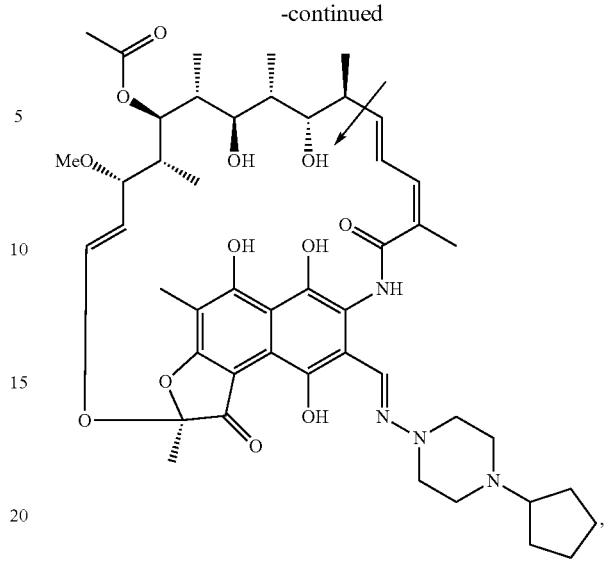
Rifapentin
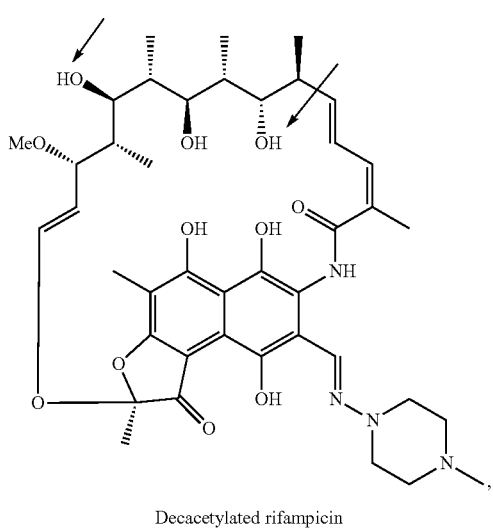
Decacetylated rifampicin
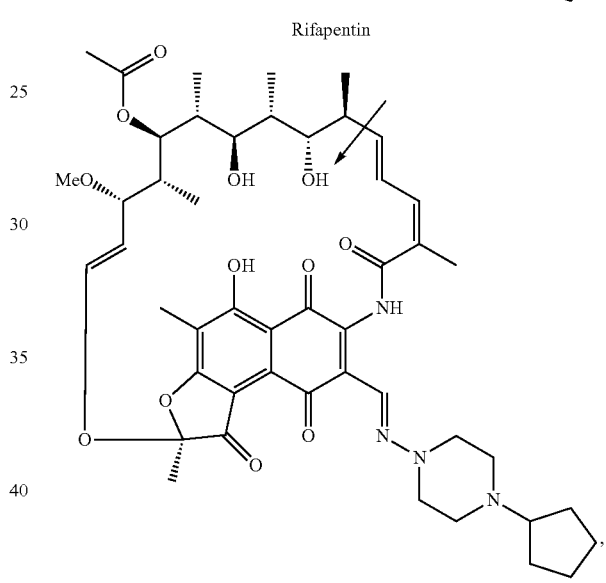
Rifapentin quinone form
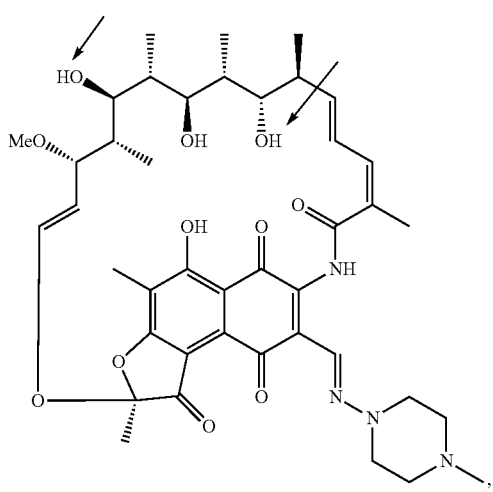
Decacetylated quinone form of Rifampicin
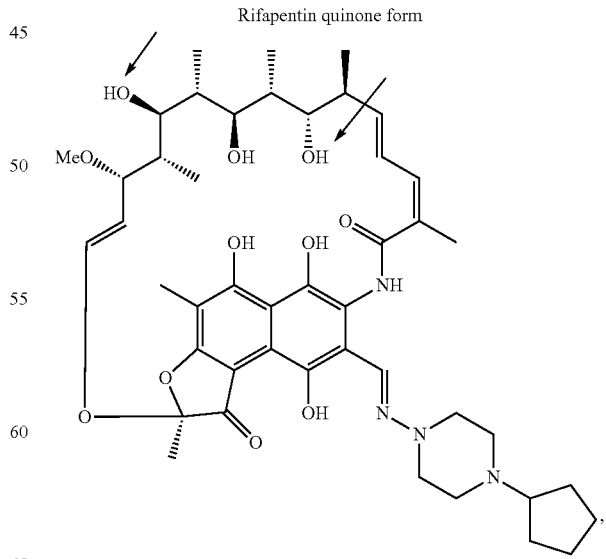
Deacetylated rifapentin

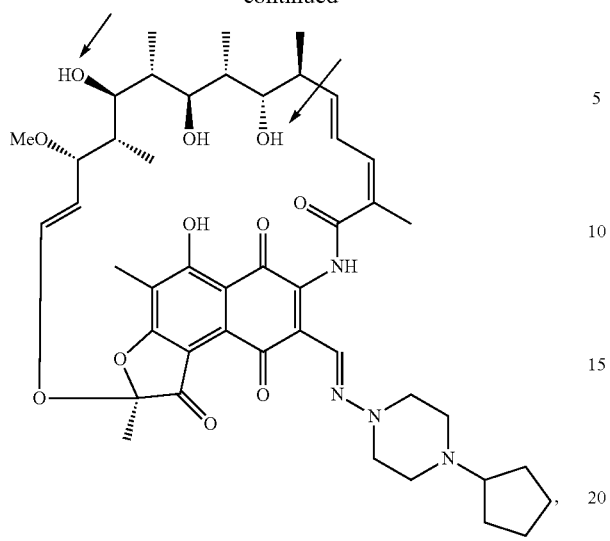
Deacetylated quinone form of rifapentin
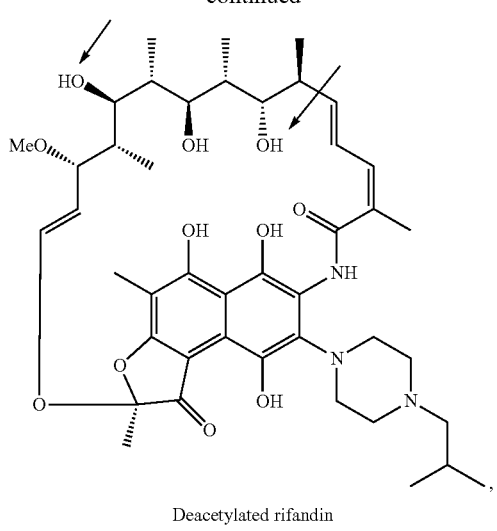
Deacetylated rifandin
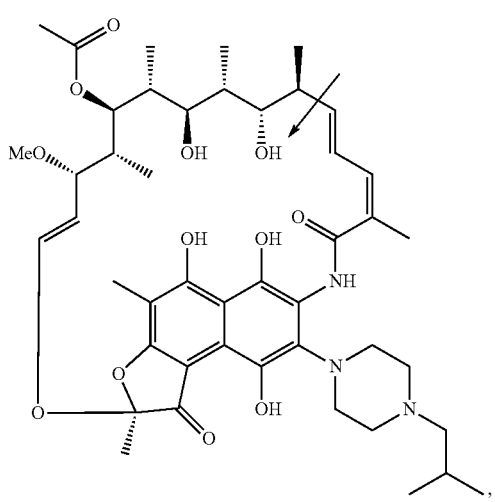
Rifandin
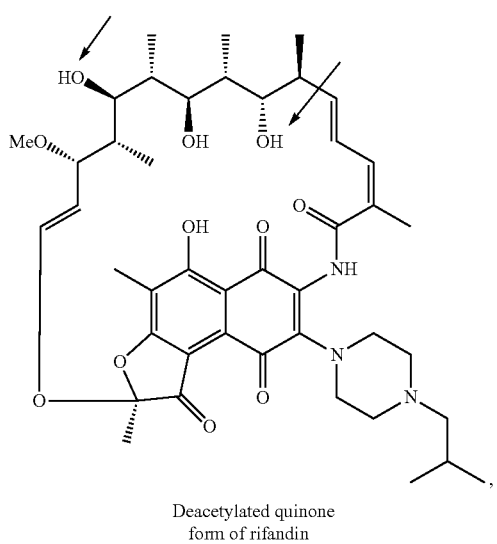
Deacetylated quinone form of rifandin
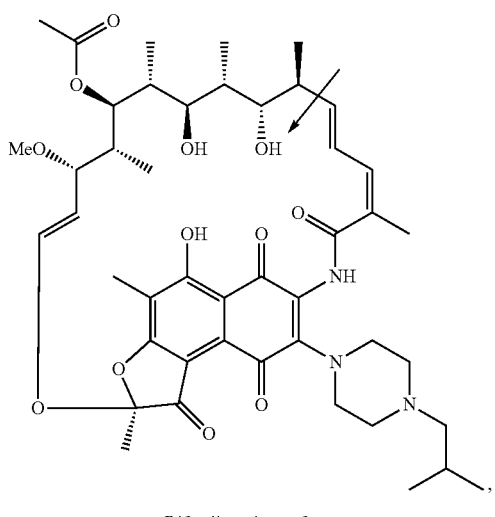
Rifandin quinone form
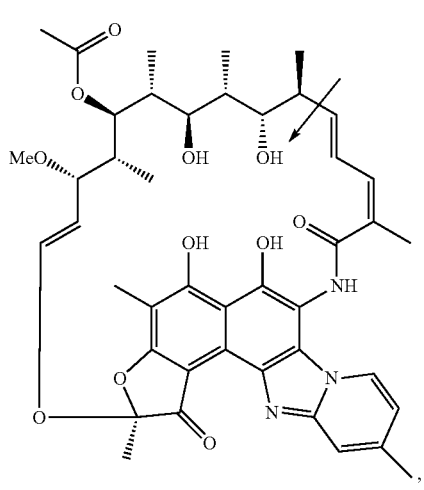
Rifamixin

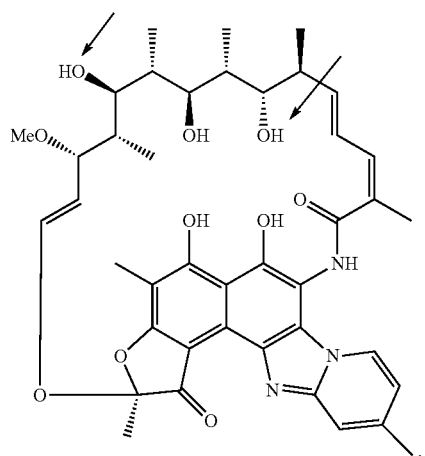
Deacetylated rifamixin
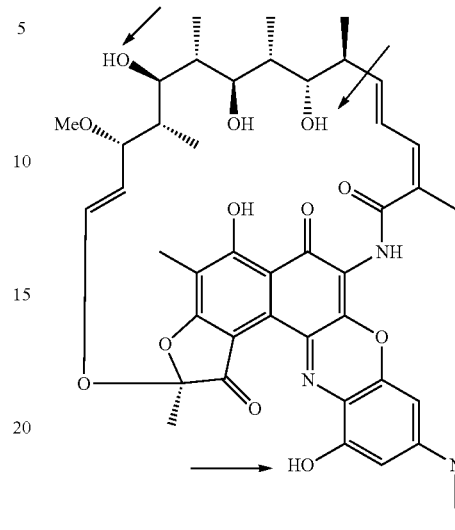
Deacetylated rifalazil
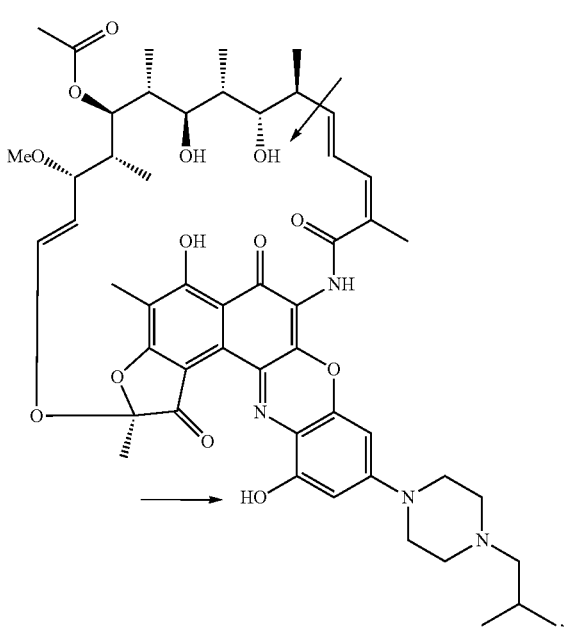
Rifalazil
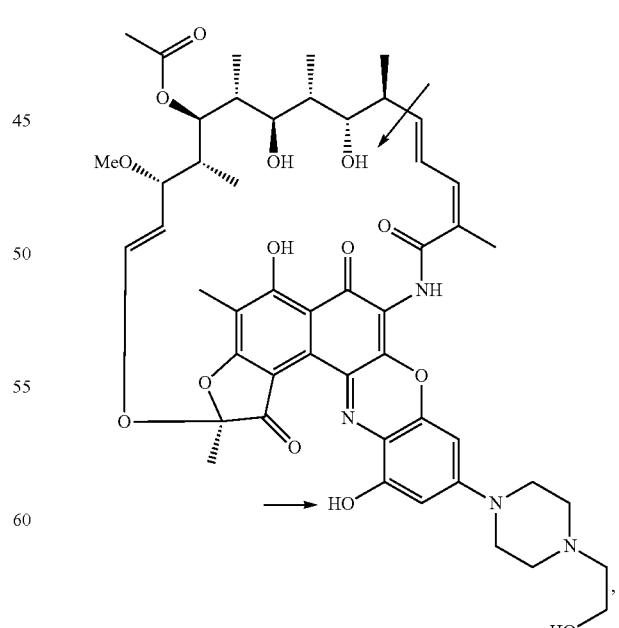
Compound 56

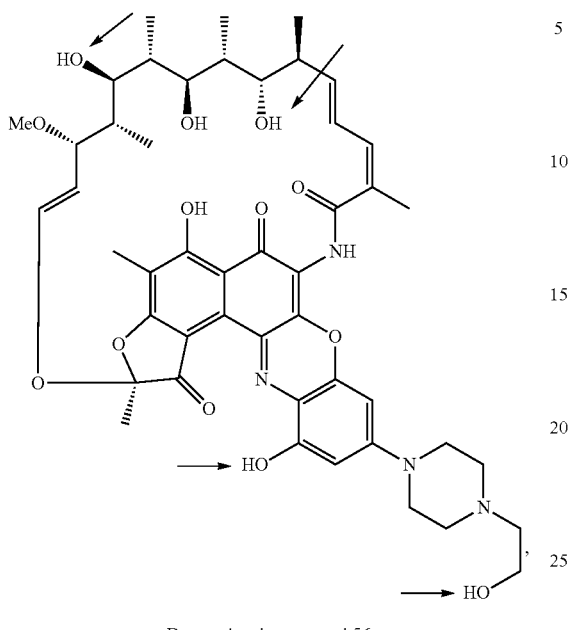
Deacetylated compound 56
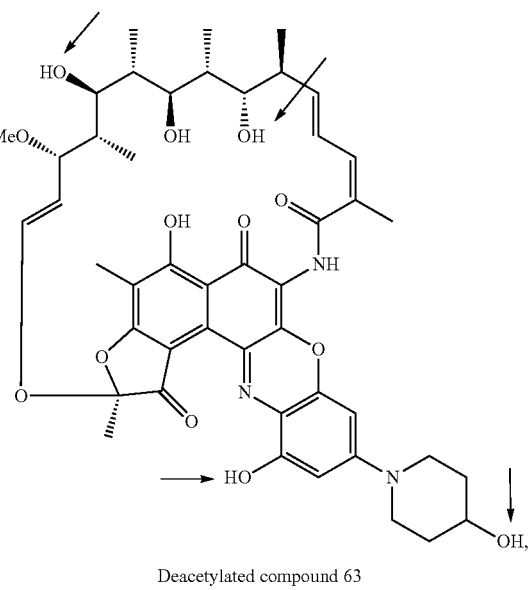
Deacetylated compound 63
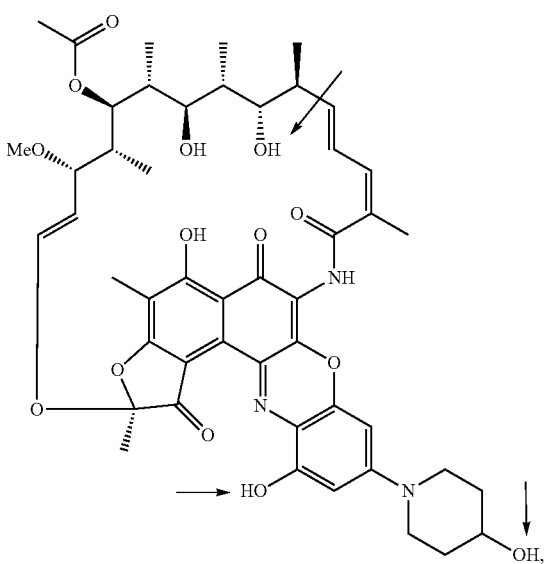
Compound 63
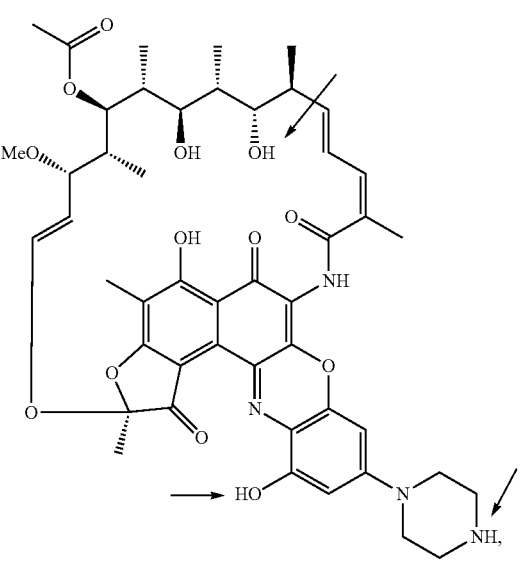
Compound 69

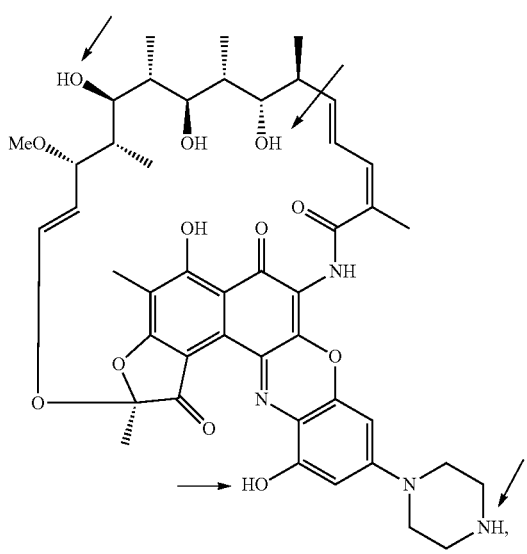

Deacetylated compound 69

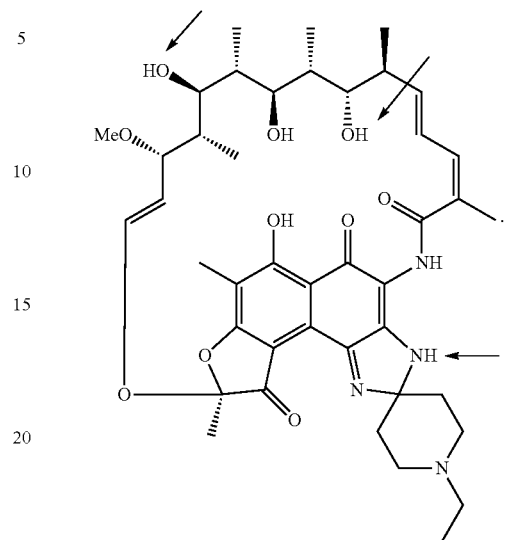

Deacetylated rifabutin

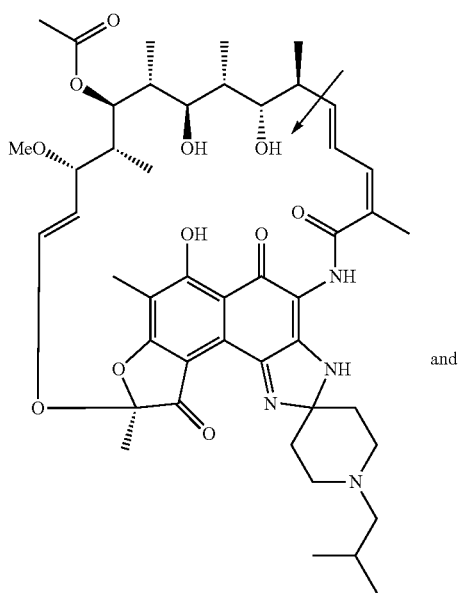

Rifabutin and

Specific examples of phosphonated Rifamycins according to the invention are shown in the Exemplification section. The present invention also encompasses phosphonated Rifamycins having more than one phosphonated group. As mentioned previously, the above identified sites of attachment are only preferred sites for tethering a phosphonated group and all other potential sites (for instance on any of the hydroxyl groups of a Rifamycin) are covered by the present invention.

Linkers

A cleavable linker L covalently and reversibly couples the phosphonated group B to a Rifamycin A. As used herein, the term "cleavable" refers to a group that is chemically or biochemically unstable under physiological conditions. The chemical instability preferably results from spontaneous decomposition due to a reversible chemical process, an intramolecular chemical reaction or hydrolysis (i.e. splitting of the molecule or group into two or more new molecules or groups due to the net insertion of one or more water molecules) when it depends on an intermolecular chemical reaction.

Cleavage of the linker may be very rapid or very slow. For instance, the half-life of the cleavable linker may be of about 1 minute, about 15 minutes, about 30 minutes, about 1 hour, about 5 hours, about 10 hours, about 15 hours, about 1 day or about 48 hours. The cleavable linker may be an enzyme-sensitive linker that is cleavable only by selected specific enzymes (e.g. amidase, esterase, metalloproteinase, etc) or may be susceptible to cleavage by other chemical means, such as but not limited to acid/base catalysis or self-cleavage. For instance, an esterase-sensitive linker that is cleavable only by bone-specific esterases (Goding et al. Biochim Biophys Acta (2003), 1638(1):1-19) or bone-specific metalloproteinase (MMP) (Kawabe et al., Clin Orthop. (1986) 211:244-51; Tuckermann et al., Differentiation (2001), 69(1):49-57; Sellers et al., Biochem J. (1978) 171(2):493-6) or by the action of alkaline phosphatases thereby releasing the Rifamycin at its desired site of action may be used. Similarly, a cleavable linker which is not too easily cleavable in the plasma, thereby permitting a sufficient amount of the phosphonated Rifamycin to reach and accumulate within the osseous tissues before being cleaved to release the Rifamycin may be used. For instance, the linker may be selected such that only 1%, 5%, 10%, 15%, 20%, 25%, 30%, 35%, 40%, 50%, 60%, or 70% of the bone-bonded antibiotic is released through a time period extending to 1 minute, 15 minutes, 30 minutes, 1 hour, 5 hours, 10 hours, 15 hours, 1 day, 2 days, 3 days, 4 days, 5 days, 6 days 7 days, one week, two weeks, three weeks or more following administration of the compound of the invention. Preferably, the linker is selected such that only about 1% to about 25% of the bone-bonded Rifamycin is released per day. The choice of the linker may vary according to factors such as (i) the site of attachment of the phosphonated group to the Rifamycin, (ii) the type of phosphonated group used; (iii) the type of Rifamycin used, and (iv) the desired ease of cleavage of the linker and associated release of the Rifamycin.

Preferably, the linker L couples the phosphonated group B to the Rifamycin A through one or more hydroxyl groups on A, through one or more nitrogen atoms on A, through one or more sulhydryl groups on A, or a combination of one or more hydroxyl groups, one or more nitrogen atoms, and/or one or more sulhydryl groups, on A. Between 1 and 7 phosphonated groups may be coupled to A through any combination of linkers L.

When L couples B to A through a hydroxyl group on A, preferably L is one of the following linkers:

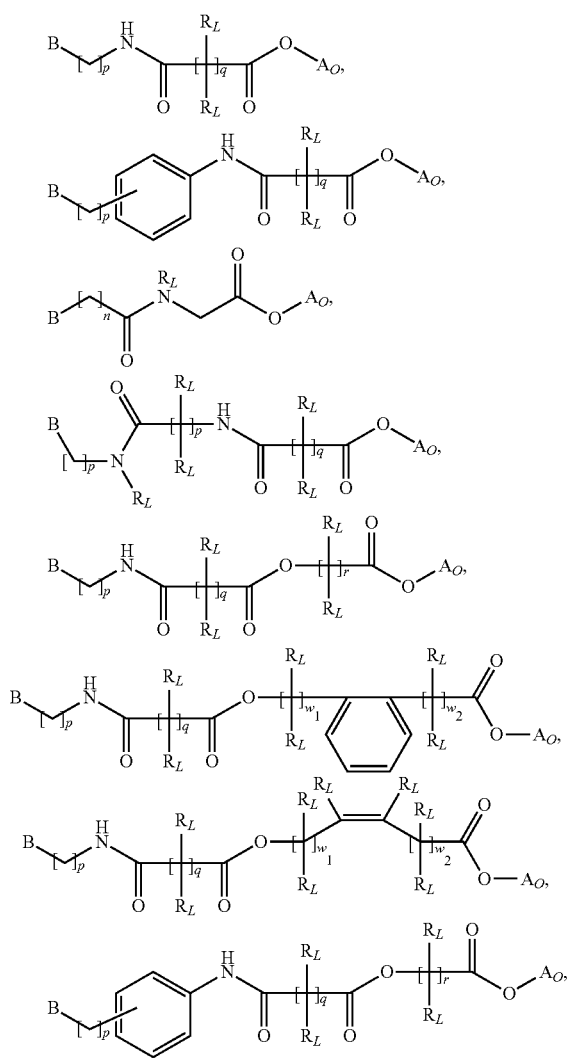

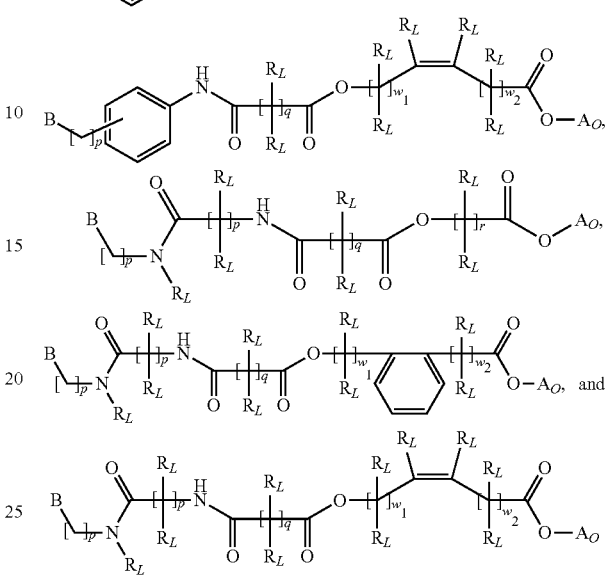

wherein:
n is an integer $\leq 10$, preferably 1, 2, 3 or 4, more preferably 1 or 2;
each p is independently 0 or an integer $\leq 10$, preferably 0, 1, 2, 3 or 4, more preferably 0 or 1;
q is 2 or 3
r is 1, 2, 3, 4 or 5
$w_1$ and $w_2$ are integers $\geq 0$ such that their sum $(w_1+w_2)$ is 1, 2 or 3
each $R_L$ is independently selected from the group consisting of H, ethyl and methyl, preferably H;
B represents the phosphonated group;
and the substructure

of the linker represents the hydroxyl moiety of A.

When L couples B to A through a nitrogen atom on A, preferably L is one of the following linkers:

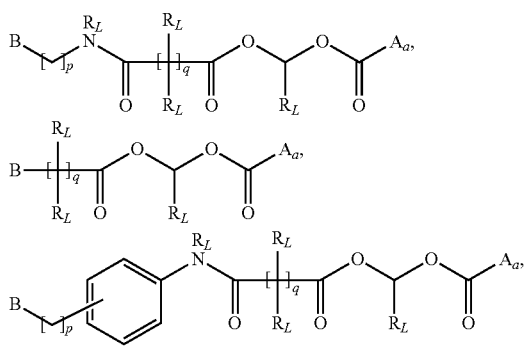

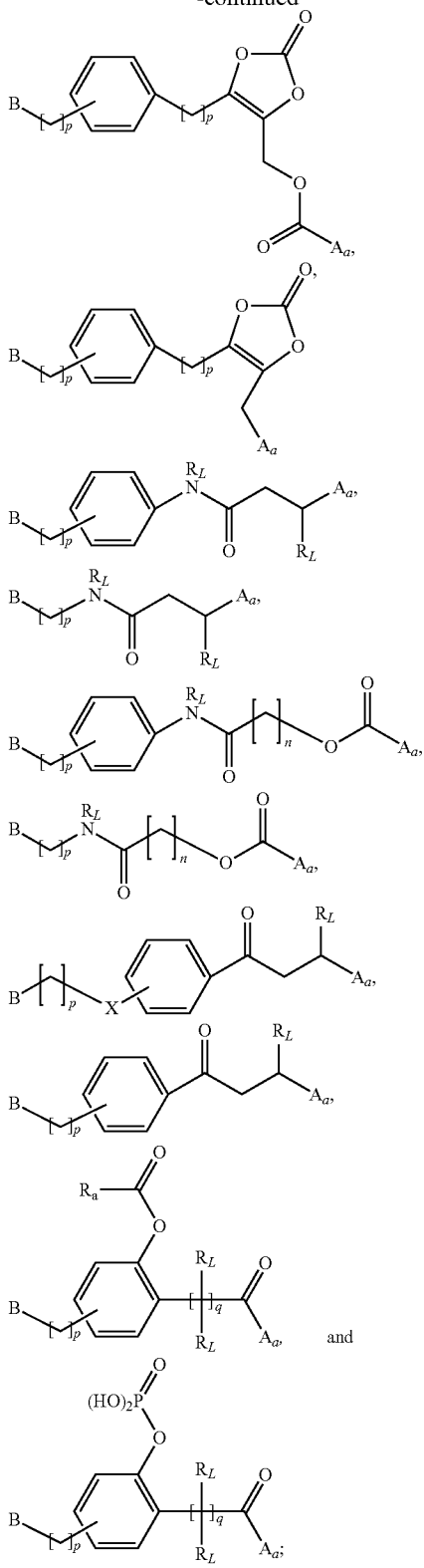

q is 2 or 3;

each $R_L$ is independently selected from the group consisting of H, ethyl and methyl, preferably H;

$R_a$ is $C_xH_y$, where x is an integer of 0 to 20 and y is an integer of 1 to 2x+1;

X is $CH_2$, —$CONR_L$—, —CO—O—$CH_2$—, or —CO—O—;

B represents the phosphonated group; and $A_a$ represents the nitrogen atom on A.

When L couples B to A through a sulfhydryl group on A, preferably L is one of the following linkers:

wherein:

n is an integer ≦10, preferably 1, 2, 3 or 4, more preferably 1 or 2;

each p is independently 0 or an integer ≦10, preferably 0, 1, 2, 3 or 4, more preferably 0 or 1;

-continued

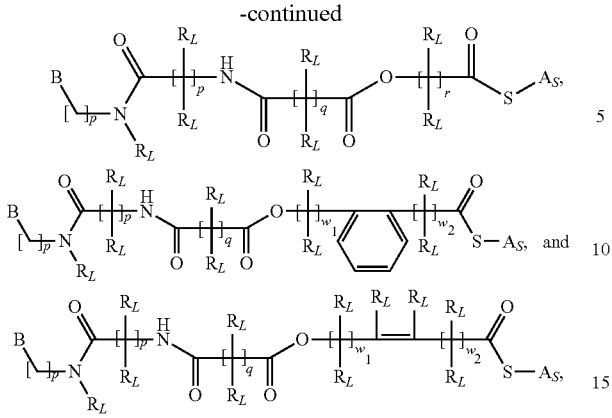

wherein:
n is an integer ≦10, preferably 1, 2, 3 or 4, more preferably 1 or 2;
each p is independently 0 or an integer ≦10, preferably 0, 1, 2, 3 or 4, more preferably 0 or 1;
q is 2 or 3;
r is 1, 2, 3, 4 or 5;
$w_1$ and $w_2$ are integers such that their sum ($w_1+w_2$) is 1, 2 or 3;
each $R_L$ is independently selected from the group consisting of H, ethyl and methyl, preferably H;
B represents the phosphonated group;
and the substructure

of the linker represents the sulfhydryl moiety of A;

According to another particular embodiment, the compounds of the invention are represented by Formula (II) or a pharmaceutically acceptable salt or prodrug thereof:

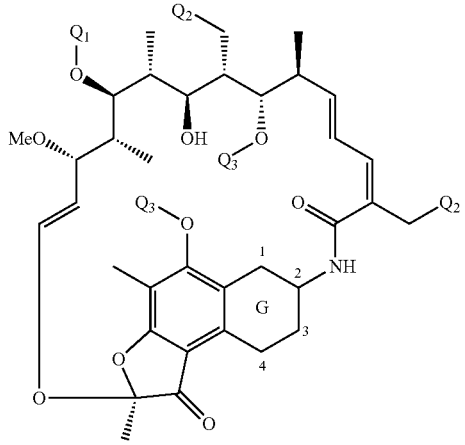

(II)

wherein:
$Q_1$ is H—, $R_1CO$— or $L_1$-, wherein $R_1$ is a substituted or unsubstituted alkyl chain of 1-6 carbons;

each $Q_2$ is independently selected from the group consisting of H—, RO— and $L_2O$—,
wherein R is H—, $R_1$— or $R_1CO$—, with $R_1$ defined as above;
each $Q_3$ is independently selected from the group consisting of H— and $L_3$-;

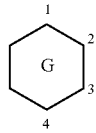

is selected from the group consisting of formulae A2-A10:

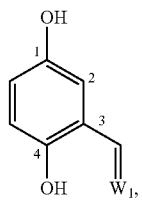
A2

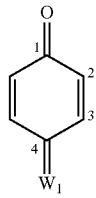
A3

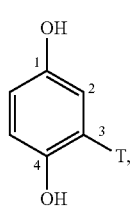
A4

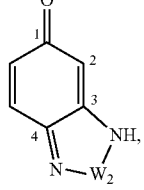
A5

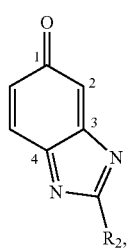
A6

-continued

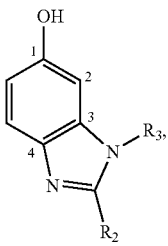
A7

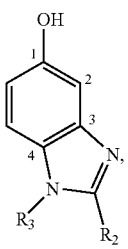
A8

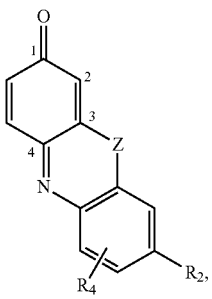
A9

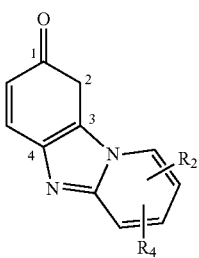
A10 wherein
R₂ is H—, a substituted or unsubstituted alkyl chain of 1-10 carbons or a dialkyl amino group, preferably said dialkyl amino group is a substituted piperidine, a substituted morpholine or a substituted piperazine, wherein when R₂ is a substituted alkyl chain of 1-10 carbons, a substituted piperidine, a substituted morpholine or a substituted piperazine, the substituent is one member selected from the group consisting of L₄O—, L₅S— and L₆NR₇—, wherein R₇ is a substituted or unsubstituted alkyl chain of 1-7 carbons;

R₃ is H—, a substituted or unsubstituted alkyl chain of 1-7 carbons or L₇-;

R₄ is a hydroxyl group, a sulfhydryl group or a substituted or unsubstituted alkyl chain of 1-3 carbons, L₅O— or L₉S—;

W₁ is oxygen or —NR₂, with R₂ defined as above;

W₂ is a substituted or unsubstituted methylene, including

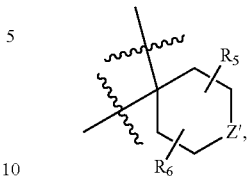

wherein R₅ and R₆ are independently H— or a substituted or unsubstituted alkyl chain of 1-5 carbons, and Z' is an oxygen atom, a sulfur atom, a substituted methylene, a carbonyl, —NR₁ or —N(O)R₁ where R₁ is defined as above;

T is a halogen or R₂, where R₂ is defined as above;

Z is O, S or NR₃, where R₃ is defined as above;

each L₁, L₂, L₃, L₄, L₅, L₈ and L₉ is a cleavable linker independently selected from the group consisting of:

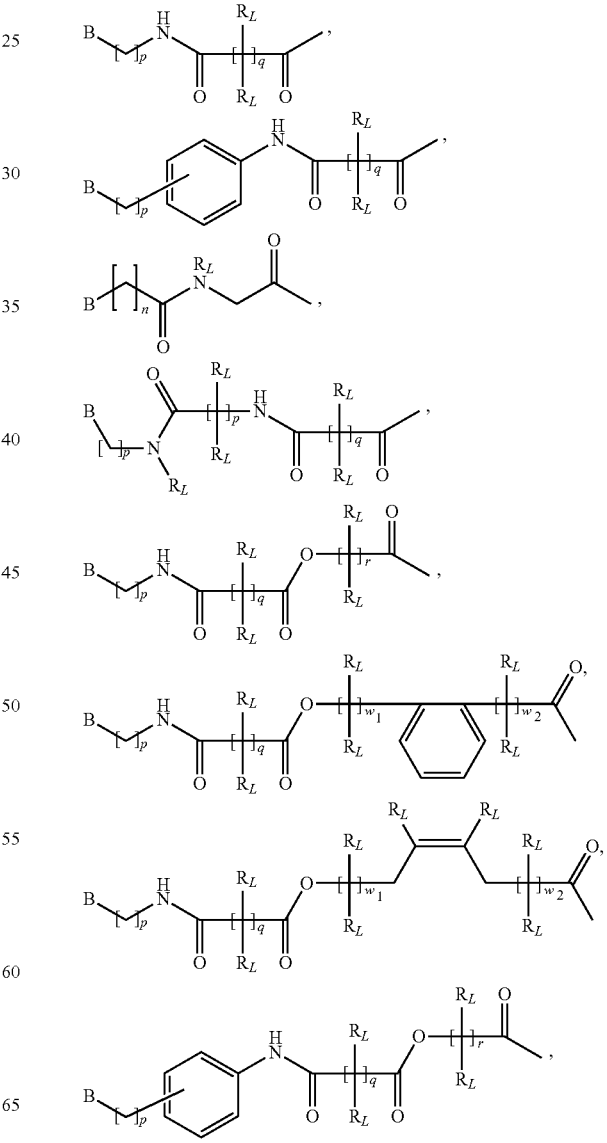

-continued

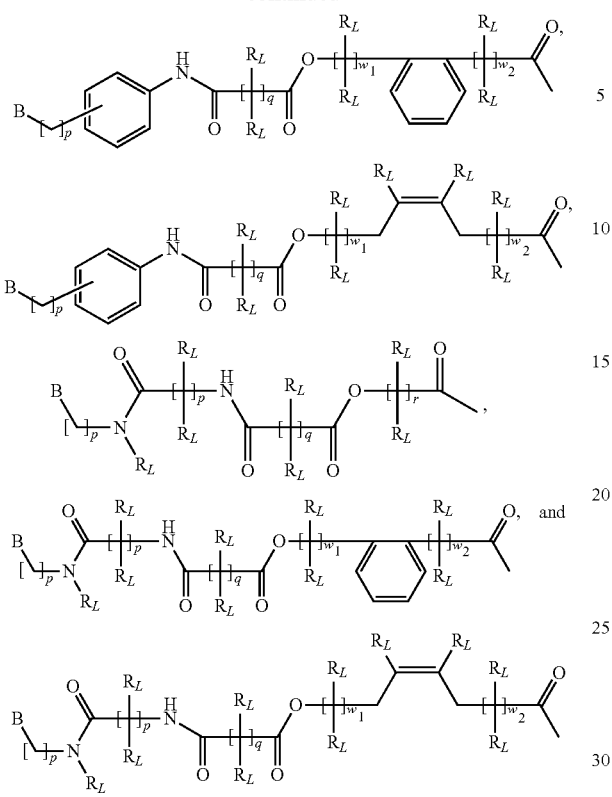

wherein:
n is an integer ≦10, preferably 1, 2, 3 or 4, more preferably 1 or 2;
each p is independently 0 or an integer ≦10, preferably 0, 1, 2, 3 or 4, more preferably 0 or 1;
q is 2 or 3;
r is 1, 2, 3, 4 or 5;
$w_1$ and $w_2$ are integers ≧0 such that their sum ($w_1+w_2$) is 1, 2 or 3;
each $R_L$ is independently selected from the group consisting of H, ethyl and methyl, preferably H;
each $L_6$ and $L_7$ is a cleavable linker independently selected from the group consisting of:

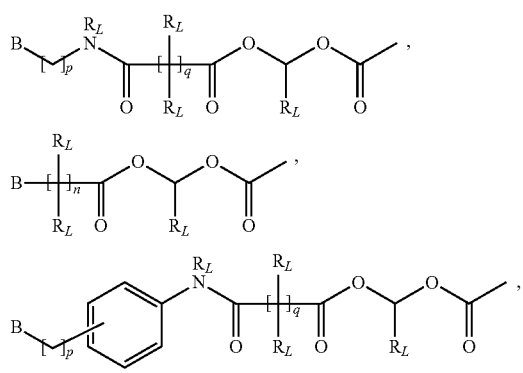

-continued

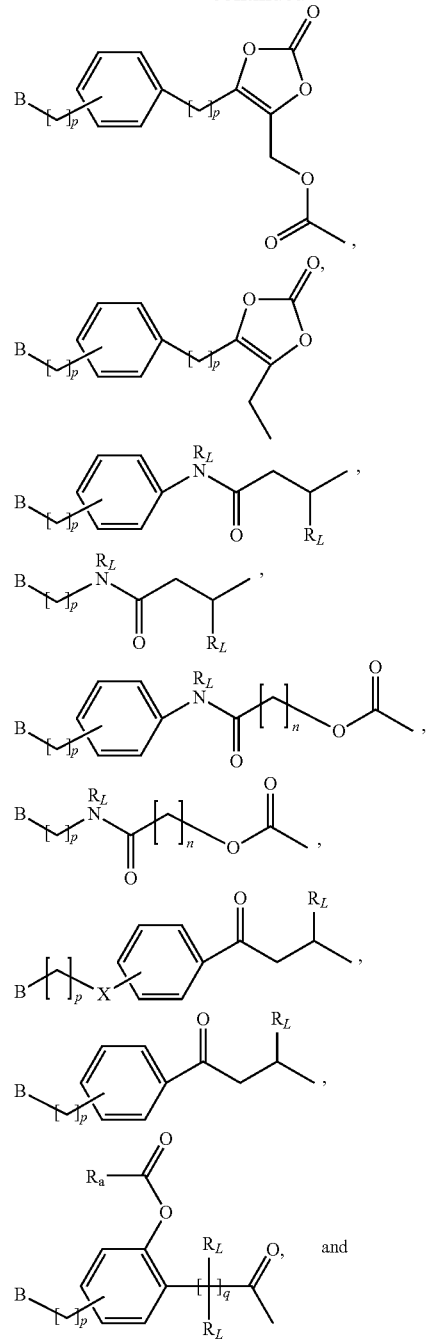

wherein:
n is an integer ≦10, preferably 1, 2, 3 or 4, more preferably 1 or 2;
each p is independently 0 or an integer ≦10, preferably 0, 1, 2, 3 or 4, more preferably 0 or 1;
q is 2 or 3;

each $R_L$ is independently selected from the group consisting of H, ethyl and methyl, preferably H;

$R_a$ is $C_xH_y$, where x is an integer of 0 to 20 and y is an integer of 1 to 2x+1; and X is $CH_2$, —$CONR_L$—, —CO—O—$CH_2$—, or —CO—O—;

B is a phosphonated group selected from the group consisting of:

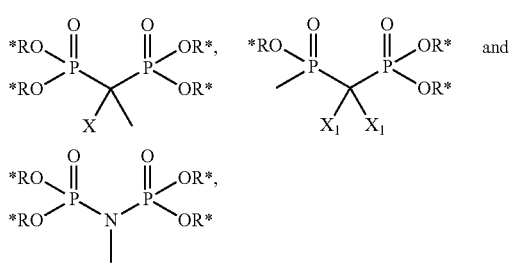

wherein:

each R* is independently selected from the group consisting of H, lower alkyl, cycloalkyl, aryl and heteroaryl, with the proviso that at least two R* are H;

X is H, OH, $NH_2$, or a halo group;

each $X_1$ is independently selected from the group consisting of H, OH, $NH_2$, and a halo group;

with the proviso that at least one of $L_1$, $L_2$, $L_3$, $L_4$, $L_5$, $L_6$, $L_7$, $L_8$ and $L_9$ is present.

The present invention also includes the use of a single phosphonated group coupled to two or more antibacterial molecules. In such circumstances, the antibacterial molecules may be the same (e.g. two molecules of a Rifamycin) or different (e.g. one molecule of the fluoroquinolone antibacterial ciprofloxacin (Cipro®; U.S. Pat. No. 4,670,444) and one molecule of a Rifamycin). The phosphonated group may also be tethered to similar groups (e.g. the hydroxyl groups) or to different groups (e.g. the carboxyl group of one fluoroquinolone molecule and the hydroxyl group of a Rifamycin).

A non-limiting list of useful antibiotics with which the compounds of the present invention might be coupled through a single phosphonated group includes: sulfonamides, beta-lactams, tetracyclines, chloramphenicol, aminoglycosides, macrolides, glycopeptides, streptogramins, quinolones, fluoroquinolones, oxazolidinones and lipopeptides. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, and daptomycin derived antibacterial agents are preferred.

Examples of potentially useful, cleavable, multi-antibacterial linkers according to the invention include, but are not limited to, those having the structures:

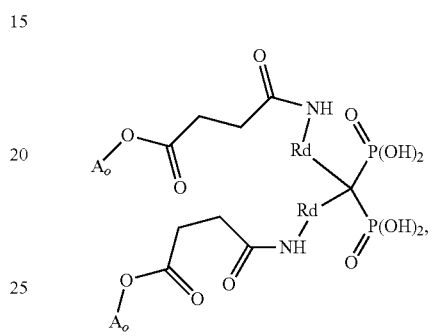

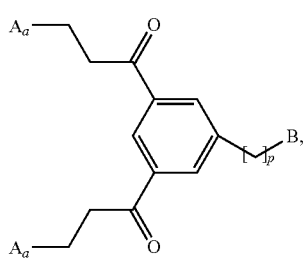

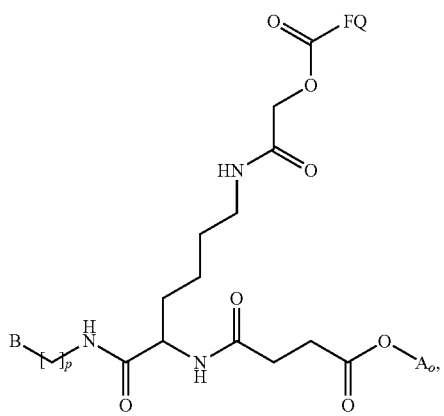

wherein: each $R_d$ is independently an alkyl or an aryl group;
p is 0 or an integer $\leq 10$, preferably 0, 1, 2, 3 or 4, more preferably 0 or 1;
the substructure

of the linker represents the hydroxyl moiety of the Rifamycin A;

$A_a$ represents an amine group of the Rifamycin A;
the substructure

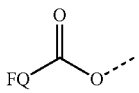

of the linker represents the carboxylic moiety of a fluoroquinolone antimicrobial.

Because of its high affinity to osseous tissues, the phosphonated group B will likely remain bound to the bones for an extended period of time (up to several years). Therefore, it is very important that the phosphonated group be endowed with low or preferably no measurable toxicity. According to another embodiment, the phosphonated group B and the linker L are selected such that the linker is hydrolyzed or cleaved in vivo (preferably mostly in osseous tissues) thereby releasing: (i) the Rifamycin A and (ii) a chosen non-toxic phosphonated molecule having a proven bone therapeutic activity. Such compounds would thus have a double utility that is to: 1) provide locally to the bones, for an extended period of time and/or at increased concentrations, an antibiotic useful in preventing and/or treating a bacterial bone infection, and 2) provide to the bones a drug stimulating bone regeneration or inhibiting bone resorption, thereby facilitating bone recovery from damages caused by an infection or other injury. Suitable phosphonated molecules with proven bone therapeutic activity useful according to the invention include but are not limited to risedronate and olpadronate (others such as (others such as pamidronate, alendronate, incadronate, etidronate, ibandronate, zolendronate or neridronate), these molecules being well known bisphosphonate bone resorption inhibitors commonly used for the treatment of osteoporosis.

The scheme below illustrates the principles of that embodiment:

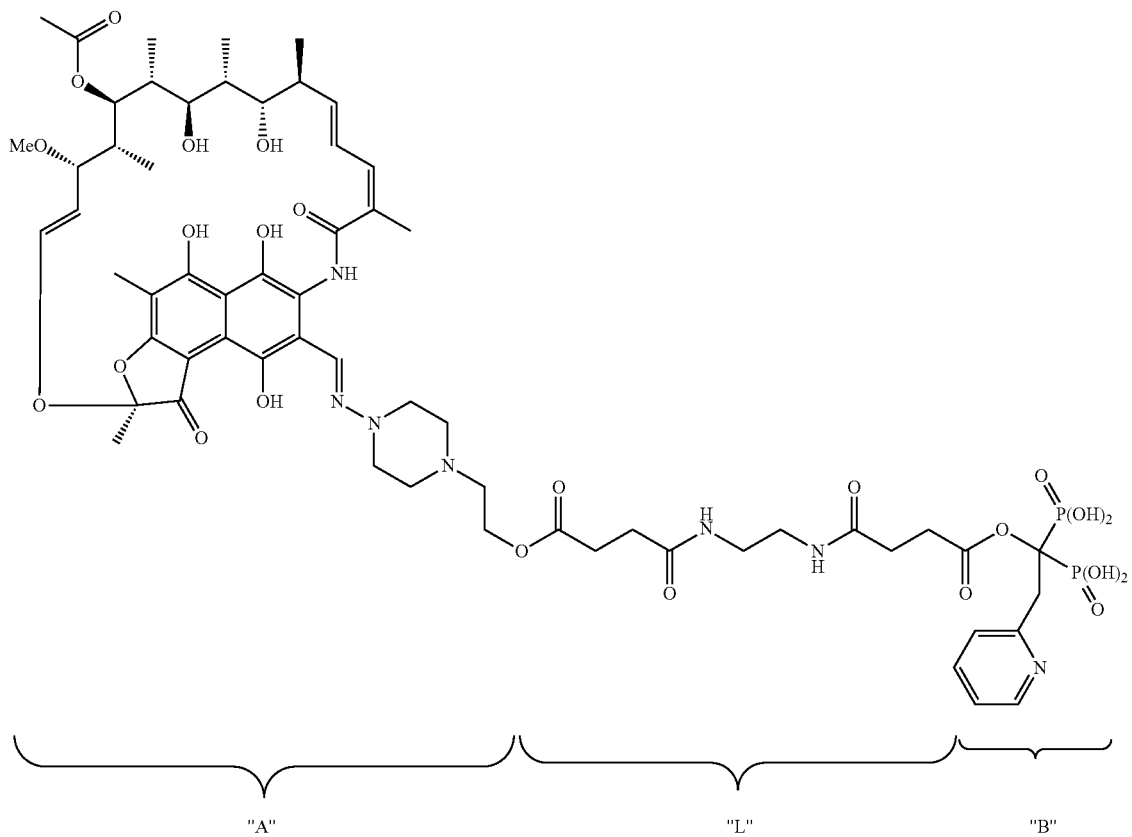

-continued

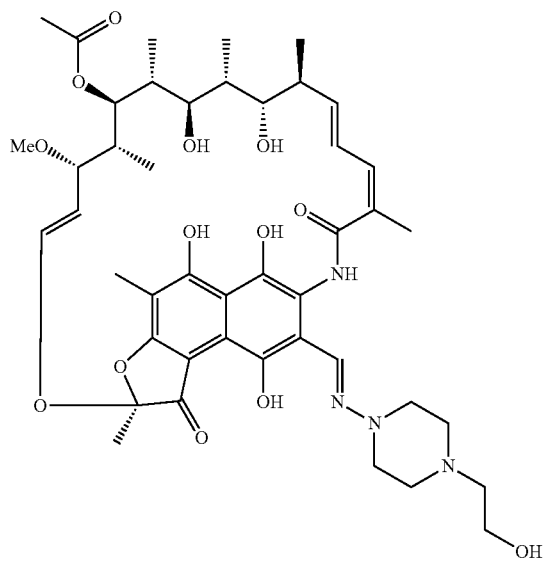
Rifamycin derivative

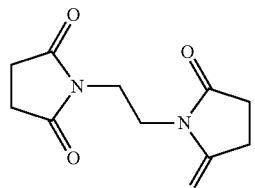

+

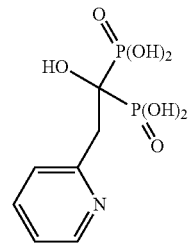
Risedronate

The present invention also includes the use of a pH-sensitive linker that is cleaved only at a predetermined range of pH. In one embodiment, the pH-sensitive linker is a base-sensitive linker that is cleaved at a basic pH ranging from about 7 to about 9. According to another embodiment, the linker is an acid-sensitive linker that is cleaved at an acidic pH ranging from about 7.5 to about 4, preferably from about 6.5 and lower. It is hypothesized that such an acid-sensitive linker would allow a specific release of the Rifamycin A mostly at a site of bacterial infection because it is known that acidification of tissues commonly occurs during infection (O'Reilley et al., Antimicrobial Agents and Chemotherapy (1992), 36(12): 2693-97).

A covalent bond or a non-cleavable linker may also covalently couple the phosphonated group B to the Rifamycin A. Such bond or linker would be selected such that it would not be cleaved or would be cleaved mainly by the bacteria present at the actual site of infection. It is hypothesized that for such compounds the phosphonated group would remain tethered to the Rifamycin A and the whole compound would gradually be released from the bone and absorbed by the bacteria, thereby exerting its antibacterial effect.

Of course, other types of linkers could be selected and synthesized by those skilled in the art. For instance the linker may also contain an in vivo hydrolyzable phosphonated group having an affinity to bones as disclosed by Ilex Oncology Research in WO 04/026315. The linker may also contain an active group (e.g. a releasable group stimulating bone formation or decreasing bone resorption). These and other suitable linkers are encompassed by the present invention.

In addition to those compounds described hereinbefore and in the Exemplification section, additional compounds of Formula (I) according to the invention include, but are not limited to, those having the following formulae:

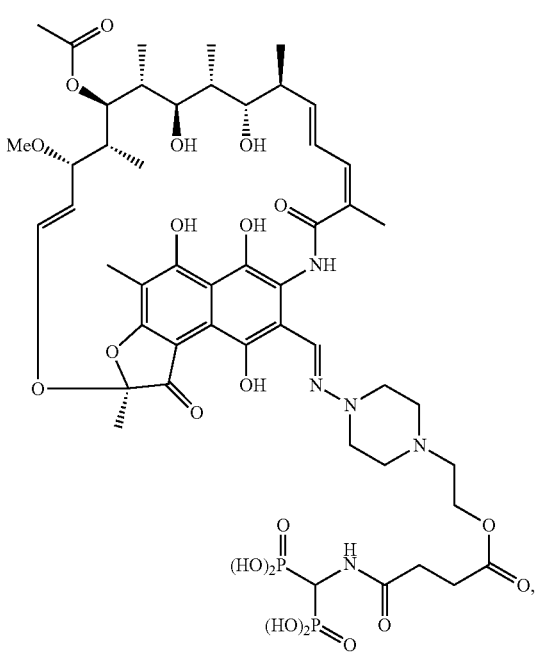

71
-continued
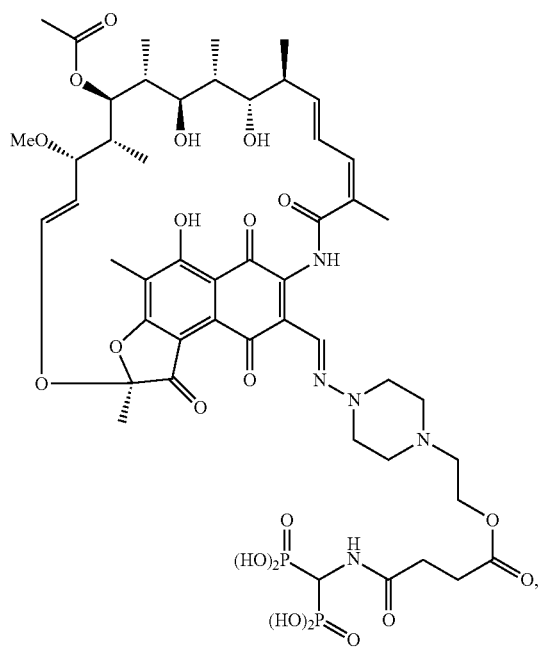
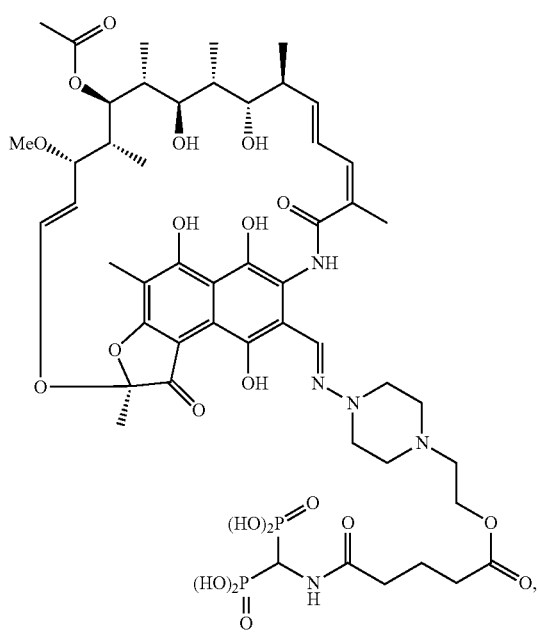
72
-continued
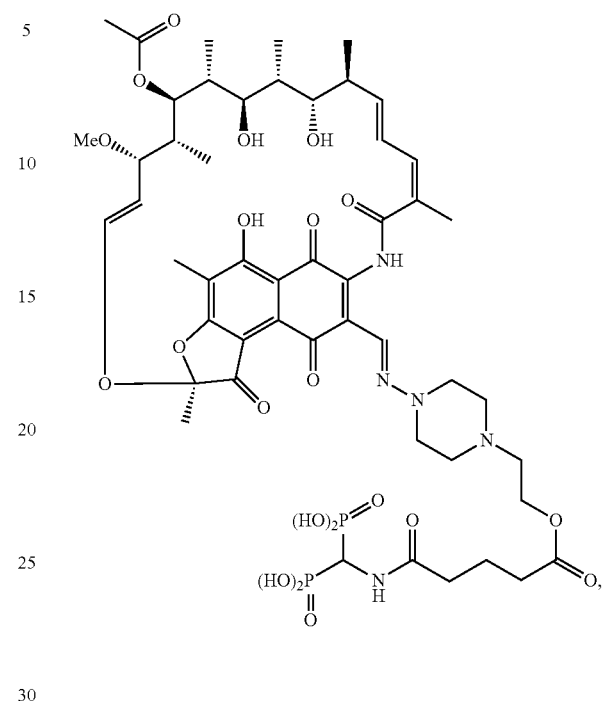
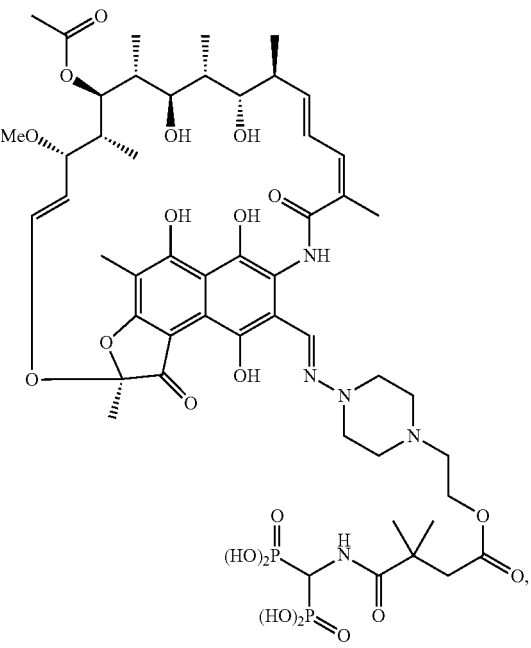

73
-continued
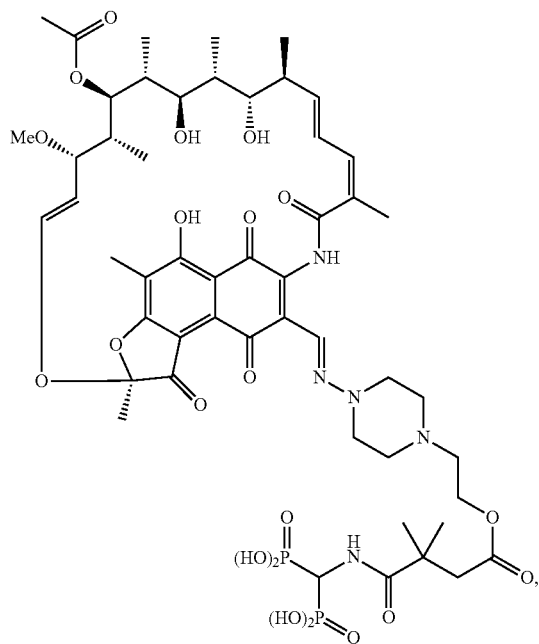
74
-continued
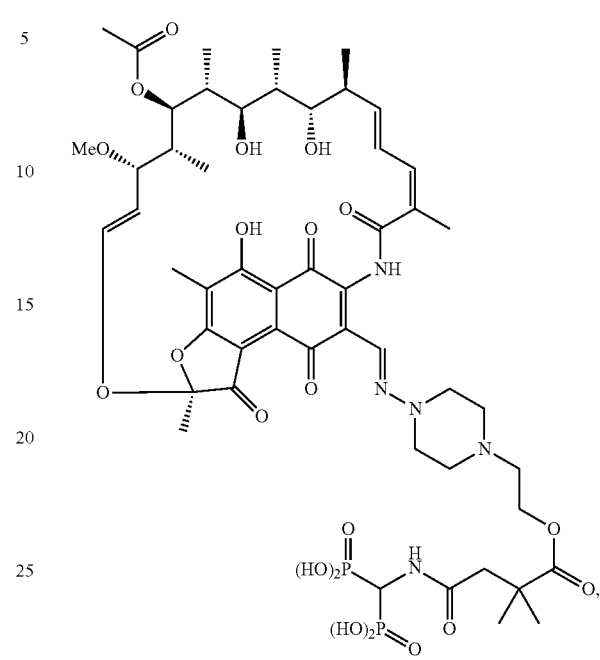
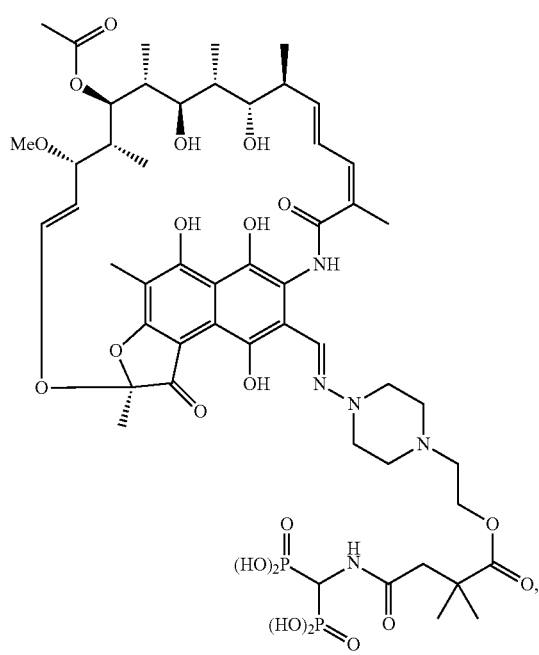
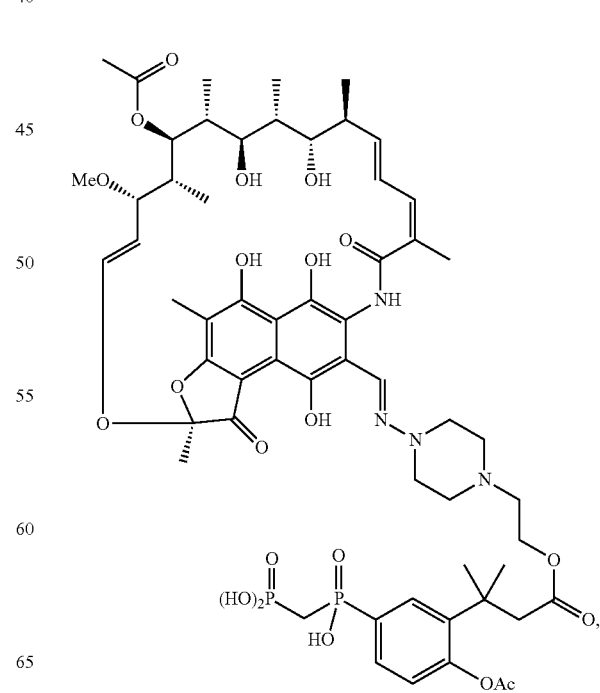

75
-continued
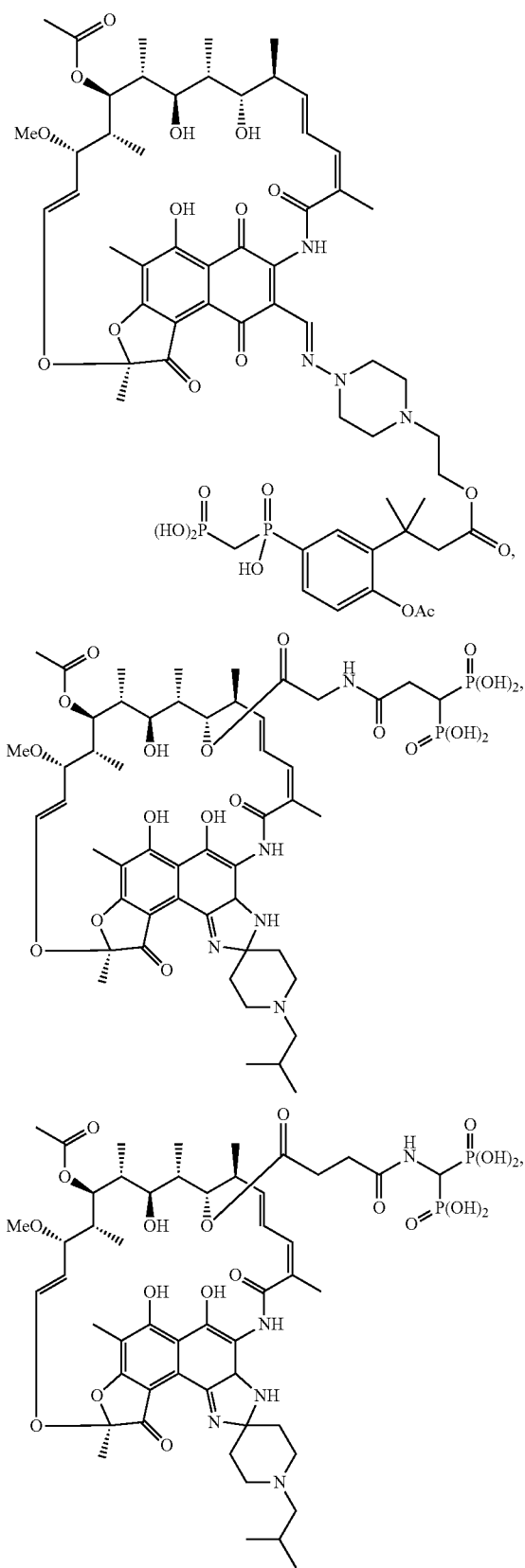
76
-continued
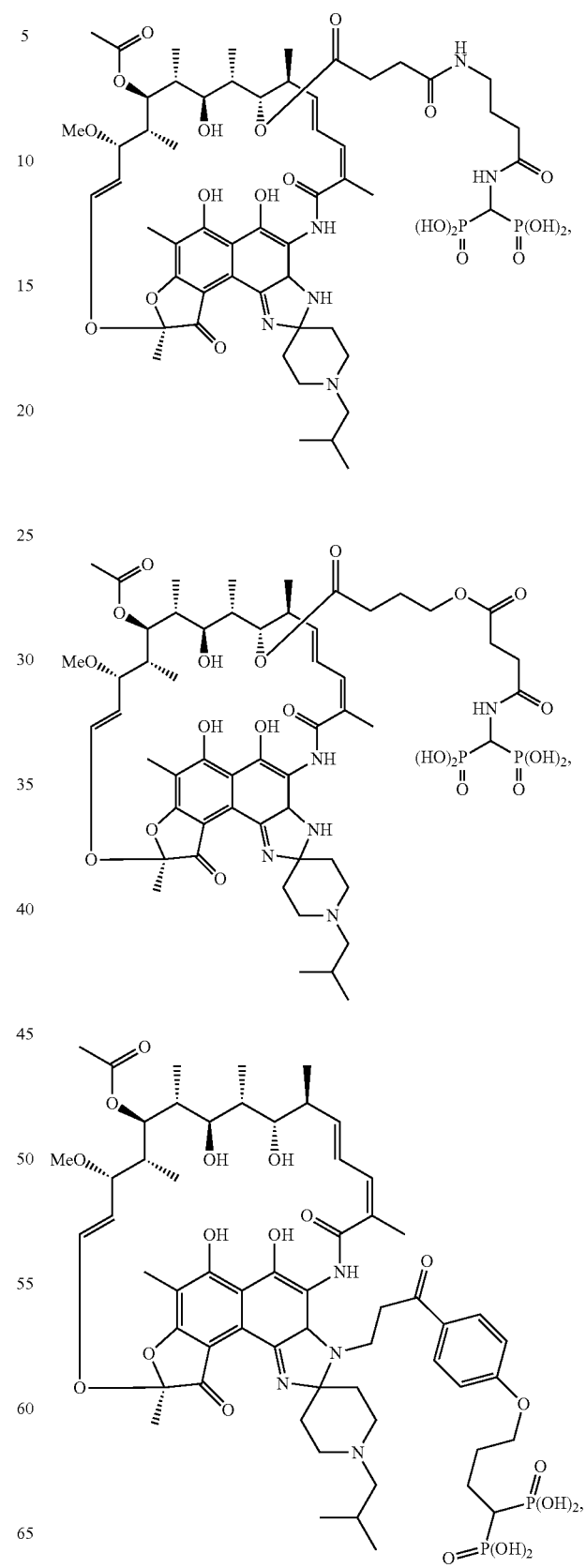

77
-continued
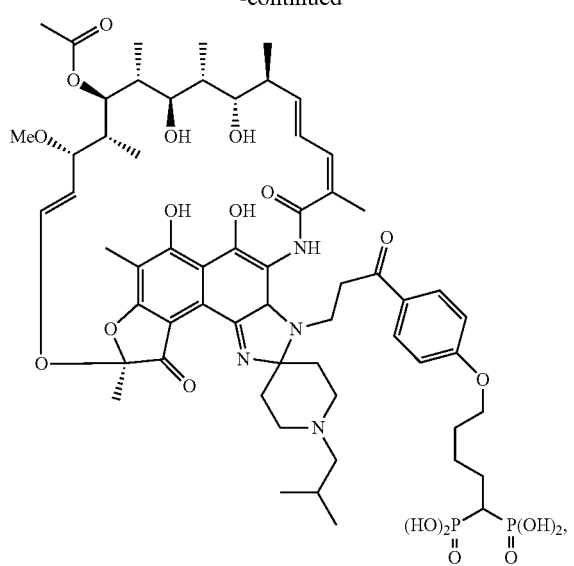
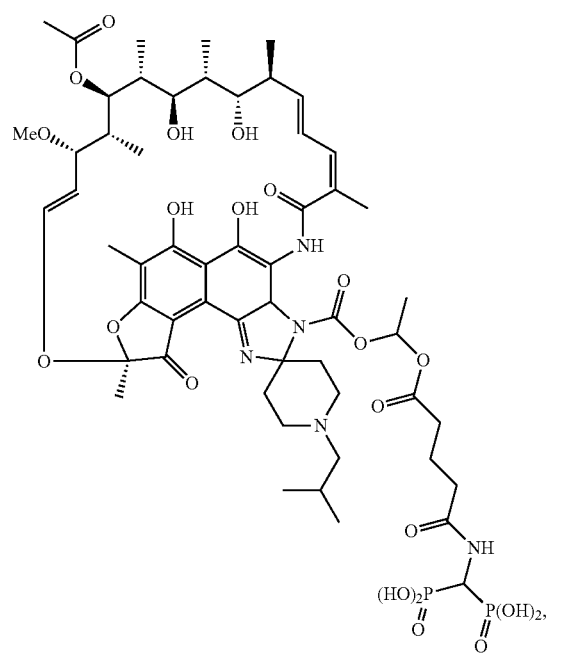
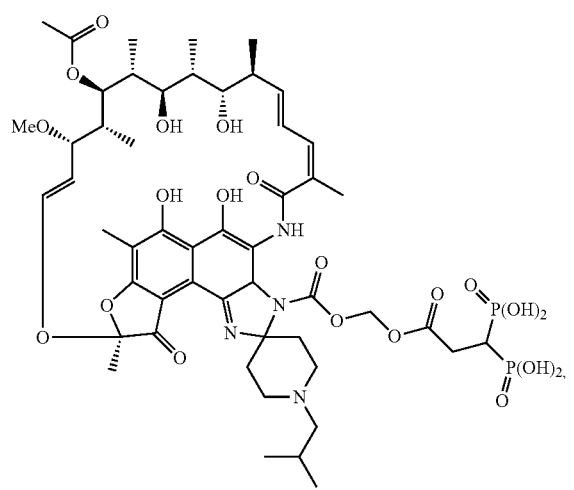
78
-continued
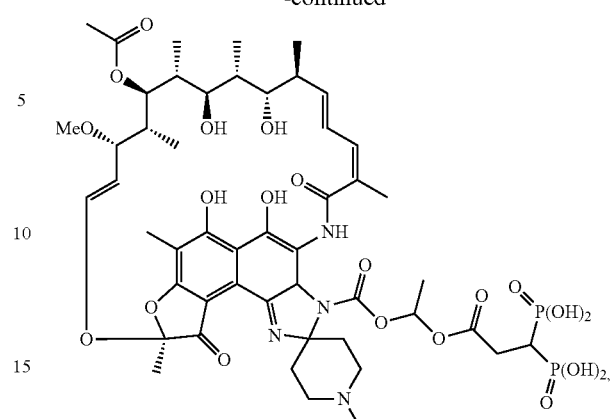
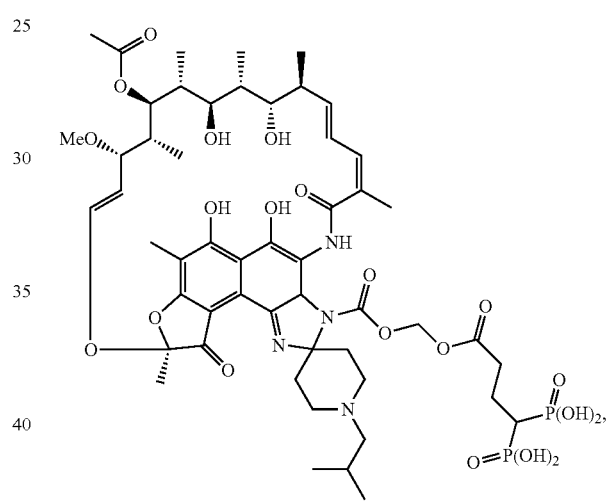
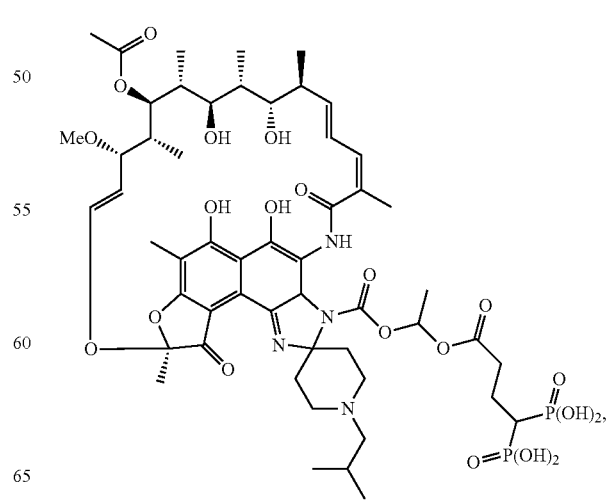

79
-continued
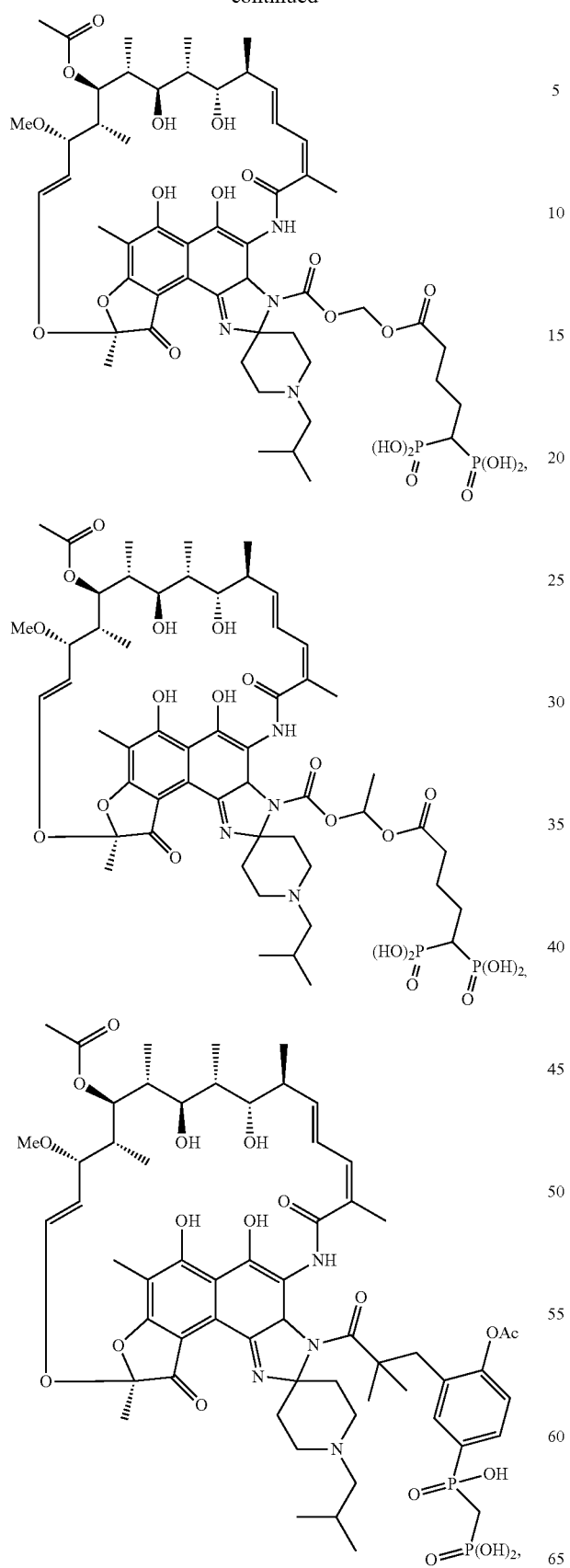
80
-continued
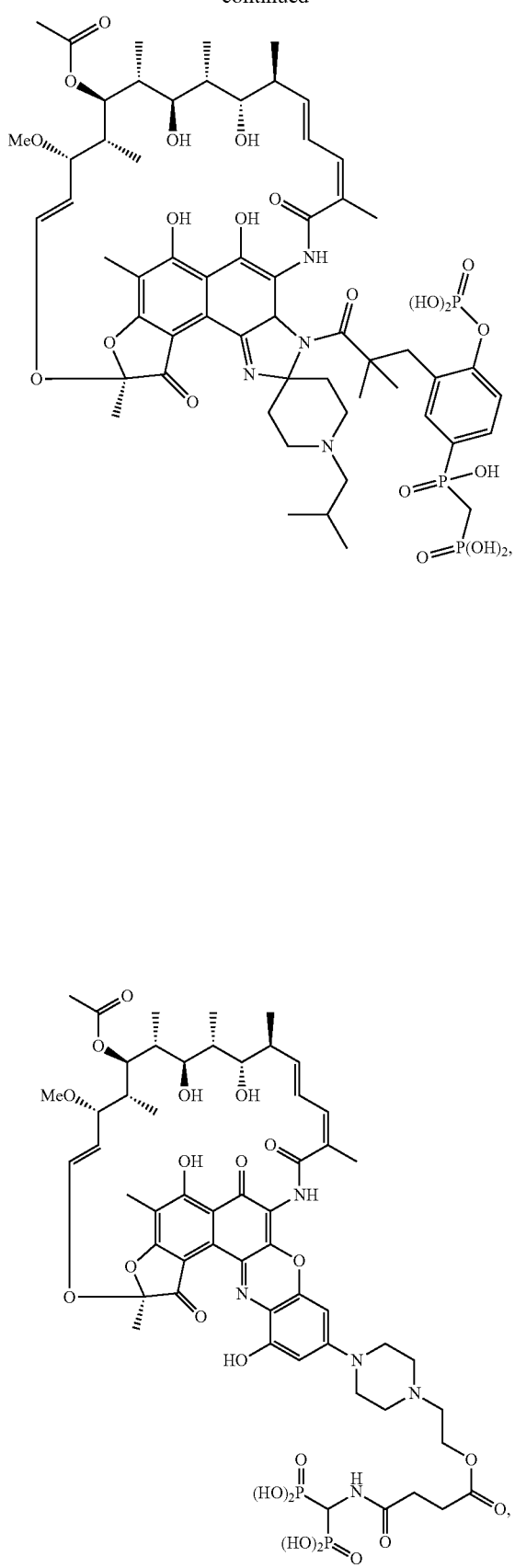

81
-continued
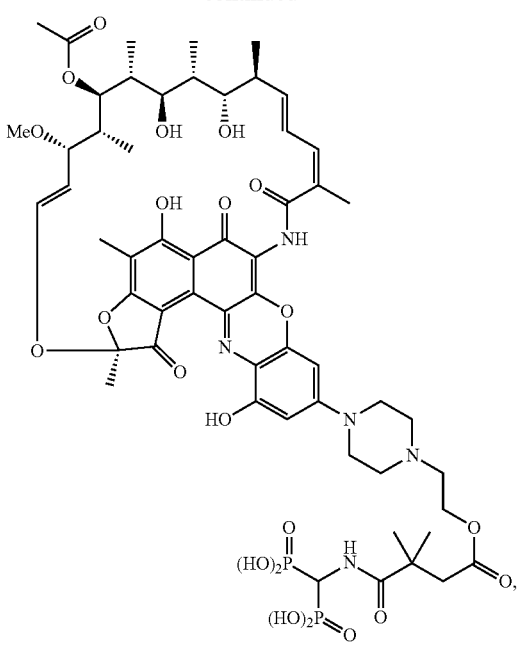
82
-continued
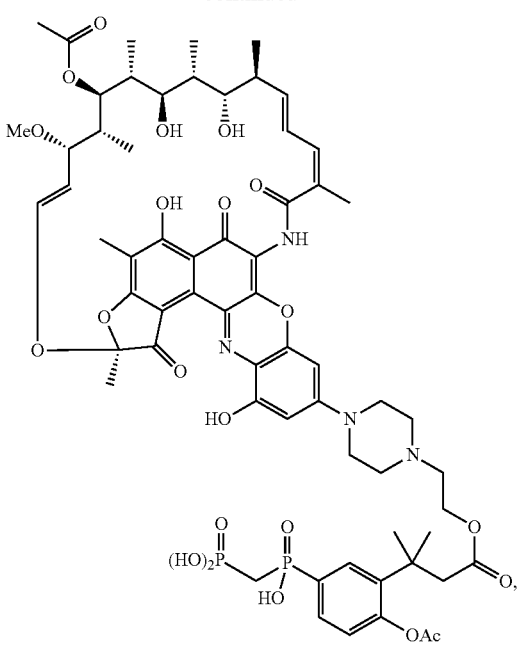
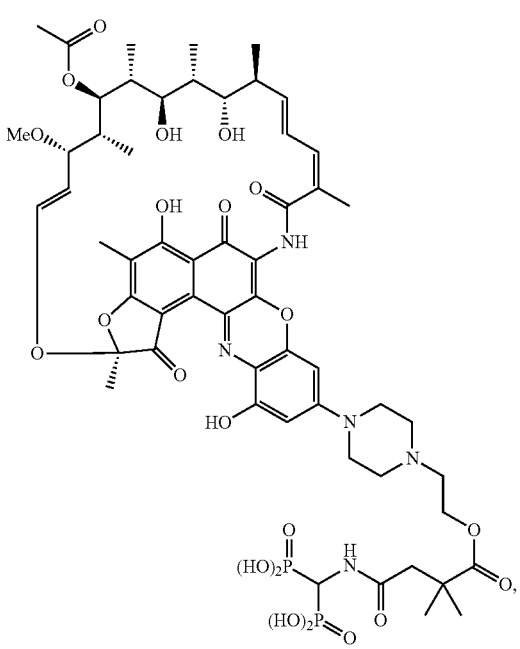
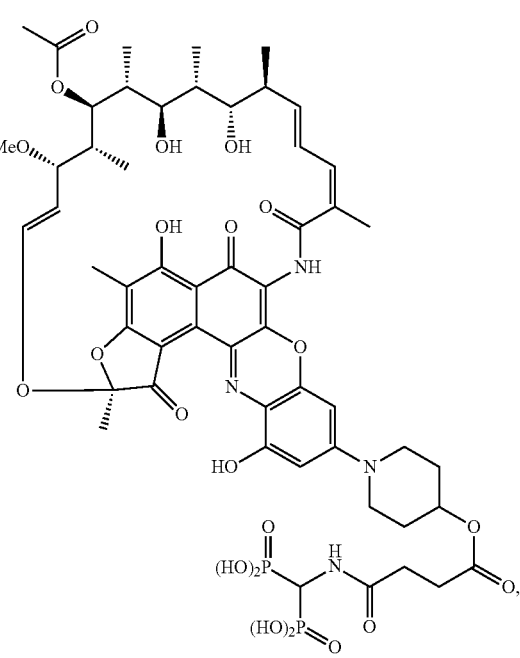

83
-continued
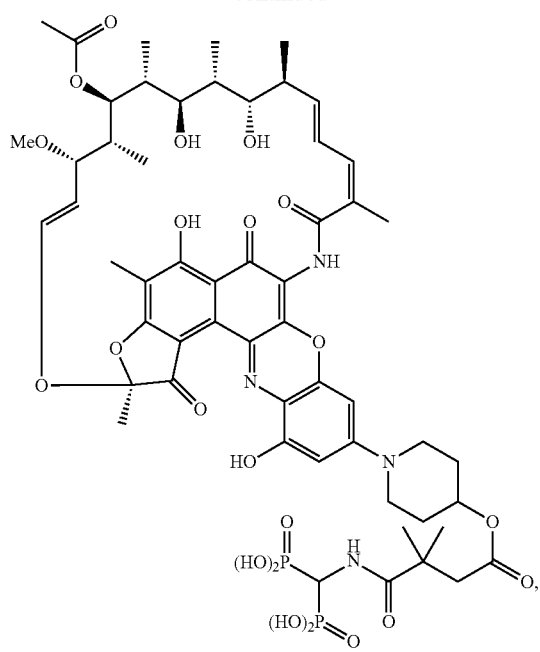
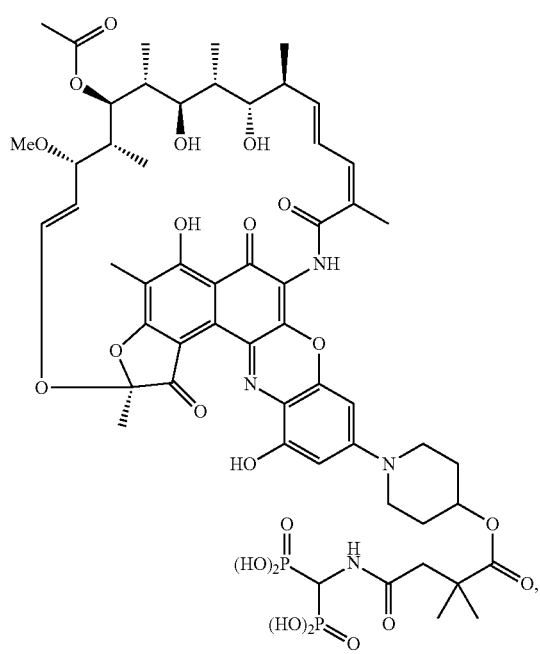
84
-continued
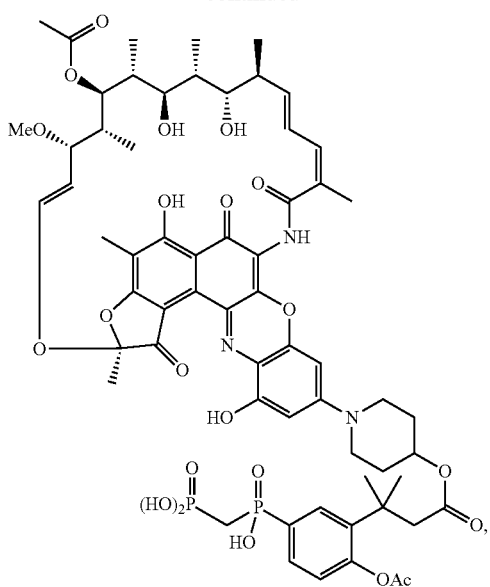
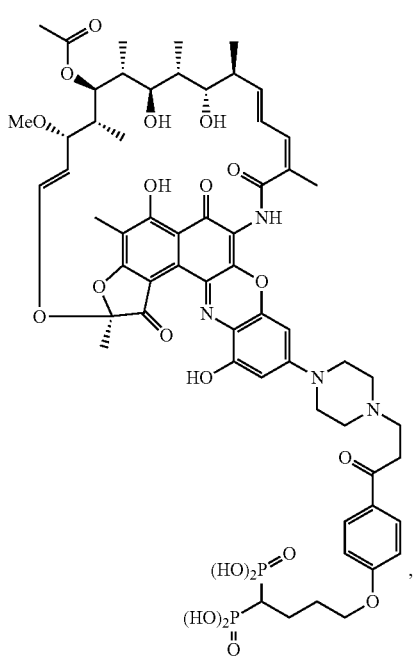

85
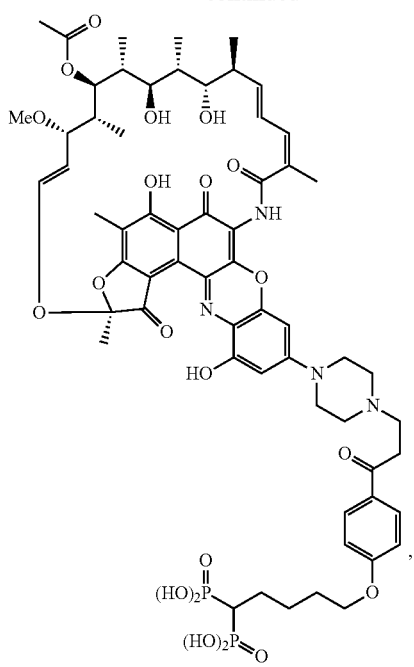
86
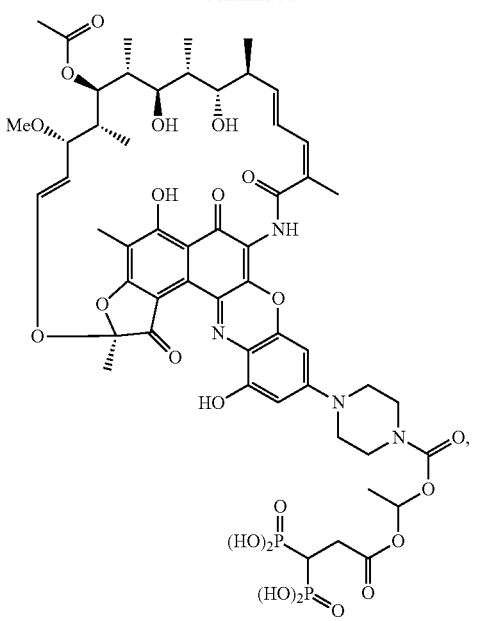
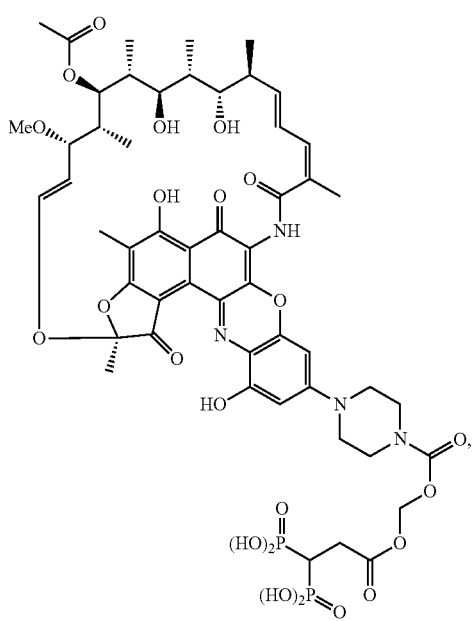
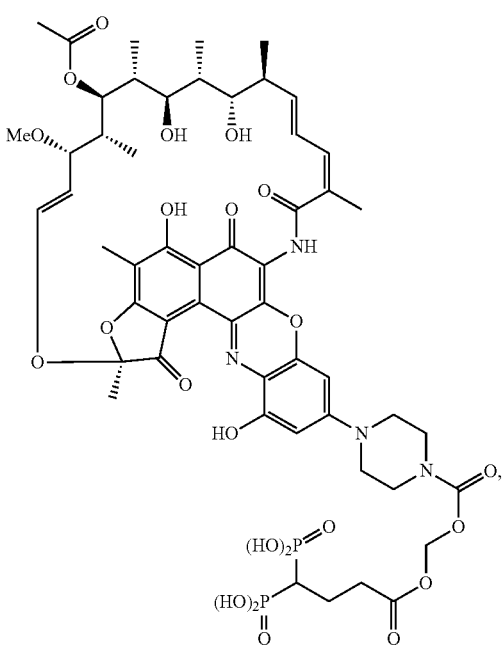

87
-continued
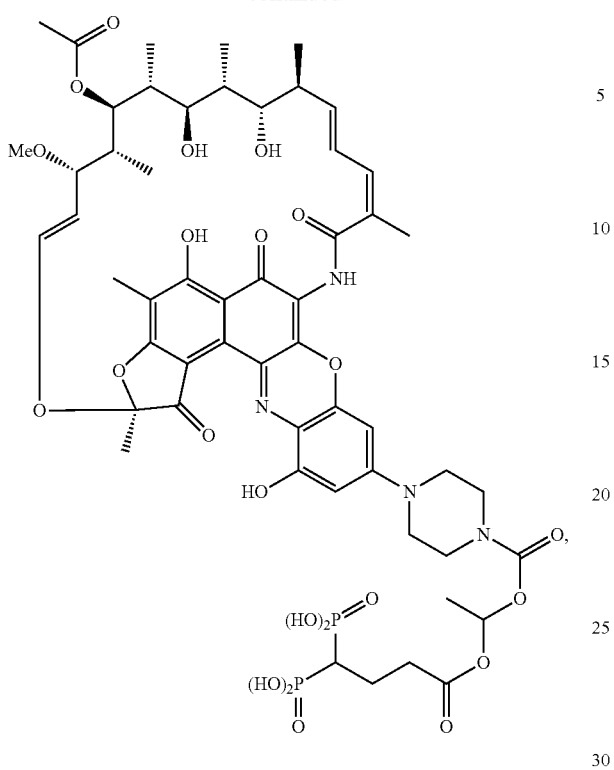
88
-continued
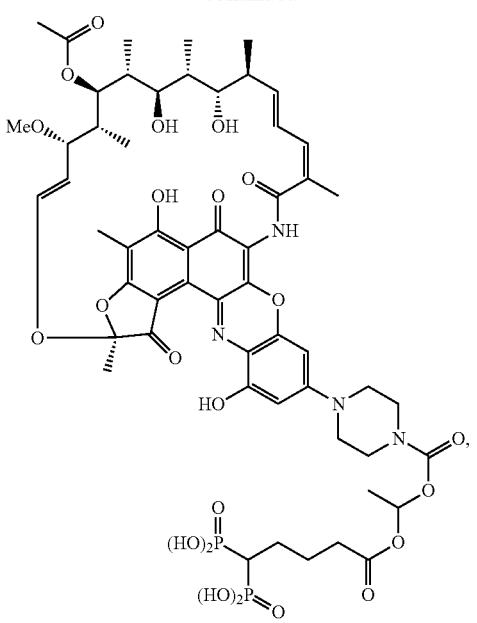
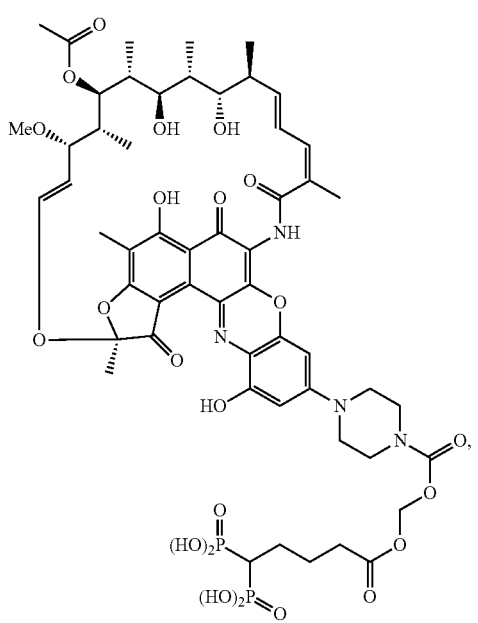
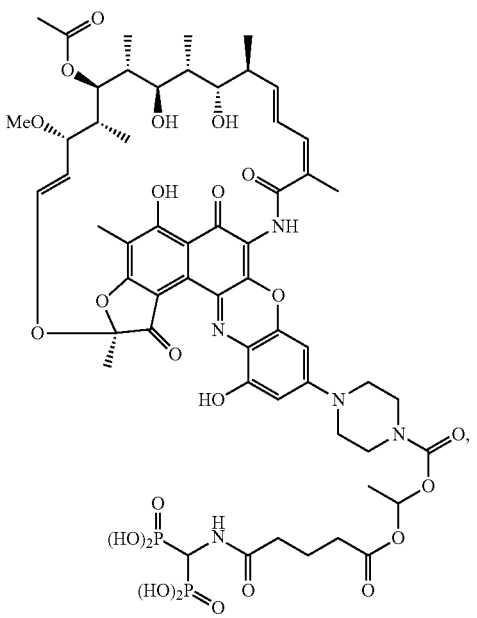

89
-continued
90
-continued
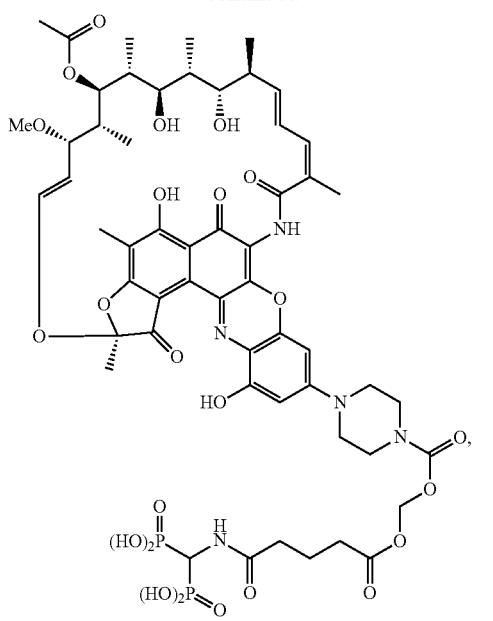
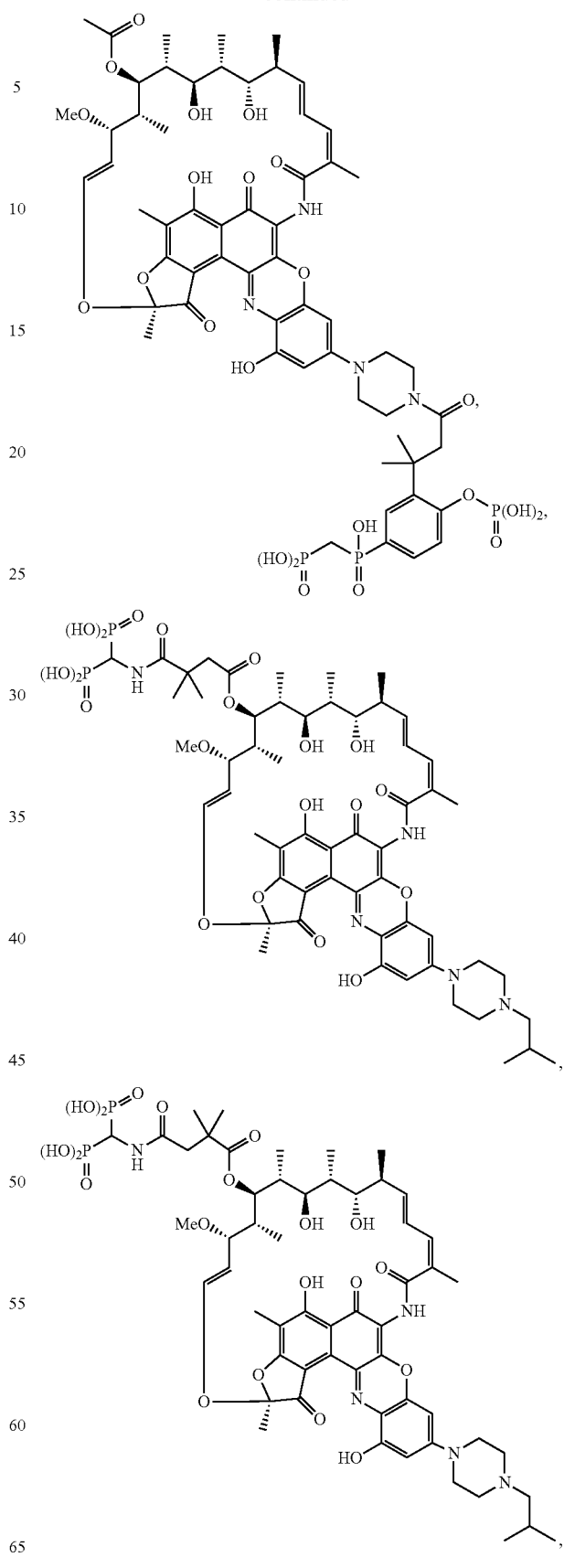

91
-continued
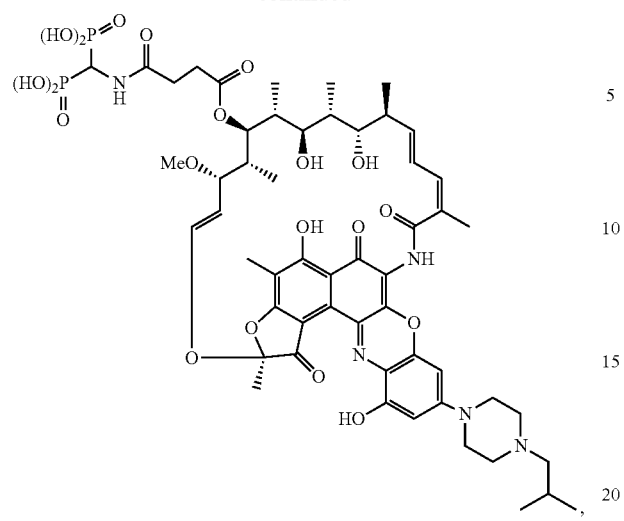
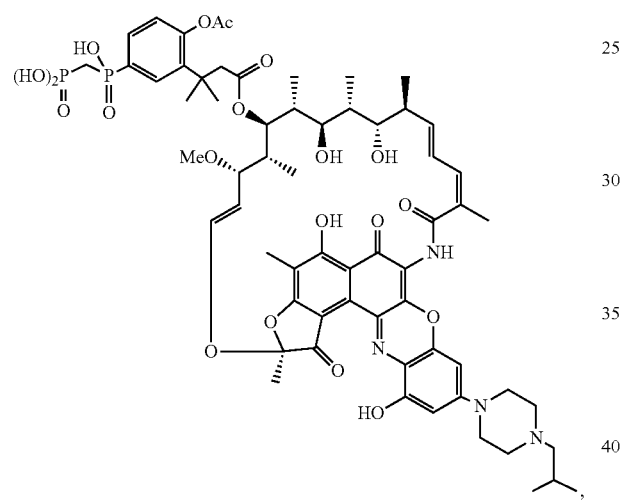
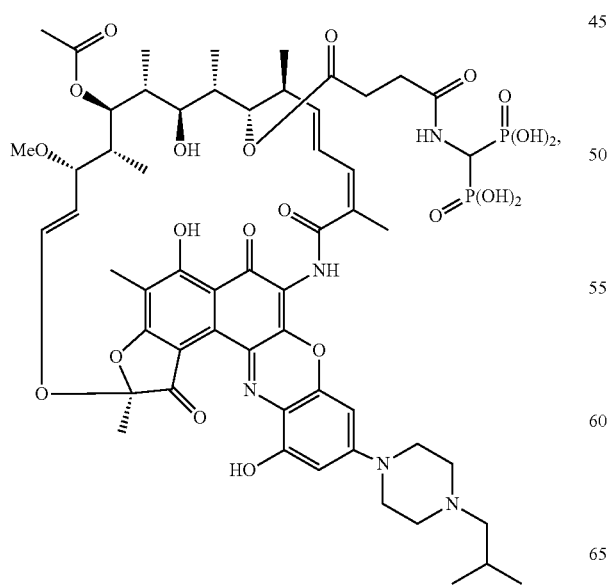
92
-continued
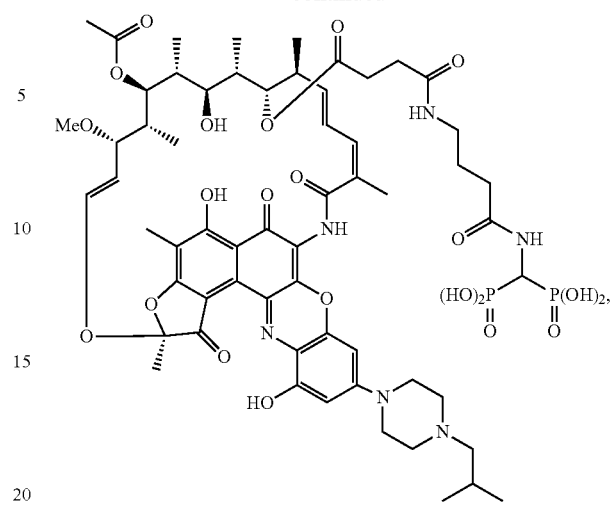
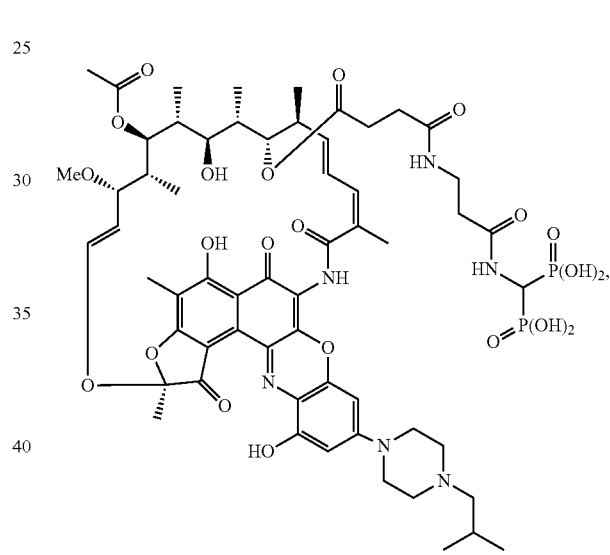
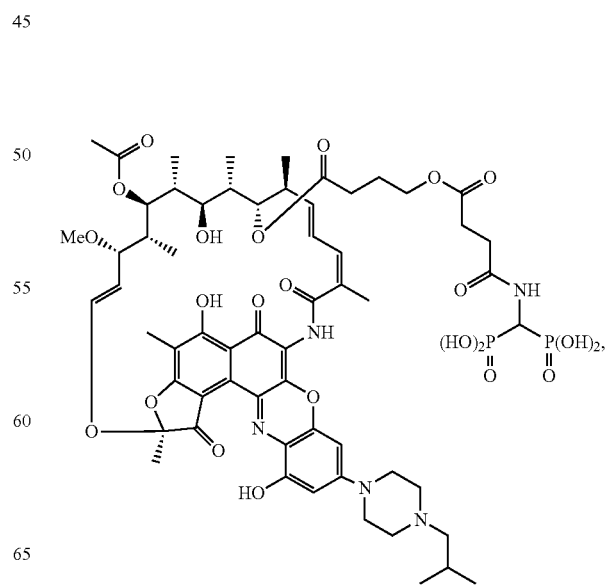

93
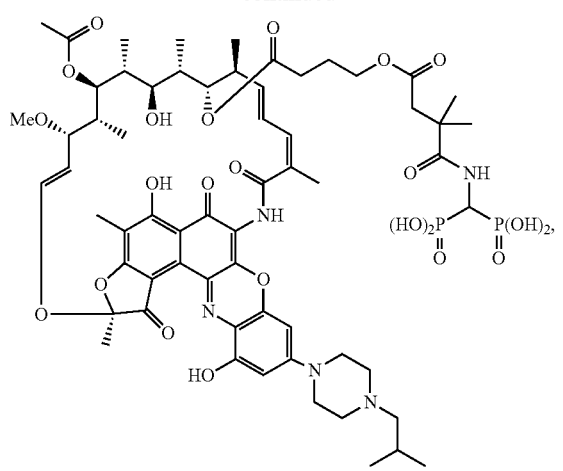
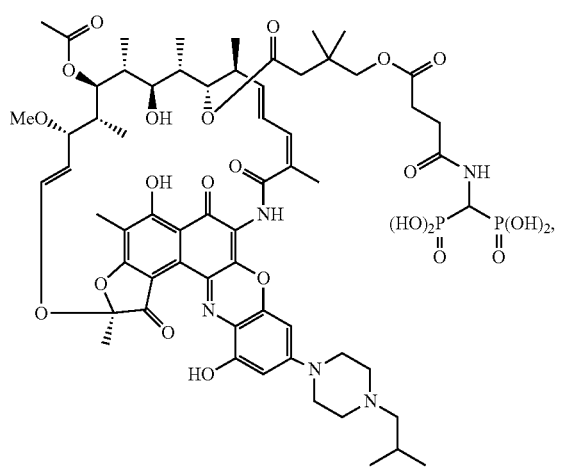
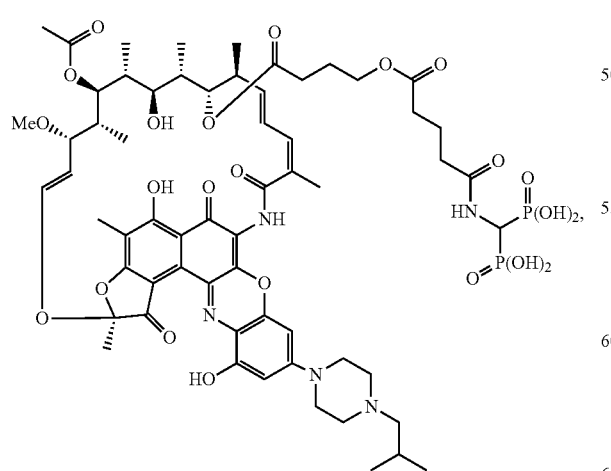
94
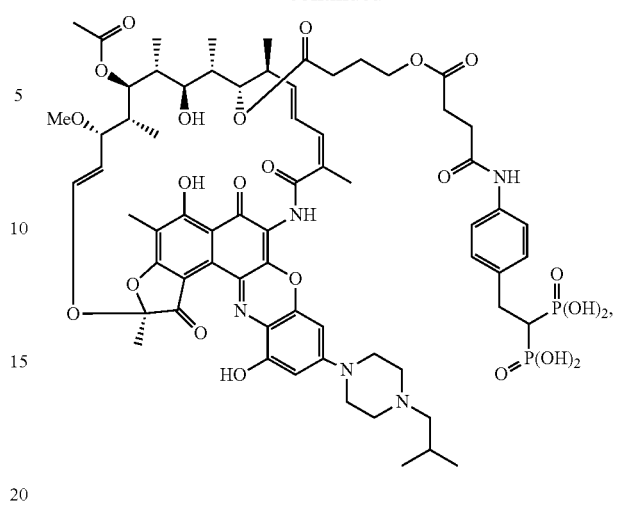
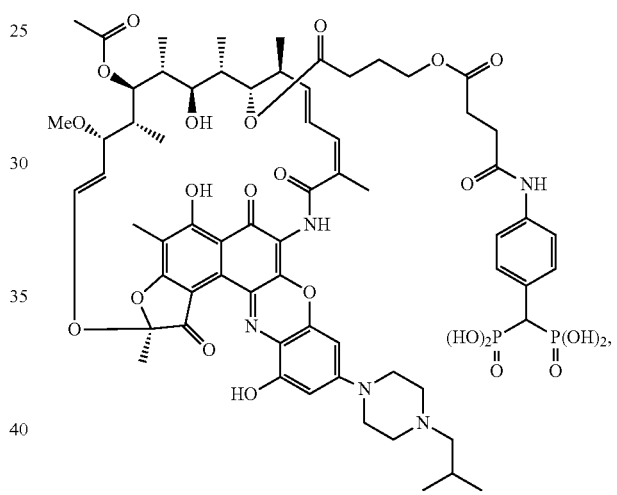
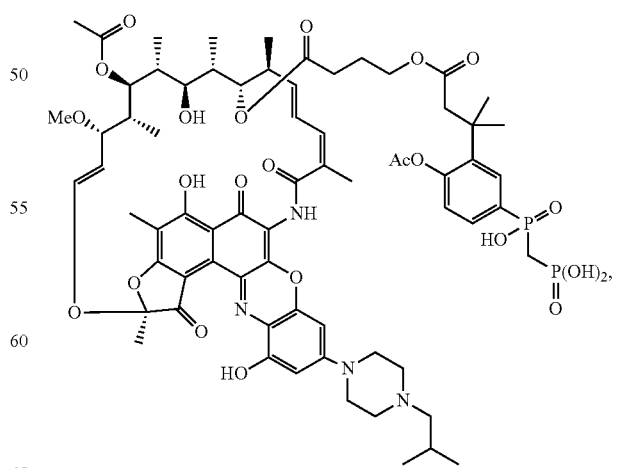

95
-continued
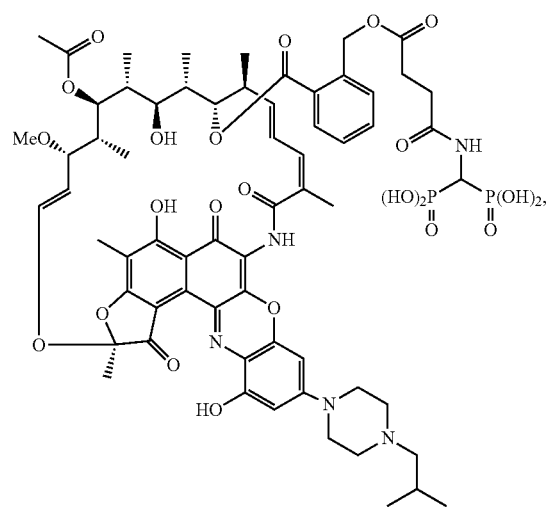
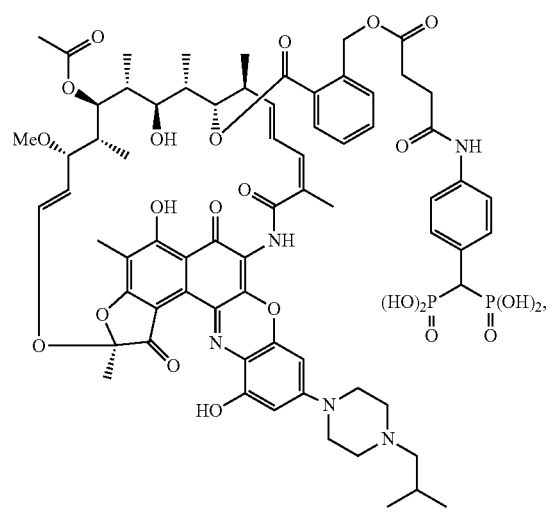
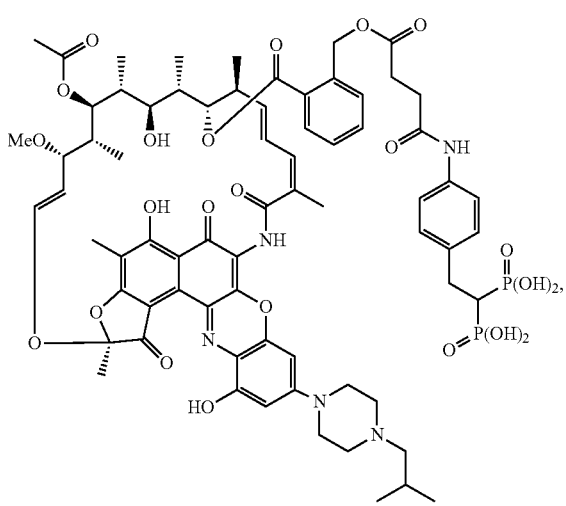
96
-continued
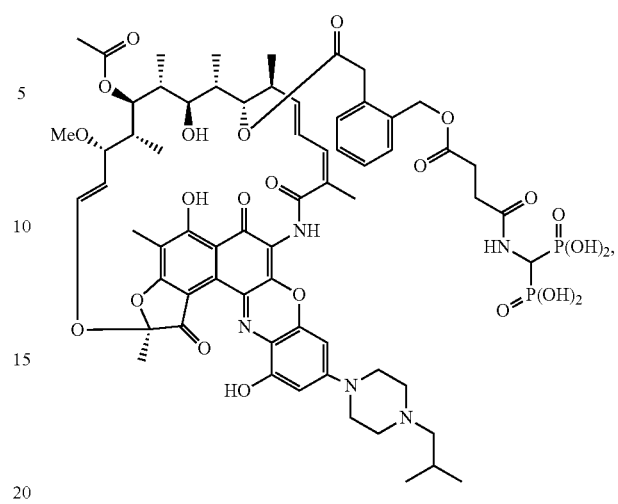
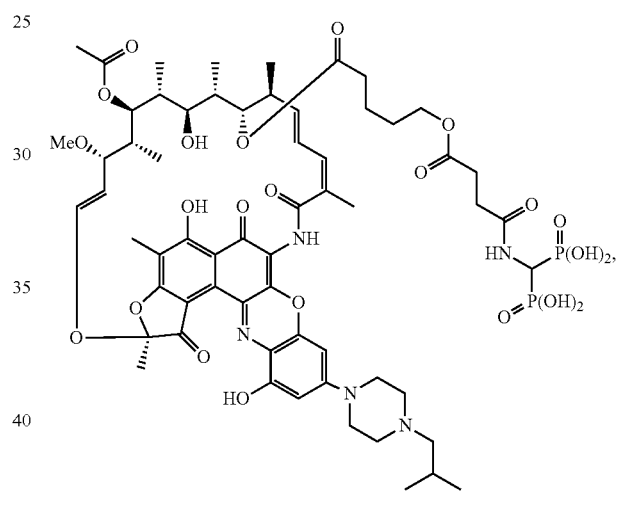
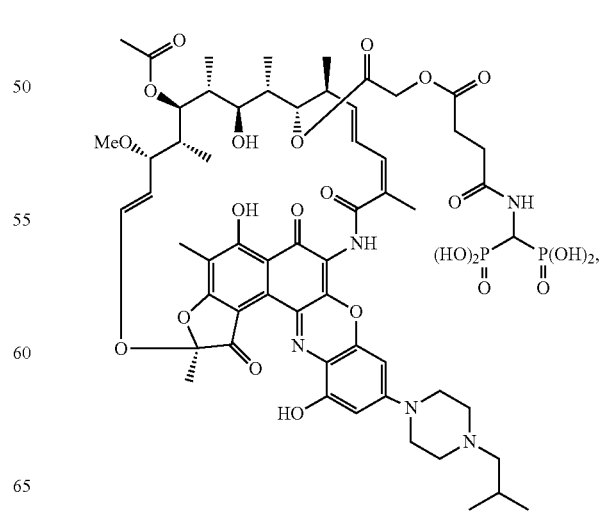

97
-continued
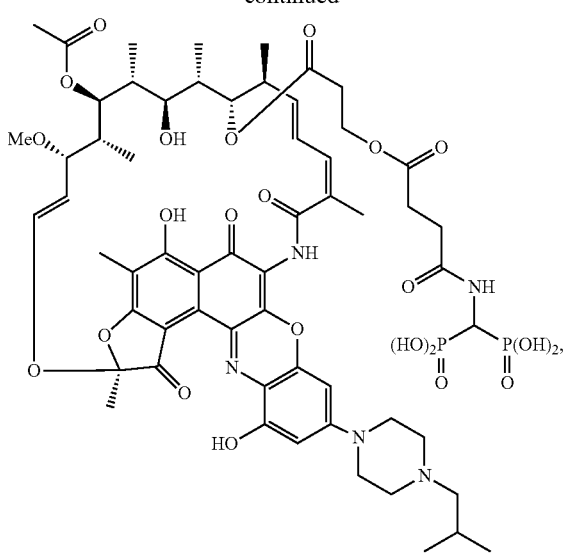
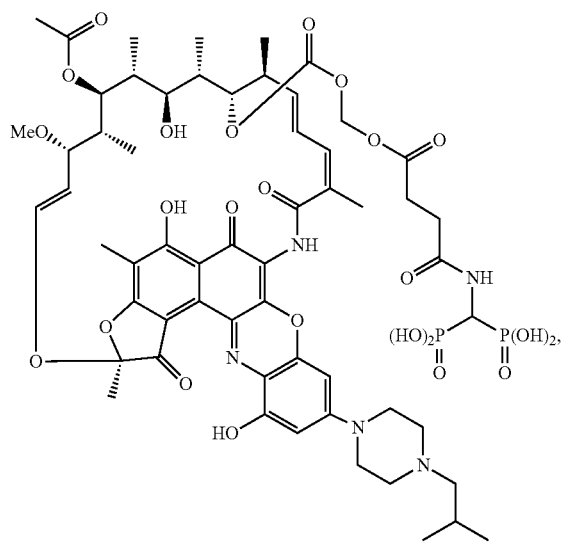
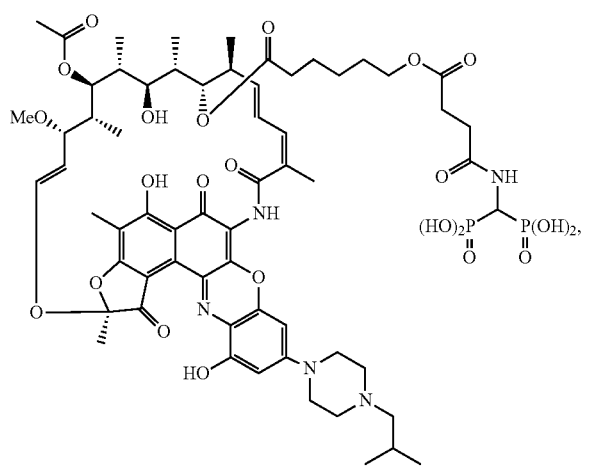
98
-continued
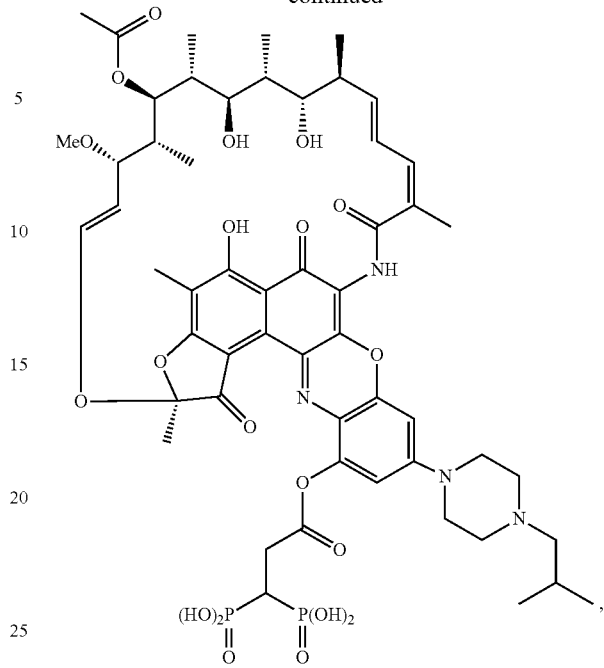
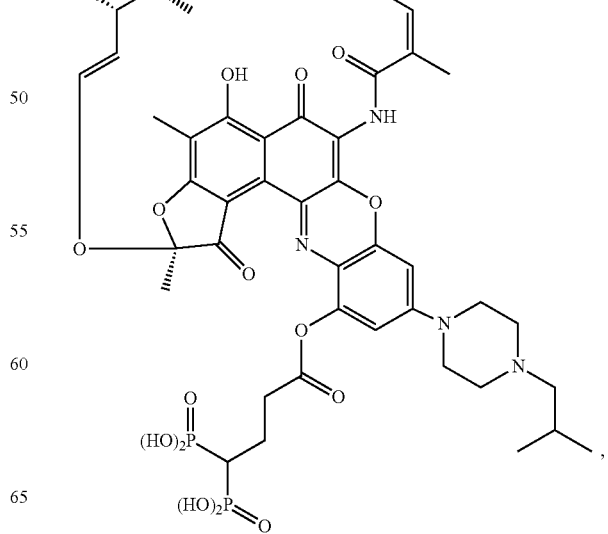

99
-continued

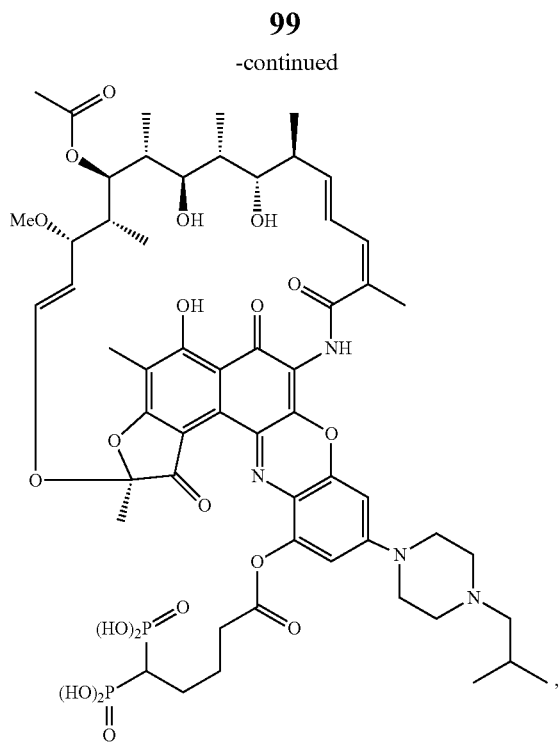

,

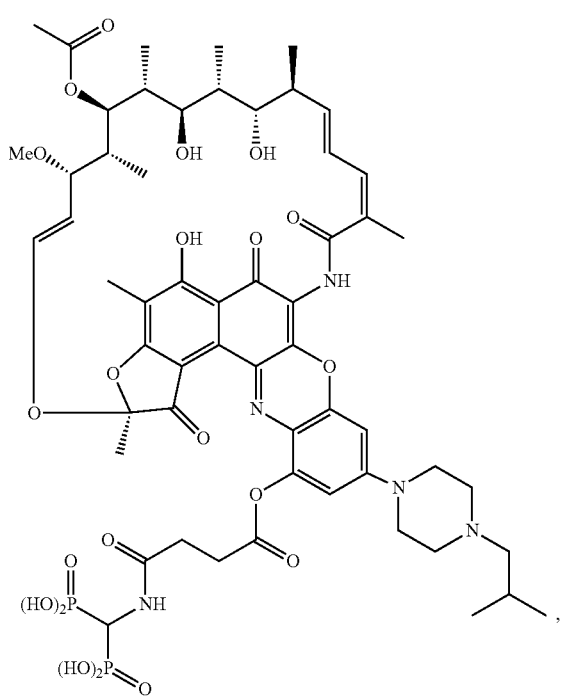

,

100
-continued

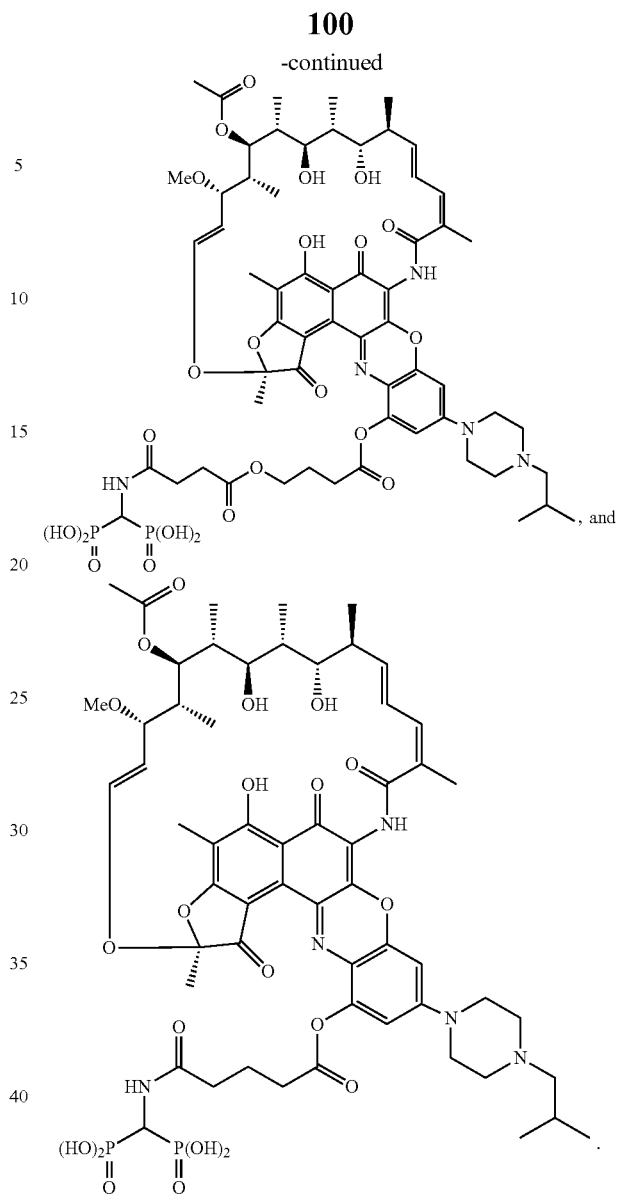

Further, the present invention covers the compounds of Formula (I) and of Formula (II), as well as pharmaceutically acceptable salts, metabolites, solvates and prodrugs thereof. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycolates, tartrates, methanesulfonates, propanesulfonates, naphthalene-1-sulfonates, naphthalene-2-sulfonates, and mandelates.

If the inventive compound is a base, the desired salt may be prepared by any suitable method known to the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid or ethanesulfonic acid, or the like.

If the inventive compound is an acid, the desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum, and lithium.

In the case of compounds, salts, prodrugs or solvates that are solids, it is understood by those skilled in the art that the inventive compounds, salts, and solvates may exist in different crystal forms, all of which are intended to be within the scope of the present invention.

The inventive compounds may exist as single stereoisomers, racemates and/or mixtures of enantiomers and/or diastereomers. All such single stereoisomers, racemates and mixtures thereof are intended to be within the scope of the present invention. Preferably, the inventive compounds are used in optically pure form.

The compounds of the Formula (I) and/or of Formula (II) be administered in the form of a prodrug which is broken down in the human or animal body to give a compound of the Formula (I) or of Formula (II). Examples of prodrugs include in vivo hydrolyzable esters of a compound of the Formula (I) and/or of Formula (II).

An in vivo hydrolyzable ester of a compound of the Formula (I) and/or of Formula (II) containing carboxy or hydroxy group is, for example, a pharmaceutically-acceptable ester which is hydrolyzed in the human or animal body to produce the parent acid or alcohol. Suitable pharmaceutically-acceptable esters for carboxy include (1-6C)alkoxymethyl esters for example methoxymethyl, (1-6C)alkanoyloxymethyl esters for example pivaloyloxymethyl, phthalidyl esters, (3-8C)cycloalkoxycarbonyloxy(1-6C)alkyl esters for example 1-cyclohexylcarbonyloxyethyl; 1,3-dioxolen-2-onylmethyl esters for example 5-methyl-1,3-dioxolen-2-onylmethyl; and (1-6C)alkoxycarbonyloxyethyl esters for example 1-methoxycarbonyloxyethyl and may be formed at any carboxy group in the compounds of this invention.

An in vivo hydrolyzable ester of a compound of the Formula (I) and/or of Formula (II) containing a hydroxy group includes inorganic esters such as phosphate esters and alpha-acyloxyalkyl ethers and related compounds which as a result of in vivo hydrolysis of the ester break down to give the parent hydroxy group. Examples of alpha-acyloxyalkyl ethers include acetoxymethoxy and 2,2-dimethylpropionyloxymethoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

D) Methods of Preparation

The inventive compounds, and their salts, solvates, crystal forms, active metabolites, and prodrugs, may be prepared by employing the techniques available in the art using starting materials that are readily available. Certain novel and exemplary methods of preparing the inventive compounds are described in the Exemplification section. Such methods are within the scope of this invention.

E) Antimicrobial Compositions and Methods of Treatment

A related aspect of the invention concerns the use of compounds of the invention as an active ingredient in a therapeutic or anti-bacterial pharmaceutical composition for treatment, prophylaxis or prevention purposes.

Pharmaceutical Compositions

The compounds of the present invention may be formulated as pharmaceutically acceptable compositions.

The present invention provides for pharmaceutical compositions comprising a compound of the present invention (e.g., those compounds of Formula (I) and (II)) in combination with a pharmaceutically acceptable carrier or excipient. Preferably, the compound of the present invention in a pharmaceutical composition is a therapeutically effective amount of the compound. Carriers include, but are not limited to saline, buffered saline, dextrose, water, glycerol, ethanol, and combinations thereof.

Acceptable methods of preparing suitable pharmaceutical forms of the pharmaceutical compositions according to the invention are known to those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for various routes of administration.

The compounds and compositions of the invention are conceived to have a broad spectrum of activity, including antibiotic resistant strains, against both Gram-positive (e.g. *Staphylococcus aureus, Staphylococcus epidermis, Streptococcus pyogenes, Enterococcus faecalis*) and Gram-negative bacteria (e.g. *E. coli, Chlamydia pneumoniae, Enterobacter* sp., *H. influenza, K. pneumoniae, Legionella pneumoniae, P. aeruginosa*).

Pharmaceutical Compositions and a Second Therapeutic Agent

A wide range of second therapeutic agents, such as antibiotics, can be used in combination with the compounds, pharmaceutical compositions and methods of the present invention. Antibiotics used as second therapeutic agents may act by interfering with cell wall synthesis, plasma membrane integrity, nucleic acid synthesis, ribosomal function, folate synthesis, etc. Second therapeutic agents may be included in a pharmaceutical composition comprising a phosphonated Rifamycin compound of the present invention, or may be administered concurrently with a pharmaceutical composition comprising a phosphonated Rifamycin compound of the present invention.

A non-limiting list of useful antibiotics with which the compounds and compositions of the present invention might be combined or co-administered includes: sulfonamides, beta-lactams, tetracyclines, chloramphenicol, aminoglycosides, macrolides, glycopeptides, streptogramins, quinolones, fluoroquinolones, oxazolidinones and lipopeptides. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, and daptomycin derived antibacterial agents are preferred.

Methods for Inhibiting Bacterial Growth

According to a related aspect, the present invention concerns methods of inhibiting bacterial growth. The method comprises contacting the bacteria for the purpose of such inhibition with an effective amount of a phosphonated Rifamycin compound according to the invention or a pharmaceutical composition comprising a compounds according to the invention (or a pharmaceutically acceptable prodrug, salt, active metabolite, or solvate thereof). For example, one can inhibit bacterial RNA polymerase, bacterial RNA polymerase dependent DNA transcription and/or bacterial translation by contacting a bacterium with a compound of the invention.

The contacting may be carried out in vitro (e.g., in laboratory tissue cultures, in biochemical and/or cellular assays), in vivo in a non-human animal, in vivo in mammals, including humans and/or ex vivo (e.g. for sterilization purposes).

The activity of the inventive compounds as inhibitors of DNA transcription and/or translation may be measured by any of the methods available to those skilled in the art, including in vivo and in vitro assays. Some examples of assays of bacterial RNA polymerase enzymes have been described in U.S. Pat. No. 5,635,349 and by Sawadogo and coworkers (Proc. Natl. Acad. Sci. USA (1985), 82:4394-4398), Doan and coworkers (FEMS Microbiol. Lett. (2001), 196:135-139) and Wu and coworkers (Anal. Biochem. (1997), 245:226-230).

Methods of Treatment

A related aspect of the invention concerns the use of a compound of the invention as an active ingredient in a pharmaceutical, therapeutic or anti-bacterial composition for treatment purposes. As defined above, "treating" or "treatment" means at least the mitigation of a disease condition associated with a bacterial infection in a subject, including mammals such as a human, that is alleviated by a reduction of growth, replication, and/or propagation of any bacterium, such as Gram-positive or Gram-negative organisms, and includes curing, healing, inhibiting, relieving from, improving and/or alleviating, in whole or in part, the disease condition.

The pharmaceutical compositions may be administered in any effective, convenient manner including, for instance, administration by topical, parenteral, oral, anal, intravaginal, intravenous, intraperitoneal, intramuscular, intraocular, subcutaneous, intranasal, intrabronchial, or intradermal routes among others.

In particular, in therapy or as a prophylactic (as further described below), the compounds and pharmaceutical compositions of the invention and/or pharmaceutically acceptable prodrugs, salts, active metabolites and solvates may be administered to an individual as an injectable composition, for example as a sterile aqueous dispersion, preferably isotonic. Alternatively the compounds and compositions may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Alternative means for systemic administration include transmucosal and transdermal administration using penetrants such as bile salts or fusidic acids or other detergents. In addition, if a compound or pharmaceutical composition of the present invention can be formulated in an enteric or an encapsulated formulation, oral administration may also be possible. Administration of these compounds and compositions may also be topical and/or localized, in the form of salves, pastes, gels, and the like.

While the treatment can be administered in a systemic manner through the means described above, it may also be administered in a localized manner. For example, the treatment may be administered directly to a bone, such as through an injection into a bone. The treatment may also be administered in other localized manners, such as application to a wound through a topical composition or directly into a subcutaneous or other form of wound.

The active compounds, pharmaceutical compositions and pharmaceutically acceptable prodrugs, salts, metabolites and solvates may be also administered to an individual as part of a bone substitute or bone-repair compound such as bone cements or fillers (e.g. Skelite™, Millenium Biologics, Kingston, ON, Canada) and calcium or hydroxyapatite beads.

A dose of the compounds or pharmaceutical compositions contains at least a pharmaceutically- or therapeutically-effective amount of the active compound (i.e., a compound of Formula (I), of Formula (II) and/or a pharmaceutically acceptable prodrug, salt, active metabolite, or solvate thereof), and is preferably made up of one or more pharmaceutical dosage units. The selected dose may be administered to a subject, for example, a human patient, in need of treatment. A "therapeutically effective amount" is intended to mean that amount of a compound of Formula (I) and/or of Formula (II) (and/or a pharmaceutically acceptable prodrug, salt, active metabolite, or solvate thereof) that confers a therapeutic effect on the subject treated. The therapeutic effect may be objective (i.e. measurable by some test or marker (e.g. lower bacterial count)) or subjective (i.e. the subject gives an indication of or feels an effect).

The amount that will correspond to a "therapeutically effective amount" will vary depending upon factors such as the particular compound, the route of administration, excipient usage, the disease condition and the severity thereof, the identity of the subject in need thereof, and the possibility of co-usage with other agents for treating a disease. Nevertheless the therapeutically effective amount can be readily determined by one of skill in the art. For administration to a subject such as a mammal, and particularly a human, it is expected that the daily dosage level of the active compound will be from 0.1 mg/kg to 200 mg/kg, typically around 1-5 mg/kg. The physician in any event will determine the actual dosage that will be most suitable for an individual and will vary with the age, weight and response of the particular individual. The above dosages are exemplary of the average case. There can, of course, be individual instances where higher or lower dosage ranges are merited, and such are within the scope of this invention.

Although the invention is preferably directed to the prophylaxis and/or treatment of bone-related infections, the invention encompasses therapeutic and prophylactic methods against other diseases caused by or related to bacterial infection, including but not limited to otitis, conjunctivitis, pneumonia, bacteremia, sinusitis, pleural emphysema and endocarditis, low grade infections in the vicinity of calcifications of atherosclerotic vessels, and meningitis. In such methods, an effective therapeutic or prophylactic amount of a compound and/or pharmaceutical composition as defined hereinbefore, is administered to a subject (preferably a human) in an amount sufficient to provide a therapeutic effect and thereby prevent or treat the infection of the subject. Exact amounts can be routinely determined by one skilled in the art and will vary depending on several factors, such as the particular bacterial strain involved and the particular antibacterial compound used.

Prophylaxis and Prevention

An additional use that is particularly contemplated for the compounds of the present invention is for prophylaxis and prevention purposes. Indeed, many orthopedic surgeons consider that humans with prosthetic joints should be considered for antibiotic prophylaxis before a treatment that could produce a bacteremia. Deep infection is a serious complication sometimes leading to loss of the prosthetic joint and is accompanied by significant morbidity and mortality. The compounds and pharmaceutical compositions of the present invention may therefore be used as a replacement for prophylactic antibiotics in this situation. For instance, the compounds and/or pharmaceutical compositions may be administered by injection to achieve a systemic and/or local effect against relevant bacteria shortly before an invasive medical treatment, such as surgery or insertion of an in-dwelling device (e.g. joint replacement (hip, knee, shoulder, etc.), bone grafting, fracture repair, dental operation or implant. Treatment may be continued after invasive medical treatment, such as post-operatively or during the in-body time of the device.

In addition, the compounds and/or pharmaceutical compositions may also be administered before the invasive medical treatment to permit the accumulation of the compound into the bone tissues prior to the treatment.

In each instance, the compounds and/or pharmaceutical compositions of the present invention may be administered once, twice, thrice or more, from 1, 2, 3, 4, 5, 6, 7 days or more, to 10, 9, 8, 7, 6, 5, 4, 3, 2, or 1 hour or less before surgery for permitting an advisable systemic or local presence of the compounds, and/or accumulation in the bones, preferably in the areas potentially exposed to bacterial contamination during the surgical procedure. Even more preferably, phosphonated compounds and/or pharmaceutical compositions of the invention may be administered such that they can reach a local concentration of about 5, 10, 20, 30, 40, 50, 75, 100, 500 or even 1000 fold higher concentration than the concentration that would normally be achieved during the administration of the unmodified parent Rifamycin, i.e. a non-phosphonated equivalent. The compound(s) may be administered after the invasive medical treatment for a period of time, such as 1, 2, 3, 4, 5 or 6 days, 1, 2, 3 or more weeks, or for the entire time in which the device is present in the body.

Therefore, the invention provides a method of inducing accumulation of Rifamycin in bones of a subject, such as mammal, wherein a phosphonated Rifamycin having high affinity to osseous tissues is administered to a subject. The phosphonated Rifamycin binds osseous tissues and accumulates in bones of the subject in amounts greater than amounts of a non-phosphonated equivalent of the Rifamycin. Preferably, the phosphonated group is coupled to the Rifamycin through a cleavable linker.

The invention further provides a method for prolonging the presence of a Rifamycin in bones of a subject, such as a mammal, wherein a phosphonated Rifamycin having a high affinity to osseous tissues is administered to a subject. The phosphonated group is coupled to the Rifamycin through a cleavable linker. The phosphonated Rifamycin binds osseous tissues and accumulates in bones of the subject, and the linker is cleaved gradually within the bones thereby releasing the Rifamycin and prolonging the presence of the Rifamycin in the bones.

F) In-Dwelling Devices and Products Coated with a Phosphonated Rifamycin

The invention further encompasses in-dwelling devices coated with the compounds and pharmaceutical compositions of the invention. As used herein, the term "in-dwelling device" refers to surgical implants, orthopedic devices, prosthetic devices and catheters, i.e., devices that are introduced to the body of an individual and remain in position for an extended time. Such devices include, but are not limited to, artificial joints and implants, heart valves, pacemakers, vascular grafts, vascular catheters, cerebrospinal fluid shunts, urinary catheters, continuous ambulatory peritoneal dialysis (CAPD) catheters.

According to one embodiment, the in-dwelling device is bathed in or sprayed with a concentration of about 1 mg/ml to about 10 mg/ml of a compound and/or pharmaceutical composition of the invention, before its insertion in the body.

According to another embodiment, the in-dwelling device is made of, or pre-coated with, an osseous-like type of material (e.g. calcium phosphate, Ca-ion and hydroxyapatite (Yoshinari et al., Biomaterials (2001), 22(7): 709-715)). Such material is likely to advantageously improve binding of the compounds and pharmaceutical compositions of the invention to the in-dwelling device, either during the coating of the device with the compounds or pharmaceutical compositions of the invention and/or after their local or systemic administration. The in-dwelling devices may also be coated with an osseous material pre-loaded with or containing bound bone-targeting compound(s) according to the invention. For the above-mentioned embodiments, hydroxyapatite would be preferred as the osseous material. More details on coating methods, uses and advantages of hydroxyapatite-coated prostheses are found in the review by Dumbleton and Manly (The Journal of Bone & Joint Surgery (2004) 86A:2526-40) which is incorporated herein by reference.

G) Methods of Preparation

The inventive compounds, and their salts, solvates, crystal forms, active metabolites, and prodrugs, may be prepared by employing the techniques available in the art using starting materials that are readily available. Certain novel and exemplary methods of preparing the inventive compounds are described in the Exemplification section below. Such methods are within the scope of this invention.

EXAMPLES

The Examples set forth herein provide exemplary syntheses of representative compounds of the invention. Also provided are exemplary methods for assaying the compounds of the invention for their bone-binding activity, assays for determining the minimum inhibitory concentration (MIC) of the compounds of the invention against microorganisms, and methods for testing in vivo activity and cytotoxicity.

Example 1

Synthesis of Phosphonated Rifamycins

A) General Experimental Procedures
A 1) Preparation of Bisphosphonate Building Blocks

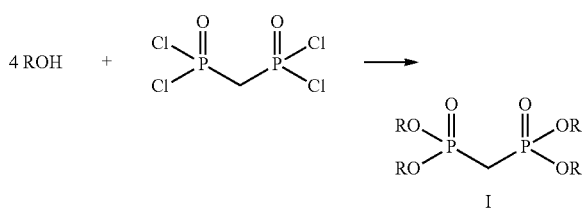

As described in Synth. Commun. (2002), 32; 211-218, tetraesters of methylenebisphosphonic acid (I) can be prepared from the parent tetrachloride and an alcohol.

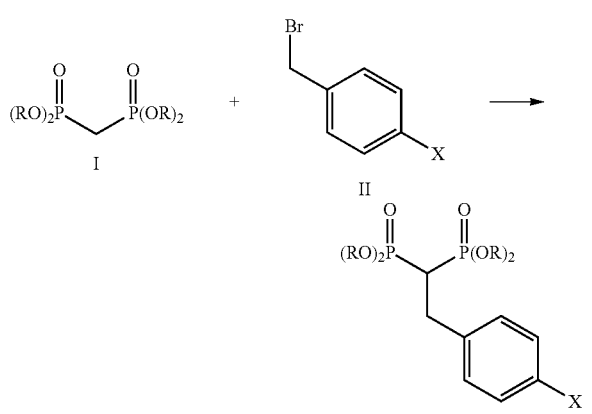

IIIa: X = NO$_2$
IIIb: X = NH$_2$
IIIc: X = CO$_2$R'
IIId: X = CO$_2$H

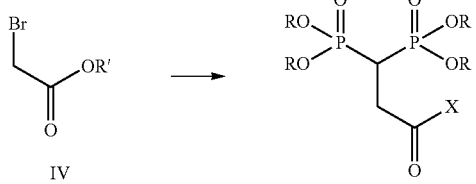

Va: X = OR'
Vb: X = OH
Vc: X = Cl

Following protocols described in Bioorg. Med. Chem. (1999), 7; 901-919, benzyl substituted bisphosphonate building blocks of the general structures III and V can be obtained by alkylation of the anion of I with 4-substituted benzyl bromide II or bromoacetate IV. Nitro compound IIIa can be converted to aniline IIIb by reduction of the nitro group under hydrogenation conditions, using a catalyst such as PtO$_2$. Esters like IIIc and Va can be converted to the corresponding acids IIId or Vb via ester cleavage. For example, ester IIIc where R'=t-Bu can be treated with TFA to afford the corresponding acid IIId. Under similar conditions, ester Va where X=Ot-Bu can be converted to acid Vb.

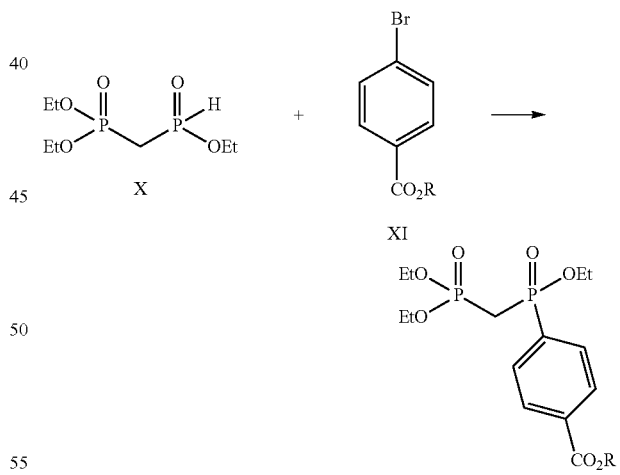

XIIa: R = t-Bu, Me
XIIb: R = H

Aryl substituted methylene bisphosphonates of general formula IX can be obtained from the parent benzylic halides VI in a sequence of two Arbuzov reactions separated by a benzylic halogenation.

Diethyl (ethoxyphosphinyl)methylphosphonate X can be prepared using the procedure described in Synth. Comm. (2002), 32; 2951-2957 and U.S. Pat. No. 5,952,478 (1999). It can be coupled with a 4-substituted bromobenzene (XI) to access acid XIIb, following cleavage of the ester intermediate XIIa.

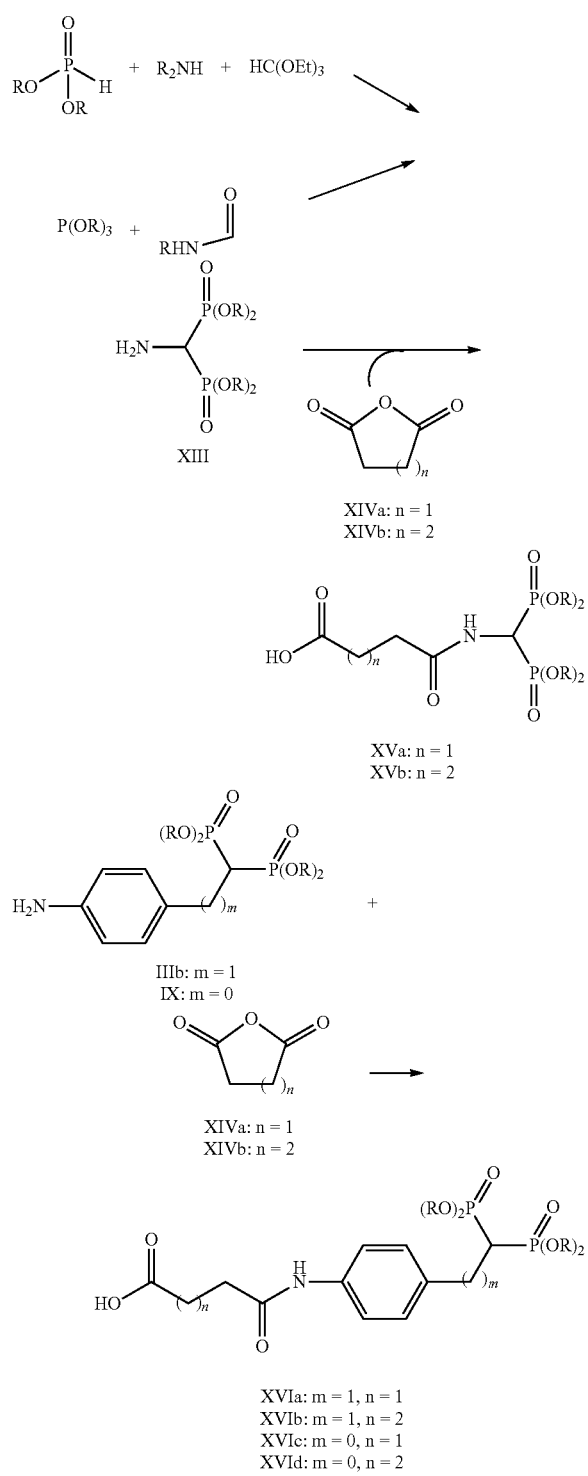

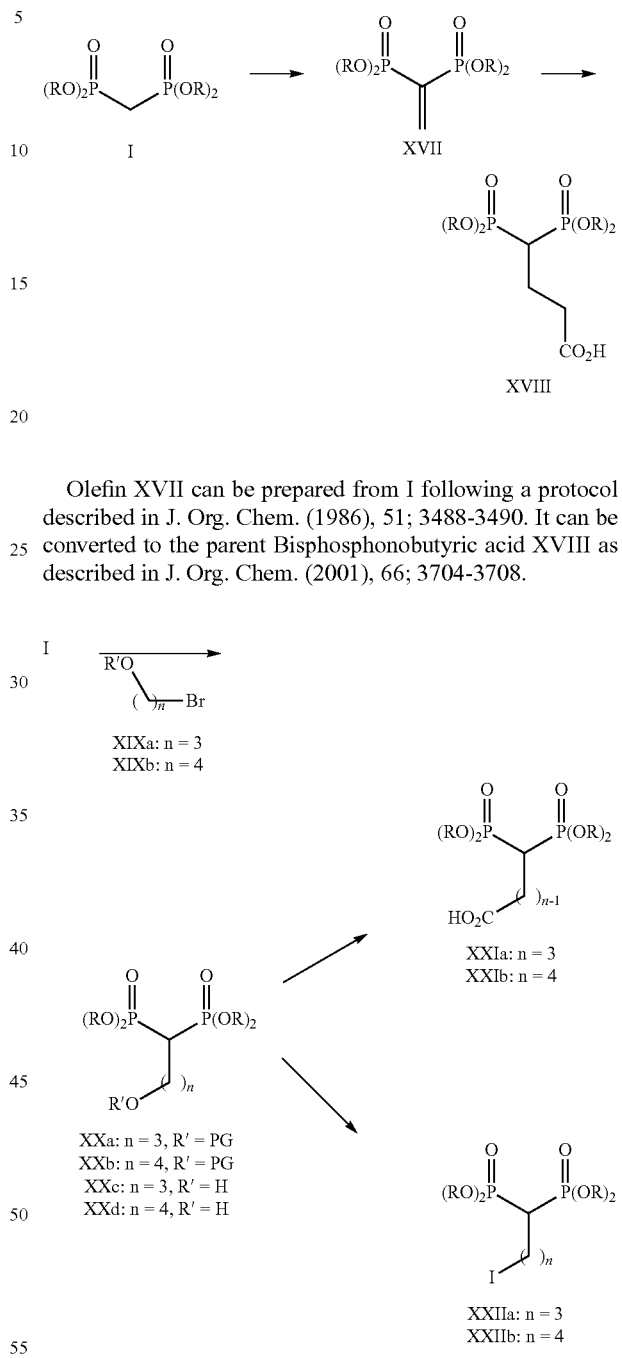

of the previously described IIIb or IX with XIV(a-b) results in the succinamic and glutaramic acids XVI(a-d).

Olefin XVII can be prepared from I following a protocol described in J. Org. Chem. (1986), 51; 3488-3490. It can be converted to the parent Bisphosphonobutyric acid XVIII as described in J. Org. Chem. (2001), 66; 3704-3708.

Amine XIII can be prepared from dibenzylamine or diallylamine, dialkyl phosphite and triethyl orthoformate following a protocol described in Synth. Commun. (1996), 26; 2037-2043, or from a trialkyl phosphite and an appropriately substituted formamide (such as allyl formamide) as in Phosphorus, Sulfur and Silicon (2003), 178, 38-46. Acylation of XIII with succinic anhydride XIVa or glutaric anhydride XIVb can provide acids XVa and XVb respectively (J. Drug Targeting (1997), 5; 129-138). In a similar fashion, treatment As described in Phosphorus, Sulfur and Silicon, (1998), 132; 219-229, alcohols of general structure XX(c-d) and iodides of general structure XXII can be prepared by alkylation of the anion of I by protected ω-hydroxy bromides of various chain length XIX(a-b). After deprotection, alcohols can be converted to the corresponding iodides via treatment with in situ generated triphenylphosphine:iodine complex. These alcohols XX(c-d) may additionally be converted to acids of general structure XX by conventional methods of oxidation, such as treatment with pyridinium dichromate.

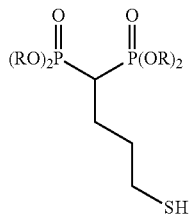
XXIII

Thiol XXIII can be prepared by alkylation of the anion of I with a protected 3-iodopropane-1-thiol following the protocol described in Bioorg. Med. Chem. (1999), 7; 901-919.

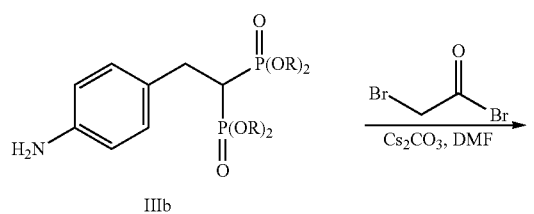
IIIb

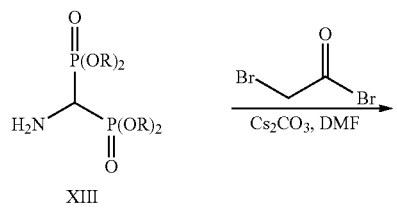
XXIV

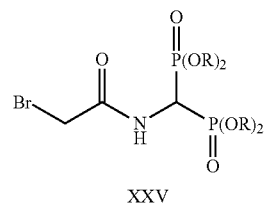
XIII

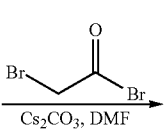
XXV

Bromoacetamides XXIV and XXV from the parent amines IIIb and XIII can be prepared according to a modification of the procedure described in J. Drug Targeting (1995), 3, 273-282.

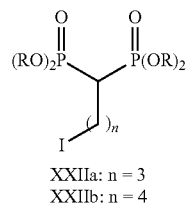
XXIIa: n = 3
XXIIb: n = 4

-continued

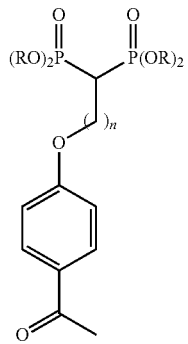
XXVIa: n = 3
XXVIb: n = 4

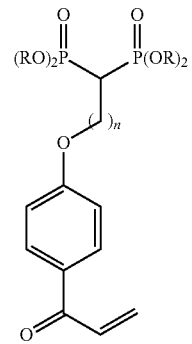
XXVIIa: n = 3
XXVIIb: n = 4

The bisphosphonated vinyl aryl ketones such as XXVII(a-b) can be prepared via treatment of the parent iodides XXII (a-b) with p-hydroxyacetophenone, followed by a methylene transfer reaction as described in Org. Syn. (1983); 60; 88-91.

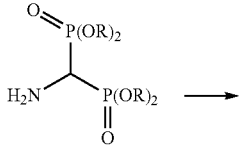
XXVIIIa n = 2
XXVIIIb n = 3

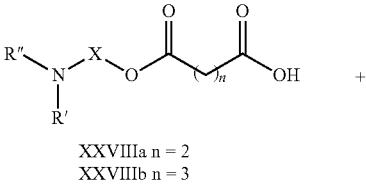
XIII

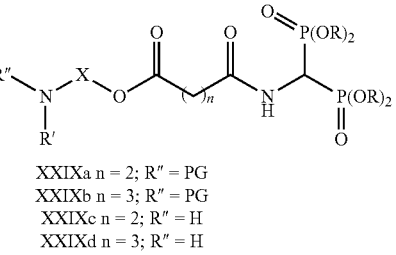
XXIXa n = 2; R″ = PG
XXIXb n = 3; R″ = PG
XXIXc n = 2; R″ = H
XXIXd n = 3; R″ = H

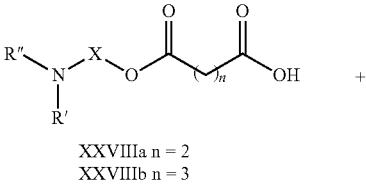
XXVIIIa n = 2
XXVIIIb n = 3

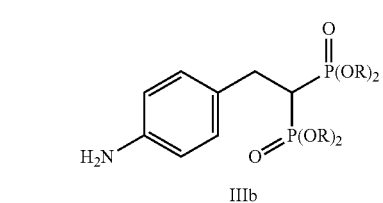
IIIb

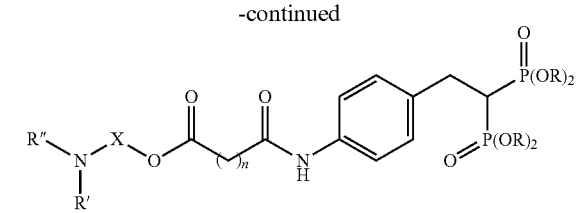

XXXa n = 2; R'' = PG
XXXb n = 3; R'' = PG
XXXc n = 2; R'' = H
XXXd n = 3; R'' = H

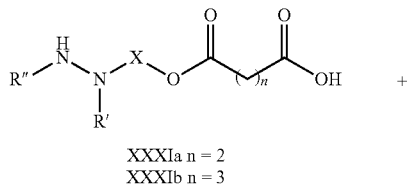

XXXIa n = 2
XXXIb n = 3

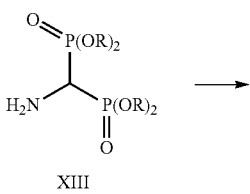

XIII

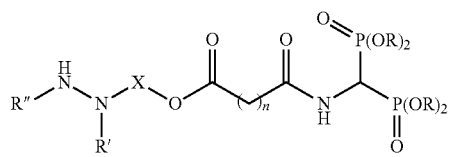

XXXIIa n = 2; R'' = PG
XXXIIb n = 3; R'' = PG
XXXIIc n = 2; R'' = H
XXXIId n = 3; R'' = H

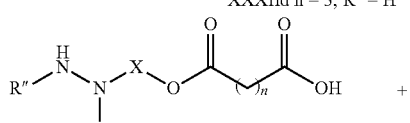

XXXIa n = 2
XXXIb n = 3

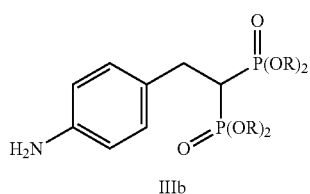

IIIb

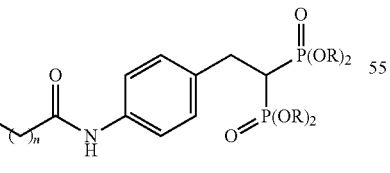

XXXIIIa n = 2; R'' = PG
XXXIIIb n = 3; R'' = PG
XXXIIIc n = 2; R'' = H
XXXIIId n = 3; R'' = H

Bisphosphonated amines XXIX(a-d) and XXX(a-d) and hydrazines XXXII(a-d) and XXXIII(a-d) are produced by the appropriately protected amines XXVIII(a-b) and hydrazines XXXI(a-b) with either IIIb or XIII, in the presence of a tertiary amine and a standard amide coupling agent (DCC, EDCl, HBTU, HATU, PyBOP, BOP-Cl). In all these cases, X is a combination of atoms separating the oxygen and nitrogen atoms and R' is another combination of atoms which could be bonded to those in X.

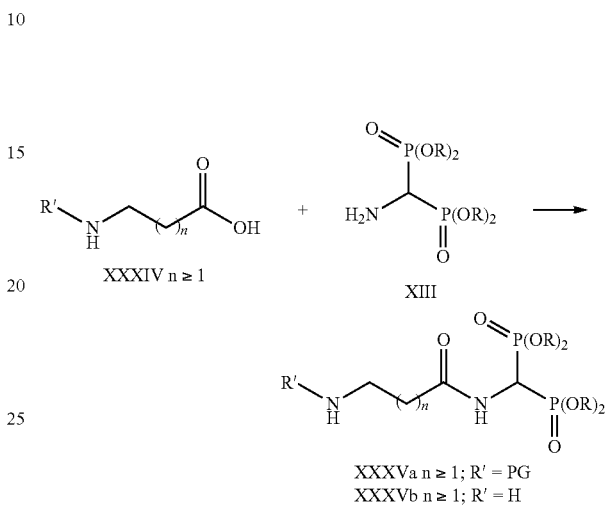

XXXIV n ≥ 1

XIII

XXXVa n ≥ 1; R' = PG
XXXVb n ≥ 1; R' = H

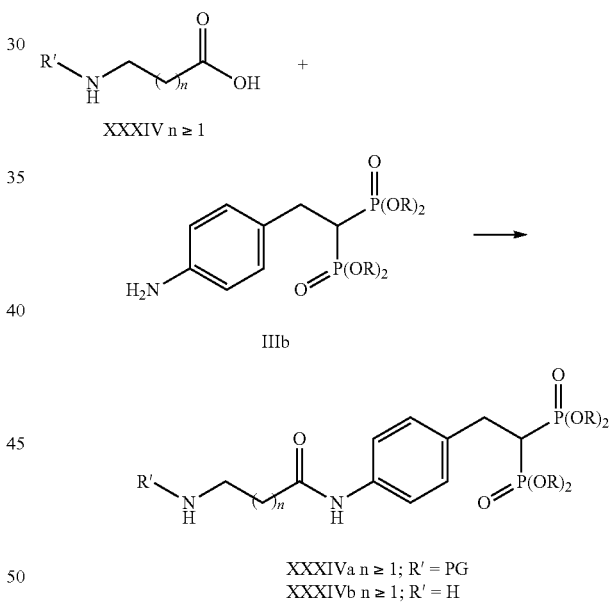

XXXIV n ≥ 1

IIIb

XXXIVa n ≥ 1; R' = PG
XXXIVb n ≥ 1; R' = H

Bisphosphonated amines XXXVa-b and XXXVIa-b are easily produced by the acylation of amines XIII and IIIb respectively with protected amino acids XXXIV under standard amide coupling conditions (Tertiary amine and a standard amide coupling agent such as DCC, EDCl, HBTU, HATU, PyBOP, BOP-Cl).

The bisphosphonate building blocks described in this section are in the form of their phosphonic esters, R being Me, Et, i-Pr or Bn; or as the free bisphosphonic acid.

A 2) Synthesis of Rifamycin-Bisphosphonate Conjugates
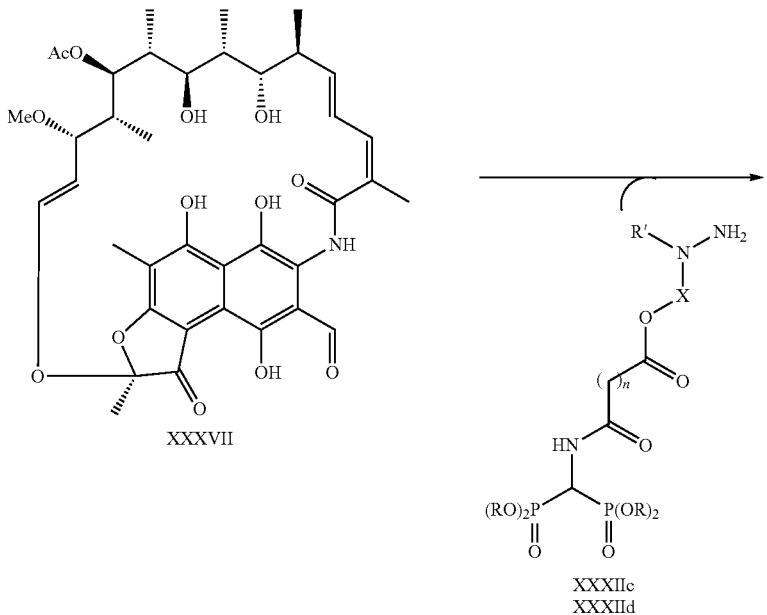
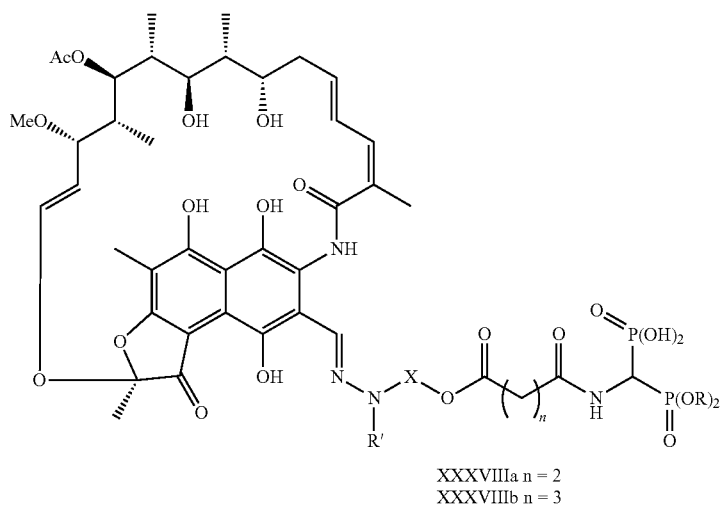
XXXVIIIa n = 2
XXXVIIIb n = 3

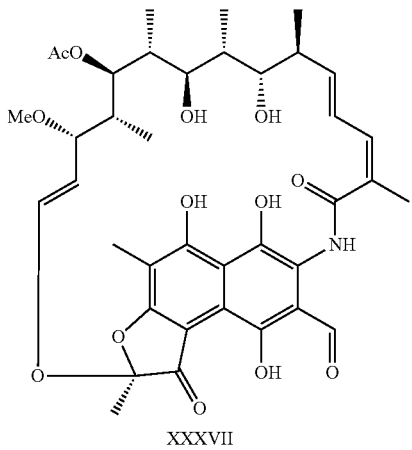
XXXVII
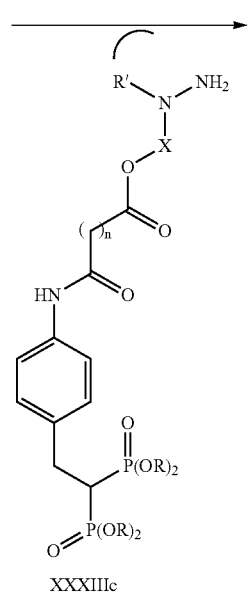
XXXIIIc
XXXIIId
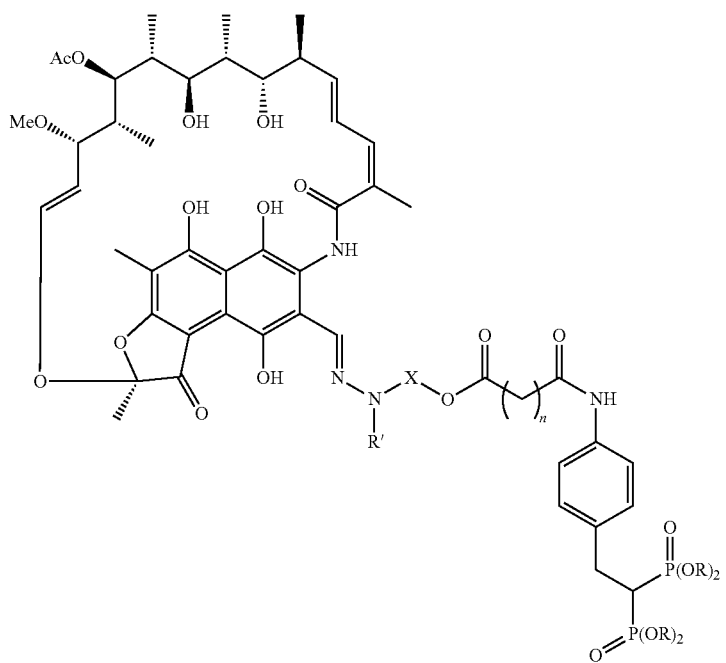
XXXIXa n = 2
XXXIXb n = 3

Bisphosphonated prodrugs XXXVIII(a-b) and XXXIX(a-b) are prepared by the condensation of 3-formyl Rifamycin S XXXVII with the hydrazines XXXII(c-d) and XXXIII(c-d) in a similar fashion as described in Farmaco, Ed. Sci. (1975), 30, 605-619.

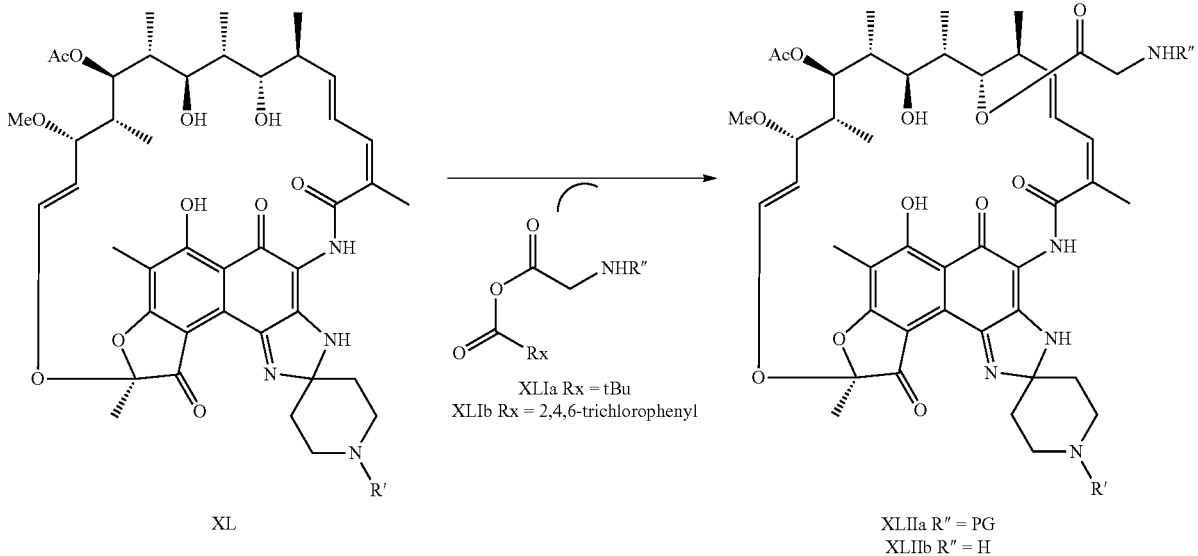

The reaction of rifamycin derived compounds XL with the mixed anhydrides prepared from protected glycines selectively produce the ester products XLIIa, in a similar manner to that described for other anhydrides in J. Mol. Struct. (2001), 563-564, 61-78. After the deprotection of the glycinyl moiety, the free amino group is reacted with acid Vb to produce the desired bisphosphonated Rifamycin derivatives XLIII.

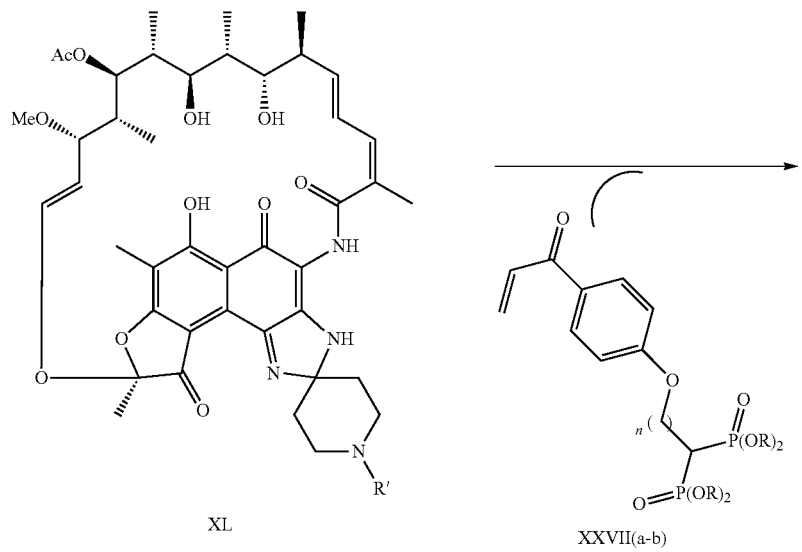
XL
XXVII(a-b)
XLIVa n = 3
XLIVb n = 4

The addition of XL to vinyl ketones XXVII(a-b) provides bisphosphonated Rifamycin derived prodrugs XLIV(a-b), in a similar fashion to that described for a non-bisphosphonated prodrug of ciprofloxacin in Ind. J. Pharm. Sci. (1999); 61, 223-226.
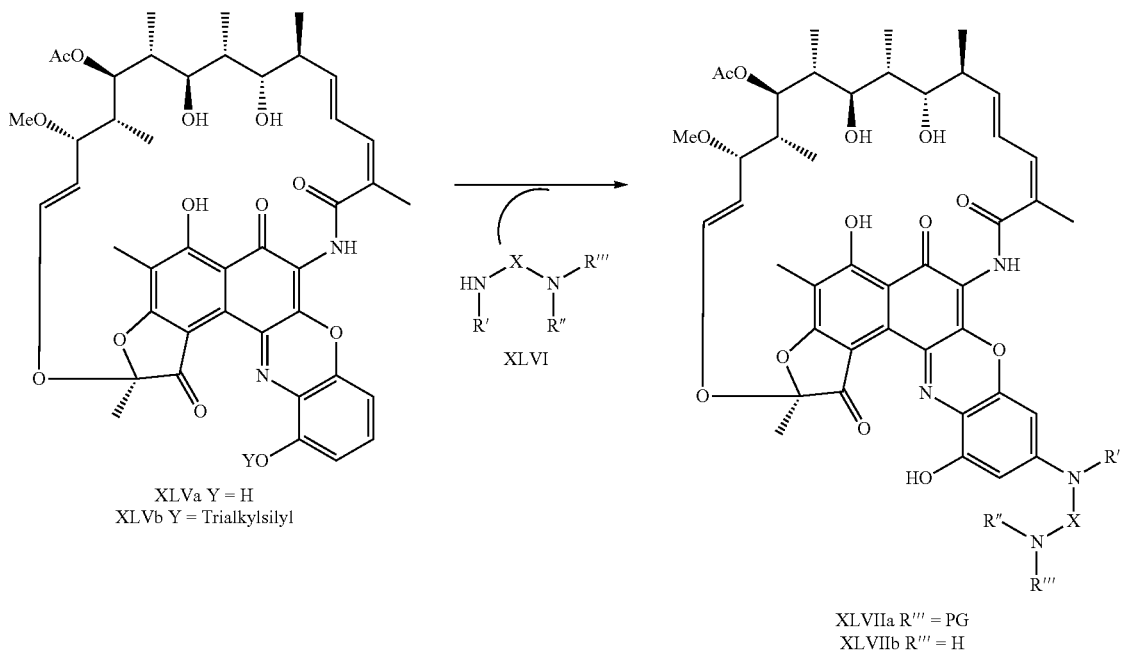
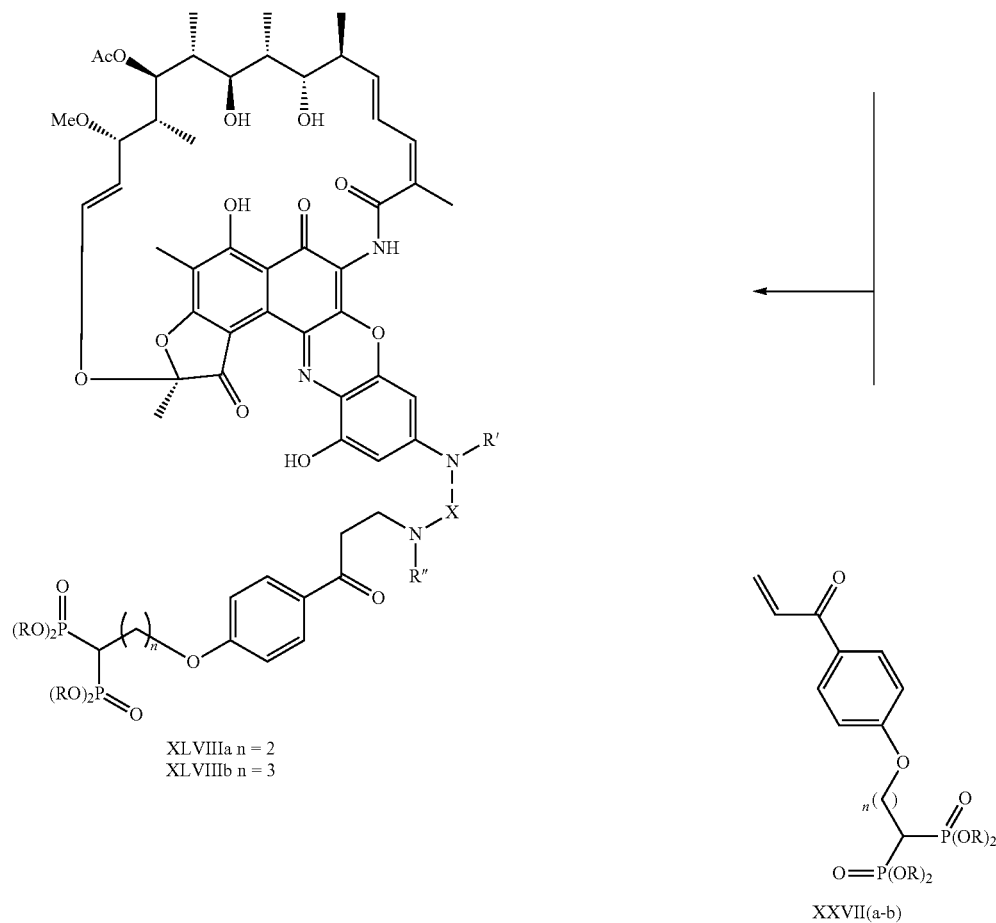

Similarly, compounds XLVIIb obtained by the condensation of benzoxazinoryfamicins XLV(a-b) with diamines XLVI In the presence of a mild oxidant such as manganese dioxide, as described in U.S. Pat. Nos. 4,690,919, 4,983,602 and Chem. Pharm. Bull. (1993), 41: 148-155, can react with vinyl ketones XXVII(a-b) to afford bisphosphonated prodrugs XLVIII(a-b).
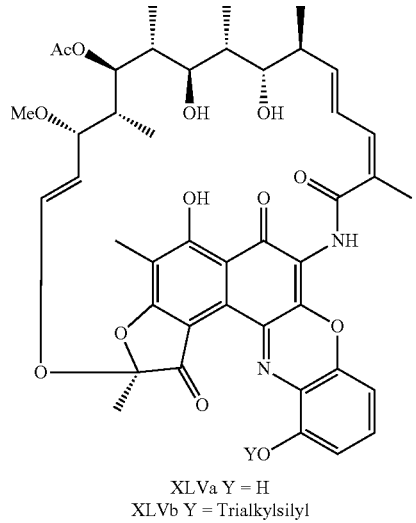
XLVa Y = H
XLVb Y = Trialkylsilyl
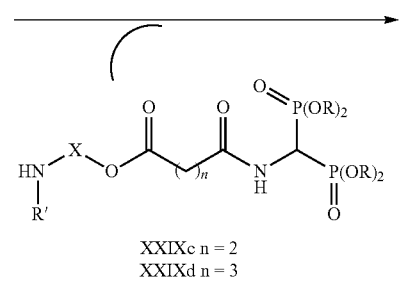
XXIXc n = 2
XXIXd n = 3
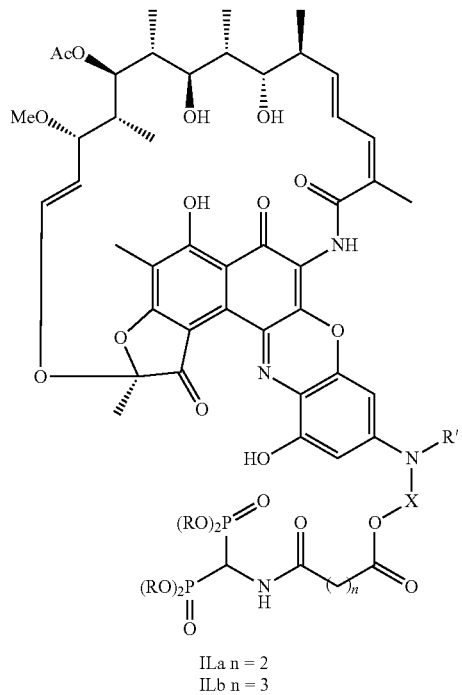
ILa n = 2
ILb n = 3

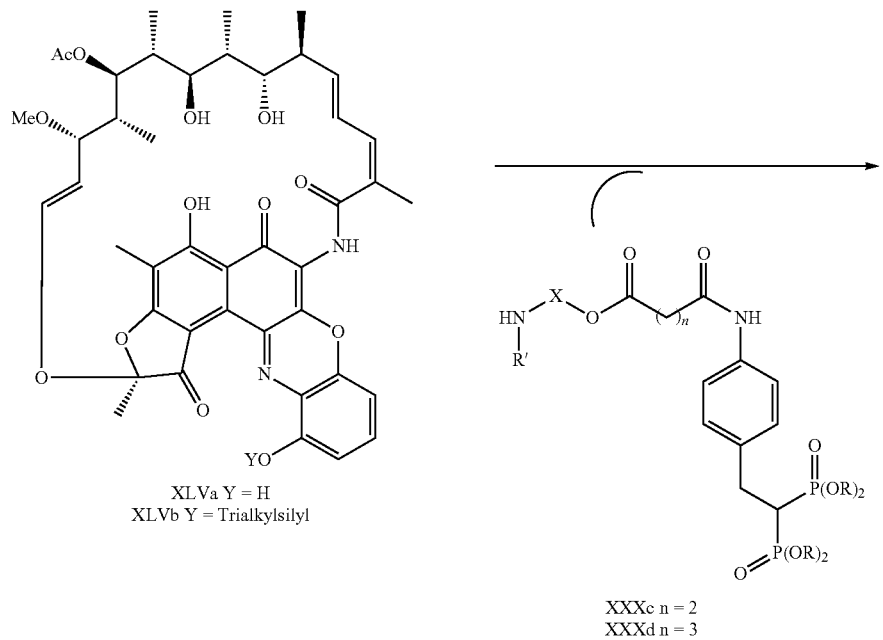
XLVa Y = H
XLVb Y = Trialkylsilyl
XXXc n = 2
XXXd n = 3
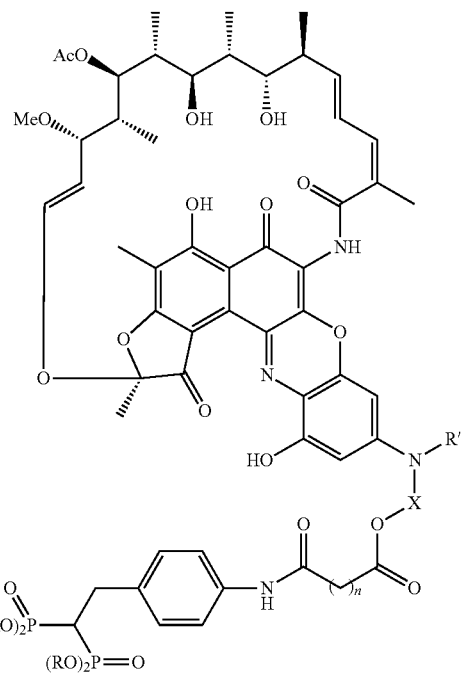
Bisphosphonated benzoxazinorifamycin derivatives IL(a-b) and L(a-b) are prepared via the condensation of bisphosphonated amines XXIX(c-d) and XXX(c-d) with the benzoxazinorifamycin derivatives XLV(a-b) in the presence of a mild oxidant such as manganese dioxide, as described in U.S. Pat. Nos. 4,690,919, 4,983,602 and Chem. Pharm. Bull. (1993), 41: 148-155.

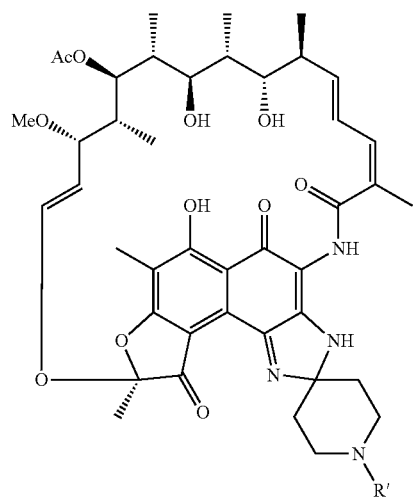
XL
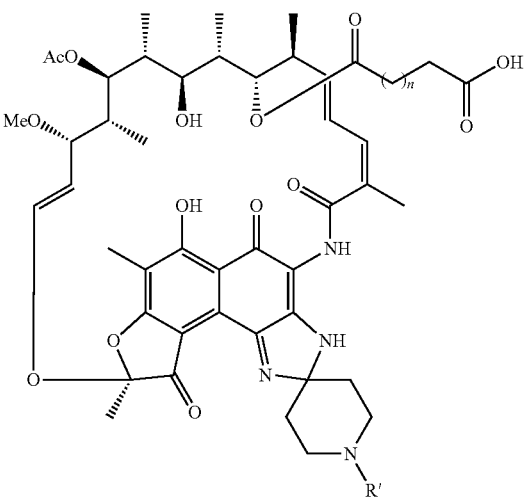
LIa n = 1
LIb n = 2
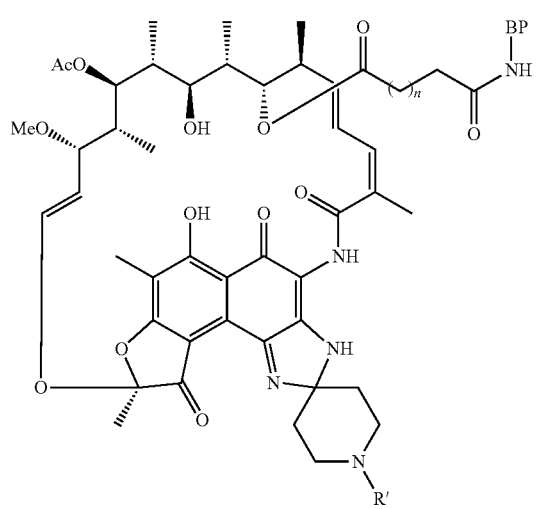
Condensation of rifamycin XL with succinic and glutaric anhydrides provides acids LIa and LIb respectively. These acids can be coupled, under standard amide coupling conditions (Tertiary amine and a standard amide coupling agent such as DCC, EDCl, HBTU, HATU, PyBOP, BOP-Cl), with amine XIII to provide bisphosphonate prodrugs LII(a-b), with amine IIIb to provide bisphosphonated prodrugs LIII(a-b), with amine XXXVb to provide bisphosphonated prodrugs LIV(a-b) and with amines XXXVIb to provide bisphosphonated prodrugs LV(a-b).
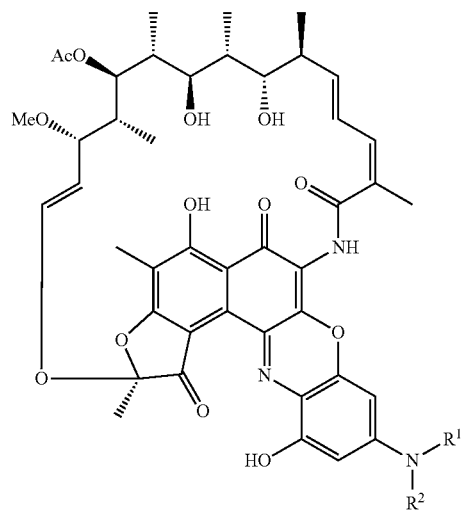
LIV
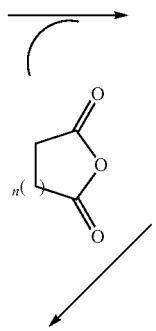
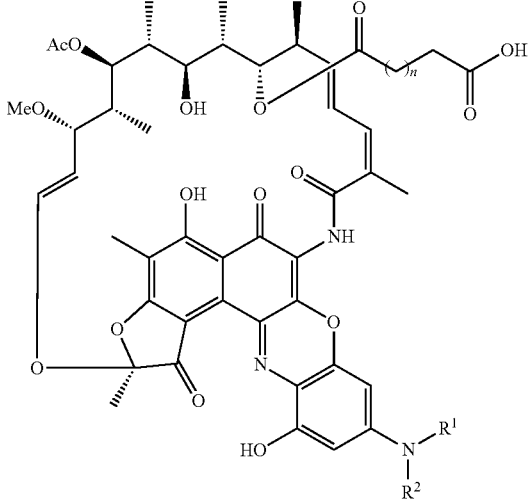
LVIIa n = 1
LVIIb n = 2
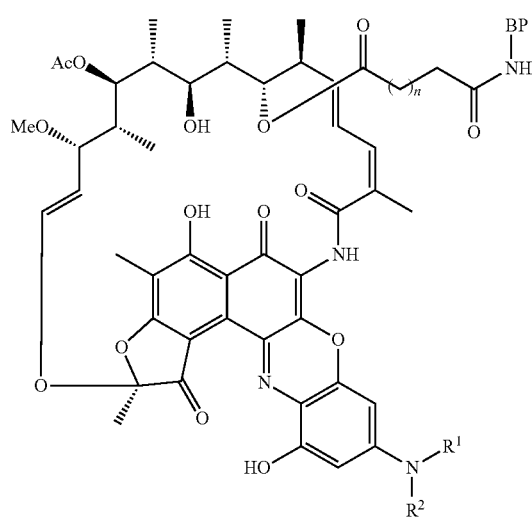
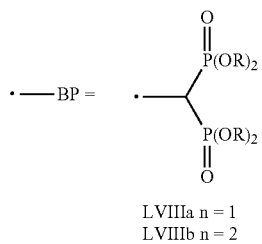
LVIIIa n = 1
LVIIIb n = 2
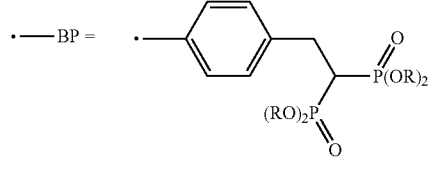
LIXa n = 1
LIXb n = 2
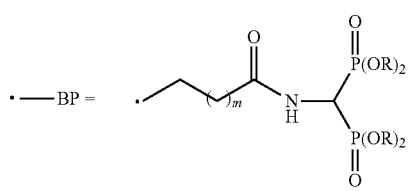
LXa n = 1, m ≥ 1
LXb n = 2, m ≥ 1
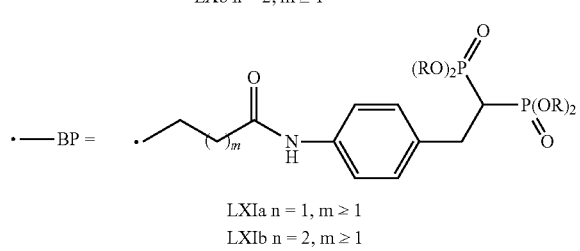
LXIa n = 1, m ≥ 1
LXIb n = 2, m ≥ 1

Similarly, the condensation of benzoxazinorifamycin LIV with succinic and glutaric anhydrides provides acids LIa and LIb which can be coupled with amines XIII, IIIb, XXXVb and XXXVIb to furnish bisphosphonated prodrugs LVII(a-b), LVIII(a-b), LIX(a-b) and LX(a-b) respectively.

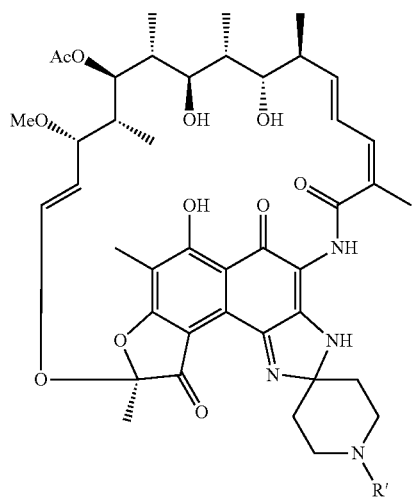

XL

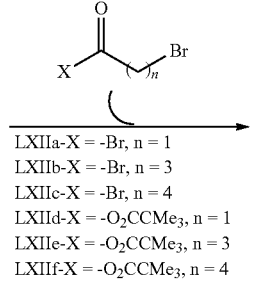

LXIIa-X = -Br, n = 1
LXIIb-X = -Br, n = 3
LXIIc-X = -Br, n = 4
LXIId-X = -O₂CCMe₃, n = 1
LXIIe-X = -O₂CCMe₃, n = 3
LXIIf-X = -O₂CCMe₃, n = 4

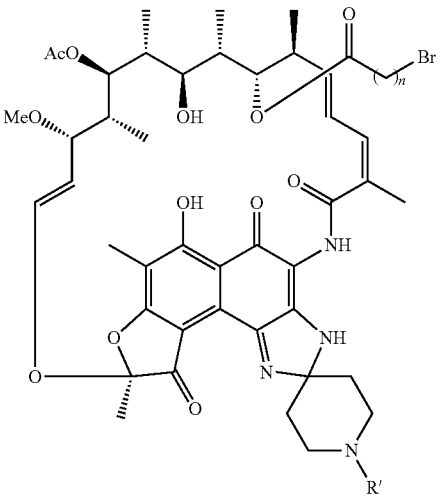

LXIIIa n = 1
LXIIIb n = 3
LXIIIc n = 4

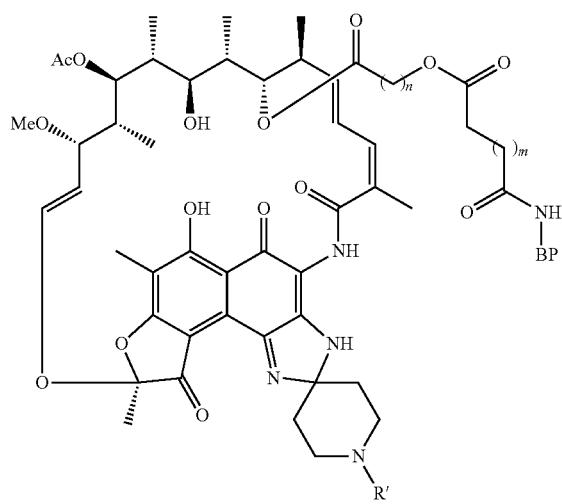

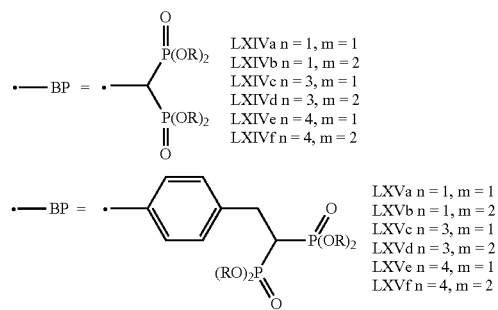

LXIVa n = 1, m = 1
LXIVb n = 1, m = 2
LXIVc n = 3, m = 1
LXIVd n = 3, m = 2
LXIVe n = 4, m = 1
LXIVf n = 4, m = 2

LXVa n = 1, m = 1
LXVb n = 1, m = 2
LXVc n = 3, m = 1
LXVd n = 3, m = 2
LXVe n = 4, m = 1
LXVf n = 4, m = 2

Treatment of rifamycins XL with bromoacyl bromides LXII(a-c) or with the mixed anhydrides LXII(d-f) in the presence of a non nucleophilic base provides bromoacyl esters LXIII(a-c). These can react with the succinamic acids XVa and XVIa and the gutaramic acids XVb and XVIb in the presence of a base to furnish bisphosphonated prodrugs LXIV(a-f) and LXV(a-f).

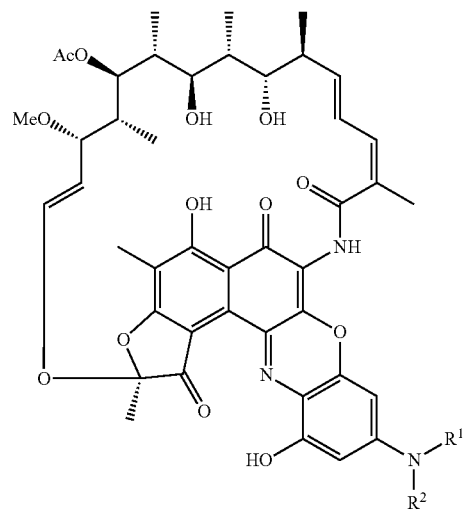

LIV

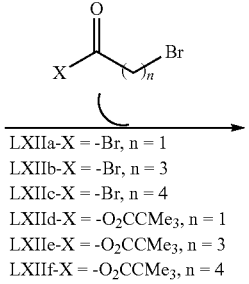

LXIIa-X = -Br, n = 1
LXIIb-X = -Br, n = 3
LXIIc-X = -Br, n = 4
LXIId-X = -O$_2$CCMe$_3$, n = 1
LXIIe-X = -O$_2$CCMe$_3$, n = 3
LXIIf-X = -O$_2$CCMe$_3$, n = 4

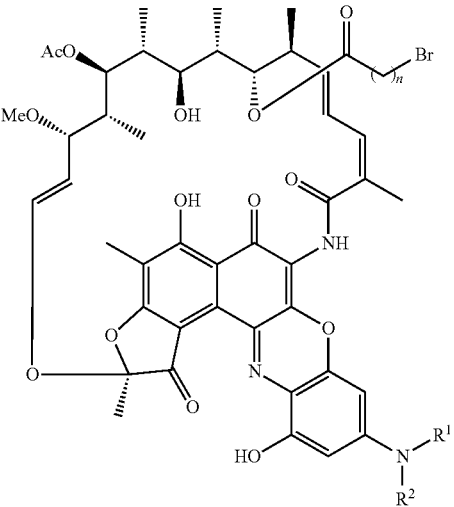

LXVIa n = 1
LXVIb n = 3
LXVIc n = 4

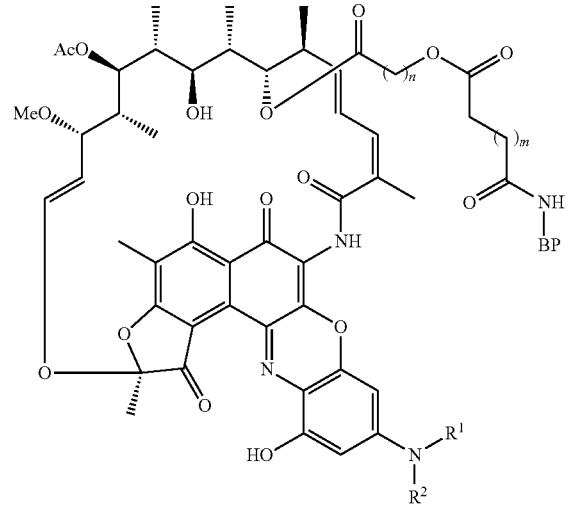

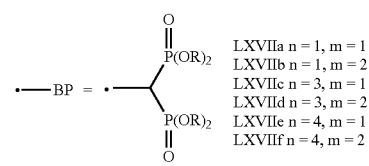

LXVIIa n = 1, m = 1
LXVIIb n = 1, m = 2
LXVIIc n = 3, m = 1
LXVIId n = 3, m = 2
LXVIIe n = 4, m = 1
LXVIIf n = 4, m = 2

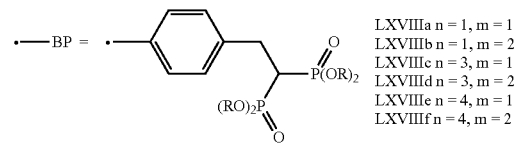

LXVIIIa n = 1, m = 1
LXVIIIb n = 1, m = 2
LXVIIIc n = 3, m = 1
LXVIIId n = 3, m = 2
LXVIIIe n = 4, m = 1
LXVIIIf n = 4, m = 2

Similarly, benzoxazinorifamycins LIV can be treated with LXII(a-f) in the presence of a base to furnish bromoacyl esters LXVI(a-c) which can react with acids XV(a-b) and XVI(a-b) to produce bisphosphonated prodrugs LXVII(a-f) and LXVIII(a-f).

The bisphosphonate building blocks described in this section are in the form of their phosphonic esters, R being Me, Et, i-Pr, allyl or Bn; or as the free bisphosphonic acids and/or free bisphosphonate salts. The bisphosphonic esters may be converted to the free acids and acid salts by conventional methods, such as the treatment with trimethylsilyl bromide or Iodide in the presence or the absence of a base, hydrogenation when the bisphosphonate esters are benzyl bisphosphonates, by treatment with a palladium catalyst and a nucleophile when the bisphosphonate esters are allyl bisphosphonates.

The other protecting groups used can be put on and removed using the conventional methods described in the literature, for instance as reviewed in "*Protective Groups in Organic Synthesis*", Greene, T. W. and Wuts, P. M. G., Wiley-Interscience, New York, 1999.

B) Detailed Experimental Procedures

Tetraethyl N,N-dibenzyl-1-aminomethylenebisphosphonate (1): Compound 1 was prepared according to a modified protocol derived from Synth. Comm. (1996), 26: 2037-2043. Triethyl orthoformate (8.89 g, 60 mmol), diethyl phosphite (16.57 g, 120 mmol) and dibenzyl amine (11.80 g, 60 mmol) were combined in a 100 mL round bottom flask fitted with a distillation head. The reaction was heated to a temperature of 180-195° C. for 1 h under Ar. When EtOH evolution was complete, the reaction mixture was cooled to room temperature, diluted with $CHCl_3$ (300 mL), washed with aqueous NaOH (2M, 3×60 mL) and brine (2×75 mL), then dried over $MgSO_4$. After evaporation, a crude yield of 25.2 g (87%) was obtained. A 4.95 g portion of the crude oil was purified by chromatography (ethyl acetate:hexane:methanol 14:4:1) to yield pure 1 (2.36 g, 41%). $^1$H NMR (400 MHz, $CDCl_3$) δ 1.32 (dt, J=2.0, 7.0, 12H), 3.55 (t, J=25.0, 1H), 3.95-4.25 (m, 12H), 7.20-7.45 (m, 10H).

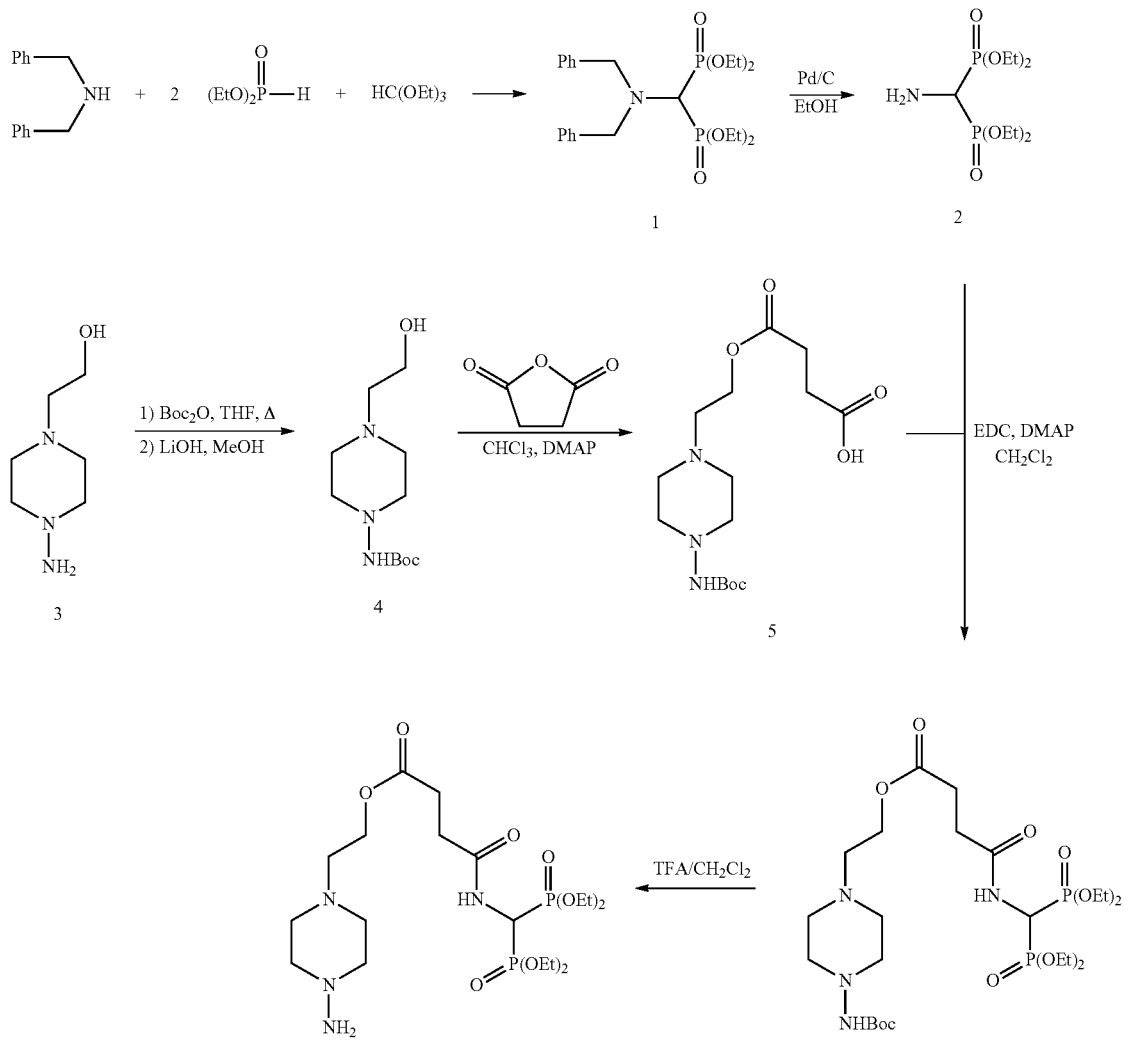

Scheme 1. Synthesis of Tetraethyl (4-(2-(1-amino-piperazin-4-yl)ethoxy)-4-oxo-butanoylamino)methylene-1,1-bisphosphonate (7)

Tetraethyl 1-aminomethylenebisphosphonate (2): Compound 1 (2.00 g, 4.14 mmol) was dissolved in EtOH (40 mL). To this solution was added palladium on carbon (10%, 1.5 g) and cyclohexene (2.5 mL, 24.7 mmol). The reaction mixture was refluxed under argon for 15 hours, filtered through celite and evaporated to give 2 as a slightly impure pale yellow oil (1.50 g, 119%), which was used directly in the next step without further purification. $^1$H NMR (400 MHz, CDCl$_3$) δ 1.35 (t, J=7.0, 12H), 3.58 (t, J=20.3, 1H), 3.65-3.90 (br s, 2H), 4.20-4.28 (m, 8H).

1-(t-Butyloxycarbonylamino)-4-(2-hydroxyethyl)piperazine (4): 1-amino-4-(2-hydroxyethyl)-piperazine 3 (1.18 g, 8.1 mmol) and Boc anhydride (4.4 g, 20.3 mmol) were added to 100 mL of THF and heated at 60° C. for 1.5 hours. The solvent was evaporated under vacuum and the residue was dissolved in MeOH (50 mL) and an aqueous solution (50 mL) of LiOH (970 mg, 40.4 mmol) was added. The resulting solution was stirred at room temperature for 16 hours. The mixture was then diluted with water (50 mL) and extracted with CH$_2$Cl$_2$ (3×75 mL), washed with brine (75 mL), dried over Na$_2$SO$_4$ and concentrated to give a colorless gum. The crude residue was triturated in Et$_2$O, cooled down to 0° C. and filtered to yield a with solid (1.21 g, 61%). $^1$H NMR (400 MHz, CDCl$_3$) δ 1.45 (s, 9H), 2.55 (apparent t, J=5.4 Hz, 2H), 2.64 (m, 4H). 2.83 (m, 4H), 3.60 (apparent t, J=5.4 Hz, 2H) 5.40 (br s, 1H).

1-(t-Butyloxycarbonylamino)-4-(2-(4-hydroxy-4-oxo-butanoyloxy)ethyl)piperazine (5): Compound 4 (250 mg, 1.0 mmol), succinic anhydride (105 mg, 1.05 mmol) and 4-DMAP (cat.) were dissolved in CHCl$_3$ (600 µL) and stirred for 12 hours. The solution was concentrated in vacuo and used without further purification. $^1$H NMR (400 MHz, CDCl$_3$) δ 1.43 (s, 9H), 2.60 (s, 4H), 2.76 (m, 6H), 2.86 (m, 4H), 4.23 (t, J=5.5 Hz, 2H), 5.71 (br s, 1H), 10.82 (br s, 1H).

Tetraethyl (4-(2-(1-(t-butyloxycarbonylamino)-piperazin-4-yl)ethoxy)-4-oxo-butanoyl-amino)methylene-1,1-bisphosphonate (6): To a solution of compounds 2 (303 mg, 1.0 mmol) and 5 (345 mg, 1.0 mmol) in CH$_2$Cl$_2$ (10 mL) were added EDC (230 mg, 1.2 mmol) and 4-DMAP (cat.). The resulting solution was stirred 4 hours under Ar at room temperature. The reaction mixture was diluted in CH$_2$Cl$_2$, washed with water, brine and dried over Na$_2$SO$_4$. After evaporation, the residue was purified by flash chromatography over SiO$_2$ (gradient from 4% to 10% MeOH/CH$_2$Cl$_2$) to yield a colorless gum (410 mg, 65%). $^1$H NMR (400 MHz, CDCl$_3$) δ 1.33 (t, J=7.1 Hz, 12H), 1.45 (s, 9H), 2.56-2.69 (m, 10H), 2.81 (br s, 4H), 4.12-4.26 (m, 10H), 5.00 (dt, J=10.1, 21.7 Hz, 1H), 5.51 (br s, 1H), 6.50 (br d, J=8.2 Hz, 1H).

Tetraethyl (4-(2-(1-amino-piperazin-4-yl)ethoxy)-4-oxo-butanoylamino)methylene-1,1-bisphosphonate (7): Compound 6 (490 mg, 0.78 mmol) was dissolved in a solution of 10% TFA/CH$_2$Cl$_2$ (8 mL). The solution was stirred at room temperature until no starting material remained (TLC monitoring). Volatiles were evaporated under vacuum and the residue was used in the next step without purification.

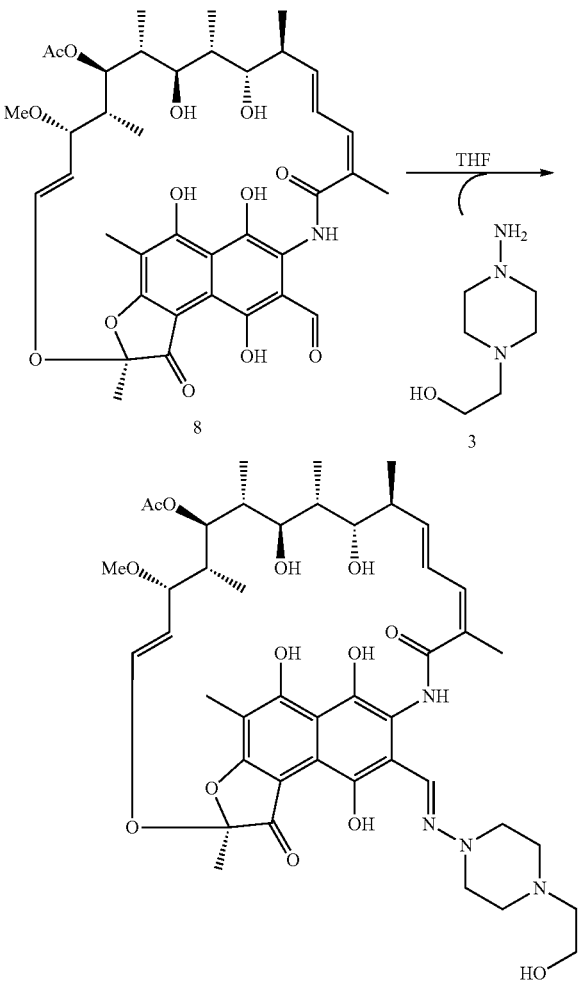

Scheme 2.
Synthesis of 3-(((4-(2-hydroxyethyl)-1-piperazinyl)imino)methyl)rifamycin (9)

3-(((4-(2-hydroxyethyl)-1-piperazinyl)imino)methyl)rifamycin (9): 3-formyl Rifamycin S (8, 724 mg, 1 mmole) was suspended in 3 mL of THF. Solid 1-amino-4-(2-hydroxyethyl)-piperazine (3, 145 mg, 1 mmole) was added in one portion. The mixture was stirred at room temperature for 15 min. It was then partitioned between 50 mL of CH$_2$Cl$_2$ and a mixture of 10 mL of saturated brine and a solution of 2 g of sodium ascorbate in 30 mL of water. The organics were collected and the aqueous layer was extracted with another 50 mL of CH$_2$Cl$_2$. The combined organics were dried over Na$_2$SO$_4$ and concentrated in vacuo to furnish 830 mg (0.97 mmoles, 97%) of 9 as a dark solid. $^1$H NMR (400 MHz, CDCl$_3$) δ −0.32 (d, J=6.9, 3H), 0.58 (d, J=6.9, 3H), 0.86 (d, J=7.0, 3H), 1.00 (d, J=7.0, 3H), 1.34 (m, 1H), 1.52 (m, 1H), 1.69 (m, 1H), 1.80 (s, 3H), 2.05 (s, 3H), 2.08 (s, 3H), 2.22 (s, 3H), 2.38 (m, 1H), 2.91 (br t, J=4.6, 2H), 3.04 (overlapping 3.04 (m, 6H) and 3.03 (s, 3H)), 3.33-3.48 (m, 6H), 3.54 (br s, 1H), 3.74 (m, 2H), 3.86 (br t, J=4.8, 2H), 4.93 (d, J=10.6, 1H), 5.09 (dd, J=6.6, 12.6, 1H), 5.36 (br s, 1H), 5.92 (dd, J=5.0, 15.4, 1H), 6.18 (d, J=12.7, 1H), 6.38 (d, J=11.1, 1H), 6.56 (dd, J=11.6, 15.5, 1H), 8.35 (s, 1H), 12.07 (s, 1H).

Scheme 3.
Synthesis of 3-(((4-(2-(3-((bisphosphonomethyl) carbamoyl)propanoyloxy)ethyl)-1-piperazinyl)imino)methyl)rifamycin (11)

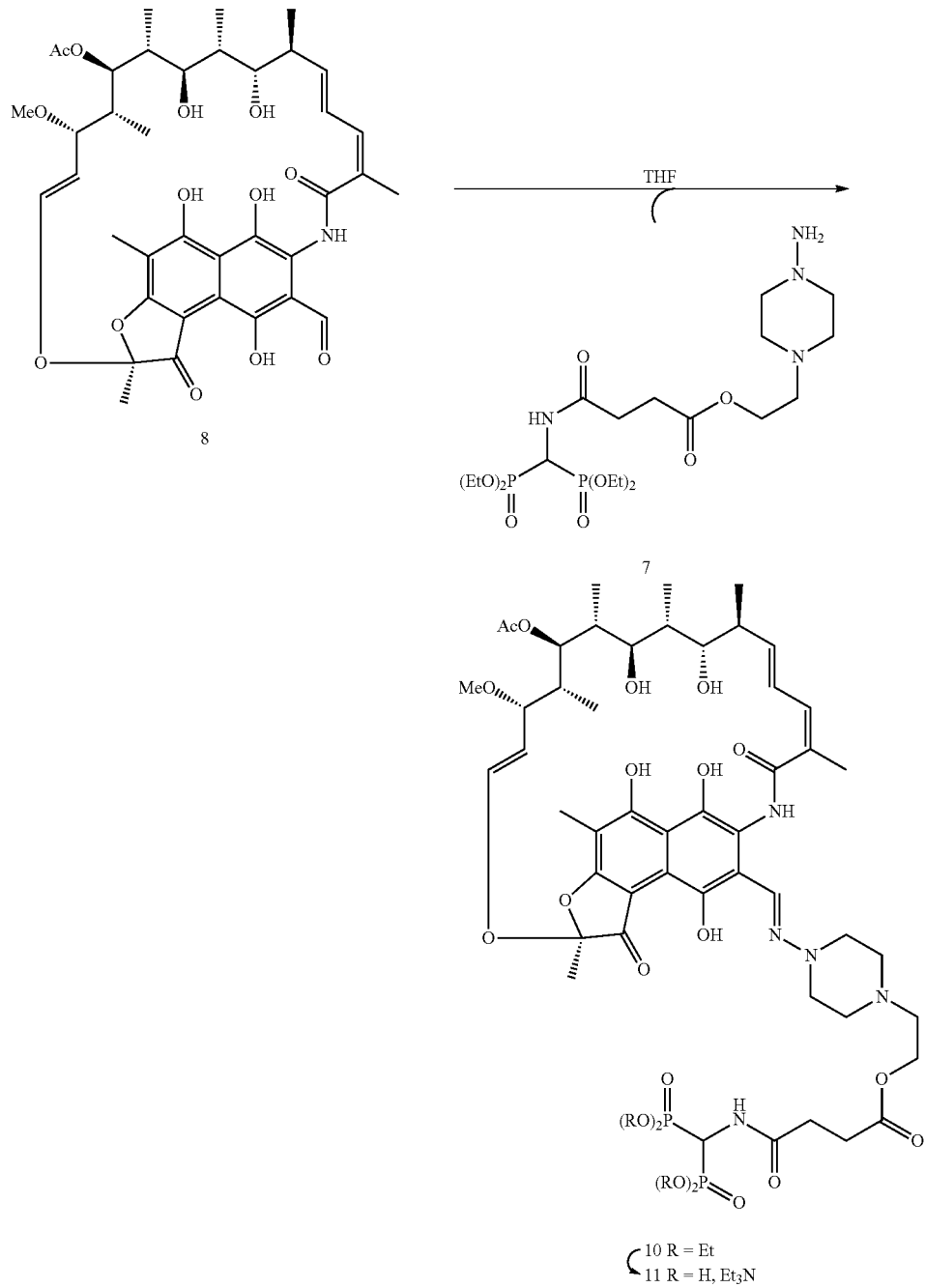

3-(((4-(2-(3-((bis(diethylphosphono)methyl)carbamoyl) propanoyloxy)ethyl)-1-piperazinyl)imino)methyl)rifamycin (10): Compound 7 (490 mg, 0.78 mmol) was diluted in THF and TEA was then added (560 µL, 4.0 mmol). Solid 3-formyl Rifamycin S 8 (537 mg, 0.74 mmol) was then added. The mixture was stirred at room temperature for 15 hours. It was then partitioned between 50 mL of $CH_2Cl_2$ and a mixture of 10 mL of saturated brine and an aqueous solution of 10% of sodium ascorbate (30 mL). The organics were collected and the aqueous layer was extracted with $CH_2Cl_2$ (2×50 mL). The combined organics were dried over $Na_2SO_4$ and concentrated in vacuo to furnish crude 10 as a deep red solid. $^1$H NMR (400 MHz, $CDCl_3$) δ −0.33 (d, J=6.9 Hz, 3H), 0.58 (d, J=6.9 Hz, 3H), 0.85 (d, J=7.0 Hz, 3H), 1.00 (d, J=7.00 Hz, 3H), 1.33 and 1.34 (t, J=7.0 Hz, 12H), 1.53 (m, 1H), 1.71 (m, 1H), 1.80 (s, 3H), 1.90 (m, 1H), 2.06 (s, 3H), 2.08 (s, 3H), 2.23 (s, 3H), 2.38 (m, 1H), 2.56-2.72 (m, 12H), 3.04 (s, 3H), 3.00-3.10 (m, 4H), 3.12-3.19 (m, 2H), 3.47 (m, 1H), 3.64 (bd, J=4.8 Hz, 1H), 3.70-3.80 (m, 2H), 4.14-4.25 (m, 12H), 4.95 (d, J=10.5 Hz, 1H), 5.00 (dt, J=10.1, 21.6 Hz, 1H), 5.10 (dd, J=6.8, 12.7 Hz, 1H), 5.94 (dd, J=4.9, 15.5 Hz, 1H), 6.21 (dd, J=0.8, 12.7 Hz, 1H), 6.53-6.63 (m, 1H), 8.27 (s, 1H), 12.01 (s, 1H).

3-(((4-(2-(3-((bisphosphonomethyl)carbamoyl)propanoyloxy)ethyl)-1-piperazinyl)imino)methyl)rifamycin (11): To a solution of 10 (1.18 g, 0.96 mmol) and 2,6-lutidine (5.6 mL, 48 mmol) in CH$_2$Cl$_2$ (30 mL) at −78° C. was added dropwise TMSBr (3.17 mL, 24 mmol) under argon. The cold bath was removed and the mixture was stirred for 24 hours at room temperature. The solvent was removed to dryness under vacuum. The residue was dissolved in a 50 mmol aqueous solution of NH$_4$OAc/AcOH adjusted at pH 5.1 and stirred at room temperature overnight. The solution was then lyophilized. The crude residue was purified by reverse phase flash chromatography at pH 5.1 (linear gradient of 10% to 40% acetonitrile in a 50 mmol aqueous solution of NH$_4$OAc/AcOH) to yield 11 as an orange solid (680 mg, 54%). $^1$H NMR (400 MHz, DMSO) δ −0.26 (d, J=6.6 Hz, 3H), 0.43 (d, J=6.5 Hz, 3H), 0.82 (d, J=7.6 Hz, 3H), 0.85 (d, J=6.7 Hz, 3H), 1.04 (m, 1H), 1.30 (m, 1H), 1.54 (m, 1H), 1.60 (s, 3H), 1.87 (s, 3H), 1.89 (s, 3H), 1.96 (s, 3H), 2.13 (m, 1H), 2.44 (br s, 4H), 2.48 (m, 10H), 2.52-2.64 (m, 6H), 2.81 (br d, J=9.6 Hz, 1H), 2.87 (s, 3H), 3.20 (br d, J=8.2 Hz, 1H), 3.70 (br d, J=8.3 Hz, 1H), 4.10 (m, 2H), 4.18 (dt, J=9.8, 19.1 Hz, 1H), 4.90 (dd, J=8.3, 12.7 Hz, 1H), 5.05 (d, J=10.7, 1H), 5.83 (dd, J=6.5, 15.8 Hz, 1H), 6.20 (m, 1H), 6.94 (dd, J=11.2, 15.6 Hz, 1H), 7.46 (m, 1H), 7.95 (s, 1H), 9.11 (s, 1H), 12.44 (s, 1H).

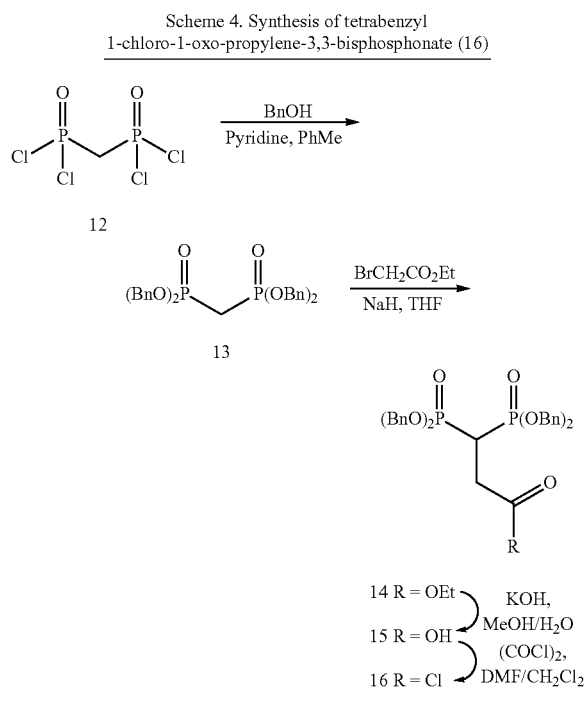

Scheme 4. Synthesis of tetrabenzyl 1-chloro-1-oxo-propylene-3,3-bisphosphonate (16)

This sequence of reactions was performed as described in J. Org. Chem. (2001), 66; 3704-3708.

Tetrabenzyl methylenebisphosphonate (13): A mixture of dry benzyl alcohol (8.66 mL, 83.0 mmol) and dry pyridine (6.15 mL, 76.1 mmol) was added, over 80 min by syringe pump, to a vigorously stirred suspension of methylene bis(phosphonic dichloride) (5.00 g, 20.0 mmol) in dry toluene (10 mL) at 0° C. After the addition was complete, the reaction was left to come to room temperature and was stirred for an additional 3 h. The solids were removed by filtration and washed twice with toluene (2×20 mL). The filtrate was washed with 2 M NaOH (2×15 mL) and water (15 mL), dried over MgSO$_4$, and concentrated in vacuo. Removal of benzyl alcohol impurity by distillation gave 13 as a colorless oil (8.1 g, 75%). Spectral data is as described in the above-mentioned article.

Tetrabenzyl 1-Ethoxy-1-oxo-propylene-3,3-bisphosphonate (14): A solution of 13 (1.00 g, 1.87 mmol) in THF (10 mL) was added to a suspension of NaH (0.047 g, 1.96 mmol) in THF (20 mL) at 0° C. over 5 min. The solution was allowed to warm up to room temperature and was stirred for an additional 30 min. Then 220 µL of ethyl bromoacetate (1.98 mmol) were added. After stirring for an overnight, the mixture was poured in a saturated solution of NH$_4$Cl, and extracted with dichloromethane. The combined organic extracts were dried over MgSO$_4$ and concentrated in vacuo. The residue was subjected to SiO$_2$ chromatography (70% EtOAc/hexanes) to yield 14 as a colorless oil (0.7 g, 60%). Spectral data is as described in the above mentioned article.

Tetrabenzyl 1-Carboxyethylene-2,2-bisphosphonate (15): A solution of 14 (1.27 g, 2.04 mmol) in methanol (6 mL) was added to a solution of KOH (0.127 g, 2.26 mmol) in water (6 mL) and methanol (6 mL) at 0° C. The reaction was left to warm to room temperature over 1 h and was stirred at this temperature for an overnight. The methanol was removed in vacuo and the remaining solution was washed with diethyl ether (20 mL). The aqueous layer was acidified to pH 2 with aqueous HCl and it was extracted with CH$_2$Cl$_2$ (3×20 mL) and EtOAc (1×20 mL). The combined organic extracts were dried over MgSO$_4$ and concentrated in vacuo to yield 15 as a colorless oil (0.95 g, 78%). Spectral data is as described in the above mentioned article.

Tetrabenzyl 1-chloro-1-oxo-propylene-3,3-bisphosphonate (16): To a solution of 15 (68 mg, 1.14×10$^{-4}$ moles) in 3 mL of dry CH$_2$Cl$_2$ was added 22 µL (2.6×10$^{-4}$ moles) of oxalyl chloride followed by 1 drop of DMF. The mixture was stirred at room temp for 10 min and then was concentrated in vacuo to furnish crude 16, which is used as such without purification.

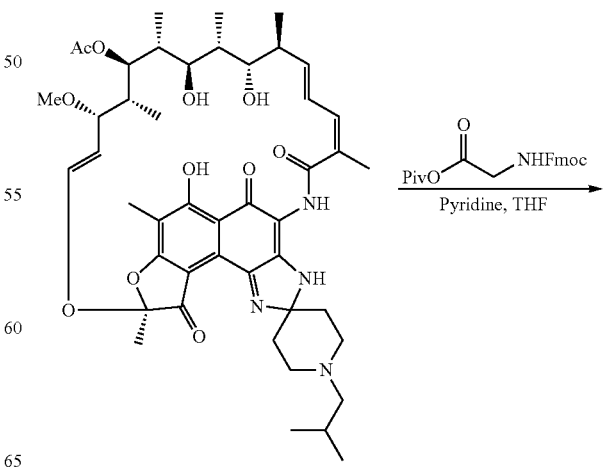

Scheme 5. Synthesis of rifabutin-bisphosphonate conjugate 21

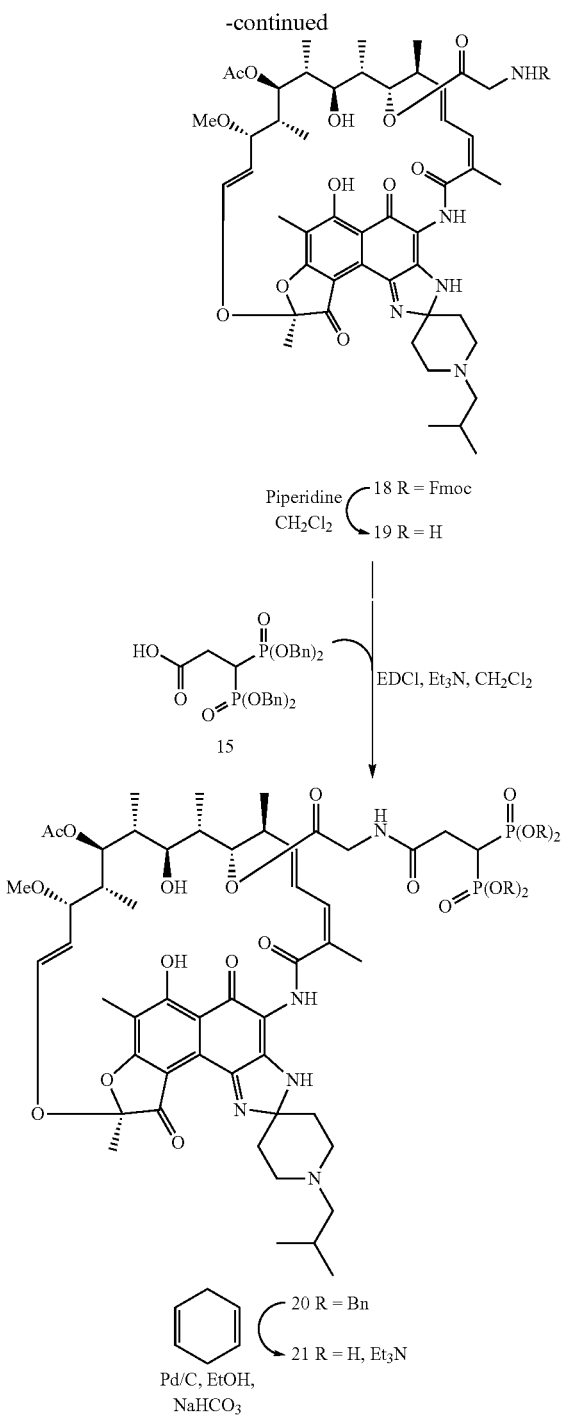

21-O-(N-((9H-fluoren-9-yl)methyloxycarbonyl)-glycinoyl)-1',4-didehydro-1-deoxy-1,4-dihydro-5'-(2-methylpropyl)-1-oxorifamycin XIV (18): Pivaloyl chloride (145 μL, 1.18 mmol) was added dropwise to a solution of N-Fmoc-glycine (351 mg, 1.18 mmol) and pyridine (95 μL, 1.18 mmol) in THF (3 mL) and the resulting solution was stirred for 1 h before being added to a stirred solution of rifabutin (100 mg, 0.118 mmol) and pyridine (38 μL, 0.47 mmol) in THF (2 mL). The resulting was stirred for 3 days under Ar before being diluted in Et$_2$O (10 mL) and H$_2$O (10 mL). After separation, the aqueous layer was extracted two times with Et$_2$O (2×10 mL). The combined organic layers were washed with a saturated solution of NaCl (10 mL), dried over MgSO$_4$ and concentrated in vacuo. The crude product was purified by reverse phase chromatography eluting with aqueous buffer (Et$_3$N/CO$_2$, pH=7)/CH$_3$CN (10% to 100% linear gradient) and afford 114 mg (0.102 mmol, 86%) of 18 as dark purple solid. $^1$H NMR (400 MHz, CDCl$_3$) δ 8.34 (br s, 1H), 7.94 (br s, 1H), 7.79-7.71 (m, 4H), 7.42 (t, J=3.0 Hz, 2H), 7.34 (t, J=3.0 Hz, 2H), 6.43 (dd, J=16 Hz, 1H), 6.14 (d, J=11 Hz, 1H), 6.08 (d, J=11.2 Hz, 1H), 5.95-5.91 (m, 2H), 5.19 (d, J=11.2 Hz, 1H), 5.05 (dd, J=9.3, 1.2 Hz, 1H), 4.97 (d, J=10.6 Hz, 2H), 4.51-2.19 (m, 3H), 3.83 (d, J=4.6 Hz, 2H), 3.55 (s, 1H), 3.14 (br d, J=1.2 Hz, 1H), 3.10 (s, 3H), 3.08-2.84 (m, 4H), 2.73-2.52 (m, 4H), 2.30 (d, J=6.0 Hz, 2H), 2.21 (s, 3H), 2.31 (m, 1H), 2.05 (s, 6H), 2.02 (m, 2H), 1.86-1.79 (m, 4H), 1.80 (s, 3H), 1.27 (m, 3H), 1.08 (d, J=6.9 Hz, 3H), 0.95 (d, J=6.6 Hz, 9H), 0.53 (d, J=6.9 Hz, 3H), −0.75 (d, J=7.0 Hz, 3H).

21-O-glycinoyl-1',4-didehydro-1-deoxy-1,4-dihydro-5'-(2-methylpropyl)-1-oxorifamycin XIV (19): Piperidine (100 μL, 1.02 mmol) was added to a stirred solution of N-Fmoc-rifabutin derivative 18 (114 mg, 0.102 mmol) in CH$_2$Cl$_2$ (5 mL). After 24 h of stirring at room temperature, the mixture was concentrated in vacuo. The crude product was purified by reverse phase chromatography eluting with aqueous buffer (Et$_3$N/CO$_2$, pH=7)/CH$_3$CN (10% to 100% linear gradient) to afford 77 mg (0.085 mmol, 84%) of 19 as dark purple solid. $^1$H NMR (400 MHz, CDCl$_3$) δ 8.32 (br s, 1H), 7.94 (s, 1H), 6.41 (t, J=11.1 Hz, 1H), 6.12-6.05 (m, 2H), 5.90 (dd, J=15.8, 7.4 Hz, 1H), 5.12 (d, J=10.3 Hz, 1H), 5.04 (dd, J=15.8, 1.5 Hz, 1H), 3.59 (br s, 1H), 3.48 (m, 1H), 3.20 (d, J=9.5 Hz, 2H), 3.05 (s, 3H), 3.04-2.91 (m, 3H), 2.86 (dd, J=10.1, 3.0 Hz, 1H), 2.72-2.63 (m, 2H), 2.58-2.47 (m, 2H), 2.31 (d, J=7.0 Hz, 2H), 2.27 (s, 3H), 2.19-2.09 (m, 2H), 2.06-1.97 (m, 8H), 1.93-1.84 (m, 2H), 1.84-1.78 (m, 2H), 1.77 (s, 3H), 1.24 (m, 1H), 1.28 (d, J=7.1 Hz, 3H), 0.92 (m, 9H), 0.97 (d, J=6.9 Hz, 3H), 0.40 (d, J=7.1 Hz, 3H).

21-O-(N-(3,3-Bis(dibenzylphosphono)propanoyl)-glycinoyl)-1',4-didehydro-1-deoxy-1,4-dihydro-5'-(2-methylpropyl)-1-oxorifamycin XIV (20): To a stirred solution of amine 19 (77 mg, 0.085 mmol) and acid 15 (51 mg, 0.085 mmol) in CH$_2$Cl$_2$ (2 mL) were added Et$_3$N (24 μL, 0.170 mmol) and EDCl (18 mg, 0.094 mmol). After being stirred 24 h at rt, the mixture was concentrated in vacuo. The crude product was purified by reverse phase chromatography eluting with aqueous buffer (Et$_3$N/CO$_2$, pH=7)/CH$_3$CN (10% to 100% linear gradient) to afford 96 mg (0.065 mmol, 76%) of 20 as dark purple solid.

21-O-(N-(3,3-Bisphosphonopropanoyl)-glycinoyl)-1',4-didehydro-1-deoxy-1,4-dihydro-5'-(2-methylpropyl)-1-oxorifamycin XIV (21): A stirred solution of tetrabenzyldiphosphonate 20 (96 mg, 0.065 mmol) and NaHCO$_3$ (22 mg, 0.26 mmol) in EtOH (5 mL) was degassed for 10 min with Ar. To this mixture was added cyclohexadiene (303 μL, 3.24 mmol) and 10% Pd/C (70 mg, 0.065 mmol). The resulting was stirred 6 h under Ar before being filtered through a pad of celite (EtOH). After removal of the solvent in vacuo, the crude product was purified by reverse phase chromatography eluting with aqueous buffer (Et$_3$N/CO$_2$, pH=7)/CH$_3$CN (10% to 50% linear gradient) to afford 34 mg (0.065 mmol, 48%) of 21 as pale purple solid. LC/MS purity: 99.2% (254 nm), 94.9% (220 nm), 99.4% (320 nm). MS (MH$^-$) 1117.9.

Scheme 6.
Synthesis of 1-(4-(5,5-bis(diethylphosphono)pentyloxy)phenyl)prop-2-en-1-one.

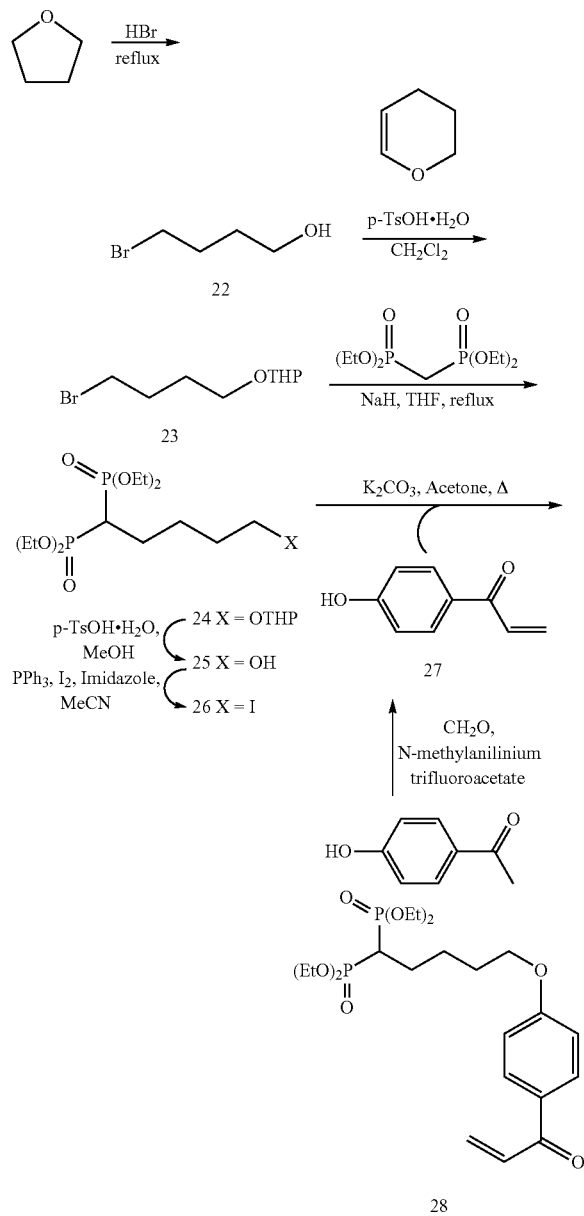

4-Bromo-1-butanol (22): To 67.5 mL (832.2 mmol) of refluxing tetrahydrofuran was added 31 mL (274 mmol) of 48% hydrobromic acid dropwise and the yellow solution was allowed to reflux for another 2 h. After cooled to room temperature, the reaction was carefully neutralized with saturated sodium bicarbonate aqueous solution. The resultant mixture was extracted with diethyl ether (3×) and dried over anhydrous sodium sulfate. Removal of the solvent afforded the product 19 as a yellow oil (10.7 g, 26%). $^1$H NMR (400 MHz, CDCl$_3$): δ 1.69-1.76 (m, 2H), 2.01-1.94 (m, 2H), 3.46 (t, J=6.6 Hz, 2H), 3.70 (t, J=6.4 Hz, 2H).

2-(4-Bromobutoxy)-tetrahydro-2H-pyran (23): 3,4-Dihydro-2H-pyran (8.5 mL, 90.96 mmol) was added dropwise to the dichloromethane (20 mL) solution of 22 (10.7 g, 69.93 mmol) and p-toluenesulfonic acid monohydrate (26.5 mg, 0.1372 mmol). The mixture was stirred at room temperature over night. After removing the solvent, the residue was purified by flash chromatography on silica gel with 5:1 hexanes/ethyl acetate as the eluent to yield product 23 as a colorless oil (15.3 g, 92%). $^1$H NMR (400 MHz, CDCl$_3$): δ 1.48-1.62 (m, 4H), 1.68-1.85 (m, 4H), 1.94-2.02 (m, 2H), 3.40-3.53 (m, 4H), 3.74-3.88 (m, 2H), 4.57-4.59 (m, 1H).

Tetraethyl 5-(2-Tetrahydro-2H-pyranyloxy)pentylene-1,1-bisphosphonate (24): To the suspension of sodium hydride (60%, 840.5 mg, 21.01 mmol) in 40 mL of THF was carefully added tetraethyl methylenebisphosphonate (6.16 g, 20.95 mmol) and the resultant pale yellow clear solution was stirred at room temperature for 45 min. Then the bromide 23 (4.97 g, 20.96 mmol) was introduced plus 5 mL of THF rinse. The reaction was brought to reflux overnight and allowed to cool to room temperature before being quenched with saturated ammonium chloride aqueous solution. Another small amount of water was required to dissolve the solid. The mixture was extracted with ethyl acetate (3×), dried over anhydrous sodium sulfate and concentrated in vacuo. Flash chromatography on silica gel with 20:1 (v/v) dichloromethane/methanol as the eluent afforded 7.3 g of impure product 24 as a slightly yellow oil. The material was used directly in the next step without further purification. Selected $^1$H NMR signals (400 MHz, CDCl$_3$): δ 2.28 (tt, J=6.1, 24.3 Hz, 1H), 3.37-3.51 (m, 2H), 3.71-3.89 (m, 2H), 4.56-4.58 (m, 1H).

Tetraethyl 5-hydroxypentylene-1,1-bisphosphonate (25): The crude compound 24 was dissolved in 20 mL of methanol and 74.6 mg (0.3863 mmol) of p-toluenesulfonic acid monohydrate was added. After overnight stirring at room temperature, the mixture was concentrated and subjected to flash chromatography with gradient elution from 15:1 ethyl acetate/methanol to 8:1 then 6:1 to afford 25 as a colorless oil (3.1 g, 41% over two steps). $^1$H NMR (400 MHz, CDCl$_3$): δ 1.24-1.36 (m, 12H), 1.55-1.72 (m, 4H), 1.89-2.03 (m, 2H), 2.16 (bs, 1H), 2.29 (tt, J=6.1, 24.3 Hz, 1H), 3.66 (bs, 2H), 4.11-4.22 (m, 8H).

Tetraethyl 5-iodopentylene-1,1-bisphosphonate (26): The alcohol 25 (1.419 g, 3.938 mmol), triphenylphosphine (1.25 g, 4.718 mmol) and imidazole (325.6 mg, 4.735 mmol) were dissolved in 15 mL of dry acetonitrile, and 1.196 g (4.703 mmol) of I$_2$ was added in several portions. After overnight stirring at room temperature, the solvent was removed in vacuo and the residue was taken up in ethyl acetate and saturated Na$_2$S$_2$O$_3$ aqueous solution. The mixture was stirred until the organic layer turned pale yellow and the two phases were separated. The organic phase was dried over anhydrous sodium sulfate and concentrated. Flash chromatography on silica gel with 15:1 ethyl acetate/methanol as the eluent afforded the product 26 as a yellow oil (1.26 g, 68%). $^1$H NMR (400 MHz, CDCl$_3$): δ 1.36 (t, J=7.0 Hz, 12H), 1.66-1.72 (m, 2H), 1.81-1.99 (m, 4H), 2.35 (tt, J=5.9, 24.1 Hz, 1H), 3.20 (t, J=6.9 Hz, 2H), 4.17-4.23 (m, 8H).

1-(4-hydroxyphenyl)prop-2-en-1-one (27): The mixture of 4-hydroxyacetophenone (2.719 g, 20 mmol), paraformaldehyde (2.702 g, 90 mmol) and N-methylanilinium trifluoroacetate (6.603 g, 30 mmol) in 20 mL of anhydrous THF was refluxed for 3.5 h and cooled to room temperature. To the red solution was added 60 mL of diethyl ether and the mixture was vigorously stirred for 15 min. The resultant yellow solution was decanted and residual brown-red sticky mud was repeatedly extracted with 50 mL portions of diethyl ether until it turned into yellow solid. The combined organic extracts were washed with half saturated sodium bicarbonate solution (2×) and the aqueous wash was extracted with ether (2×). The combined organic layers were dried over anhydrous sodium sulfate prior to concentration. Flash chromatography on silica gel with 5:1 hexanes/ethyl acetate as the eluent afforded product 27 (1.21 g, 41%) as a pale yellow solid. $^1$H NMR (400 MHz, CDCl$_3$): δ 5.89 (dd, J=1.8, 10.6 Hz, 1H), 5.91 (s, 1H), 6.43 (dd, J=1.6, 16.9 Hz, 1H), 6.92 (d, J=8.4 Hz, 2H), 7.17 (dd, J=10.6, 17.2 Hz, 1H), 7.93 (d, J=8.4 Hz, 2H).

1-(4-(5,5-bis(diethylphosphono)pentyloxy)phenyl)prop-2-en-1-one (28): The mixture of iodide 26 (1.066 g, 2.267 mmol), enone 27 (373 mg, 2.514 mmol) and potassium carbonate (369 mg, 2.673 mmol) in 10 mL of acetone was refluxed until iodide 26 was consumed as monitored by $^1$H NMR. Normally it took 6-8 h. Upon the removal of the solvent in vacuo, the residue was taken up in dichloromethane and the insolubles were filtered off. The filtrate was washed with saturated sodium bicarbonate (2×) and dried over anhydrous sodium sulfate. Concentration under vacuum afforded a yellow oil in quantitative yield (1.14 g), which was used directly in the next step without further purification. $^1$H NMR (400 MHz, CDCl$_3$): δ 1.31-1.37 (m, 12H), 1.70-1.86 (m, 4H), 1.92-2.08 (m, 2H), 2.31 (tt, J=6.2, 24.2 Hz, 1H), 4.04 (t, J=6.2 Hz, 2H), 4.14-4.22 (m, 8H), 5.87 (dd, J=1.8, 10.6 Hz, 1H), 6.42 (dd, J=1.8, 17.2 Hz, 1H), 6.93 (d, J=9.2 Hz, 2H), 7.17 (dd, J=10.6, 16.9 Hz, 1H), 7.95 (d, J=9.2 Hz, 2H).

Scheme 7. Preparation of Rifabutin bisphosphonate conjugate 30

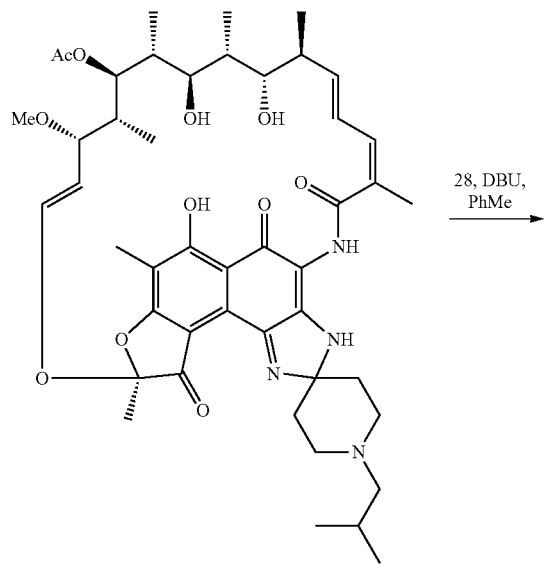

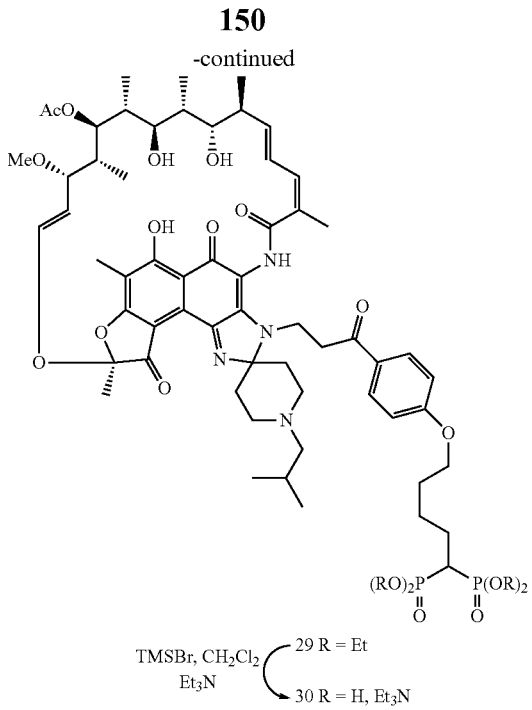

Rifabutin-bisphosphonate conjugate 29: The mixture of rifabutin (573.8 mg, 0.6774 mmol), bisphosphonate 28 (351.7 mg, 0.7171 mmol) and DBU (0.22 mL, 1.471 mmol) in 7 mL of toluene was stirred at room temperature overnight. After the removal of the solvent, the residue was taken up in ethyl acetate and was washed with saturated ammonium chloride (2×) before being dried over anhydrous sodium sulfate. Flash chromatography on silica gel with 30:1 dichloromethane/methanol then 25:1 as the eluant produced the rifabutin-bisphosphonate conjugate 29 as a red solid (400 mg, 44%) as well as recovered unreacted rifabutin (275 mg, 48%) that was contaminated with trace amount of linker-like impurities. $^1$H NMR (400 MHz, CDCl$_3$): δ 0.19 (d, J=7.0 Hz, 3H), 0.60 (d, J=6.6 Hz, 3H), 0.73 (d, J=7.0 Hz, 3H), 0.92 (d, J=5.9 Hz, 6H), 0.99 (d, J=7.0 Hz, 3H), 1.32 (t, J=7.0 Hz, 12H), 1.56-1.85 (m, 13H), 1.91-2.05 (m, 3H), 2.07 (s, 3H), 2.12 (s, 3H), 2.16-2.45 (m, 9H), 2.64-2.74 (m, 2H), 2.80-2.88 (m, 1H), 2.92-3.04 (m, 3H), 3.07-3.18 (m, 4H), 3.24-3.32 (m, 2H), 3.54-3.58 (m, 2H), 3.79 (d, J=9.9 Hz, 1H), 3.97 (d, J=5.5 Hz, 1H), 4.03 (t, J=5.5 Hz, 2H), 4.13-4.22 (m, 8H), 5.15 (d, J=10.2 Hz, 1H), 5.25 (dd, J=4.8, 12.5 Hz, 1H), 6.02 (dd, J=6.6, 16.1 Hz, 1H), 6.20-6.25 (m, 2H), 6.90 (d, J=9.2 Hz, 2H), 7.04 (dd, J=10.6, 15.8 Hz, 1H), 7.88 (d, J=9.2 Hz, 2H), 8.19 (s, 1H).

Rifabutin-bisphosphonate conjugate 30: To the mixture of compound 29 (397.6 mg, 0.2973 mmol) and triethylamine (2.10 mL, 15.05 mmol) in 5 mL of anhydrous dichloromethane was added 0.98 mL (7.425 mmol) of bromotrimethylsilane. The dark mixture was stirred at room temperature for over 20 h. Upon concentration in vacuo, the residue was stirred in a mixture of 15 mL of 0.1 N hydrochloric acid and 15 mL of acetonitirile at room temperature for 2.5 h prior to the neutralization with 0.38 mL (2.723 mmol) of triethylamine. The mixture was freeze-dried and subjected to a 10 g (35 cc) Waters C18 Sep-Pak cartridge with gradient elution from water to 10:1 water/acetonitrile then 8:1 to 6:1 to 5:1. The yellow fractions were concentrated and freeze-dried to afford compound 30 as a yellow to orange solid (50 mg, 14%). Selected $^1$H NMR (400 MHz, DMSO-$d_6$): δ 0.01 (d, J=6.9 Hz, 3H), 0.49 (d, J=6.6 Hz, 3H), 0.72 (d, J=6.9 Hz, 3H), 0.85 (d, J=7.0 Hz, 3H), 0.88 (d, J=6.6 Hz, 6H), 1.09 (t, J=7.3 Hz, 6H), 1.16 (tt, J=1.8, 7.3 Hz, 2H), 1.20-1.28 (m, 3H), 2.00 (s, 3H), 2.09 (s, 3H), 2.98 (s, 3H), 3.40 (d, J=6.2 Hz, 1H), 3.53-3.54 (m, 1H), 5.07 (dd, J=6.2, 12.8 Hz, 1H), 5.18 (d, J=10.3 Hz, 1H), 5.92 (d, J=7.3, 15.4 Hz, 1H), 6.20-6.23 (m, 2H), 6.82 (dd, J=11.0, 15.8 Hz, 1H), 7.00 (d, J=8.8 Hz, 2H), 7.74 (d, J=8.8 Hz, 2H), 8.74 (s, 1H). $^{31}$P (162 MHz, DMSO-$d_6$): δ 20.53.

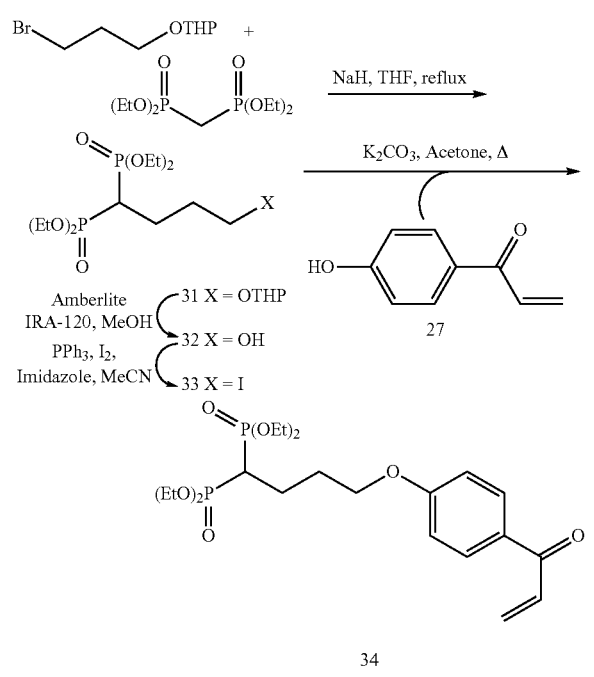

Scheme 8.
Synthesis of 1-(4-(5,5-bis(diethylphosphono)pentyloxy)phenyl)prop-2-en-1-one.

Tetraethyl 4-(2-Tetrahydro-2H-pyranyloxy)butylene-1,1-bisphosphonate (31): To a suspension of NaH (60% suspension in mineral oil, 900 mg, 22.0 mmol) in dry THF (20 mL) was added dropwise tetraethyl methylenebisphosphonate (6.46 g, 22.4 mmol). The resulting clear solution was stirred 15 min at room temperature, after which 2-(3-bromopropoxy)tetrahydro-2H-pyran (5.05 g, 22.6 mmol) was added dropwise. The reaction mixture was heated to reflux for 6 h, diluted with CH$_2$Cl$_2$ (75 mL) and washed with brine (2×50 mL), dried (MgSO$_4$) and evaporated. It was used as such in the following step.

Tetraethyl 4-hydroxybutylene-1,1-bisphosphonate (32): To a stirred solution of the crude product 31 (max. 22.4 mmol) in MeOH (40 mL) was added Amberlite IR-120 (0.6 g). The reaction mixture was heated to 50° C. for 4 h, filtered and evaporated. The crude product was purified by flash chromatography on silica gel with gradient elution from 5-10% methanol/ethyl acetate to give pure 32 (2.67 g, 34% from tetraethyl methylenebisphosphonate). $^1$H NMR (400 MHz, CDCl$_3$) δ 1.30-1.36 (m, 12H), 1.75-1.85 (m, 2H), 1.97-2.13 (m, 2H), 2.30-2.64 (m, 2H), 3.66 (t, J=5.8, 2H), 4.12-4.23 (m, 8H).

Tetraethyl 4-iodobutylene-1,1-bisphosphonate (33): To a solution of 32 (1.52 g, 4.39 mmol) in CH$_2$Cl$_2$ (50 mL) were added triphenylphosphine (1.32 g, 5.033 mmol) and imidazole (0.45 g, 6.61 mmol). The reaction mixture was cooled to 0° C., before the addition of iodine (1.22 g, 4.81 mmol). The mixture was then removed from the cooling bath, stirred for 2 h, diluted with hexanes (100 mL) and filtered washing the precipitate with further hexanes (2×30 mL). The filtrate was evaporated and purified by flash chromatography on silica gel with gradient elution from 0-10% methanol/ethyl acetate to give pure 33 (1.6 g, 80%). $^1$H NMR (400 MHz, CDCl$_3$) δ 1.32-1.38 (m, 12H), 1.95-2.15 (m, 4H), 2.28 (tt, J=24.1, 6.1, 1H), 3.18 (t, J=6.6, 2H), 4.12-4.24 (m, 8H).

1-(4-(4,4-bis(diethylphosphono)butoxy)phenyl)prop-2-en-1-one (34): A mixture of iodide 33 (3.1 g, 6.8 mmol), phenol 27 (1.21 g, 8.17 mmol) and K$_2$CO$_3$ (1.033 g, 7.47 mmol) in acetone (75 mL) was refluxed for 6.5 h. The mixture was cooled, filtered and evaporated. The residue was redissolved in CH$_2$Cl$_2$ (170 mL), filtered through Celite and evaporated to give crude 34 (3.2 g, 99%) which was used directly in the next step. $^1$H NMR (400 MHz, CDCl$_3$) δ 1.28-1.39 (m, 12H), 1.89-2.25 (m, 4H), 2.26-2.48 (m, 1H), 4.05 (t, J=5.7, 2H), 4.12-4.26 (m, 8H), 5.87 (dd, J=10.6, 1.8, 1H), 6.42 (dd, J=16.9, 1.8, 1H), 6.93 (d, J=8.8, 2H), 7.17 (dd, J=17.0, 10.4, 1H), 7.95 (d, J=8.8, 2H).

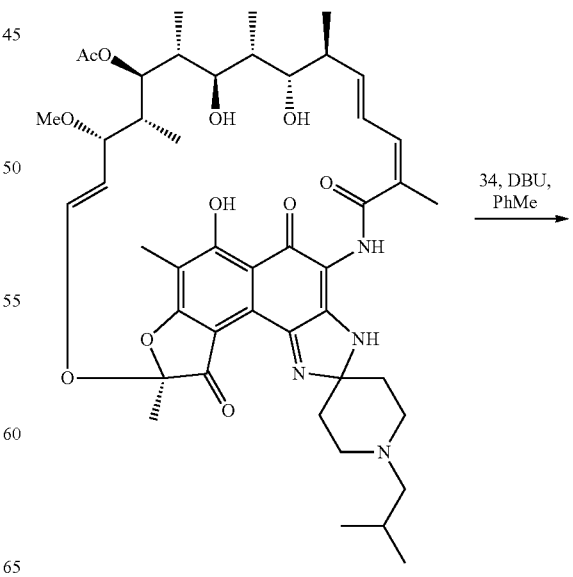

Scheme 9. Preparation of Rifabutin bisphosphonate conjugate 36.

-continued

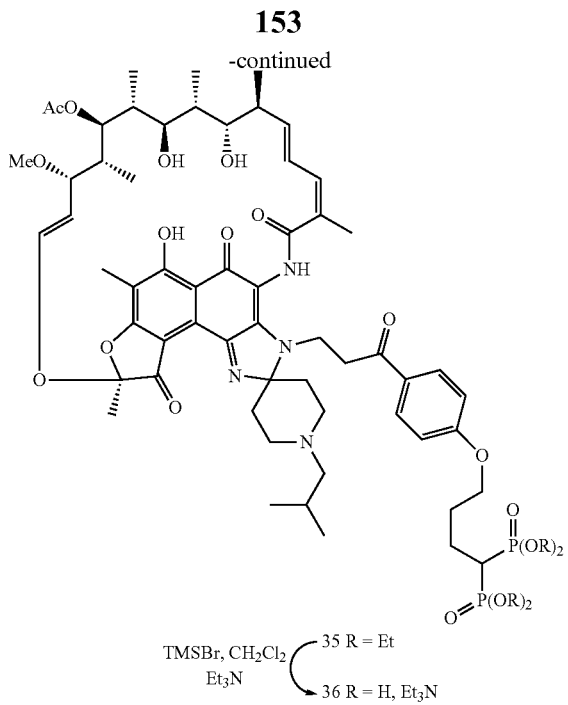

Rifabutin-bisphosphonate conjugate 35: The mixture of 6 g (7.088 mmol) of rifabutin, compound 34 (3.656 g, 7.431 mmol) and DBU (2.20 mL, 14.71 mmol) in 70 mL of toluene was stirred at room temperature overnight. The reaction was washed with a saturated aqueous solution of ammonium chloride (twice) and dried over anhydrous sodium sulfate. Flash chromatography on silica gel using a gradient elution of 40:1 then 30:1, 20:1, 15:1 and 10:1 (v/v) dichloromethane/methanol. The product 35 was obtained as a red-brown solid (4.4 g, 47%). $^1$H NMR (400 MHz, CDCl$_3$) δ 0.20 (d, J=7.0, 3H), 0.60 (d, J=6.6, 3H), 0.72 (d, J=6.6, 3H), 0.91 (d, J=6.6, 3H), 0.92 (d, J=6.6, 3H), 0.99 (d, J=7.0, 3H), 1.34 (dt, J=7.0, 1.1, 12H), 1.56-1.85 (m, 10H), 2.00-2.46 (m, 20H), 2.64-2.74 (m, 2H), 2.80-2.88 (m, 1H), 2.92-3.02 (m, 3H), 3.11 (s, 3H), 3.12-3.18 (m, 1H), 3.25-3.32 (m, 1H), 3.55-3.57 (m, 1H), 3.79 (d, J=9.5, 1H), 3.95 (d, J=5.1, 1H), 4.02-4.06 (m, 2H), 4.14-4.23 (m, 8H), 5.14 (d, J=10.2, 1H), 5.24 (dd, J=12.6, 5.1, 1H), 6.02 (dd, J=16.1, 6.6, 1H), 6.19-6.24 (m, 2H), 6.90 (d, J=9.2, 2H), 7.06 (dd, J=16.1, 11.0, 1H), 7.88 (d, J=8.8, 2H), 8.17 (s, 1H); $^{31}$P NMR (162 MHz, CDCl$_3$) δ 24.58.

Rifabutin-bisphosphonate conjugate 36: Compound 35 (4.4 g, 3.325 mmol) was dissolved in 50 mL of anhydrous dichloromethane. To this solution was added 23 mL (164.1 mmol) of triethylamine followed by 11 mL (83.34 mmol) of bromotrimethylsilane. The mixture was stirred at room temperature for over 20 h. Upon the removal of the solvent, the residue was taken up in the mixture of 200 mL of 0.1 N hydrochloric acid and 75 mL of acetonitrile and stirred at room temperature for 5 h. At the end of the treatment, 4.7 mL of triethylamine was added and the insolubles were filtered. The organic solvents were removed and the residue was lyophilized. The resulting material was subjected to a C18 reverse phase flash chromatography with a linear gradient elution of 20% acetonitrile in 30 mM triethylamine/carbon dioxide aqueous solution (pH 6.8) to pure acetonitrile. For the fractions containing the product, acetonitrile was removed in vacuo and the resulting aqueous solution was lyophilized to afford compound 36 as an orange-brown solid bis-triethylammonium salt form (1.137 g, 24%). $^1$H NMR (400 MHz, D$_2$O) δ 0.01 (d, J=6.6, 3H), 0.63 (d, J=6.6, 3H), 0.81 (d, J=7.0, 3H), 0.95 (d, J=7.0, 3H), 1.01 (d, J=6.2, 6H), 1.26 (t, J=7.3, 18H), 1.60 (s, 3H), 1.54-1.62 (m, 1H), 1.68-2.16 (m, 11H), 2.03 (s, 3H), 2.09 (s, 3H), 2.13 (s, 3H), 2.30-2.37 (m, 2H), 2.42-2.50 (m, 2H), 2.66-2.75 (m, 2H), 3.00-3.28 (m, 3H), 3.07 (s, 3H), 3.18 (q, J=7.3, 12H), 3.53-3.59 (m, 4H), 3.76 (d, J=8.8, 1H), 4.13-4.16 (m, 3H), 5.10 (d, J=11, 1H), 5.35 (dd, J=12.5, 7.0, 1H), 6.04 (dd, J=15.8, 1H), 6.26 (d, J=12.5, 1H), 6.38 (d, J=11.4, 1H), 6.74 (dd, J=16.1, 11.4, 1H), 6.99 (d, J=8.8, 2H), 7.71 (d, J=8.8, 2H); $^{31}$P NMR (162 MHz, D$_2$O) δ 21.00.

Scheme 10. Preparation of Rifabutin-bisphosphonate conjugate 39

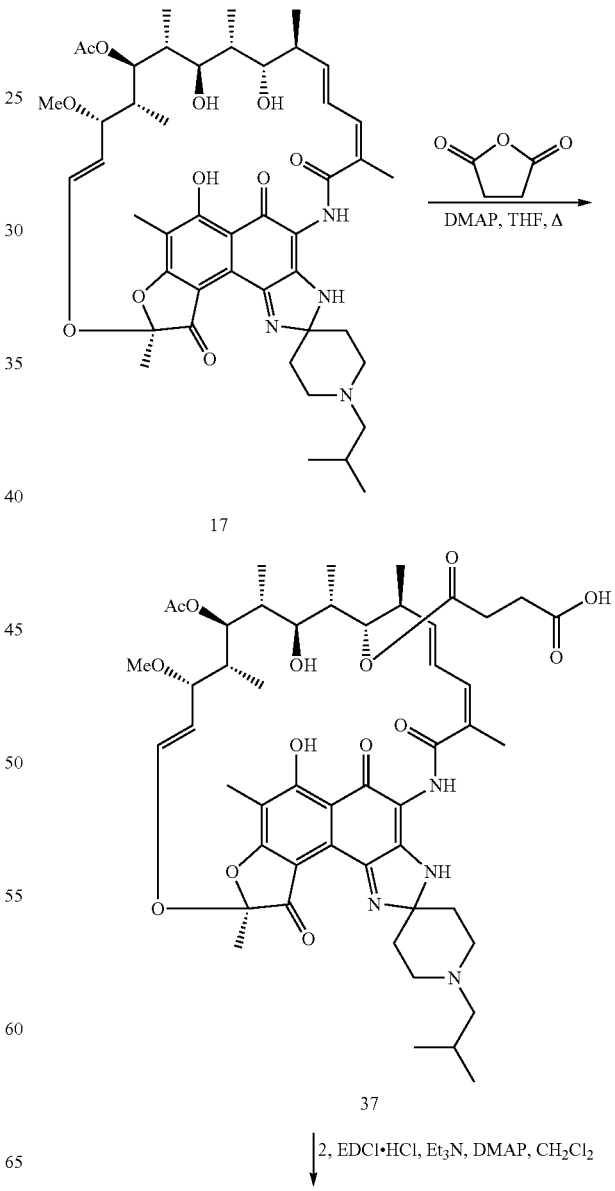

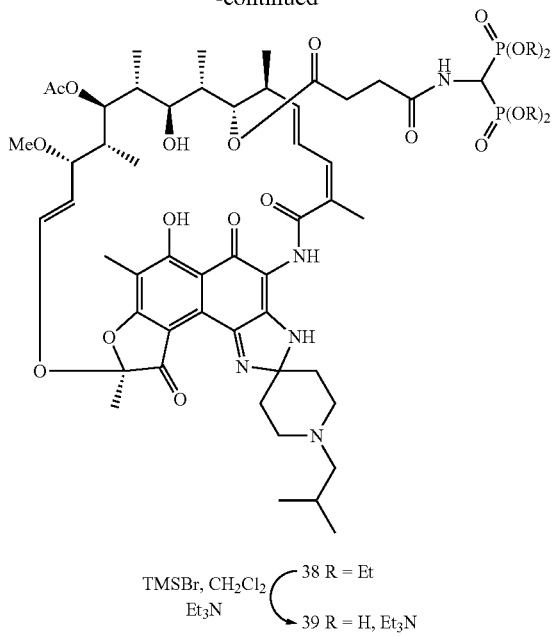

21-O-(3-carboxypropanoyl)-1',4-didehydro-1-deoxy-1,4-dihydro-5'-(2-methylpropyl)-1-oxorifamycin XIV (37): Rifabutin 17 (153.8 mg, 0.1816 mmol) was refluxed overnight with 44.3 mg (0.4427 mmol) of succinic anhydride and 6.4 mg (0.05239 mmol) of DMAP in 3 mL of anhydrous THF. After concentration, the material obtained was subjected to flash chromatography on silica gel eluting with dichloromenthane/methanol (30:1 (v/v) then 20:1 then 10:1) to afford the product 37 (136.4 mg, 80%) as a dark purple solid. $^1$HNMR (400 MHz, CDCl$_3$): δ −0.15 (d, J=7.0, 3H), 0.50 (d, J=6.6, 3H), 0.88-1.00 (m, 9H), 1.07 (d, J=7.0, 3H), 1.20-1.26 (m, 2H), 1.57 (s, 1H), 1.79 (s, 3H), 1.80-1.98 (m, 4H), 2.02 (s, 3H), 2.04 (s, 3H), 2.26 (s, 3H), 2.30-2.66 (m, 9H), 2.86-3.21 (m, 5H), 3.08 (s, 3H), 3.47 (br s, 1H), 3.66 (s, 1H), 4.98-5.06 (m, 2H), 5.76-5.86 (m, 1H), 6.02 (d, J=12.5, 1H), 6.15 (d, J=11.0, 1H), 6.30-6.37 (m, 1H), 7.99 (s, 1H), 8.35 (br s, 1H).

21-O-(3-((bis(diethylphosphono)methyl)carbamoyl)propanoyl)-1',4-didehydro-1-deoxy-1,4-dihydro-5'-(2-methylpropyl)-1-oxorifamycin XIV (38): Acid 37 (136 mg, 0.1436 mmol) and amine 2 (44 mg, 0.1446 mmol) were dissolved into 2 mL of anhydrous dichloromethane and 40 μL (0.2854 mmol) of triethylamine was added followed by EDCl.HCl (64 mg, 0.3338 mmol) and DMAP (3.5 mg, 0.02865 mmol). After stirring overnight at room temperature, the mixture was concentrated and subjected to flash chromatography on silica gel. The column was initially eluted with 10:1 (v/v) ethyl acetate/acetic acid until the dark purple band of unreacted rifabutin was flushed out. Then elution dichloromethane/methanol (20:1 (v/v) then 10:1) was applied to yield the product 38 (58.9 mg, 33%) as a dark purple solid. $^1$HNMR (400 MHz, CDCl$_3$): δ −0.18 (d, J=7.3, 3H), 0.47 (d, J=7.0, 3H), 0.92 (d, J=6.6, 3H), 0.95-1.03 (m, 9H), 1.12-1.32 (m, 2H), 1.35 (t, J=7.0, 12H), 1.79 (s, 3H), 1.80-1.98 (m, 4H), 2.02 (s, 3H), 2.08 (s, 3H), 2.00-2.10 (m, 3H), 2.29 (s, 3H), 2.32-2.76 (m, 8H), 2.80-3.10 (m, 5H), 3.07 (s, 3H), 3.49 (br s, 1H), 4.14-4.28 (m, 8H), 4.95 (d, J=10.7, 1H), 4.98-5.12 (m, 2H), 5.86 (dd, J=15.4, 7.7, 1H), 6.08-6.15 (m, 1H), 6.40 (dd, J=15.4, 11.4, 1H), 6.65 (d, J=10.3, 1H), 8.15 (s, 1H), 8.28 (br s, 1H).

21-O-(3-((bisphosphonomethyl)carbamoyl)propanoyl)-1',4-didehydro-1-deoxy-1,4-dihydro-5'-(2-methylpropyl)-1-oxorifamycin XIV (39): Compound 38 (57.4 mg, 0.04658 mmol) was dissolved in 0.5 mL of anhydrous dichloromethane and 0.33 mL (2.355 mmol) of triethylamine and 0.16 mL (1.212 mmol) of TMSBr were added sequentially. The mixture was stirred at room temperature overnight and concentrated. After drying in vacuo for at least 30 min, the material was dissolved in a mixture of 2.8 mL of 0.1 N HCl (aq) and 2.8 mL of acetonitrile. After stirring for 1.5 h, the solution was basified with 0.07 mL of triethylamine and the organic solvent was carefully removed. The residue was filtered and lyophilized. The solid material after lyophilization was applied to a C18 column on an automated Biotage® separation apparatus with linear gradient elution of 10% acetonitrile in 30 mM triethylammonium bicarbonate buffer (pH=6.8) to 60% followed by a pure acetonitrile wash to afford a dark purple solid 39 as bis-triethylamine salt (20.5 mg, 33%). Selected $^1$HNMR (400 MHz, D$_2$O): δ 0.16 (bs, 3H), 0.40 (d, J=5.5, 3H), 0.74 (br s, 1H), 0.88 (d, J=6.6, 3H), 1.00 (d, J=6.6, 3H), 1.06 (d, J=6.6, 6H), 1.27 (t, J=7.3, 18H), 1.55 (br s, 1H), 1.78 (s, 3H), 1.99 (s, 3H), 2.01 (s, 3H), 2.19 (s, 3H), 2.20-2.26 (m, 1H), 2.39 (br s, 1H), 2.65 (br s, 5H), 2.97-3.00 (m, 1H), 3.02 (s, 3H), 3.10-3.24 (m, 5H), 3.19 (q, J=7.3, 12H), 3.29-3.32 (m, 2H), 3.65 (br s, 5H), 4.28 (t, J=19.0, 1H), 5.01-5.04 (m, 1H), 5.32 (bs, 1H), 5.99 (dd, J=15.4, 9.2, 1H), 6.19 (d, J=12.5, 1H), 6.43 (d, J=11.0, 1H), 6.80 (br s, 1H). $^{31}$PNMR (162 MHz, D$_2$O): δ 14.15. MS (M−H): 1118.2.

Scheme 11. Preparation of tetraethyl (4-aminobutanoylamino)methylene-1,1-bisphosphonate

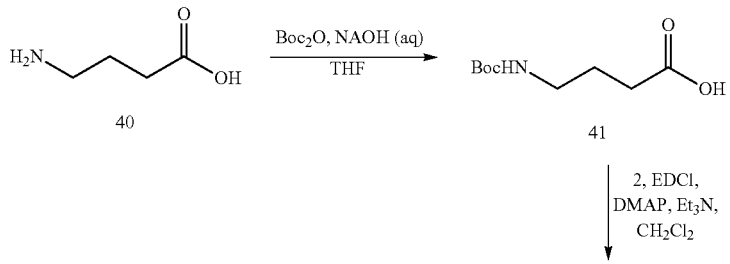

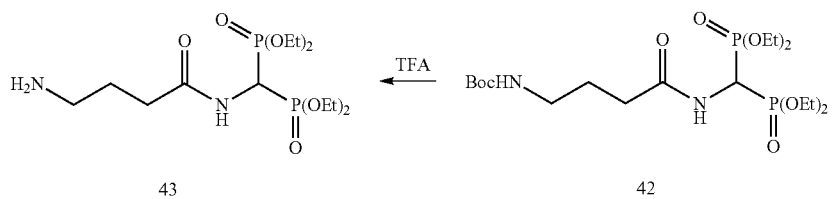

4-(t-butoxycarbonylamino)butanoic acid (41): Amino-acid 40 (956.2 mg, 9.273 mmol) was stirred with Boc$_2$O (2.037 g, 9.333 mmol) and 23 mL of 1N NaOH (aq) in 5 mL of THF at room temperature overnight. The solution was acidified with diluted hydrochloric acid until the pH reached around 2 when a turbid mixture was obtained. The reaction was extracted with ethyl acetate (3×) and dried over anhydrous sodium sulfate prior to the removal of the solvent to yield a colorless oil 41 (1.759 g, 93%). $^1$HNMR (400 MHz, CDCl$_3$): δ 1.44 (s, 9H), 1.83 (quint. J=7.0, 2H), 2.41 (t, J=7.0, 2H), 3.12-3.24 (m, 2H), 4.66 (br s, 1H).

Tetraethyl (4-(t-butoxycarbonylamino)butanoylamino)methylene-1,1-bisphosphonate (42): The acid 41 (314.6 mg, 1.547 mmol) and amine 2 (466.8 mg, 1.539 mmol) were dissolved in 15 mL of dry dichloromethane. Triethylamine (0.44 mL, 3.14 mmol) was added followed by DMAP (37.6 mg, 0.3078 mmol) and EDCl.HCl (592.4 mg, 3.09 mmol). The mixture was stirred at room temperature overnight before being concentrated. Flash chromatography on silica gel with elution in 15:1 (v/v) ethyl acetate/methanol afforded 469.3 mg (62%) of compound 42 as a pale yellow oil. $^1$HNMR (400 MHz, CDCl$_3$): δ 1.34 (t, J=7.0, 12H), 1.44 (s, 9H), 1.83 (quint. J=7.0, 2H), 2.31 (t, J=7.0, 2H), 3.16-3.24 (m, 2H), 4.16-4.26 (m, 8H), 4.78 (br s, 1H), 5.06 (dt, J=21.6, 9.9, 1H), 6.61 (br d, J=10.3, 1H).

Tetraethyl (4-aminobutanoylamino)methylene-1,1-bisphosphonate (43): Compound 42 (469 mg, 0.9602 mmol) was dissolved in small amount of TFA and the solution was concentrated. The residue was taken up in 1N NaOH aqueous solution and was extracted with ethyl acetate (5×). The combined extracts were dried over sodium sulfate and concentrated to dryness in vacuo to afford compound 43 as a colorless oil (82 mg, 22%). $^1$HNMR (400 MHz, CDCl$_3$): δ 1.34 (dt, J=7.0, 2.6, 12H), 1.79 (quint. J=7.0, 2H), 2.38 (t, J=7.0, 2H), 2.79 (t, J=7.0, 2H), 4.14-4.26 (m, 8H), 5.05 (dt, J=21.3, 8.5, 1H), 7.08 (br d, J=8.0, 1H).

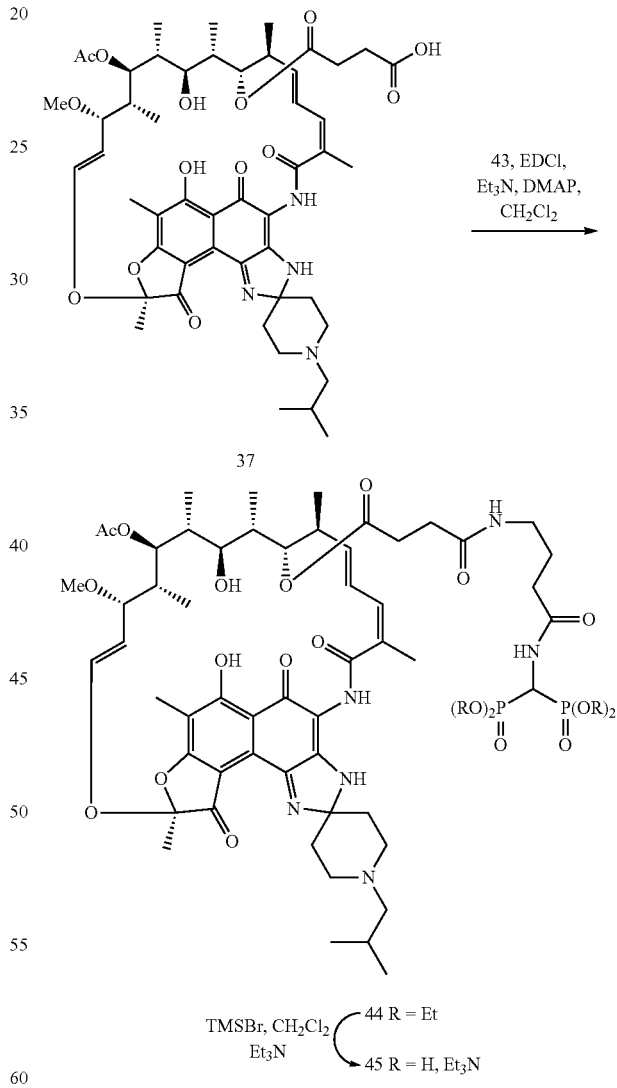

Scheme 12. Preparation of Rifabutin-bisphosphonate conjugate 45.

21-O-(3-(3-((bis(diethylphosphono)methyl)carbamoyl)propylcarbamoyl)propanoyl)-1',4-didehydro-1-deoxy-1,4-dihydro-5'-(2-methylpropyl)-1-oxorifamycin XIV (44): A mixture of acid 37 (432.5 mg, 0.4567 mmol), amine 43 (176.3 mg, 0.4540 mmol), EDCl.HCl (180.1 mg, 0.9394 mmol), DMAP (11.9 mg, 0.09741 mmol) and triethylamine (0.13 mL, 0.9277 mmol) in 5 mL of dichloromethane was stirred at room temperature over night. After concentration to dryness, the residue was purified by SiO$_2$ chromatography on a Biotage® automated flash purification system with a gradient elution of 2-10% methanol in dichloromethane over 15 column volumes to furnish 44 as a dark purple solid (404.8 mg, 68%). $^1$HNMR (400 MHz, CDCl$_3$): δ −0.21 (d, J=7.0, 3H), 0.47 (d, J=7.0, 3H), 0.91 (d, J=7.0, 3H), 0.98 (br s, 3H), 1.03 (d, J=7.0, 6H), 1.41 (t, J=7.3, 12H), 1.79 (s, 3H), 1.72-2.00 (m, 11H), 2.01 (s, 3H), 2.02 (s, 3H), 2.28 (s, 3H), 2.28-2.54 (m, 10H), 2.84-2.92 (m, 2H), 3.05 (s, 3H), 3.18-3.23 (m, 2H), 3.32-3.37 (m, 2H), 3.45-3.49 (m, 2H), 4.11-4.28 (m, 8H), 4.96 (d, J=11.0, 1H), 5.00-5.14 (m, 2H), 5.92 (dd, J=15.4, 7.0, 1H), 6.07 (d, J=13.2, 1H), 6.17 (d, J=11.4, 1H), 6.39 (dd, J=15.4, 11.4, 1H), 6.68 (br s, 1H), 6.79 (br s, 1H), 8.00 (br s, 1H), 8.18 (br s, 1H).

21-O-(3-(3-((bisphosphonomethyl)carbamoyl)propylcarbamoyl)propanoyl)-1',4-didehydro-1-deoxy-1,4-dihydro-5'-(2-methylpropyl)-1-oxorifamycin XIV (45): Compound 44 (396.5 mg, 0.3010 mmol) was dissolved in 3 mL of dichloromethane and 2.1 mL (14.99 mmol) of triethylamine was added followed by 1 mL (7.577 mmol) of TMSBr. The red mixture was stirred for at least 20 hours at room temperature and was concentrated to dryness. After drying under high vacuum for at least 30 min, the solid material was taken up in the mixture of 18 mL of 0.1 N HCl and 10 mL of acetonitrile and stirred at room temperature for 1 h, at which time a clear solution was obtained. After basification by the addition of 0.43 mL of triethylamine (end pH=9.6), the organic solvent was carefully removed and the insoluble material was filtered off. The filtrate was lyophilized and the residue was subjected to a C18 column on a Biotage® automated flash chromatography system with a gradient elution in 10-60% MeCN in 30 mM triethylammonium bicarbonate buffer (pH=6.5) over 15 column volumes to afford 45 as a dark purple solid (194 mg, 46%) as the bistriethylammonium salt. $^1$HNMR (400 MHz, D$_2$O): δ −0.04 (d, J=6.6, 3H), 0.39 (d, J=6.2, 3H), 0.76 (br s, 1H), 0.88 (d, J=7.0, 3H), 0.95 (d, J=6.6, 3H), 1.08 (d, J=6.6, 6H), 1.26 (t, J=7.3, 18H), 1.53 (br s, 1H), 1.80-2.32 (m, 8H), 1.81 (s, 3H), 1.98 (s, 3H), 2.02 (s, 3H), 2.10 (s, 3H), 2.32-2.72 (m, 10H), 2.96-3.02 (m, 2H), 2.99 (s, 3H), 3.18 (q, J=7.3, 12H), 3.35 (d, J=7.3, 1H), 3.60-3.84 (m, 4H), 4.33 (t, J=19.1, 1H), 4.95 (d, J=10.3, 1H), 5.04-5.06 (m, 1H), 5.21 (dd, J=12.4, 5.1, 1H), 5.97 (dd, J=15.0, 7.7, 1H), 6.10 (d, J=12.5, 1H), 6.39 (d, J=10.6, 1H), 6.63 (dd, J=15.1, 11.4, 1H); $^{31}$PNMR (162 MHz, D$_2$O): δ 13.99; Mass (M−H): 1203.

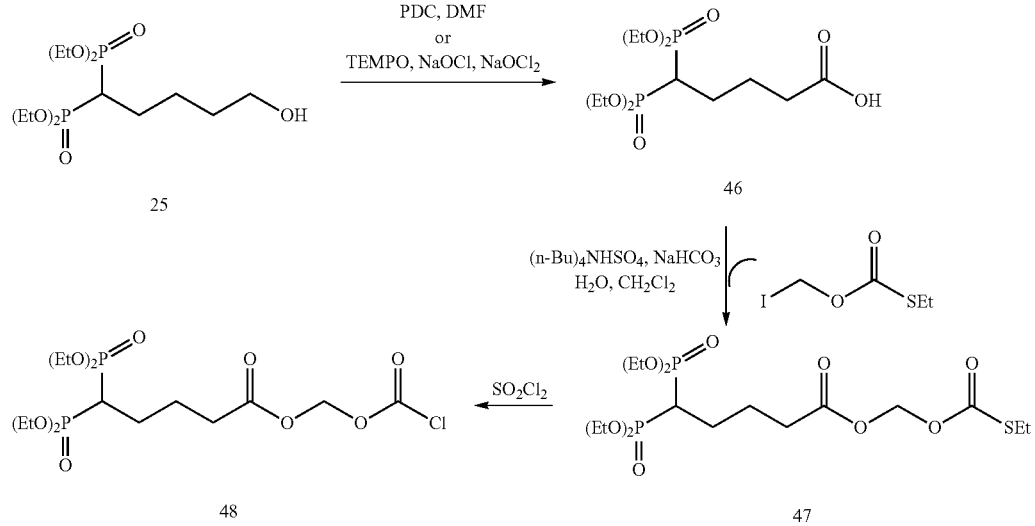

Scheme 13. Preparation of (carbonochloridoyloxy)methyl 5,5-bis(diethylphosphono)pentanoate Tetraethyl 5-carboxypentylene-1,1-bisphosphonate (46): Alcohol 25 (1.3942 g, 3.869 mmol) was dissolved in 40 mL of anhydrous DMF and 5.098 g (13.55 mmol) of pyridinium dichromate was added. The dark solution was stirred at room temperature over night. The reaction was concentrated to half the original volume and diluted with water. The mixture was extracted with ethyl acetate (3×) and the combined extracts were dried over sodium sulfate and concentrated to dryness. Flash chromatography on silica gel with elution in 15:1 (v/v) dichloromethan/methanol afforded acid 46 (606 mg, 42%) as a colorless oil. Alternatively, to a mixture of alcohol 25 (475 mg, 1.318 mmol), TEMPO (15 mg, 0.095 mmol), MeCN (6 mL) and sodium phosphate buffer (6 mL, 0.67 M, pH=6.7) heated to 35° C. were added dropwise a sodium chlorite solution (300 mg in 2 mL of water) and dilute bleach (0.75 mL of solution of 1 mL of commercial bleach in 19 mL of water) simultaneously from separate syringes. The mixture turned from yellow to red. After 5 h, reaction was complete by TLC and $^1$H NMR and was cooled to room temperature. 30 mL of water was added and the pH was adjusted to about 9 with the addition of 3 mL of 1N NaOH. The reaction was quenched by pouring into a cold Na$_2$SO$_3$ solution (500 mg in 10 mL of water) and maintained below 20° C. After 30 min stirring at the same temperature, 30 mL of diethyl ether was used to extract the mixture and the organic phase was discarded. The pH of the aqueous phase was readjusted to between 3-4 by adding 5 mL of 1N HCl and the mixture was extracted with dichloromethane (3×). The combined extracts were dried over sodium sulfate and concentrated to afford the acid 46 quantitatively, which could be used in the following steps without further purification. $^1$HNMR (400 MHz, CDCl$_3$): δ 1.34 (t, J=7.0, 12H), 1.86-2.06 (m, 4H), 2.33 (tt, J=24.2, 5.9, 1H), 2.36 (t, J=7.3, 2H), 4.14-4.22 (8H).

S-Ethyl O-(5,5-bis(diethylphosphono)pentanoyloxy)methyl carbonothioate (47): Acid 46 (606 mg, 1.619 mmol), tetrabutylammonium hydrogensulfate (552 mg, 1.626 mmol) and sodium bicarbonate (274.2 mg, 3.264 mmol) were added to the mixture of 4 mL of water and 4 mL of dichloromethane. After the evolution of gas stopped, 310.8 mg (1.263 mmol) of S-ethyl O-iodomethyl carbonothioate (synthesized according to Folkmann, M.; Lund, F. J. *Synthesis*, 1990, 1159-1166) in 1 mL of dichloromethane was added and the mixture was stirred for 2 h. The organic phase was separated, washed with water (1×) and dried over sodium sulfate. After filtration and concentration, the residue was stirred in ether for 10 min. The solid was removed and the filtrate was concentrated and subjected to flash chromatography on silica gel with elution in 20:1 (v/v) dichloromethane/methanol to afford compound 47 (519.2 mg, 83%) as a colorless oil. $^1$HNMR (400 MHz, CDCl$_3$): δ1.33 (t, J=7.3, 3H), 1.35 (t, J=7.7, 12H), 1.86-2.04 (m, 4H), 2.28 (tt, J=23.8, 6.2, 1H), 2.40 (t, J=7.3, 2H), 2.90 (q, J=7.3, 2H), 4.14-4.22 (m, 8H), 5.80 (s, 2H).

(Carbonochloridoyloxy)methyl 5,5-bis(diethylphosphono)pentanoate (48): Compound 47 neat (519.2 mg, 1.054 mmol) was cooled in an ice/water bath and sulfuryl chloride (128 μL, 1.579 mmol) was carefully added. The reaction mixture was allowed to warm to room temperature and was stirred overnight. After removal of the excess sulfuryl chloride in vacuo, the crude acid chloride 48 was used directly in the next step without further purification. $^1$HNMR (400 MHz, CDCl$_3$): δ 1.35 (t, J=7.0, 12H), 1.86-2.06 (m, 4H), 2.28 (tt, J=23.8, 6.2, 1H), 2.45 (t, J=7.0, 2H), 2.90 (q, J=7.3, 2H), 4.14-4.24 (m, 8H), 5.82 (s, 2H).

Scheme 14. Preparation of rifabutin-bisphosphonate conjugate 50.

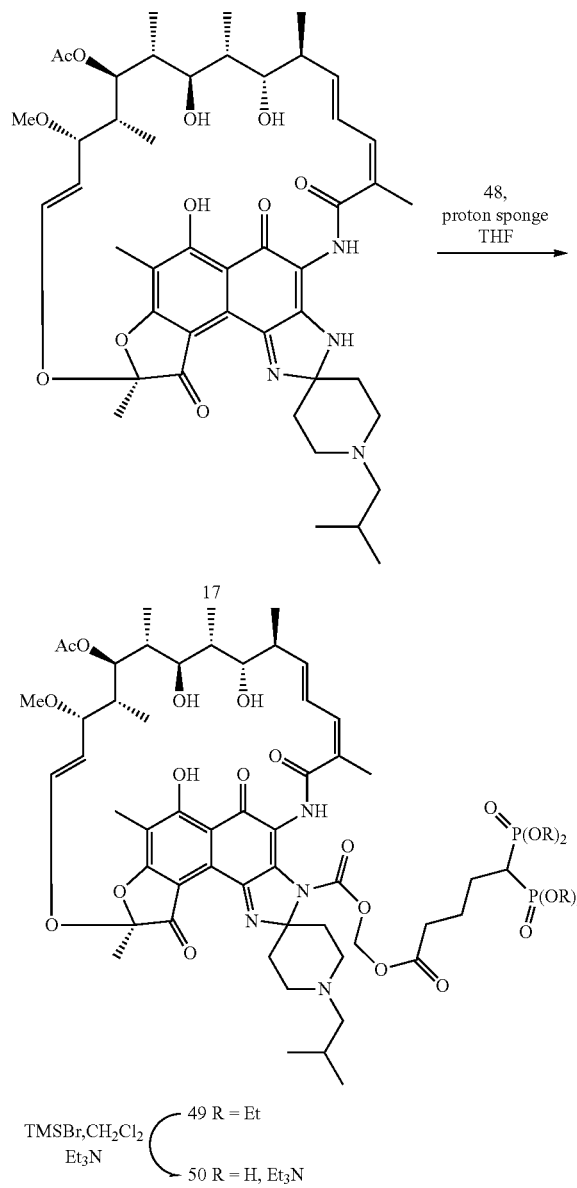

Rifabutin-bisphosphonate conjugate 49: Rifabutin 17 (899 mg, 1.061 mmol) was dissolved in 10 mL of THF and proton sponge (453.5 mg, 2.116 mmol) and crude acid chloride 48 (1.054 mmol) were added. The mixture was stirred at room temperature overnight and was diluted with ethyl acetate. The solution was washed with water (2×), dried over sodium sulfate and concentrated to dryness. The residue was purified by a flash chromatography on silica gel, eluting the dark purple rifabutin band with 19:1 (v/v) ethyl acetate/methanol and switching to a gradient elution with dichloromethane/methanol (30:1 (v/v) to 20:1 to 10:1) to afford compound 49 (504.3 mg, 37%) as a dark red-orange solid. $^1$HNMR (400 MHz, CDCl$_3$): δ −0.07 (br d, J=7.0, 3H), 0.59 (d, J=6.6, 3H), 0.85 (d, J=7.0, 3H), 0.96 (d, J=6.6, 6H), 1.02 (d, J=7.0, 3H), 1.31-1.36 (m, 12H), 1.50-2.02 (m, 10H), 1.76 (s, 3H), 2.05 (s, 3H), 2.09 (br s, 3H), 2.20-2.40 (m, 6H), 2.32 (s, 3H), 2.84-3.04 (m, 6H), 3.09 (s, 3H), 3.38-3.44 (m, 2H), 3.74-3.82 (m, 2H), 4.12-4.22 (m, 8H), 4.98 (br d, J=9.5, 1H), 5.15 (br, s, 1H), 5.75-5.92 (m, 2H), 6.00-6.28 (m, 3H), 6.79 (br s, 1H), 8.03 (br s, 1H).

Rifabutin bisphosphonate conjugate 50: Compound 49 (499.1 mg, 0.3907 mmol) was dissolved in 4 mL of dichloromethane and 2.7 mL (19.27 mmol) of triethylamine and 1.3 mL (9.850 mmol) of TMSBr were added sequentially. The bright red-orange mixture was stirred at room temperature for at least 20 h prior to concentration in vacuo. The residue was taken up in a mixture of dilute HCl aqueous solution (20 mL, pH=4.5) and 15 mL of MeCN and stirred at room temperature for 1 h, at which point a clear dark red solution was obtained. Triethylamine (0.22 mL, 4 eq) was added to adjust the end pH to 9.4. The organic solvent was carefully removed and the insoluble materials were filtered off. The resulting aqueous mixture was lyophilized to remove water. The solid material was subjected to a C18 column on a Biotage® automated flash chromatography system with gradient elution in 10-60% MeCN in 30 mM triethylammonium bicarbonate buffer (pH=6.5) over 12 column volumes to furnish the bis-triethylammonium salt of 50 as a dark red solid (166 mg, 31%). $^1$H-NMR (400 MHz, D$_2$O): δ −0.08 (br d, J=5.9, 3H), 0.61 (d, J=6.3, 3H), 0.89 (d, J=5.9, 3H), 0.96 (d, J=7.0, 6H), 1.08 (d, J=6.6, 3H), 1.09 (d, J=6.6, 3H), 1.26 (t, J=7.3, 18H), 1.58-2.14 (m, 24H), 2.20-2.30 (m, 2H), 2.41 (br s, 3H), 3.06 (s, 3H), 3.10-3.22 (m, 2H), 3.18 (q, J=7.3, 12H), 3.55 (br s, 2H), 3.72-3.88 (m, 4H), 3.99 (br s, 1H), 4.28 (br s, 1H), 4.98 (br s, 1H), 5.25 (br s, 1H), 5.83 (br s, 2H), 5.96-6.16 (m, 2H), 6.43 (br s, 1H), 7.35 (br s, 1H); $^{31}$PNMR (162 MHz, D$_2$O): δ 20.81; Mass (M−H):1163.

Scheme 15. Preparation of 3-[(tetraethylbisphosphonomethyl)carbamoyl]propanoic acid

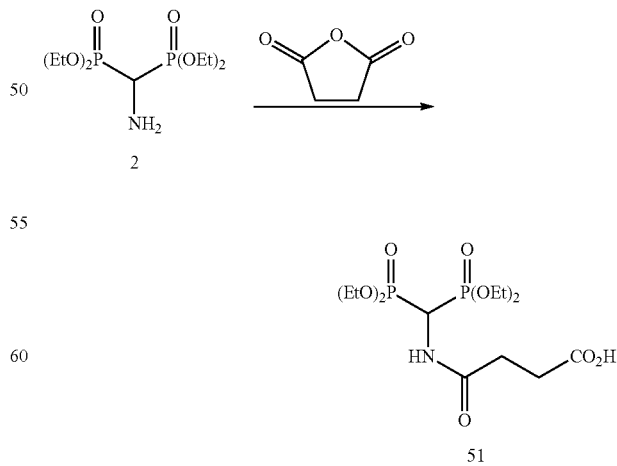

3-[(tetraethylbisphosphonomethyl)carbamoyl]propanoic acid (51): Compound 51 was prepared as described in *J. Drug*

Targeting, 1997, 5, 129-138. It was obtained as an oil which slowly solidified, in 57% crude yield from 2. The crude product could be purified by chromatography (10% AcOH/EtOAc) to give a white solid. $^1$H NMR (400 MHz, CDCl$_3$) δ 1.31 (t, J=7.0, 6H), 1.33 (t, J=7.1, 6H), 2.61-2.73 (m, 4H), 4.05-4.28 (m, 8H), 5.07 (td, J=21.6, J=9.8, 1H), 7.90 (d, J=9.4, 1H).

mL) and H$_2$O (30 mL). The organic phase was collected and the aqueous layer was extracted two more times with CH$_2$Cl$_2$ (2×10 mL). The combined organic layers were washed with a saturated solution of NaCl (20 mL), dried over Na$_2$SO$_4$ and concentrated in vacuo. The crude product was purified by silica gel chromatography eluting with 1% to 5% MeOH in CH$_2$Cl$_2$ (linear gradient) to afford 1.2 g (1.1 mmol, 56%) of 52 as dark purple solid. $^1$H NMR (400 MHz, CDCl$_3$) δ −0.18

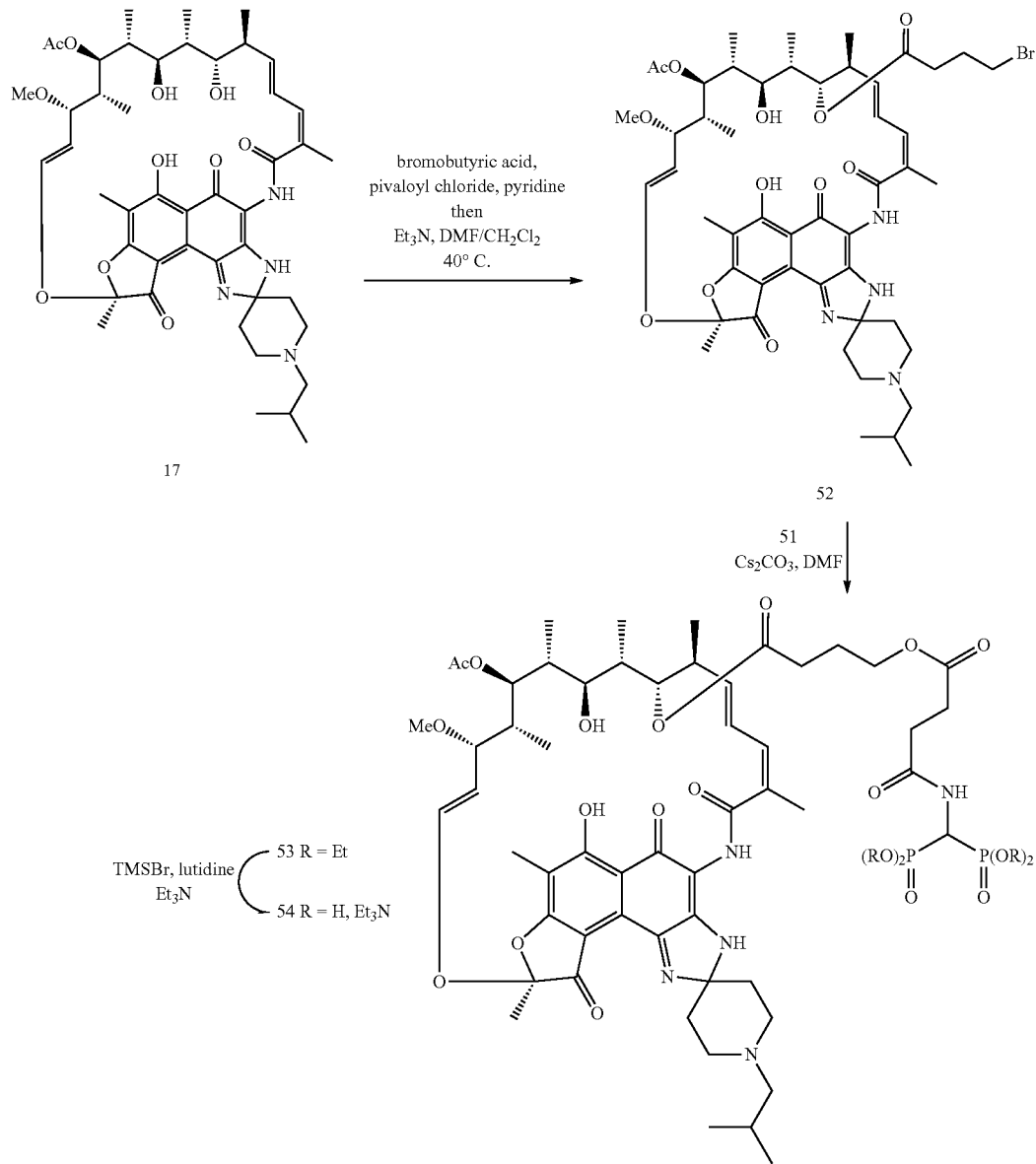

Scheme 16. Preparation of rifabutin-bisphosphonate conjugate 54

21-O-(4-bromobutanoyl)-1',4-didehydro-1-deoxy-1,4-dihydro-5'-(2-methylpropyl)-1-oxorifamycin XIV (52): Pivaloyl chloride (1.2 mL, 10 mmol) was added dropwise to a solution of 4-bromobutyric acid (1.7 g, 10 mmol) and pyridine (810 μL, 10 mmol) in CH$_2$Cl$_2$ (3 mL) and the resulting solution was stirred for 0.5 h before being filtered and added to a stirred solution of rifabutin (1.2 g, 2.0 mmol) and pyridine (320 μL, 4 mmol) in THF (5 mL). The resulting was stirred for 11 days under Ar at 40° C. before being diluted in CH$_2$Cl$_2$ (50

(d, J=7, 3H), 0.48 (d, J=7, 3H), 0.92 (d, J=7, 3H), 0.94 (m, 6H), 1.04 (d, J=7, 3H), 1.22 (m, 2H), 1.79 (s, 3H), 1.84-2.15 (m, 9H), 2.01 (s, 3H), 2.03 (s, 3H), 2.25-2.37 (m, 4H), 2.29 (s, 3H), 2.50 (m, 1H), 2.67 (m, 2H), 2.87 (m, 1H), 2.93-3.11 (m, 2H), 3.05 (s, 3H), 3.35-3.40 (m, 2H), 3.44 (m, 1H), 3.57-3.77 (m, 1H) 4.97 (d, J=10, 1H), 5.03 (dd, J=12, 5, 1H), 5.11 (d, J=10, 1H), 5.92 (dd, J=16, 7, 1H), 6.08 (d, J=12, 1H), 6.12 (d, J=11, 1H), 6.42 (dd, J=16, 11, 1H), 7.72 (bs, 1H), 8.35 (bs, 1H).

21-O-(4-((3-(bis(diethylphosphono)methyl)carbamoyl) propanoyloxy)butanoyl)-1',4-didehydro-1-deoxy-1,4-dihydro-5'-(2-methylpropyl)-1-oxorifamycin XIV (53): A solution of 51 (260 mg, 0.65 mmol), 52 (643 mg, 0.65 mmol) and $Cs_2CO_3$ (212 mg, 0.65 mmol) in DMF (1 mL) was stirred overnight at room temperature under Ar. The mixture was diluted in $CH_2Cl_2$ (20 mL), washed with water (10 mL) followed by brine (10 mL), dried over $Na_2SO_4$ and concentrated in vacuo. The crude product was used without further purification in the next step.

21-O-(4-((3-(bisphosphonomethyl)carbamoyl)propanoyloxy)butanoyl)-1',4-didehydro-1-deoxy-1,4-dihydro-5'-(2-methylpropyl)-1-oxorifamycin XIV (54): Compound 53 (maximum of 857 mg, 0.65 mmol) was dissolved in 20 mL of anhydrous dichloromethane at −78° C. To this solution was added 2,6-lutidine (3.8 mL, 32.5 mmol) followed by bromotrimethylsilane (2.2 mL, 16.3 mmol). The cooling bath was removed and the mixture was stirred at room temperature for over 20 h. Upon complete removal of the volatiles, the residue was taken up in the mixture of 50 mL of 0.1 N hydrochloric acid and 10 mL of acetonitrile and stirred at room temperature for 2 h. At the end of the treatment, the solution was brought to pH 7 by the addition of triethylamine. The organic volatiles were removed in vacuo and the residue was lyophilized. The resulting material was subjected to a C18 reverse phase flash chromatography with a linear gradient elution of 5% acetonitrile in 30 mM triethylamine/carbon dioxide aqueous solution (pH 6.8) to pure acetonitrile. For the fractions containing the product, the acetonitrile was removed in vacuo and the resulting aqueous solution was lyophilized to afford compound 54 as purple solid of bis-triethylammonium salt form (8.6 mg). LC/MS purity: 97.0% (254 nm), 96.4% (220 nm), 97.6% (320 nm). MS (M+H) 1206.4.

Scheme 17. Preparation of 3'-hydroxybenzoxazinorifamycin derivative 56.

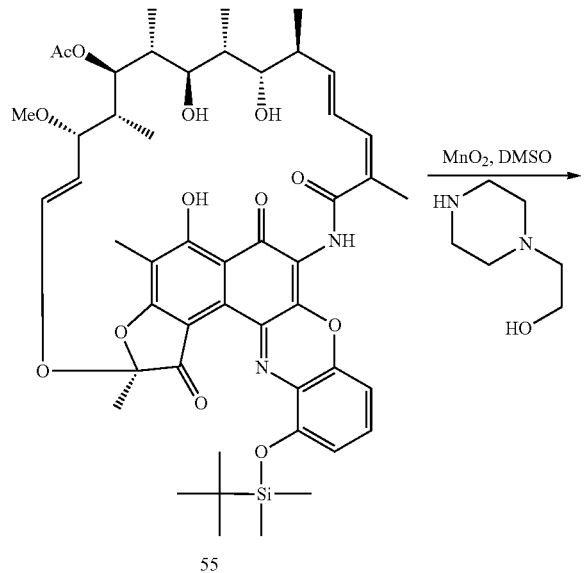

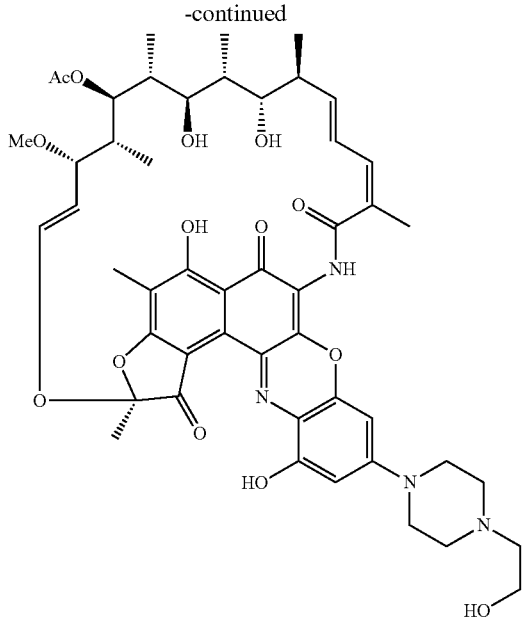

56

Preparation of 1',4-Didehydro-1-deoxy-1,4-dihydro-3'-tert-butyldimethylsilyloxy-1-oxorifamycin VIII (compound 37) is described by Yamane et al (Chem. Pharm. Bull. (1993), 41: 148-155).

1',4-Didehydro-1-deoxy-1,4-dihydro-3'-hydroxy-5'-[4-(2-hydroxyethyl)-1-piperazinyl]-1-oxorifamycin VIII (56): To a solution of 1',4-Didehydro-1-deoxy-1,4-dihydro-3'-tert-butyldimethylsilyloxy-1-oxorifamycin VIII (compound 55) (2.236 g, 2.44 mmol) in 60 mL of DMSO were added 1-(2-hydroxyethyl)piperazine (635 mg, 4.88 mmol) and manganese dioxide (2.227 g, 25.62 mmol). Within 30 min, the mixture turned from red to blue. After stirring overnight at room temperature, the mixture was filtered trough Celite and evaporated under vacuum to half the initial volume. The resulting mixture was poured in water and extracted with $CH_2Cl_2$. The organic extracts were washed with brine and dried over $MgSO_4$. After evaporation, the residue was purified by flash chromatography over $SiO_2$ (gradient from 0% to 10% MeOH/$CH_2Cl_2$) to yield 56 as a blue solid (975 mg, 43%). LCMS 98.0% (254 nm), 97.1% (220 nm), 96.3% (320 nm); mass calculated for $C_{49}H_{60}N_4O_{14}$ 929. found 929.2

Scheme 18. preparation of Tetraethyl (4-(2-(piperazin-4-yl)ethoxy)-4-oxo-butanoylamino)methylene-1,1-bisphosphonate.

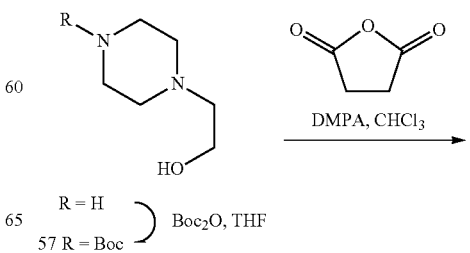

R = H  
57 R = Boc  } Boc$_2$O, THF

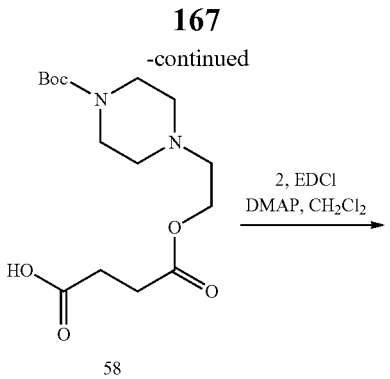

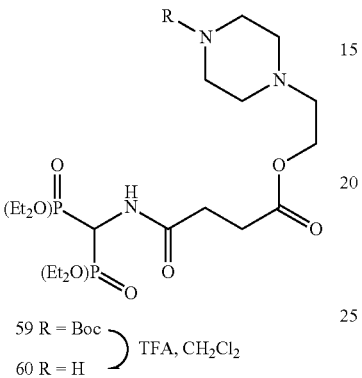

water (3×) and MeOH (3×) beforehand. The resin was filtered and the filtrate was concentrated to yield a colorless solid (0.85 g, quant.) which was used in the next step without further purification. $^1$H NMR (400 MHz, CDCl$_3$) δ 1.29 (t, J=7.1, 6H), 1.35 (t, J=7.1, 6H), 2.65-2.74 (m, 4H), 3.22-3.24 (m, 2H), 3.44-3.46 (m, 4H), 3.56-3.59 (m, 4H), 4.06-4.23 (m, 8H), 4.38-4.41 (m, 2H), 5.06 (dt, J=21.6, 10.0, 1H), 7.93 (d, J=10.1, 1H).

Scheme 19. Preparation of 3'-hydroxybenzoxazinorifamycin bisphosphonate conjugate 62.

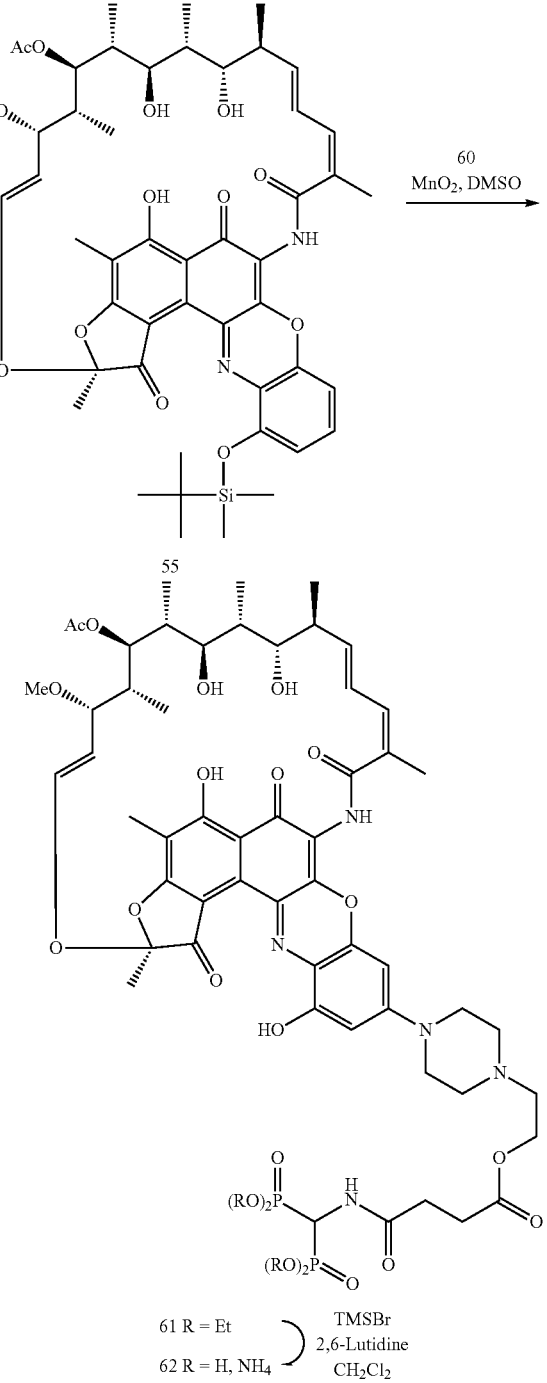

tert-butyl 4-(2-hydroxyethyl)piperazine-1-carboxylate (57): To 1-(2-hydroxyethyl)piperazine (3.0 g, 23.0 mmol) in THF was added di-tert-butyl dicarbonate (5.5 g, 25.3 mmol). The mixture was stirred for 2 hours. The solvent was evaporated under vacuum to half the initial volume and the mixture was poured in water, extracted with CH$_2$Cl$_2$, washed with brine, dried over Na$_2$SO$_4$ and concentrated to give a pale yellow oil (5.3 g, quant.). $^1$H NMR (400 MHz, CDCl$_3$) δ 1.46 (s, 9H), 2.44-2.46 (m, 4H), 2.54-2.57 (m, 2H), 2.66 (m, J=5.3, 1H), 3.42-3.45 (m, 4H), 3.62 (q, J=5.3, 2H).

1-(t-Butyloxycarbonyl)-4-(2-(4-hydroxy-4-oxo-butanoyloxy)ethyl)piperazine (58): Compound 57 (5.3 g, 23.0 mmol), succinic anhydride (2.30 g, 23.0 mmol) and 4-dimethylaminopyridine (281 mg, 2.30 mmol) were dissolved in CHCl$_3$ (14 mL) and stirred for 18 h. The solution was concentrated in vacuo and used without further purification. $^1$H NMR (400 MHz, CDCl$_3$) δ 1.42 (s, 9H), 2.54-2.60 (m, 8H), 2.72 (t, J=5.6, 2H), 3.43-3.46 (m, 4H), 4.23 (t, J=5.5, 2H).

Tetraethyl (4-(2-(1-(t-butyloxycarbonyl)-piperazin-4-yl) ethoxy)-4-oxo-butanoyl-amino)methylene-1,1-bisphosphonate (59): To a solution of compounds 2 (3.0 g, 9.9 mmol) and 58 (3.3 g, 9.9 mmol) in CH$_2$Cl$_2$ (50 mL) were added EDC (2.08 g, 10.9 mmol) and 4-dimethylaminopyridine (121 mg, 0.99 mmol). The resulting solution was stirred for 3 h under Ar at room temperature. The reaction mixture was poured into saturated NaHCO$_3$, the layers were separated, and the aqueous layer was extracted twice with CH$_2$Cl$_2$. The combined organic layers were washed with brine, dried over Na$_2$SO$_4$ and concentrated in vacuo. The residue was purified by flash chromatography over SiO$_2$ (gradient from 0% to 10% MeOH/CH$_2$Cl$_2$) to yield a pale yellow oil which solidifies over time (4.5 g, 74%). $^1$H NMR (400 MHz, CDCl$_3$) δ 1.33 (t, J=7.1, 12H), 1.45 (s, 9H), 2.42-2.44 (m, 4H), 2.55-2.60 (m, 6H), 3.41-3.43 (m, 4H), 4.14-4.25 (m, 10H), 5.00 (dt, J=21.7, 10.1, 1H), 6.18 (d, J=9.9, 1H).

Tetraethyl (4-(2-(piperazin-4-yl)ethoxy)-4-oxo-butanoylamino)methylene-1,1-bisphosphonate (60): Compound 59 (1.0 g, 1.62 mmol) was dissolved in a solution of 20% TFA/ CH$_2$Cl$_2$ (8 mL). The solution was stirred at room temperature until no starting material remained (TLC monitoring). Volatiles were removed under vacuum. The TFA salt was dissolved in MeOH and treated with 13 cc of Dowex 1×2 Cl$^-$ form resin, which was washed with saturated NaHCO$_3$ (3×), 3'-hydroxybenzoxazinorifamycin bisphosphonate conjugate 61: Compound 60 (2.37 g, 4.59 mmol) was added to a solution of 55 (2.8 g, 3.06 mmol) in dry DMSO (16 mL). NaHCO$_3$ (2.57 g, 30.6 mmol) and MnO$_2$ (2.66 g, 30.6 mmol) were added. The mixtured was stirred under Ar for 9 days at 40° C. The reaction mixture was diluted with CH$_2$Cl$_2$, most solids were removed by filtration over celite. Solids were washed with CH$_2$Cl$_2$ and combined organic layers were washed with half-saturated brine. The organic layer was separated and filtered over paper to remove the remaining fine black solid. The filtrate was washed with water, brine, dried over MgSO$_4$. After evaporation, the residue was purified by flash chromatography over SiO$_2$ (gradient from 0% to 10% MeOH/CH$_2$Cl$_2$) to yield 61 as a blue solid (1.3 g, 33%). LCMS purity: 96.3% (254 nm), 95.9% (220 nm), 94.2% (320 nm); mass calculated for C$_{62}$H$_{85}$N$_5$O$_{22}$P$_2$ 1313. found 1312.0 (M–H)$^-$. Desilylated 37 was also recovered as a dark red solid (1.1 g, 45%).

3'-hydroxybenzoxazinorifamycin bisphosphonate conjugate 62: To a solution of 61 (168 mg, 0.13 mmol) and 2,6-lutidine (594 µL, 5.11 mmol) in CH$_2$Cl$_2$ (5 mL) at –78° C. was added dropwise TMSBr (337 µL, 2.55 mmol) under argon. The cold bath was removed and the mixture was stirred for 24 hours at room temperature. The solvent was removed under vacuum until dryness. The residue was dissolved in aqueous 50 mM NH$_4$OAc/AcOH buffer (pH 5) and stirred for 18 hours at room temperature and the sample was lyophilized. The crude residue was purified by reverse phase flash chromatography at pH 5 (linear gradient of 5% to 100% acetonitrile in aqueous 50 mM NH$_4$OAc/AcOH buffer). Combined pure fractions were concentrated and lyophilized to yield 62 as a dark blue bis-ammonium salt (120 mg, 76%). LCMS purity: 96.2% (254 nm), 96.6% (220 nm), 96.3% (320 nm); mass calculated for C$_{54}$H$_{69}$N$_5$O$_{22}$P$_2$ 1201. found 1200.3 (M–H)$^-$.

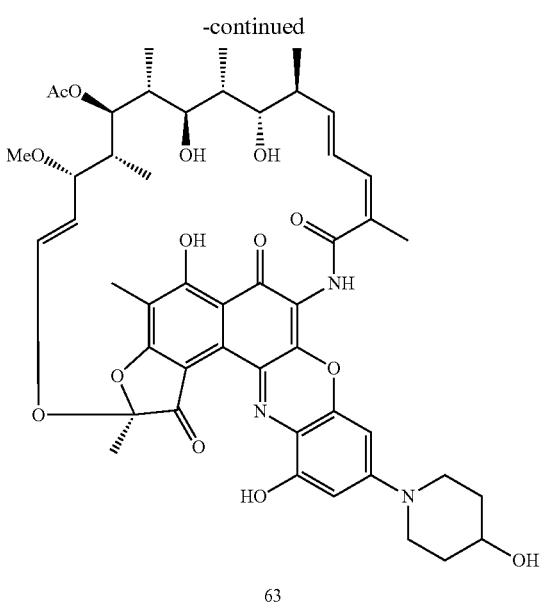

63

1',4-Didehydro-1-deoxy-1,4-dihydro-3'-hydroxy-5'-[4-hydroxy-1-piperidinyl]-1-oxorifamycin VIII (63): To a stirred solution of 55 (0.60 g, 0.65 mmol) in dry DMSO (10 mL) was added 4-hydroxypiperidine (0.132 g, 1.31 mmol) and MnO$_2$ (0.57 g, 6.56 mmol). The mixture was stirred at room temperature for 24 h. The reaction mixture was diluted with ethyl acetate (100 mL), filtered through celite and washed through with ethyl acetate (100 mL). The combined filtrates were washed successively with water (2×75 mL), brine (2×75 mL), dried over Na$_2$SO$_4$ and concentrated. The residue was purified by flash chromatography over SiO$_2$ (8% MeOH/CH$_2$Cl$_2$) to yield 63 as a blue solid (197 mg, 33%). LCMS purity: 97.8% (254 nm), 95.1% (220 nm), 97.1% (320 nm); Mass calculated for C$_{48}$H$_{57}$N$_3$O$_{14}$: 899. found: 898 (M–H).

Scheme 20. Preparation of 3'-hydroxybenzoxazinorifamycin derivative 63.

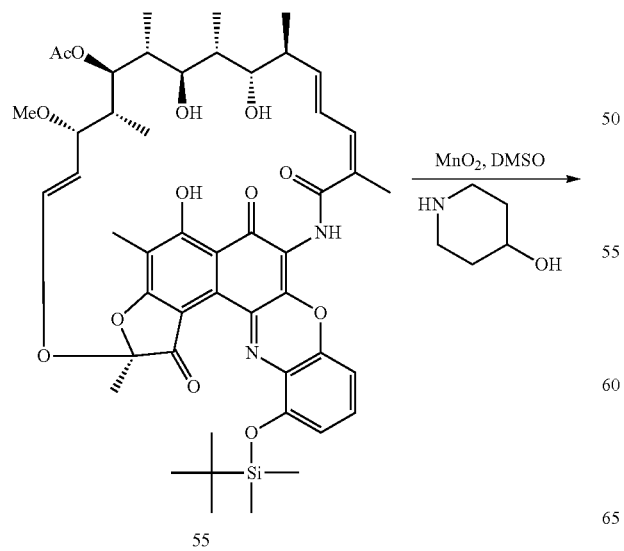

55

Scheme 21. Preparation of Tetraethyl (4-(2-(1-benzyloxycarbonyl)-piperidin-4-yl)ethoxy)-4-oxo-butanoyl-amino)methylene-1,1-bisphosphonate

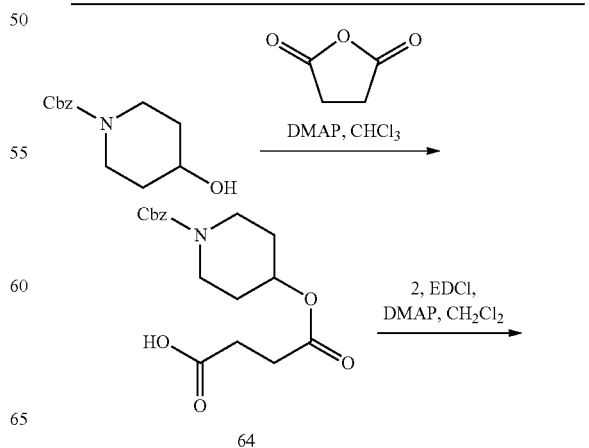

64

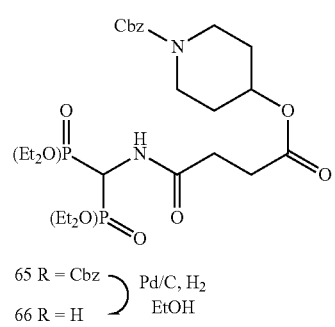

65 R = Cbz  ⎤ Pd/C, H₂
66 R = H   ⎦ EtOH 3-((1-((benzyloxy)carbonyl)piperidin-4-yloxy)carbonyl) propanoic acid (64): Benzyl 4-hydroxy-1-piperidinecarboxylate (1.0 g, 4.25 mmol), succinic anhydride (0.425 g, 4.25 mmol) and 4-DMAP (52 mg, 0.425 mmol) were dissolved in CHCl₃ (10 mL) and stirred for 24 hours. The volatiles were removed in vacuo. Aqueous NaHCO₃ (100 mL) was added and the mixture was washed with Et₂O (2×50 mL). The aqueous layer was acidified to pH=6 to 7 with 2N HCl and extracted with CH₂Cl₂ (2×60 mL). The combined organic extracts were washed with brine (60 mL), dried over Na₂SO₄ and concentrated in vacuo to afford compound 64 (768 mg, 54%) which was used without further purification. ¹H NMR (400 MHz, CDCl₃) δ 1.62 (m, 2H), 1.85 (m, 2H), 2.60-2.70 (m, 4H), 3.38 (m, 2H), 3.74 (m, 2H), 4.97 (m, 1H), 5.12 (s, 2H), 7.35 (m, 5H).

Tetraethyl (4-(1-(benzyloxycarbonyl)-piperidin-4-yloxy)-4-oxo-butanoyl-amino)methylene-1,1-bisphosphonate (65): To a stirred solution of compounds 64 (0.76 g, 2.26 mmol) and 2 (0.687 g, 2.26 mmol) in CH₂Cl₂ (10 mL) were added EDC (0.52 g, 2.72 mmol) and 4-DMAP (55 mg, 0.45 mmol). The resulting solution was stirred for 16 h under nitrogen at room temperature. The reaction mixture was diluted with CH₂Cl₂, washed with aqueous NaHCO₃ (2×50 mL), brine (50 mL) and dried over Na₂SO₄. After evaporation, the residue was purified by flash chromatography over SiO₂ with 5% MeOH/CH₂Cl₂ to yield the product 65 (1.20 g, 85%). ¹H NMR (400 MHz, CDCl₃) δ 1.33 (t, J=7.1 Hz, 12H), 1.62 (m, 2H), 1.85 (m, 2H), 2.57-2.62 (m, 4H), 3.35 (m, 2H), 3.76 (m, 2H), 4.16 (m, 8H), 4.90-5.08 (m, 2H), 5.12 (s, 2H), 6.33 (d, J=9.8 Hz, 1H), 7.35 (m, 5H).

Tetraethyl (4-(piperidin-4-yl)-4-oxo-butanoyl-amino)methylene-1,1-bisphosphonate (66): To a solution of compound 65 (1.20 g, 1.93 mmol) in EtOH (20 mL) was added 10% Pd/C (200 mg) and the mixture was stirred under an atmosphere of hydrogen for 3.5 h. The catalyst was filtered through celite, washed with ethanol and the filtrates were concentrated to dryness to give 66 (1.0 g) which was used in the next step without further purification. ¹H NMR (400 MHz, CDCl₃) δ 1.33 (t, J=7.1 Hz, 12H), 1.82 (m, 2H), 2.08 (m, 2H), 2.64 (s, 4H), 3.02 (m, 2H), 3.20 (m, 2H), 4.16 (m, 8H), 4.90-5.08 (m, 2H), 6.88 (d, J=9.8 Hz, 1H).

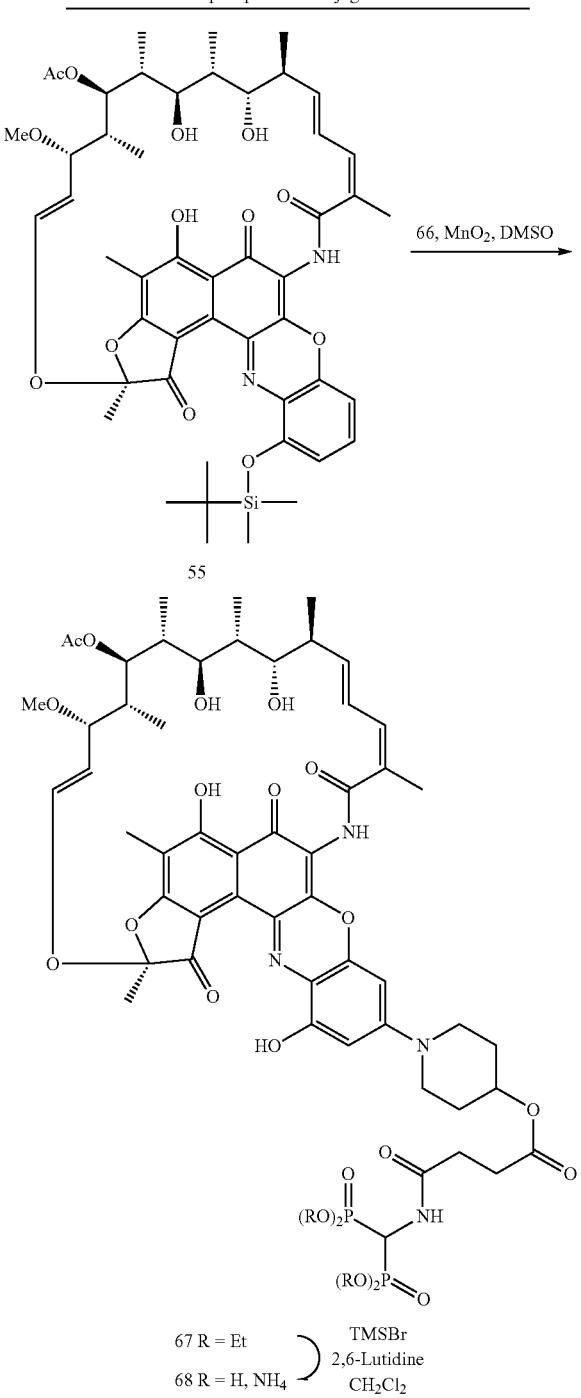

Scheme 22. Preparation of 3'-hydroxybenzoxazinorifamycin bisphosphonate conjugate 68.

3'-hydroxybenzoxazinorifamycin bisphosphonate conjugate 67: MnO₂ (1.45 g, 16.66 mmol) was added to a stirred solution of 55 (1.52 g, 1.66 mmol) and compound 66 (0.81 g, 1.66 mmol) in dry DMSO (20 mL). The mixture was stirred under argon for 4 days at room temperature. The reaction mixture was diluted with CH₂Cl₂ (50 mL), filtered through celite and washed through with further CH$_2$Cl$_2$ (100 mL) and the combined filtrates were washed successively with water (3×100 mL) and brine (2×100 mL), dried over Na$_2$SO$_4$ and concentrated. The residue was purified by flash chromatography over SiO$_2$ (gradient from 0% to 5% MeOH/ CH$_2$Cl$_2$) to yield 67 as a blue solid (0.42 g, 19.7%). LCMS Mass calculated for C$_{61}$H$_{82}$N$_4$O$_{22}$P$_2$: 1284. found: 1285 (M+H).

3'-hydroxybenzoxazinorifamycin bisphosphonate conjugate 68: To a solution of 67 (0.42 g, 0.32 mmol) in 10 mL of anhydrous dichloromethane at −78° C. was added 2,6-lutidine (1.52 mL, 13.08 mmol) followed by bromotrimethylsilane (0.86 mL, 6.54 mmol). The mixture was stirred at room temperature for 24 h. Upon the removal of the solvent, the residue was dissolved in 8 mL of 50 mM NH$_4$OAc/AcOH buffer (pH=5) and stirred at room temperature for 20 h and lyophilized. The residue was dissolved in water and filtered to remove insolubles. The resulting solution was subjected to a C18 reverse phase flash chromatography with a linear gradient elution of 5% acetonitrile in 50 mM NH$_4$OAC/AcOH buffer (pH=5) to pure acetonitrile. For the fractions containing only the product, the acetonitrile was removed in vacuo and the resulting aqueous solution was lyophilized to afford compound 68 as a dark blue solid (0.31 g, 81%). LCMS 97.9% (254 nm), 97.7% (220 nm), 96.4% (320 nm); Mass calculated for C$_{53}$H$_{66}$N$_4$O$_{22}$P$_2$: 1172. found: 1171 (M−H).

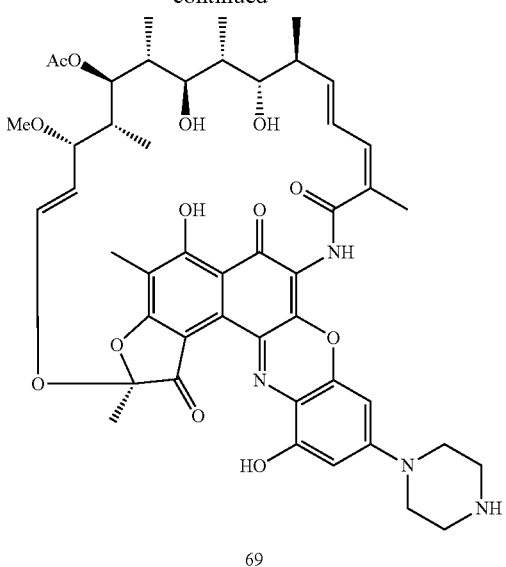

69

1',4-Didehydro-1-deoxy-1,4-dihydro-3'-hydroxy-5'-[1-piperazinyl]-1-oxorifamycin VIII (69): To a stirred solution of 55 (3.0 g, 3.28 mmol) in dry DMSO (60 mL) were added piperazine (1.13 g, 13.12 mmol) and MnO$_2$ (2.85 g, 32.82 mmol). The mixture was stirred for 48 h, diluted with CH$_2$Cl$_2$ (200 mL), filtered through celite and washed through with further CH$_2$Cl$_2$ (200 mL). The combined filtrate was washed successively with water (2×300 mL) and brine (2×200 mL), dried over Na$_2$SO$_4$ and concentrated. The residue was purified by flash chromatography over SiO$_2$ (gradient from 10% to 20% MeOH/CH$_2$Cl$_2$) to yield 69 as a blue solid (2.28 g, 78%). LCMS 99.2% (254 nm), 99.3% (220 nm), 99.2% (320 nm); Mass calculated for C$_{47}$H$_{56}$N$_4$O$_{13}$: 884. found: 883 (M−H).

Scheme 23. Preparation of 3'-hydroxybenzoxazinorifamycin derivative 69.

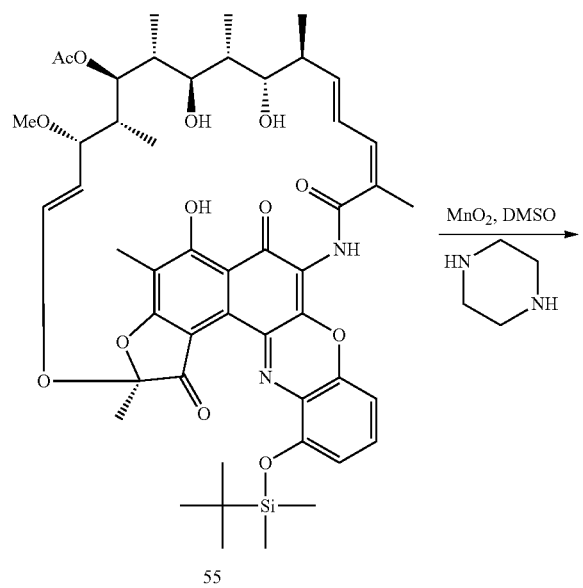

55

Scheme 24. Preparation of 3'-hydroxybenzoxazinorifamycin bisphosphonate conjugate 71

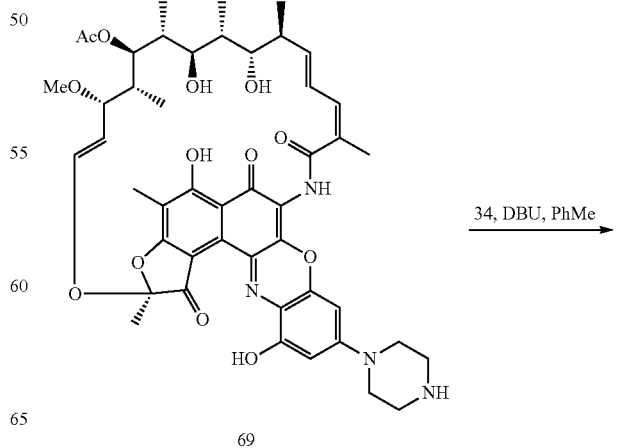

69

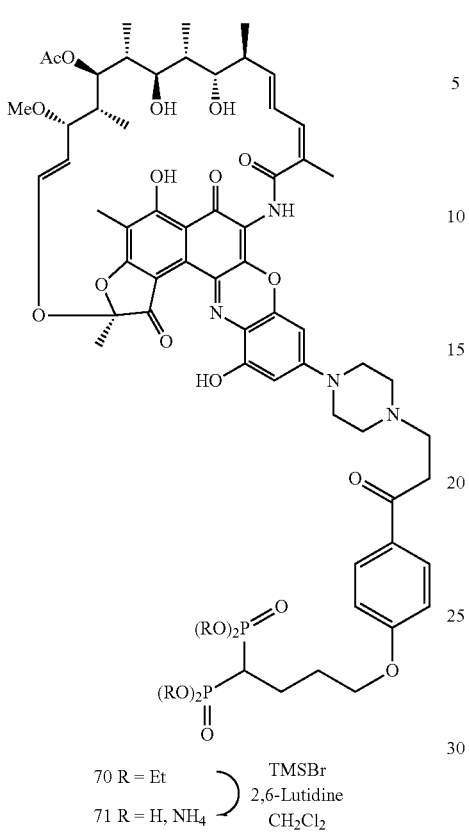

70 R = Et
71 R = H, NH₄

TMSBr
2,6-Lutidine
CH₂Cl₂

3'-hydroxybenzoxazinorifamycin bisphosphonate conjugate 70: A mixture of compound 69 (1.92 g, 2.17 mmol), compound 34 (1.03 g, 2.17 mmol) and DBU (0.714 mL, 4.77 mmol) in 25 mL of toluene was stirred at room temperature for 16 h and the volatiles were removed under reduced pressure. The residue was dissolved in CH₂Cl₂ (200 mL) and washed with saturated ammonium chloride aqueous solution (2×80 mL), brine (1×80 mL), dried over Na₂SO₄, and concentrated under reduced pressure. Flash chromatography on silica gel with gradient elution using 0-6% methanol/dichloromethane afforded the product 70 (1.92 g, 65%). LCMS: Mass calculated for $C_{68}H_{90}N_4O_{21}P_2$: 1360, found: 1361 (M+H).

3'-hydroxybenzoxazinorifamycin bisphosphonate conjugate 71: Compound 70 (1.92 g, 1.41 mmol) was dissolved in 25 mL of anhydrous dichloromethane. To this solution was added triethylamine (9.83 mL, 70.58 mmol) followed by bromotrimethylsilane (4.65 mL, 35.29 mmol). The mixture was stirred at room temperature for 23 h. Upon the removal of the solvent, the residue was taken up in a mixture of 70 mL of 0.1 N hydrochloric acid and 70 mL of acetonitrile and stirred at room temperature for 3 h, then neutralized with triethylamine. The organic solvents were removed in vacuo and the residue was lyophilized. The residue was dissolved in water and filtered to remove insolubles. The resulting filtrate was subjected to a C18 reverse phase flash chromatography with the linear gradient elution of 0-40% acetonitrile in 30 mM triethylamine/carbon dioxide aqueous solution (pH 6.8) to pure acetonitrile. For the fractions containing the product, the acetonitrile was removed in vacuo and the resulting aqueous solution was lyophilized to afford compound 71 as a dark blue solid (0.82 g, 46%). LCMS purity: 96.0% (254 nm), 92.1% (220 nm), 95.5% (320 nm); Mass calculated for $C_{60}H_{74}N_4O_{21}P_2$: 1248. found: 1247 (M−H).

Scheme 25. Preparation of tetraethyl (3-aminopropanoylamino) methylene-1,1-bisphosphonate

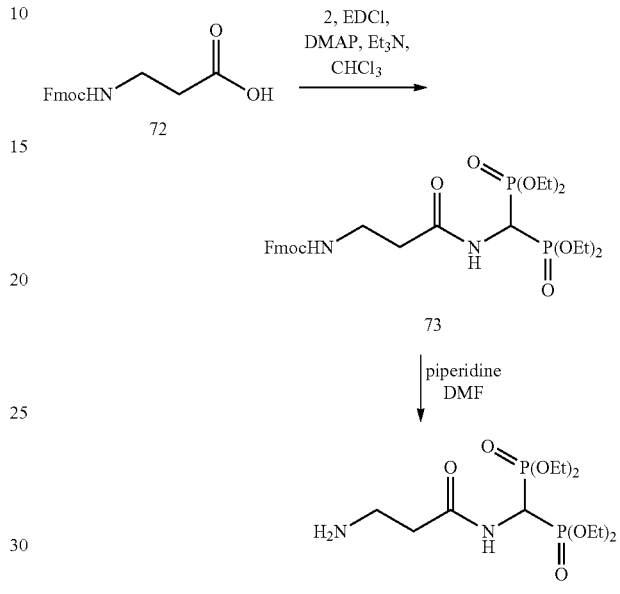

Tetraethyl (3-(((9h-fluoren-9-yl)methoxy)carbonylamino) propanoylamino)methylene-1,1-bisphosphonate (73): To a solution of compounds 72 (200 mg, 0.642 mmol) and 2 (195 mg, 0.642 mmol) in anhydrous and ethanol-free CHCl₃ (5 mL) were added EDCl (147 mg, 0.77 mmol) and DIPEA (0.14 ml, 0.77 mmol). The resulting solution was stirred overnight under Ar at room temperature. The reaction mixture was concentrated to dryness and the residue was purified by flash chromatography over SiO₂ (gradient from 5% to 15% MeOH/CH₂Cl₂) to yield a colorless gum (240 mg, 65%). ¹H NMR (400 MHz, CDCl₃) δ 1.30-1.34 (m, 12H), 2.50-2.24 (m, 2H), 3.51-3.54 (m, 2H), 4.14-4.24 (m, 8H), 4.36 (d, J=7.0 Hz, 2H), 5.03 (dt, J=22.0, 9.9 Hz, 1H), 5.66 (br s, 1H), 6.21 (br s, 1H), 7.30 (t, J=7.3 Hz, 2H), 7.39 (t, J=7.7 Hz, 2H), 7.59 (d, J=7.3 Hz, 2H), 7.75 (d, J=7.3 Hz, 2H); ³¹PNMR (162 MHz, CDCl₃): δ 17.46.

Tetraethyl (3-aminopropanoylamino)methylene-1,1-bisphosphonate (74): Piperidine (1.5 ml, 15.15 mmol) was added to a solution of compound 73 (240 mg, 0.402 mmol) in DMF (3.5 mL). The resulting solution was stirred for 1 h under Ar at room temperature. The reaction mixture was concentrated to dryness and the residue was purified by flash chromatography over SiO₂ (gradient from 5% to 15% MeOH/ CH₂Cl₂) to yield a colorless gum (78 mg, 64%). ¹H NMR (400 MHz, CDCl₃) δ 1.27-1.31 (m, 12H), 2.38-2.40 (m, 3H), 3.00 (m, 2H), 4.11-4.21 (m, 8H), 5.04 (t, J=22.0 Hz, 1H), 8.20 (bs, 1H); ³¹PNMR (162 MHz, CDCl₃): δ 17.82.

Scheme 26. Preparation of rifalazil bisphosphonate conjugate 78
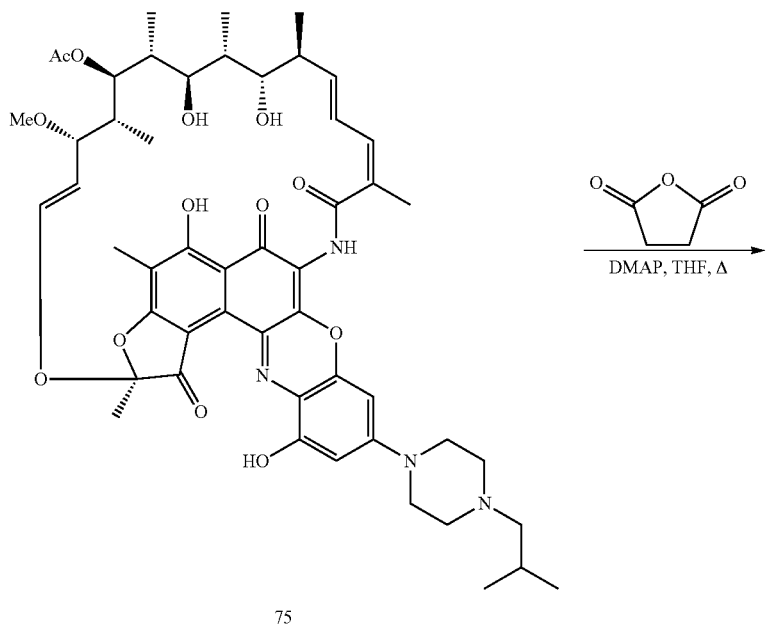
75
76
74, EDCl,
Et$_3$N, DMAP,
CHCl$_3$ -continued

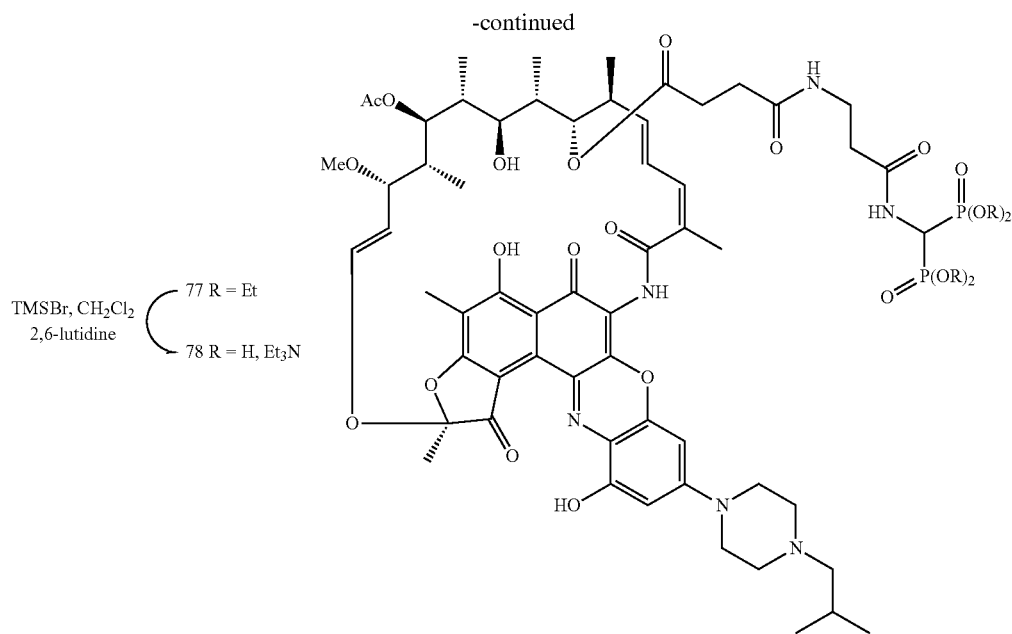

Preparation of 1',4-Didehydro-1-deoxy-1,4-dihydro-3'-hydroxy-5'-[4-(2-methylpropyl)-1-piperazinyl]-1-oxorifamycin VIII (compound 75) is described by Yamane et al (Chem. Pharm. Bull. (1993), 41: 148-155).

21-O-(3-carboxypropanoyl)-1',4-Didehydro-1-deoxy-1,4-dihydro-3'-hydroxy-5'-(4-[2-methylpropyl)-1-piperazinyl]-1-oxorifamycin VIII (76): To a solution of compound 75 (400 mg, 0.425 mmol) in anhydrous THF (50 mL) were added succinic anhydride (376 mg, 3.74 mmol) and DMAP (60 mg, 0.49 mmol). The resulting solution was heated to reflux overnight. The reaction mixture was concentrated to dryness and the residue was purified by flash chromatography over $SiO_2$ (50/45/5, Hexanes/EtOAc/MeOH) to yield a deep blue solid (323 mg, 73%). $^1$HNMR (400 MHz, $CDCl_3$): δ −0.35 (d, J=7.0 Hz, 3H), −0.06 (d, J=7.0 Hz, 3H), 0.90-0.99 (m, 15H), 1.62 (m, 1H), 1.73-1.77 (m, 2H), 1.82 (s, 3H), 1.97 (s, 3H), 2.13 (s, 3H), 2.14- (m, 4H), 2.31 (s, 3H), 2.49-2.61 (m, 7H), 2.75 (m, 1H), 2.99 (s, 3H), 3.35 (d, J=7.3 Hz, 1H), 3.53 (bs, 3H), 4.69 (d, J=10.6 Hz, 1H), 4.96 (d, J=11.0 Hz, 1H), 5.04 (dd, J=12.9, 7.3 Hz, 1H), 5.97 (dd, J=16.1, 7.3 Hz, 1H), 6.19-6.26 (m, 2H), 6.34 (s, 1H), 6.46 (s, 1H), 6.83 (dd, J=16.1, 11.0 Hz, 1H), 7.90 (s, 1H), 10.23 (s, 1H); mass calculated for $C_{55}H_{68}N_4O_{16}$ 1041. found 1042 (M+H)⁻.

21-O-(3-(2-((bis(diethylphosphono)methyl)carbamoyl)ethylcarbamoyl)propanoyl)-1',4-Didehydro-1-deoxy-1,4-dihydro-3'-hydroxy-5'-[4-(2-methylpropyl)-1-piperazinyl]-1-oxorifamycin VIII (77): To a solution of compounds 76 (268 mg, 0.257 mmol) and 74 (78 mg, 0.257 mmol) in anhydrous and ethanol-free $CHCl_3$ (10 mL) were added EDCl (100 mg, 0.514 mmol) and DMAP (63 mg, 0.514 mmol). The resulting solution was stirred overnight under Ar at room temperature. The reaction mixture was concentrated to dryness and the residue was purified by flash chromatography over $SiO_2$ (eluant $CH_2Cl_2$/AcOEt/MeOH, 50/40/10) to yield a blue solid (52 mg, 15%). $^1$HNMR (400 MHz, $CDCl_3$): δ −0.37 (d, J=7.0 Hz, 3H), −0.03 (d, J=7.0 Hz, 3H), 0.90-0.99 (m, 15H), 1.33 (m, 12H), 1.52-1.75 (m, 2H), 1.80 (s, 3H), 1.95 (s, 3H), 2.09-2.79 (m, 28H), 2.97 (s, 3H), 3.32-3.69 (m, 10H), 4.19 (m, 8H), 4.75 (d, J=11.0 Hz, 1H), 4.99-5.14 (m, 3H), 5.97 (dd, J=16.1, 7.3 Hz, 1H), 6.23 (dd, J=22.0, 11.0 Hz, 2H), 6.31 (s, 1H), 6.45 (s, 1H), 6.88-6.92 (m, 3H), 7.03 (m, 1H), 7.68 (s, 1H), 10.11 (s, 1H). $^{31}$PNMR (162 MHz, $CDCl_3$): δ 18.21; mass calculated for $C_{67}H_{94}N_6O_{22}P_2$ 1396. found 1398.2 (M+2H)⁻.

21-O-(3-(2-((bisphosphonomethyl)carbamoyl)ethylcarbamoyl)propanoyl)-1',4-Didehydro-1-deoxy-1,4-dihydro-3'-hydroxy-5'-[4-(2-methylpropyl)-1-piperazinyl]-1-oxorifamycin VIII (78): Compound 77 (50 mg, 0.0358 mmol) was dissolved in 10 mL of dichloromethane and 0.21 mL (1.789 mmol) of 2,6-lutidine was added followed by 116 uL (0.8945 mmol) of TMSBr. The red mixture was stirred for at least 48 hours at room temperature and was concentrated to dryness. After drying under high vacuum for at least 120 min, the solid material was taken up in the mixture of 2.15 mL of 0.1 N HCl and 2.5 mL of acetonitrile and stirred at room temperature for 2 h, at which time a clear solution was obtained. After basification by the addition of 0.05 mL of triethylamine (end pH=7.0), the organic volatiles were carefully removed under vacuum and the insoluble material was filtered off. The filtrate was lyophilized and the residue was subjected to a C18 column on a Biotage® automated flash chromatography system with a gradient elution of 10-60% MeCN in 30 mM triethylammonium bicarbonate buffer (pH=6.5) over 15 column volumes to afford 78 as a dark blue solid (15 mg, 30%) as the bistriethylammonium salt. $^1$H-NMR (400 MHz, $CDCl_3$): key signals δ −0.57 (bs, 3H), −0.38 (bs, 3H), 0.88 (s, 6H), 1.16 (t, 18H), 3.05 (q, 12H), 4.20 (t, 1H); $^{31}$PNMR (162 MHz, $CDCl_3$): δ 14.02; LCMS purity: 99.0% (254 nm), 98.5% (220 nm), 99.1% (320 nm); mass calculated for $C_{59}H_{78}N_6O_{22}P_2$ 1284. found 1283.2 (M−H)⁻.

Scheme 27. Preparation of rifalazil bisphosphonate conjugate 81
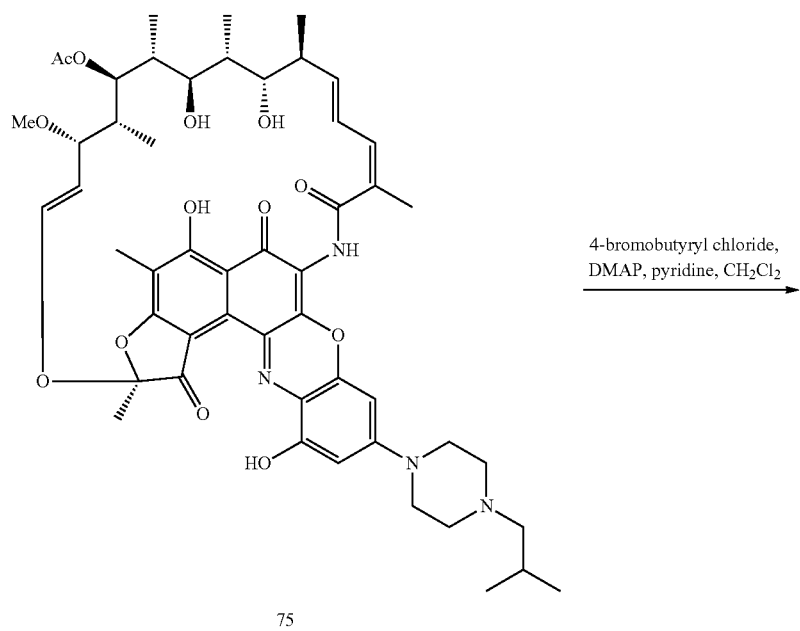
75
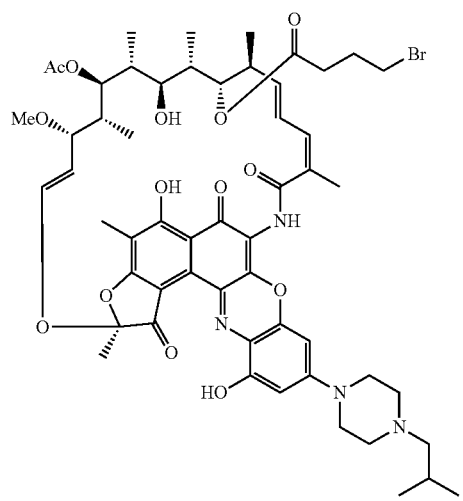
79
51
Cs₂CO₃, DMF

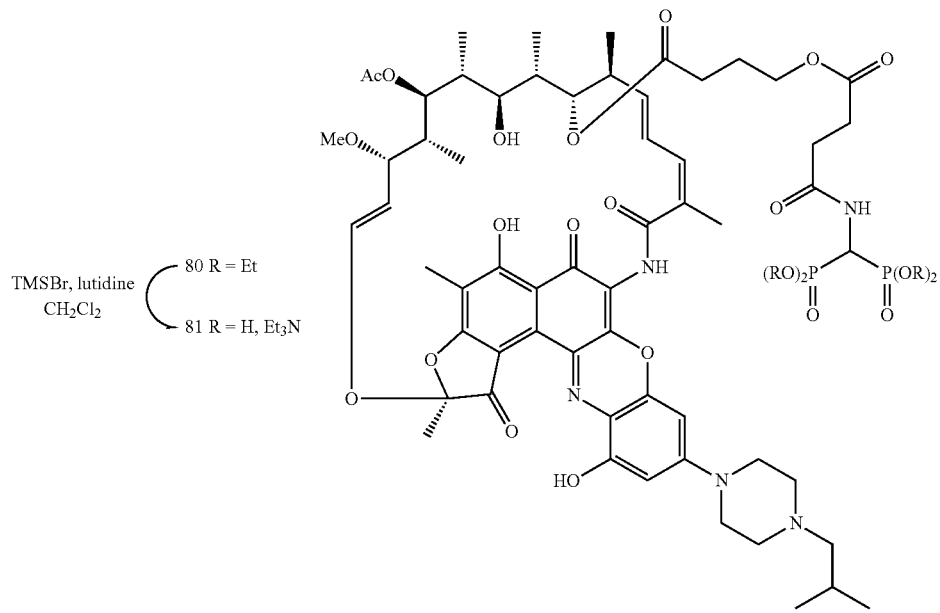

21-O-(4-bromobutanoyl)-1',4-Didehydro-1-deoxy-1,4-dihydro-3'-hydroxy-5'-[4-(2-methylpropyl)-1-piperazinyl]-1-oxorifamycin VIII (79): 4-Bromobutyryl chloride (2.18 mL, 18.82 mmol) was added drop wise to a cooled (0° C.) solution of rifalzil (11.80 g, 12.55 mmol), pyridine (3.04 mL, 37.65 mmol) and DMAP (153 mg, 1.25 mmol) in dichloromethane (150 mL). After stirring for 16 h at ambient temperature, the reaction mixture was diluted with dichloromethane (800 mL) and washed successively with water (2×500 mL) and brine (2×500 mL), dried over $Na_2SO_4$, filtered and concentrated to dryness. The residue was purified by silica gel chromatography with 60-100% ethyl acetate/hexanes and then 1-5% $MeOH/CH_2Cl_2$ to afford 79 (12.40 g, 90% yield). Mass calculated for $C_{55}H_{69}BrN_4O_{14}$: 1090. found: 1091 (M+H).

21-O-(4-((3-(bis(diethylphosphono)methyl)carbamoyl)propanoyloxy)butanoyl)-1',4-Didehydro-1-deoxy-1,4-dihydro-3'-hydroxy-5'-[4-(2-methylpropyl)-1-piperazinyl]-1-oxorifamycin VIII (80): A mixture of 79 (12.40 g, 11.37 mmol), 51 (4.58 g, 11.37 mmol), and $Cs_2CO_3$ (3.70 g, 11.37 mmol) in dry DMF (150 mL) was stirred at room temperature for 16 h. The reaction mixture was diluted with water and extracted with ethyl acetate (2×700 mL). The combined organic extracts were washed with brine (2×700 mL), dried over $Na_2SO_4$ and concentrated to dryness. The residue was purified by flash chromatography over $SiO_2$ with 5% $MeOH/CH_2Cl_2$ to yield the product 80 (9.20 g, 57% yield). LCMS: Mass calculated for $C_{68}H_{95}N_5O_{23}P_2$: 1411. found: 1412 (M+H).

21-O-(4-((3-(bisphosphonomethyl)carbamoyl)propanoyloxy)butanoyl)-1',4-Didehydro-1-deoxy-1,4-dihydro-3'-hydroxy-5'-[4-(2-methylpropyl)-1-piperazinyl]-1-oxorifamycin VIII (81): To a solution of 80 (9.20 g, 6.52 mmol) and 2,6-lutidine (30.37 mL, 260.80 mmol) in $CH_2Cl_2$ (180 mL) at −78° C. was added dropwise bromotrimethylsilane (17.21 mL, 130.40 mmol) under argon. The cold bath was removed and the mixture was stirred for 24 h at room temperature. The volatiles were removed under vacuum until dryness. The residue was dissolved in 240 mL of aqueous 50 mM $NH_4OAc/AcOH$ buffer (pH 5) and stirred for 18 hours at room temperature and the sample was lyophilized. The resultant material was subjected to a C18 reverse phase flash chromatography with the linear gradient elution of 0 to 100% acetonitrile in 50 mM $NH_4OAc/AcOH$ buffer (pH=5). The fractions containing the product were mixed, the acetonitrile was removed in vacuo and the resulting aqueous solution was lyophilized to afford compound 81 as a dark blue solid (5.30 g, 62% yield). LCMS: 94.2% (254 nm), 94.2% (220 nm), 94.2% (320 nm); Mass calculated for $C_{60}H_{79}N_5O_{23}P_2$: 1299. found: 1298 (M−H).

Scheme 28. Preparation of rifalazil bisphosphonate conjugate 84
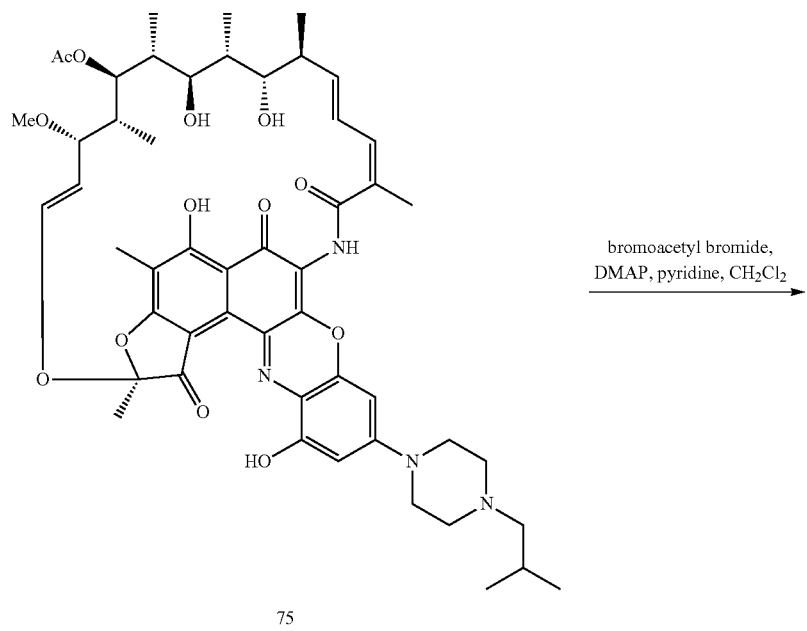
75
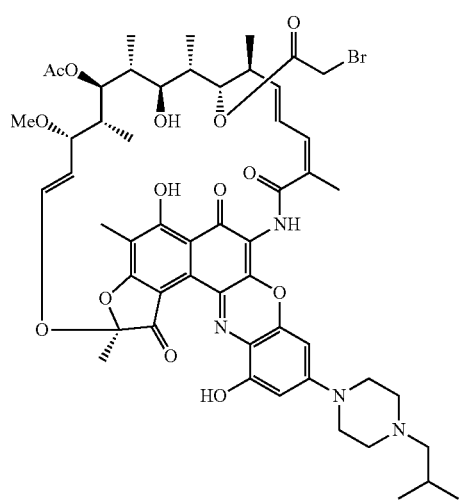
82
51
Cs$_2$CO$_3$, DMF -continued

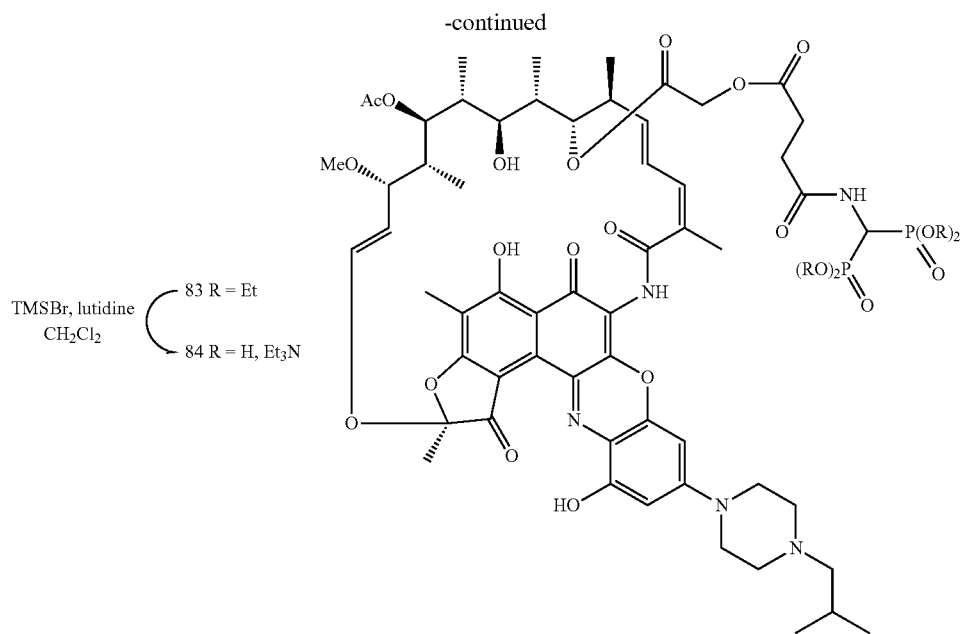

21-O-(2-bromoacetyl)-1',4-Didehydro-1-deoxy-1,4-dihydro-3'-hydroxy-5'-[4-(2-methylpropyl)-1-piperazinyl]-1-oxorifamycin VIII (82): Bromoacetyl bromide (37 µL, 0.42 mmol) was added drop wise to a solution of rifalzil (200 mg, 0.21 mmol), DMAP (31 mg, 0.25 mmol) in dichloromethane (10 mL) cooled in an ice bath. After stirring for 16 h at ambient temperature, the reaction mixture was diluted with dichloromethane (800 mL) and washed successively with water (2×500 mL) and brine (2×500 mL), dried over $Na_2SO_4$ and concentrated to dryness. The residue was purified by silica gel chromatography with 60-100% ethyl acetate/hexanes and then 2-6% $MeOH/CH_2Cl_2$ to afford 79 (200 mg, 88% yield). Mass calculated for $C_{55}H_{69}BrN_4O_{14}$: 1062. found 1063 (M+H).

21-O-(2-((3-(bis(diethylphosphono)methyl)carbamoyl)propanoyloxy)acetyl)-1',4-Didehydro-1-deoxy-1,4-dihydro-3'-hydroxy-5'-[4-(2-methylpropyl)-1-piperazinyl]-1-oxorifamycin VIII (83): A mixture of 82 (200 mg, 0.18 mmol), 51 (76 mg, 1.88 mmol), and $Cs_2CO_3$ (61.4 mg, 1.88 mmol) in dry DMF (8 mL) was stirred at room temperature for 3 h. The reaction mixture was diluted with dichloromethane (80 mL), washed with water (2×50 mL) and brine (60 mL), dried over $Na_2SO_4$ and concentrated to dryness. The residue was purified by flash chromatography over $SiO_2$ with 2 to 6% MeOH/$CH_2Cl_2$ to yield the product 83 (140 mg, 54% yield). LCMS: Mass calculated for $C_{66}H_{91}N_5O_{23}P_2$. 1383. found: 1384 (M+H).

21-O-(2-((3-(bisphosphonomethyl)carbamoyl)propanoyloxy)acetyl)-1',4-Didehydro-1-deoxy-1,4-dihydro-3'-hydroxy-5'-[4-(2-methylpropyl)-1-piperazinyl]-1-oxorifamycin VIII (84): To a solution of 83 (140 mg, 0.10 mmol) and 2,6-lutidine (0.47 mL, 4.0 mmol) in $CH_2Cl_2$ (10 mL) at −78° C. was added dropwise bromotrimethylsilane (0.26 mL, 20.0 mmol) under argon. The cold bath was removed and the mixture was stirred for 24 h at room temperature. The volatiles were removed under vacuum until dryness. The residue was dissolved in 10 mL of aqueous 50 mM $NH_4OAc/AcOH$ buffer (pH 5) and stirred for 16 hours at room temperature and the sample was lyophilized. The resulting material was subjected to a C18 reverse phase flash chromatography with a linear gradient elution of 0 to 100% acetonitrile in 50 mM $NH_4OAc/AcOH$ buffer (pH=5). The fractions containing the product were mixed, the acetonitrile was removed in vacuo and the resulting aqueous solution was freeze dried to afford compound 84 as a dark blue solid (50 mg, 39% yield). LCMS: 95.8% (254 nm), 96.0% (220 nm), 96.3% (320 nm); Mass calculated for $C_{58}H_{75}N_5O_{23}P_2$: 1271. found: 1270 (M−H).

Example 2

Determination of In Vitro Antibacterial Activity and Cytotoxicity

In Vitro Antibacterial Activity

Susceptibility of *S. aureus* strains to the known antibiotics and synthesized compounds was determined by following the guidelines set by NCCLS (M26-A). Compounds were diluted two-fold serially in DMSO and transferred to cation-adjusted Mueller Hinton broth (CAMHB; Becton Dickinson). 50 µL of compounds diluted in CAMHB was mixed with 100 µL of bacteria diluted in CAMHB in 96-well microtiter plates. The final concentration of micro-organisms in the assay was $5×10^5$ c.f.u. per mL and the final concentration of DMSO in the assay was 1.25%. Assays were set up in duplicate and incubated at 37° C. for 18 h. The lowest concentration of compound that inhibited visible growth was reported as the minimum inhibitory concentration (MIC).

Susceptibility testing experiments were also carried out in the presence of serum.

These experiments were carried out similar to the susceptibility testing with the following modifications. 75 µL of compounds diluted in CAMHB was mixed with 75 µL of bacteria diluted in 100% serum from any given source (commercial pooled mouse serum (MS) and human serum (HS), Equitech-Bio Inc.) or diluted in 8% purified human serum albumin (HSA) (Calbiochem). The final concentration of animal serum in the assay was 50% and the final concentration of purified human serum albumin in the assay was 4%; the concentrations of all other components were identical to those described for susceptibility testing. The data is summarized in Table 1.

TABLE 1

Antibacterial susceptibility of bacteria to selected compounds (Minimum inhibitory concentrations in μg/mL)

| | Species and Strain | | | | | | | | |
|---|---|---|---|---|---|---|---|---|---|
| | S. aureus | | | | | | | | |
| Compound | RN4220 | BK85[a] | ATCC 43300[b] | ATCC 13709 | ATCC 13709[c] | ATCC 13709 + 50% Mouse Serum | ATCC 13709 + 50% Human Serum | ATCC 13709 + 50% Rat Serum | E. coli LBB925[d] |
| Rifampicin | 0.008 | 0.008 | 0.008 | 0.008 | >128 | 0.125 | 0.062 | 0.125 | 8 |
| Rifabutin (17) | 0.016 | 0.031 | 0.016 | 0.031 | — | 0.062 | 0.031 | 0.031 | 4 |
| Rifalazil (75) | 0.00048 | 0.001 | 0.001 | 0.001 | 16 | 0.032 | 0.032 | 0.0078 | 16 |
| 9 | 0.016 | 0.016 | 0.016 | 0.016 | — | 0.062 | 0.062 | 0.062 | 16 |
| 11 | 0.25 | 0.25 | 0.25 | 0.125 | — | 0.25 | 0.25 | 0.25 | 32 |
| 21 | 32 | 16 | 16 | 16 | — | — | — | — | >128 |
| 30 | 1 | 0.5 | 0.5 | 1 | — | 1 | 1 | 0.25 | 1 |
| 36 | 1 | 1 | 1 | 1 | >128 | 2 | 2 | 1 | 128 |
| 39 | >128 | >128 | >128 | >128 | >128 | >128 | >128 | 64 | 128 |
| 45 | 64 | 64 | 64 | 32 | >128 | 128 | 64 | — | >128 |
| 50 | 0.25 | 0.25 | 0.25 | 0.25 | >128 | 0.125 | 0.125 | 0.032 | 16 |
| 54 | 64 | 64 | 64 | 64 | >128 | >128 | >128 | >128 | >128 |
| 56 | 0.00025 | — | 0.00025 | 0.00025 | — | 0.002 | 0.001 | 0.002 | 8 |
| 62 | 0.0078 | 0.0078 | 0.0078 | 0.0039 | >128 | 0.032 | 0.032 | 0.0156 | >128 |
| 63 | 0.00048 | 0.00048 | 0.00048 | 0.00048 | 2 | 0.0156 | 0.0078 | 0.032 | 8 |
| 68 | 0.25 | 0.25 | 0.0625 | 0.0625 | >128 | 1 | 1 | 2 | 64 |
| 69 | — | 0.00024 | — | 0.00048 | — | 0.0019 | 0.0019 | 0.0019 | 4 |
| 71 | 0.0039 | 0.0019 | 0.0019 | 0.0019 | 128 | 0.032 | 0.032 | 0.032 | >128 |
| 78 | 16 | 16 | 8 | 8 | >128 | >128 | >128 | >128 | >128 |
| 81 | 0.001 | 0.001 | 0.001 | 0.001 | >128 | 0.0625 | 0.125 | 0.03125 | >128 |
| 84 | 1 | 1 | 1 | 1 | >128 | 16 | 16 | 1 | >128 |

[a]Fluoroquinolone resistant MRSA.
[b]Fluoroquinolone sensitive MRSA.
[c]Novobiocin and Rifampicin resistant variant.
[d]tolC mutant It can be broadly deduced that the bisphosphonated prodrugs 11, 21, 30, 36, 39, 45, 50, 54, 68, 78 and 84 possess antibacterial activities which are at least orders of magnitude weaker than the parent drugs. In fact, the near complete loss of activity in the cases of 39, 45, 54 and 78 suggests the introduction of a bisphosphonated moiety to be detrimental to the antibacterial nature of the molecules. The other prodrugs 62, 71 and 81 yielded very low MICs, which are likely the result of the cleavage of the bisphosphonated moieties and liberation of the active parental antibacterial agent during the course of the experiment. The complete lack of activity of prodrugs 36, 39, 45, 50, 54, 62, 68, 71, 78, 81 and 84 against the Rifampicin resistant variant of S. aureus ATCC13709 confirms that these compounds are not capable of antibacterial activity through an alternative mechanism of action. Table 1 also demonstrates that the parent antimicrobial molecules 9, 56, 63, 69, rifampicin, rifabutin and rifalazil display antibacterial activities which are within the same range of one another.

The impact of serum on the MIC values correlated well between the parent drugs and the prodrugs. For rifampicin, and particularly for the benzoxazinorifamycin derivatives (rifalazil and compounds 56, 63 and 69), MICs increase significantly (>4x) in the presence of 50% mouse or rat serum. The same occurs for the benzoxazinorifamycin prodrugs (62, 68, 71, 78, 81 and 84). In addition, there was no impact of serum on the MICs of compounds 11, 30, 36, 39, 45, 50, and 54 which suggests that participation from serum hydrolytic enzymes is unlikely to be required or responsible for the cleavage of these prodrugs in solution.

Example 3

Binding of Compounds to Bone Powder In Vitro and Subsequent Regeneration of the Parent Drug Bone Powder Binding The ability of the molecules from Example 1 to bind to bone powder was established using a microbiological assay for detection. An individual compound was dissolved in PBS and resuspended at a concentration of 1 mg/ml in a slurry of bone meal powder (Now Foods, Bloomingdale, Ill., USA) in PBS at 10 mg/ml. The suspension of drug/prodrug in bone meal powder was incubated at 37° C. for 1 h to allow for binding, and centrifuged at 13 000 rpm for 2 min, before recovering the supernatant. The bone meal powder pellet was then washed three times with 1 ml of PBS+2% DMSO. The supernatants were assessed for the amount of prodrug by microbiological assay measurements as follows: Isolated colonies of the indicator strain (Staphylococcus aureus K1758) were resuspended in 0.85% saline to $OD_{600}$=0.1 and streaked on Cation-adjusted Miller Hinton agar (CAMHA) plates. Known volumes of the supernatants were applied to discs and dried. The discs were then placed on the seeded CAMHA plates. The plates were incubated at 37° C. for 18 hrs after which the diameters of the zone of inhibition generated by the discs were measured. The amount of prodrug was deduced from standard curves of known amounts that were used as reference for each experiment.

This experiment requires the prodrug to have a low MIC in order to allow for a satisfactory limit of detection. Hence the binding of 21 and 39 could not be assessed using this method.

When applied to compounds 11, 30, 36, 45, 50, 62, 68, 71, 78, 81 and 84, the in vitro binding experiment showed that >90%, and generally >95%, of each compound was bound to the bone meal powder, as shown in Table 2.

This confirms that the bisphosphonated prodrugs are very efficiently removed from solution by osseous matter. The results also undeniably lend credence to the use of bisphosphonates as mediators for bone delivery. It is reasonable to believe that a portion of the unbound material detected by this method was not bisphosphonated prodrug but rather contaminating or regenerated parent drug. Nevertheless, it is also probable that the extent of binding to the osseous matter is reflective of the kinetics of bone absorption/adsorption.

Regeneration of Drug from Bone Powder-Bound Prodrug

The ability of the prodrug to release the active entity at the site of infection is paramount for use in vivo. This can be predicted by measuring the release of the drug from prodrug bound to osseous matter in vitro.

Amounts of parent drug "regenerated" from the phosphonated prodrug were measured as follows. Washed bone powder-bound prodrugs from the above experiment were resuspended in 400 μL PBS+2% DMSO or in 400 μL 50% (v/v in PBS+2% DMSO) human or rat serum. The suspension was incubated overnight at 37° C., centrifuged at 13,000 rpm for 2 min and the supernatant was recovered. The amount of regenerated parent drug in the supernatant was determined by measurements using the microbiological assay that was previously described for the prodrugs themselves. The amount of prodrug was deduced from standard curves of known amounts of parent drug that were used as reference for each experiment. The amount of regenerated drug assessed by this bioassay was corroborated by MIC determination. The percentage of drug regenerated in PBS or serum after the overnight incubation (Table 2) was deduced from the difference between the amount of bound prodrug and the amount of regenerated drug (not shown).

TABLE 2

Bone binding and Conversion of bisphosphonated Rifamycin prodrugs to parent drugs after binding to bone (expressed as % prodrug converted after 24 h incubation)

| Compound | Parent | % Bone binding | Medium | % Conversion |
|---|---|---|---|---|
| 11 | 9 | 95 | PBS | 0.97 |
| | | | 50% Human Serum | 1.01 |
| | | | 50% Rat Serum | 1.01 |
| 21 | Rifabutin | ?? | PBS | <lod |
| | | | 50% Human Serum | nd |
| | | | 50% Rat Serum | 0.02 |
| 30 | Rifabutin | 90 | PBS | 0.07 |
| | | | 50% Human Serum | 0.05 |
| | | | 50% Rat Serum | 0.07 |
| 36 | Rifabutin | 99.4 | PBS | 0.38 |
| | | | 50% Human Serum | 0.25 |
| | | | 50% Rat Serum | 0.38 |
| 39 | Rifabutin | ?? | PBS | ?? |
| | | | 50% Human Serum | ?? |
| | | | 50% Rat Serum | ?? |
| 45 | Rifabutin | 99.8 | PBS | <lod |
| | | | 50% Human Serum | — |
| | | | 50% Rat Serum | 0.002 |
| 50 | Rifabutin | 96.8 | PBS | 2.65 |
| | | | 50% Human Serum | nd |
| | | | 50% Rat Serum | 2.68 |
| 54 | Rifabutin | ?? | PBS | ?? |
| | | | 50% Human Serum | nd |
| | | | 50% Rat Serum | ?? |
| 62 | 56 | 99.8 | PBS | 0.21 |
| | | | 50% Human Serum | 0.86 |
| | | | 50% Rat Serum | 0.91 |
| 68 | 63 | 99.9 | PBS | 0.02 |
| | | | 50% Human Serum | nd |
| | | | 50% Rat Serum | 0.24 |
| 71 | 69 | 99.9 | PBS | 0.1 |
| | | | 50% Human Serum | 0.46 |
| | | | 50% Rat Serum | 0.38 |
| 78 | Rifalazil | 99.9 | PBS | <lod |
| | | | 50% Human Serum | nd |
| | | | 50% Rat Serum | 0.01 |
| 81 | Rifalazil | 94.8 | PBS | 1.98 |
| | | | 50% Human Serum | nd |
| | | | 50% Rat Serum | 2.50 |
| 84 | Rifalazil | 99.8 | PBS | <lod |
| | | | 50% Human Serum | nd |
| | | | 50% Rat Serum | 0.12 |

<lod: below the limit of detection. nd: not determined. ??: cannot be measured using current technique This data shows that compounds 21, 39, 45, 78 and 84 are not able to regenerate their respective parent drug once bound to bone and therefore would predict these not to display any significant activity in vivo. The other prodrugs release significant amounts of the parent Rifamycin antibacterial agents under these conditions. Comparing the rates of regeneration of prodrugs 11 and 62—with appreciable rates of regeneration—on the one side, 68—which only slightly regenerates—and 39—which is apparently not regenerating-demonstrates the importance of the point of attachment of the linker. These prodrugs use a particular succinamate ester as a linker which cyclizes to the parent succinimide over time, the cyclization being slower in the cases involving hindered esters. The distance separating the bisphosphonated moiety from the point of cleavage is also important. Thus a comparison of the rates of cleavage of bone-bound prodrugs 30 on the one hand and 36 and 71 on the other shows that the greater length of the chain leading to the bisphosphonate in 30 detrimentally affects the rate of cleavage.

Furthermore, the rates of regeneration of parent drug from prodrugs 11, 21, 30, 36, 45, 50, and 81 were not significantly impacted by the medium, suggesting a chemical cleavage to be sufficient for the release of the parent Rifamycins, and that an enzymatically assisted process is either not required or not represented in the serum conditions of the assay (data not shown). On the other hand, there is a significant acceleration in the conversion of 62, 68, 71, 78 and 84 to their parent drugs in the presence of serum compared to PBS. This as such does not necessarily imply that biocatalysis is involved, with potentially other sources of variation such as medium effects. Again, a comparison of 62 and 68 on the one hand and 9 on the other hand shows that serum might have a different impact on the rates of cleavage of prodrugs bearing the same linker. A similar conclusion can be drawn by comparing 36 and 71. This further stresses that the unique nature of each drug-linker combination determines the nature (serum esterase requirement, rate) of the cleavage process.

Example 4

Comparisons of the Prophylactic Efficacy of Rifamycin Antibacterials and their Bisphosphonated Prodrugs in Rat Models of Bone Infections To determine the in vivo activity of bisphosphonated prodrugs of Rifamycin derived antibacterials in comparison to their non-bisphosphonated parents, compound 11 and its parent drug 9, compounds 21, 30, 36, 50 and their parent drug rifabutin, compound 62 and its parent drug 56, compound 68 and its parent drug 63, compound 71 and its parent drug 63 and compound 81 and its parent drug rifalazil were used as prophylactic therapeutics in an animal model of infection. Specifically, a spontaneous Novobiocin resistant mutant strain of S. aureus ATCC 13709 (a clinical osteomyelitis isolate), was grown overnight at 37° C. in brain heart infusion broth (BHIB). After 16 h of growth, cells were subcultured into fresh BHIB and incubated for 4 to 5 h at 37° C. The cells were washed twice with phosphate-buffered saline (PBS) and resuspended in BHIB supplemented with 10% (vol./vol.) fetal bovine serum at a density of approximately $10^{10}$ colony forming units (CFU)/ml (based upon turbidimetry). The suspension was aliquoted and a portion was used to check the CFU count. The culture was stored frozen (−80° C.) and was used without subculture. For use as an inoculum the culture was thawed, diluted in PBS and kept in an ice bath until it was used.

Animals were infected as described by O'Reilly et al. (Antimicrobial Agents and Chemotherapy (1992), 36(12): 2693-97) to generate the bone infection. Female CD rats (age, 57 to 70 days; n=5/group; Charles River, St-Constant, Canada) were anaesthetized by isofluorane before and during the surgery. Following complete induction of anesthesia, the rat was placed ventral side up and hair was shaved from the surgical site. The skin over the leg was cleaned and disinfected (proviodine-ethanol 70%). A longitudinal incision below the knee joint was made in the sagital plane. The incision was made over the bone below the "knee joint" (tibia head or condyle) but not completely extending to the ankle. A high speed drill fitted with a 2 mm bulb bit was used to drill a hole into the medullar cavity of the tibia. Rats were injected intra-tibially with 0.05 ml 5% sodium morrhuate (sclerosing agent) and then with 0.05 ml of S. aureus suspension (ca. $2 \times 10^7$ CFU/rat). The hole was sealed by applying a small amount of dry dental cement which immediately absorbs fluids and adheres to the site. The wound was closed using 3 metal skin clips. Moxifloxacin (as a positive control) was injected once at 10 mg/kg intravenously 1 h postinfection in saline, while the Rifamycin derived prodrugs (prepared in 0.9% saline) were injected at the dose indicated in Table 3 as a single intravenous bolus at different time points prior to the infection.

Infected rats were sacrificed by $CO_2$ asphyxiation 24 h postinfection to monitor the bacterial CFU count. Infected tibiae were removed, dissected free of soft tissue, and weighed. The bones were ground, resuspended in 5 ml 0.9% NaCl, serially diluted and processed for quantitative cultures. For compounds 50, 68 and 81, 1 ml of the 0.9% NaCl solution was added to 50 mg of charcoal before serial dilutions. Treatment efficacy was measured in terms of Log viable bacteria (Log CFU per gram of bone). The results obtained for each group of rats were evaluated by calculating the mean Log CFU and standard deviation. The limit of detection is 2 Log CFU. Statistical comparisons of viable bacterial counts for the different treated and untreated groups were performed with the Dunnett's multiple-comparison test. Differences were considered significant when the P value was <0.05 when comparing treated infected animals to the untreated infected ones. The doses used, the amount of time separating the treatment from the time of infection and the treatment outcomes are shown in Table 3.

TABLE 3

Retrieved bacterial titers following prophylactic treatment in rat model of S. aureus bone infection

| Compound No. | Dose (mg/kg parent drug equivalent) | Time of administration (days prior to infection) | Measured bacterial titer (Log CFU/g of bone) | | |
|---|---|---|---|---|---|
| | | | Untreated | Positive control | Parent drug | Test compound |
| Parent drug: 9 | | | | | | |
| 11 | 11 | 3 | 5.49 ± 1.22 | 2.36 ± 0.21 | 6.38 ± 0.90 | 3.01 ± 0.47 |
| Parent drug: Rifabutin | | | | | | |
| 21 | 12 | 1 | 6.32 ± 1.34 | 2.53 ± 0.39 | nd | 6.59 ± 0.90 |
| 30 | 23 | 2 | 5.53 ± 0.79 | 2.59 ± 0.56 | 2.15 ± 0.07 | 2.49 ± 0.35 |
| 36 | 23 | 5 | 6.14 ± 0.73 | 2.46 ± 0.52 | 5.75 ± 0.55 | 2.73 ± 0.86 |
| 50 | 20 | 3 | 6.24 ± 0.83 | 2.56 ± 0.64 | 4.72 ± 1.84 | 6.31 ± 0.82 |
| Parent drug: 56 | | | | | | |
| 62 | 20 | 2 | 4.89 ± 1.04 | 2.20 ± 0.33 | 3.61 ± 1.57 | 1.98 ± 0.06 |
| Parent drug: 63 | | | | | | |
| 68 | 20 | 3 | 6.14 ± 0.95 | 2.32 ± 0.33 | 2.84 ± 0.93 | 4.86 ± 0.66 |
| Parent drug: 69 | | | | | | |
| 71 | 20 | 3 | 5.28 ± 0.73 | 2.06 ± 0.04 | 4.08 ± 1.53[a] | 2.77 ± 1.00 |
| Parent drug: Rifalazil | | | | | | |
| 81 | 10 | 3 | 6.14 ± 0.95 | 2.32 ± 0.33 | 2.21 ± 0.34 | 2.05 ± 0.06 | nd: not determined.
[a]Rifalazil used instead of 69

The results clearly indicate a statistically significant (t-test; p<0.05) prophylactic effect of bisphosphonated Rifamycin derived prodrugs 11, 30, 36, 62, 71 and 81 in contrast to a lack of efficacy of the parent drugs used under the same experimental conditions. The exception is rifabutin which is able to provide efficacious prophylaxis when used two days, but not five days, prior to infection. These results and the in vitro regeneration data strongly support the notion that these bisphosphonated prodrugs are targeted to the osseous matter in vivo, where they are able to release their bioactive moieties at concentrations above those needed for antibacterial activity.

A relationship between cleavage and antibacterial activity is clearly displayed by prodrug 21. This compound is unable to significantly release its parent drug rifabutin in vitro and lacks efficacy under the conditions of the in vivo assay (Table 3). The clear relationship between chemical or biochemical instability of the prodrug and prophylactic activity demonstrates the ability to modulate an in vivo effect of the phosphonated compounds of the invention by altering the rate of regeneration of the prodrug. It also supplies further evidence to support the importance of a cleavable bisphosphonated prodrug over a non-cleaving bisphosphonated conjugate to provide the desired treatment outcome in an in vivo model.

These experiments demonstrate the clear advantage of the invention in the prevention of bone infections.

Example 5

Comparative Use of Rifamycin Derivatives 9, 56, 69, Rifabutin and Rifalazil and their Respective Bisphosphonated Prodrugs 11, 62, 71, 36 and 81 in a Rat Model of Chronic Osteomyelitis Caused by *S. aureus*

To appraise the ability of bisphosphonated prodrugs of Rifamycin derivatives in treating chronic bone infections, a comparison was made between parent compounds 9, 56, 69, rifabutin and rifalazil (all of which are non-bisphosphonated rifamycin derivatives), and their corresponding bisphosphonated prodrugs, respectively 11, 62, 71, 36 and 81, when used to treat chronically (14- to 28-day) infected rats for 4 weeks of antimicrobial therapy.

In this experiment, rats were infected as described in Example 4 and treated with either 20 mg/kg of body weight of the specific rifamycin derived antibacterial agent subcutaneously, or a molar equivalent dose of its bisphosphonated prodrug intravenously according to the indicated schedule after instillation of bacteria. The standard controls involving no treatment and a subcutaneous treatment of 20 mg/kg of Rifampicin daily were also included. The rats were humanely sacrificed at the conclusion of the experiment and the bacterial titers in the infected tibiae were determined.

This experiment was performed with 20 mg/kg of body weight of rifamycin derivative 9 subcutaneously or with 32 mg/kg of its prodrug 11 (corresponding to 20 mg/kg of 9) intravenously on each of the $20^{th}$, $24^{th}$, $28^{th}$, $32^{nd}$, $36^{th}$, $40^{th}$ and $47^{th}$ days (q4 days) after instillation of bacteria. Alternatively, 11 was administered by the same route and at the same dose on the $20^{th}$, $21^{st}$, $22^{nd}$, $23^{rd}$, $30^{th}$, $37^{th}$, $44^{th}$ and $47^{th}$ days (q24hx4+q7d) after the instillation of bacteria. The same controls (no treatment or daily subcutaneous 20 mg/kg dose of rifampicin) were used. The rats were humanely sacrificed on the $48^{th}$ day after the initiation of infection and the bacterial titers in the infected tibiae were determined. The results are show in FIG. 1.

Figure 2:
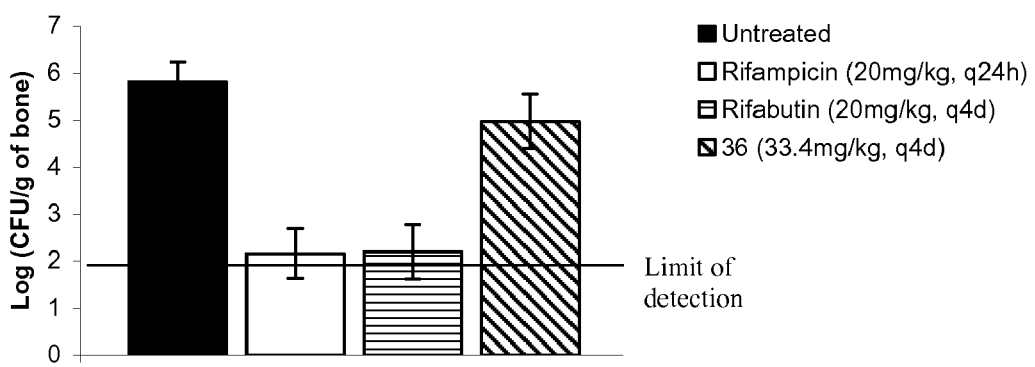
FIG. 2 is a bar graph showing the testing of 20 mg/kg of rifabutin and the small but statistically significant effect (versus the untreated control) of 33.4 mg/kg of its parent bisphosphonated prodrug 36 on bacterial titer in bone infection when used every four days for 4 weeks post-infection.

This experiment was also executed in which similarly infected rats were treated with either 20 mg/kg of body weight of rifabutin subcutaneously or with 33.4 mg/kg of its prodrug 36 (corresponding to 20 mg/kg of rifabutin) intravenously on each of the $28^{th}$, $32^{nd}$, $36^{th}$, $40^{th}$, $44^{th}$, $48^{th}$ and $52^{nd}$ days (q4 days) after instillation of bacteria. The same controls (no treatment or daily subcutaneous 20 mg/kg dose of rifampicin) were used. The rats were humanely sacrificed on the $55^{th}$ day after the initiation of infection and the bacterial titers in the infected tibiae were determined. The results are shown in FIG. 2.

Figure 3:
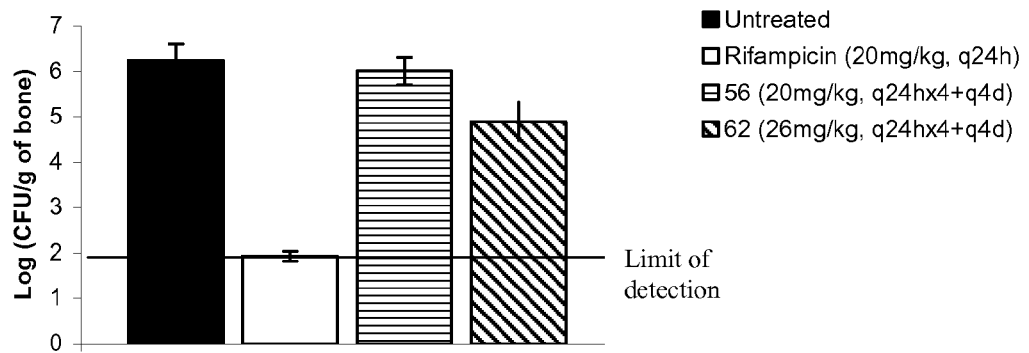
FIG. 3 is a bar graph showing the testing of 20 mg/kg of benzoxazinorifamycin 56 and the small but statistically significant effect (versus both the untreated control and benzoxazinorifamycin 56) of 26 mg/kg of its parent bisphosphonated prodrug 62 on bacterial titer in bone infection when used for four consecutive days and then every four days for 4 weeks post-infection.

This experiment was also executed in which similarly infected rats were treated with either 20 mg/kg of body weight of the rifamycin derived antibacterial agent 56 subcutaneously or with 26 mg/kg of its prodrug 62 (corresponding to 20 mg/kg of 56) intravenously on each of the $27^{th}$, $28^{th}$, $29^{th}$, $30^{th}$, $34^{th}$, $38^{th}$, $42^{nd}$, $46^{th}$ and $50^{th}$ days (q24hx4+q4 days) after instillation of bacteria. The same controls (no treatment or daily subcutaneous 20 mg/kg dose of rifampicin) were used. The rats were humanely sacrificed on the $51^{St}$ day after the initiation of infection and the bacterial titers in the infected tibiae were determined. The results are shown in FIG. 3.

Figure 4:
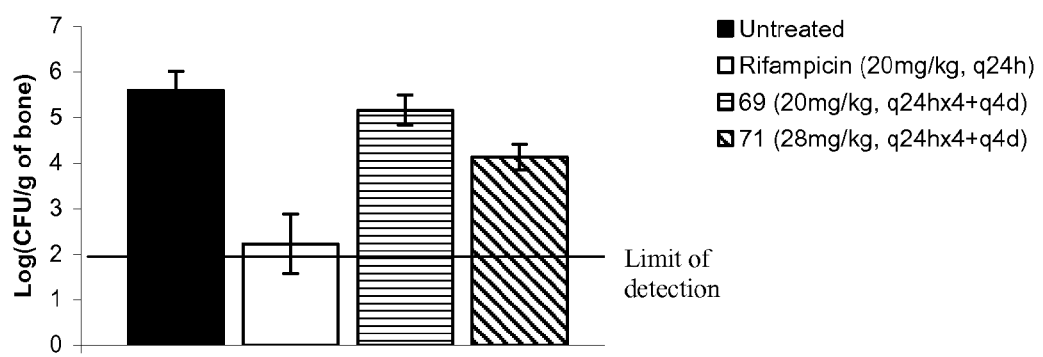
FIG. 4 is a bar graph showing the testing of 20 mg/kg of benzoxazinorifamycin 69 and the small but statistically significant effect (versus both the untreated control and benzoxazinorifamycin 69) of 28 mg/kg of its parent bisphosphonated prodrug 71 on bacterial titer in bone infection when used for four consecutive days and then every four days for 4 weeks post-infection.

This experiment was also executed in which similarly infected rats were treated with either 20 mg/kg of body weight of the rifamycin derived antibacterial agent 69 subcutaneously or with 28 mg/kg of its prodrug 71 (corresponding to 20 mg/kg of 69) intravenously on each of the $18^{th}$, $19^{th}$, $20^{th}$, $21^{st}$, $25^{th}$, $29^{th}$, $33^{rd}$, $37^{th}$, $41^{st}$ and $45^{th}$ days (q24hx4+q4 days) after instillation of bacteria. The same controls (no treatment or daily subcutaneous 20 mg/kg dose of rifampicin) were used. The rats were humanely sacrificed on the $46^{th}$ day after the initiation of infection and the bacterial titers in the infected tibiae were determined. The results are shown in FIG. 4.

Figure 5:
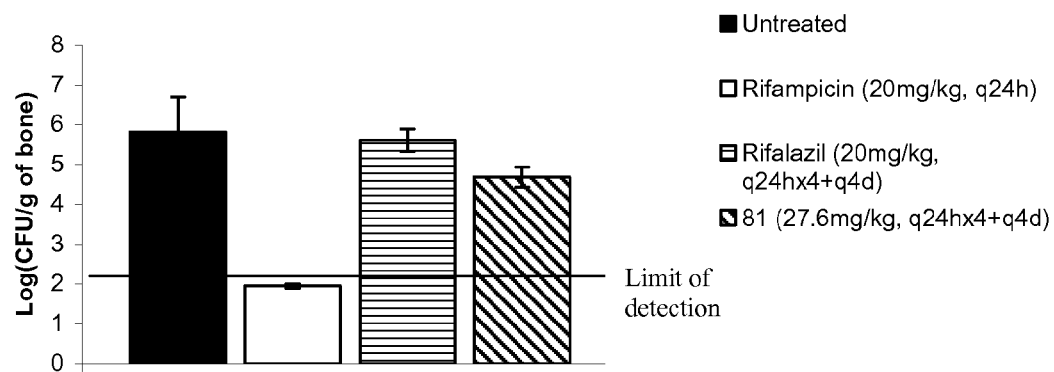
FIG. 5 is a bar graph showing the testing of 20 mg/kg of rifalazil and the small but statistically significant effect (versus both the untreated control and rifalazil) of 27.6 mg/kg of its parent bisphosphonated prodrug 81 on bacterial titer in bone infection when used for four consecutive days and then every four days for 4 weeks post-infection.

This experiment was also executed in which similarly infected rats were treated with either 20 mg/kg of body weight of rifalazil subcutaneously or with 28 mg/kg of its prodrug 81 (corresponding to 20 mg/kg of rifalazil) intravenously on each of the $22^{nd}$, $23^{rd}$, $24^{th}$, $25^{th}$, $29^{th}$, $33^{rd}$, $37^{th}$, $41^{st}$ and $45^{th}$ days (q24hx4+q4 days) after instillation of bacteria. The same controls (no treatment or daily subcutaneous 20 mg/kg dose of rifampicin) were used. The rats were humanely sacrificed on the $46^{th}$ day after the initiation of infection and the bacterial titers in the infected tibiae were determined. The results are shown in FIG. 5.

In addition, a separate experiment was performed using a once daily subcutaneous dose of 20 mg/kg of body weight of either Rifampicin, Rifabutin or compound 9 from the $15^{th}$ to the $28^{th}$ day after infection. The rats were humanely sacrificed on the $29^{th}$ day and the bacterial titers in the infected tibiae were determined. The results are in FIG. 6.

Figure 6:
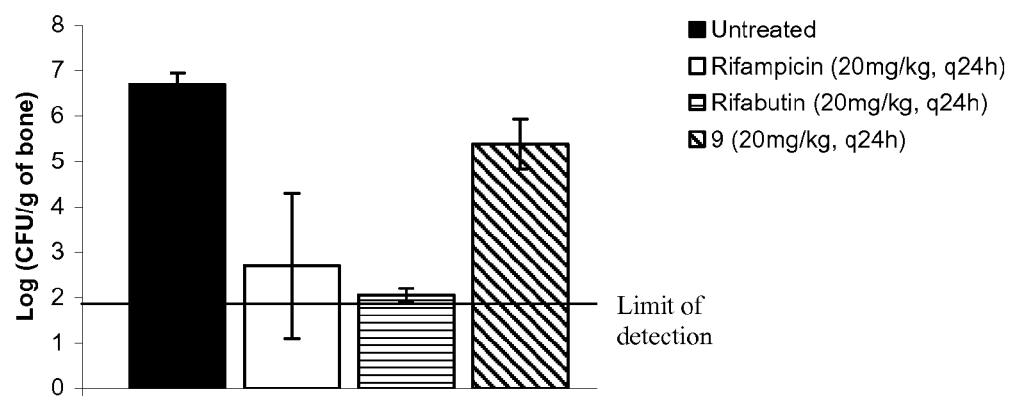
FIG. 6 is a bar graph showing the effect of 20 mg/kg of Rifampicin, Rifabutin and Rifamycin derivative 9 on bacterial titer in bone infection when used once daily for 4 weeks post-infection.

Whereas daily treatment with either Rifampicin or Rifabutin resulted in a large, statistically significant decrease in bacterial titer (p<0.0001), daily treatment with Rifamycin derivative 9 showed a smaller but still statistically significant reduction in the bacterial titer in bone (FIG. 6, p-value 0.0022). The derivative 9 was completely ineffective when used every four days (FIG. 1, p-value 0.7272). Whereas the bisphosphonated prodrug 11 demonstrates a small decrease in the bacterial titer under the two dosing regimens examined (FIG. 1), this decrease is not statistically significant (p-values of 0.4107 and 0.2082 for the q4d and the q24hx4+q7d regimens respectively). With prodrug 36, the decrease in bacterial titer by 1 logarithmic order of magnitude was statistically significant (FIG. 2, p-value 0.0036), even though it has a poorer rate of regeneration in vitro than 11. On the other hand, the parent drug Rifabutin, even at a dosing interval of 4 days, still results in an excellent decrease in bacterial titer (greater than 3 logarithmic orders of magnitude, FIG. 2). It could be speculated that the positive outcome of 36 is the result not only of its targeting to the bone, but also of reduced clearance of Rifabutin from bone relative to rifamycin derivative 9. The decreases in bacterial titers by approximately 1 logarithmic order of magnitude associated with the use of prodrugs 62, 71 and 81 are all statistically significant (FIGS. 3, 4, and 5, respectively; p-values$\leq$0.001) not only with respect to the untreated group but with respect to the parent rifamycin antibacterials, all of which were not efficacious under the dosing regimens examined.

This emphasizes the role of the bisphosphonate linker in producing the desirable therapeutic outcome and demonstrates the usefulness of the invention in treating bone infections.

Example 6

Determination of Levels of Compound 9 Resulting from the Use of Compound 11 or Compound 9 in Rat Tibiae when Used as Prophylaxis or Treatment of Bone Infection The experimentally obtained intact uninfected (contra lateral) tibia of the treated and infected rats described above was ground to a powder which was suspended in PBS+2% DMSO. The mixture was centrifuged for 2 min at 13,000 rpm. The amount of compound 9 released in the supernatant was determined by microbiological assay as described previously (Example 3).

When used at 10 mg/kg of body weight three days prior to infection, the amount of compound 9 in the uninfected tibiae of animals treated with compound 9 was below the limit of quantification (0.17 µg/g). On the other hand, a concentration of 0.88±0.11 µg/g of bone was determined for the animals treated with 15.5 mg/kg of body weight (equivalent to 10 mg/kg of 9) of compound 11 three days prior to infection.

When compound 11 was used at 32 mg/kg of body once weekly for 4 weeks after the infection, the level of compound 9 was determined to be of 1.28±0.18 µg/g of bone.

The data indicates that a high concentration of parent drug 9 is present in bone even a week after the last treatment in tibiae of animals treated with compound 11, at concentrations estimated to be nearly two orders of magnitude above minimum inhibitory concentration (MIC) for the bacterial strain used to establish the infection in vivo. This is in stark contrast with the direct use of 9 which is unable to sustain a significant concentration in bone for even three days. It lends credence to the concept of using bisphosphonated prodrugs to concentrate the dose of antibacterial in the bone matter and to release it over an extended period.

Example 7

Determination of Levels of Rifabutin Resulting from the Use of Compounds 30 and 36 in Various Tissues when Used as Prophylaxis or Treatment of Bone Infection Ground bone samples and tissue homogenates were suspended in PBS, vortexed and centrifuged at 13000 rpm for 2 min. The supernatant was collected and was applied in a microbiological assay to determine the levels of Rifabutin released as described previously (Example 3). The levels displayed in Table 4 are those detected for the use of 30 at 33.8 mg/kg of body weight two days prior to infection, 36 used at five days prior to infection and 36 used at for 4 weeks starting on the 14$^{th}$ day after infection.

TABLE 4

Levels of Rifabutin (µg/g of tissue or µg/ml in the case of plasma) detected as a result of using Rifabutin or prodrugs 30 or 36 in various tissues.

| | Measured levels of Rifabutin (µg/g of tissue or µg/mL of plasma) | | | | |
|---|---|---|---|---|---|
| Tissue | 30 (33.8 mg/kg) Treatment A | Rifabutin (20 mg/kg) Treatment B | 36 (33.4 mg/kg) Treatment B | Rifabutin (20 mg/kg) Treatment C | 36 (32 mg/kg) Treatment C |
| Tibia | <LoD | <LoD | <LoD | <LoD | 0.69 ± 0.14 |
| Liver | 1.23 ± 0.12 | <LoD | 0.33 ± 0.05 | 0.08 ± 0.02 | 0.87 ± 0.23 |
| Kidney | 3.27 ± 1.19 | <LoD | 0.31 ± 0.18 | <LoD | 0.42 ± 0.10 |
| Spleen | <LoD | <LoD | <LoD | 1.40 ± 0.40 | 1.21 ± 0.08 |
| Plasma | <LoD | <LoD | <LoD | <LoD | <LoD |

Treatment A: Single dose two days prior to infection; Sacrifice one day after infection. Treatment B: Single dose five days prior to infection; Sacrifice one day after infection. Treatment C: One dose every four days starting on the 28$^{th}$ day after infection and ending on the 52$^{nd}$; Sacrifice on the 55$^{th}$ day. <LoD: below the limit of detection.

Surprisingly, the levels in tibia were very low or below the limit of detection, but a significant amount of regenerated Rifabutin was found in liver and kidney. This might result from the occurrence of precipitate due to the presence of calcium ions in blood. The precipitate will either concentrate in the kidneys as a result of glomerular filtration or in the liver. It is possible that the rate of cleavage of the prodrugs is higher in these organs, resulting in higher measurable titers.

Example 8

Determination of Levels of Prodrugs 11, 36 and 62 in Bone after Administration

Determination of the Levels of Prodrug 11 in Tibiae, Femurs and Mandibles

To determine the levels of prodrug 11 found in the bones of rats treated with compound 11, an analytical method was developed using liquid chromatography coupled with mass spectrometry (LC/MS) for analyte determination. The whole experimentally-obtained bones (tibiae, femurs or mandibles) were ground and regenerated 9 was extracted with phosphate buffer (25 mM, pH 7; 1 mL for 50 mg of ground bone). The mixture was vortexed for 10 minutes and centrifuged 10 minutes at 10 000 g. The resulting pellet was dried, weighed and kept for the determination of the compound 11.

For the determination of the levels of the bisphosphonated prodrug 11 in bone, the standards, controls and blanks were prepared (in duplicate) as follows: to weighed (~20 mg) dry blank bone powder was added the spiking solution (10 µL) of 11 prepared in acetonitrile and 990 µL of buffer (0.1 M tris-HCl, pH 7, 0.15 M NaCl). The mixture was vortexed for 30 minutes (RT), centrifuged for 15 minutes at 10000 g (RT), the supernatant discarded and the pellet kept for the cleavage procedure. The range of the standards (6 levels) was from 0.1 to 20 µM (0.1 to 20 nmol) and the control levels were at 0.25 and 8.5 µM (0.25 and 8.5 nmol).

To each standard, control, blank and experimental sample (~20 mg from the pellet obtained previously) was added 500 µL 100 mM phosphate buffer containing ascorbic acid (1 mg/mL) adjusted to pH 9. The cleavage of the prodrug 11 into the drug 9 was achieved by an incubation period of 4 hours at 50° C. At the end of this period the solution was brought to neutral pH with a solution of 10% formic acid (20 µL) and the internal standard (rifaximin) was added. After centrifugation for 10 minutes at 10000 g (RT) 20 µL of the supernatant was injected into the LC/MS.

The amount of compound 9 resulting from this process was analyzed with the same method on an Agilent 1100™ series LC/MSD Trap. The supernatant was injected into an Inertsil ODS-3™ column (4.6×50 mm, 3µ), using (A) 0.01% formic acid in water and (B) 0.01% formic acid in acetonitrile:methanol (50:50) with a gradient of 55 to 100% (B) in (A) over 5 minutes then remaining at 100% (B) for 1 minute) at a flow rate of 0.4 mL/min. The MS was set as follows: ESI probe, positive polarity, nebulizer 45 psi, dry gas temperature 350° C., dry gas flow 10 L/min, capillary exit 120 V (2.5 to 6 min.) or 140 V (6 to 12 min) and skimmer 30 V. The run time was 12 minutes with the divert valve set to the waste for the first 2.5 minutes. Compound 9 was analyzed in SRM mode for m/z 853.3→821.1 and the internal standard (rifaximin) for m/z 786.2→754.2.

Figure 7:
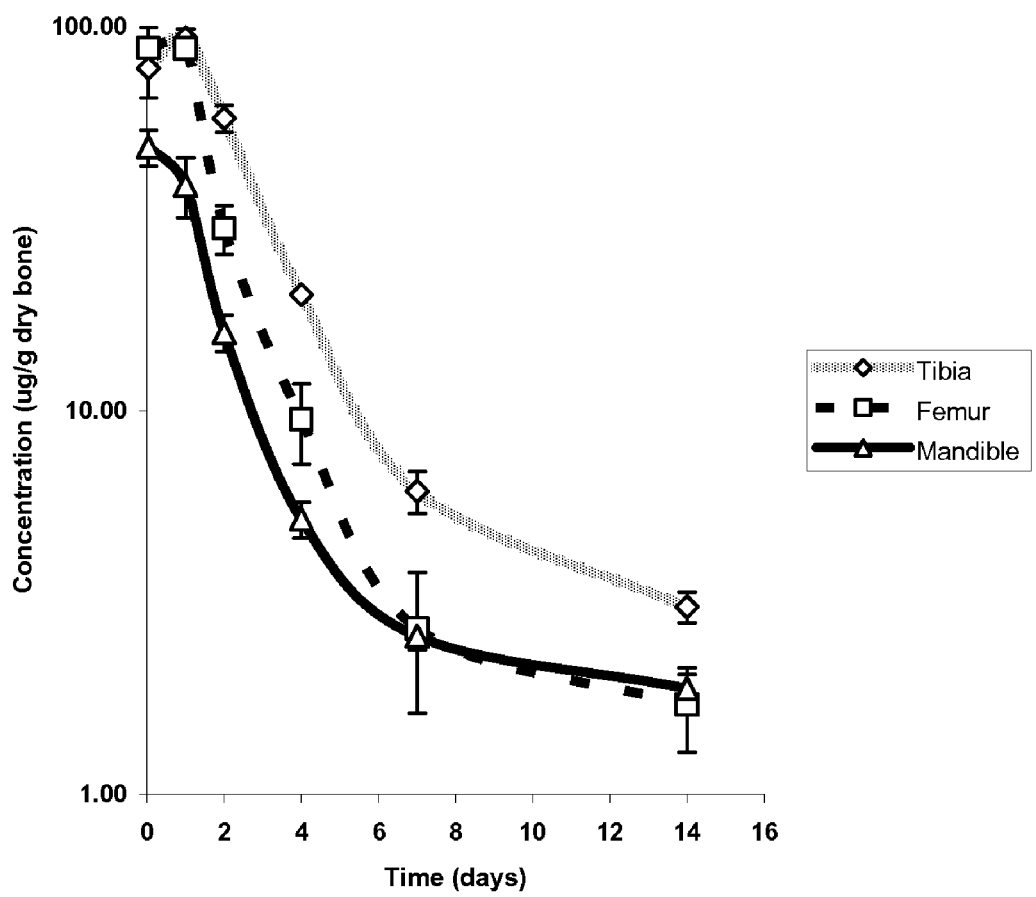
FIG. 7 is a line graph showing concentration of compound 11 in rat tibia, femur and mandible at 1 h to 14 days after an IV bolus injection at 32 mg/Kg.

The results from these determinations after a single intravenous bolus administration of 11 at 32 mg/kg of body weight are shown in FIG. 7.

Determination of the Levels of Prodrug 36 in Tibiae

To determine the levels of prodrug 36 found in the tibiae of rats treated with compound 36, an analytical method was developed using liquid chromatography coupled with mass spectrometry (LC/MS) for analyte determination. The whole experimentally obtained tibiae were ground to a powder and the regenerated rifabutin was extracted from 50 mg of powder with 1 mL acetonitrile. The mixture was vortexed for 15 minutes and centrifuged 10 minutes at 10000 g (RT).

The pellet of the experimental bone was dried, weighed and kept for the determination of the pro-drug. For the dosage of pro-drug in the bone, the standards, Qcs and blanks were prepared (in duplicate) as follow: to weighted (~20 mg) dry blank bone powder was added spiking solution (10 µL) of the pro-drug prepared in water and 990 µL of buffer (0.1 M tris-HCl, pH 7, 0.15M NaCl). The mixture was vortexed for 30 minutes (RT), centrifuge 10 minutes at 10000 g (RT), the supernatant discarded and the pellet kept for the cleavage procedure. The range of the standards (6 levels) was from 0.05 to 10 µM (0.05 to 10 nmol) and the Qcs levels were at 0.075, 0.75 and 7.5 µM (0.075, 0.75 and 7.5 nmol).

To each standard, Qc, blank and experimental sample (~20 mg weighted from the dried experimentally obtained bone) bone pellet was added 500 µL of sodium phosphate buffer 100 mM pH adjusted to 9. The cleavage of the pro-drug into the drug (rifabutin) was achieved by a sequence of five 1 h incubation periods at 70° C. At the end of each 1 h period, the supernatant was brought to a neutral pH with a solution of 10% formic acid (15 µl), the mixture vortexed and centrifuged (10 minutes at 10000 g, RT). The supernatant was kept at 4° C. and the pellet was resuspended in the phosphate buffer (500 µL) and incubated for the next period of one hour. At the end of the sequence the internal standard (compound 56) was added to the combined supernatants and the drug (rifabutin) and the internal standard extracted by SPE on Strata-X (30 mg/1 ml) using acetonitrile as the eluent. The eluent was evaporated to dryness and the dried residue was reconstituted in the mobile phase (500 µL). After vortexing for 20 minutes, the supernatant (10 µL) was injected into the LC/MS.

The amount of rifabutin resulting from this process was determined on an Agilent 1100 series LC/MSD Trap. The supernatant was injected into an Inertsil ODS-3 column (4.6× 50 mm, 3µ), using (A) 0.01% formic acid in water and (B) 0.01% formic acid in acetonitrile:methanol (50:50) with a gradient of 45 to 65% (B) in (A) over 5 minutes followed by 65 to 95% (B) over 1 minute and maintaining at 95% (B) for an additional minute at a flow rate of 0.4 mL/min.

The MS was set as follows: ESI probe, positive polarity, nebulizer 45 psi, dry gas temperature 350° C., dry gas flow 10 l/min, capillary exit 110V and skimmer 34.5V. The run time was 13 minutes with the divert valve sets to the waste for the first 3 minutes. The rifabutin was analyzed in SRM mode for m/z 847.3→815.4 and the internal standard (compound 56) for m/z 929.3.3→897.4.

Figure 8:
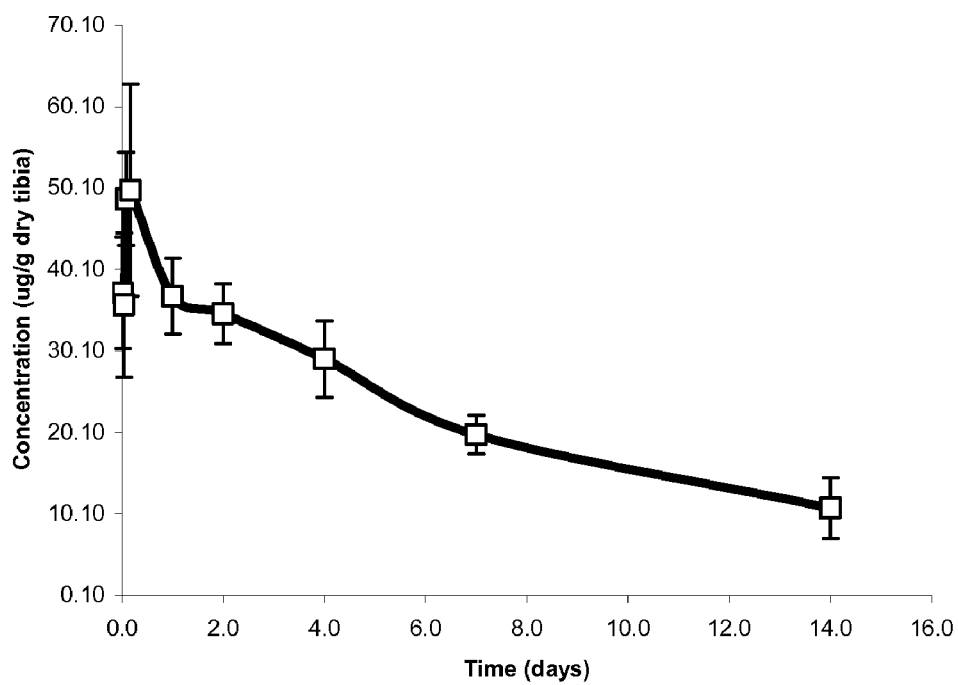
FIG. 8 is a line graph showing concentration of compound 36 in rat tibia at ½ h to 14 days after an IV bolus injection at 15.5 mg/Kg.

The results from these determinations after a single intravenous bolus administration of 36 at 15.5 mg/kg of body weight are shown in FIG. 8.

Determination of the Levels of Prodrug 62 in Tibiae

To determine the levels of prodrug 62 found in the tibiae of rats treated with compound 62, an analytical method was developed using liquid chromatography coupled with mass spectrometry (LC/MS) for analyte determination. The whole experimental bone was ground to a powder and the regenerated 56 was extracted by suspending 50 mg of this powder in 1 mL methanol. The mixture was vortexed for 15 minutes and centrifuged 10 minutes at 10000 g. The resulting pellet was dried, weighted and used for the determination of the prodrug.

For the dosage, the standards, Qcs and blanks were prepared (in duplicate) as follow: to weighted (~20 mg) dry blank bone powder was added a spiking solution (10 µL) of 62 prepared in water:methanol (50:50) and 990 µL of buffer (0.1 M tris-HCl, pH 7, 0.15M NaCl). The mixture was vortexed for 10 minutes (room temperature), centrifuged for 15 minutes at 10000 g (room temperature), the supernatant discarded and the pellet kept for the cleavage procedure. The range of the standards (6 levels) was from 0.05 to 10 µM (0.05 to 10 nmol) and the Qcs levels were at 0.075, 0.75 and 7.5 µM (0.075, 0.75 and 7.5 nmol).

To each standard, Qc, blank and experimental sample (~20 mg weighted from the dried pellet) bone pellet was added 500 µL of sodium phosphate buffer 100 mM pH adjusted to 10. The cleavage of the pro-drug into the drug (56) was achieved by a sequence of 10 incubation periods of 1 hour at 70° C. At the end of each period of 1 hour, the supernatant was brought to a neutral pH with a solution of 10% formic acid (20 µL), the mixture vortexed and centrifuged (10 minutes at 10000 g, RT). The supernatant was kept at 4° C. and the pellet was resuspended in the phosphate buffer (500 µL) and incubated for the next period of one hour. At the end of the sequence, the internal standard (rifabutin) was added to the combined supernatants which were loaded on conditioned StrataX™ cartridge (30 mg/1 mL) for the extraction (SPE). After washing with 1% formic acid in water (1 mL) and 100% water (1 mL), compound 56 and the internal standard were eluted with 1 mL acetonitrile. The eluent was evaporated to dryness and the dried residue was reconstituted in the mobile phase (500 µL). After vortexing for 15 minutes, the supernatant (20 µL) was injected into the LC/MS.

The amount of compound 56 generated by this process was analyzed on an Agilent 1100 series LC/MSD Trap. The sample solution was injected into an Inertsil ODS-3 column (4.6×50 mm, 3µ), using (A) 0.01% formic acid in water and (B) 0.01% formic acid in acetonitrile:methanol (50:50) with a gradient of 45 to 65% (B) in (A) over 5 minutes followed by 65 to 95% (B) over 1 minute and maintaining at 95% (B) for an additional minute at a flow rate of 0.4 mL/min.

The MS was set as follows: ESI probe, positive polarity, nebulizer 45 psi, dry gas temperature 350° C., dry gas flow 10 l/min, capillary exit 110V and skimmer 34.5V. The run time was 13 minutes with the divert valve sets to the waste for the first 3 minutes. Compound 56 was analyzed in SRM mode for m/z 929.3→897.2 and the internal standard (rifabutin) for m/z 847.3→815.3

Figure 9:
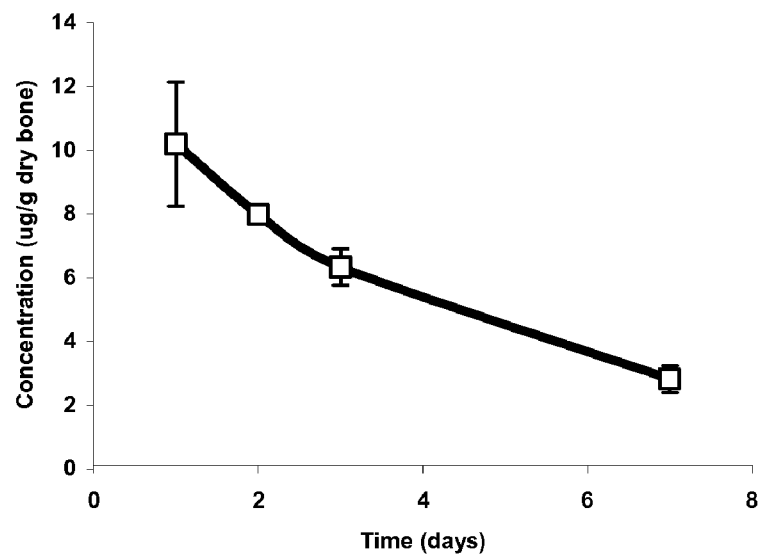
FIG. 9 is a line graph showing concentration of compound 62 in rat tibia at 1 to 7 days after an IV bolus injection at 26 mg/Kg.

The results from these determinations after a single intravenous bolus administration of 62 at 26 mg/kg of body weight are shown in FIG. 9.

These determinations provide further in vivo evidence that the bisphosphonated Rifamycins are able to concentrate in bone where they can reside for days releasing their parent drugs at the potential loci of infection. This confirms the role of the bisphosphonate linker in delivering such rifamycin agents to bone, and further supports the use of the invention for the prevention and the treatment of bone infections.

It is understood that the examples and embodiments described herein are for illustrative purposes only and that various modifications or changes in light thereof will be suggested to persons skilled in the art and are to be included within the spirit and purview of this application and scope of the appended claims.

All documents, papers and published materials referenced herein, including books, journal articles, manuals, patent applications, published patent applications and patents, are expressly incorporated herein by reference in their entireties.

What is claimed is:
1. A compound of Formula (I) or a pharmaceutically acceptable salt thereof:

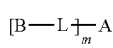

(I)

wherein:
B is a bisphosphonate is selected from the group consisting of:

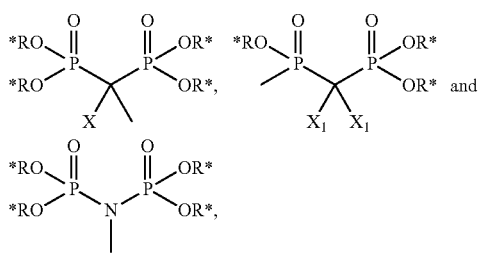

wherein:
each R* is independently selected from the group consisting of H, lower alkyl, cycloalkyl, aryl and heteroaryl, with the proviso that at least two R* are H;
X is H, OH, $NH_2$, or a halo group; and
$X_1$ are both H, or each is independently selected from the group consisting of H, OH, $NH_2$, and a halo group;
L is a cleavable linker for coupling B to A;
m is 1, 2, 3 or 4; and
A is a Rifamycin having a structure represented by the following Formula A1:

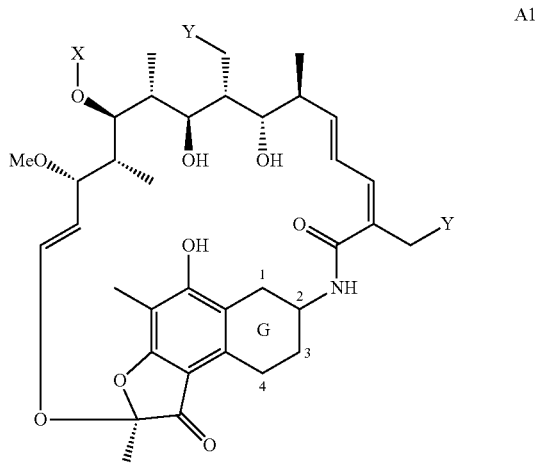

A1 wherein:
X is H— or $R_1CO$—, wherein $R_1$ is a substituted or unsubstituted alkyl chain of 1-6 carbons;
each Y is independently selected from the group consisting of H— and RO—, wherein R is H—, $R_1$—, or $R_1CO$—, ith $R_1$ defined as above;

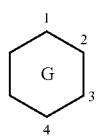

is selected from the group consisting of formulae A2-A10:

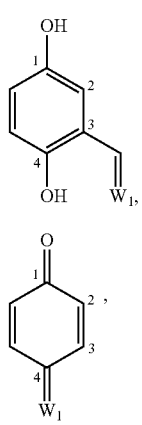

A2

A3

-continued

A4 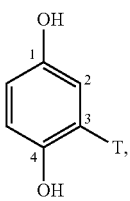

A5 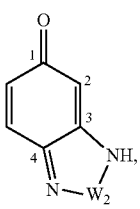

A6 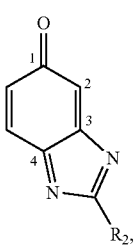

A7 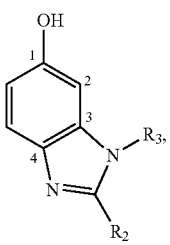

A8 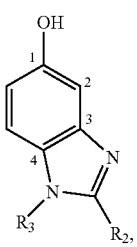

A9 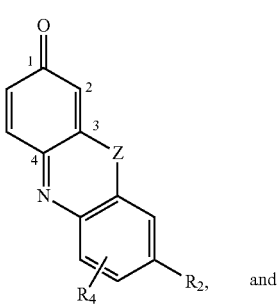

-continued

A10 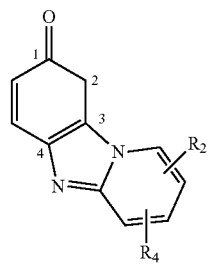

wherein $R_2$ is H—, a substituted or unsubstituted alkyl chain of 1-10 carbons, or a dialkyl amino group;

$R_3$ is H— or a substituted or unsubstituted alkyl chain of 1-7 carbons;

$R_4$ is a hydroxyl group, a sulfhydryl group or a substituted or unsubstituted alkyl chain of 1-3 carbons;

$W_1$ is oxygen or —$NR_2$ with $R_2$ defined as above;

$W_2$ is a substituted or unsubstituted methylene, comprising

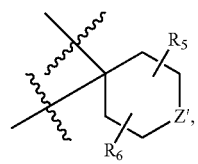

wherein $R_5$ and $R_6$ are independently H— or a substituted or unsubstituted alkyl chain of 1-5 carbons, and Z' is an oxygen atom, a sulfur atom, a substituted methylene, a carbonyl, —$NR_1$ or —$N(O)R_1$ where $R_1$ is defined as above;

T is a halogen or $R_2$, where $R_2$ is defined as above; and

Z is O, S or $NR_3$, where $R_3$ is defined as above, wherein at least one of said B-L- is coupled to a nitrogen atom on said Rifamycin A, and wherein each of said B-L- coupled to a nitrogen atom is independently selected from the group consisting of:

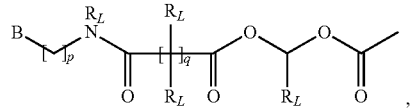

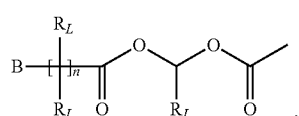

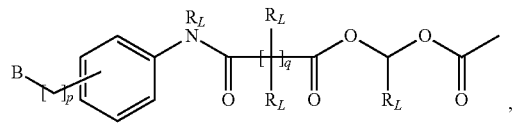

205

-continued

[structures continued]

wherein:
B represents said bisphophonate;
n is an integer ≦10;
each p is independently 0 or an integer ≦10;
each $R_L$ is independently selected from the group consisting of H, ethyl and methyl;

q is 2 or 3;
X is O, —CONR$_L$—, —CO—O—CH$_2$—, or —CO—O—; and
$R_a$ is $C_xH_y$, where x is an integer of 0 to 20 and y is an integer of 1 to 2x+1.

2. The compound of claim 1, wherein $R_2$ is a dialkyl amino group selected from the group consisting of a substituted piperidine, a substituted morpholine or a substituted piperazine.

3. The compound of claim 1, wherein said Rifamycin A has a structure represented by the following formula or an antimicrobial derivative thereof:

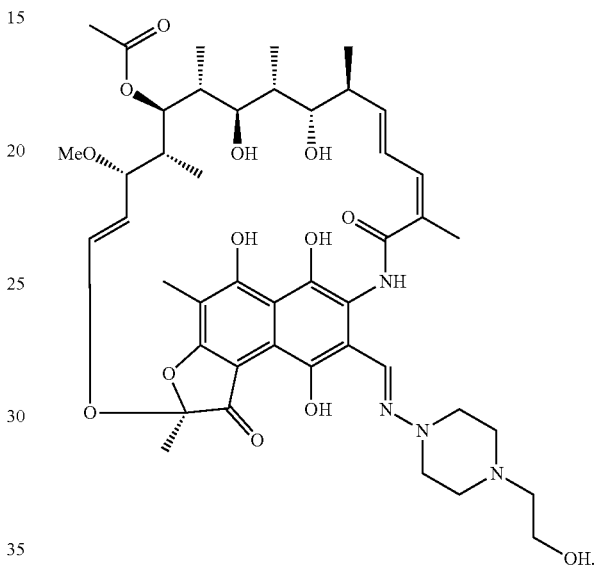

4. The compound of claim 1, wherein said Rifamycin A has a structure represented by the following formula or an antimicrobial derivative thereof:

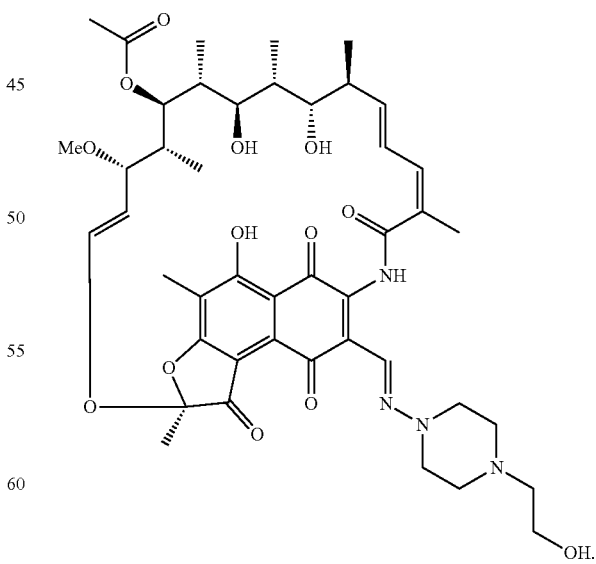

5. The compound of claim 1, wherein said Rifamycin A has a structure represented by the following formula or an antimicrobial derivative thereof:

207

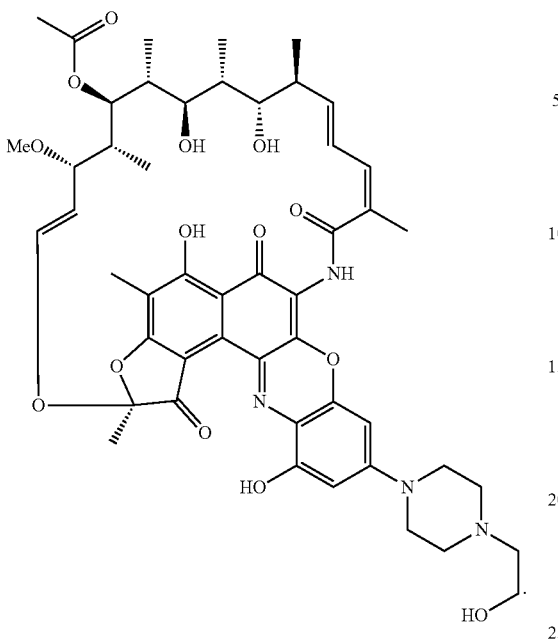

6. The compound of claim 1, wherein said Rifamycin A has a structure represented by the following formula or an antimicrobial derivative thereof:

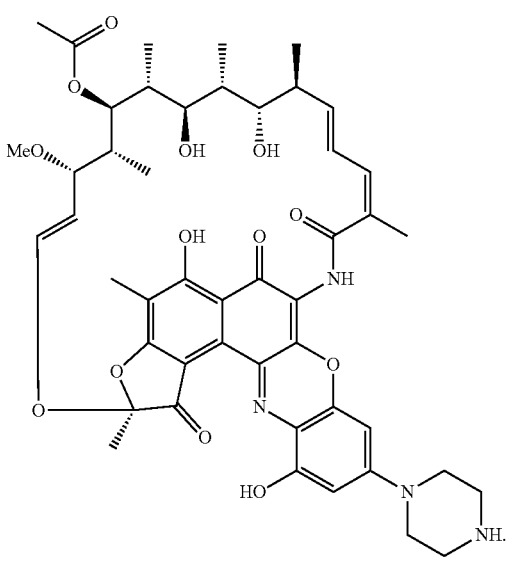 [SMILES: CO[C@H]1/C=C/O[C@@]2(C)Oc3c(C)c(O)c4c(=O)c(c5oc6cc(N7CCNCC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

7. The compound of claim 1, wherein said Rifamycin A has a structure represented by the following formula or an antimicrobial derivative thereof:

208

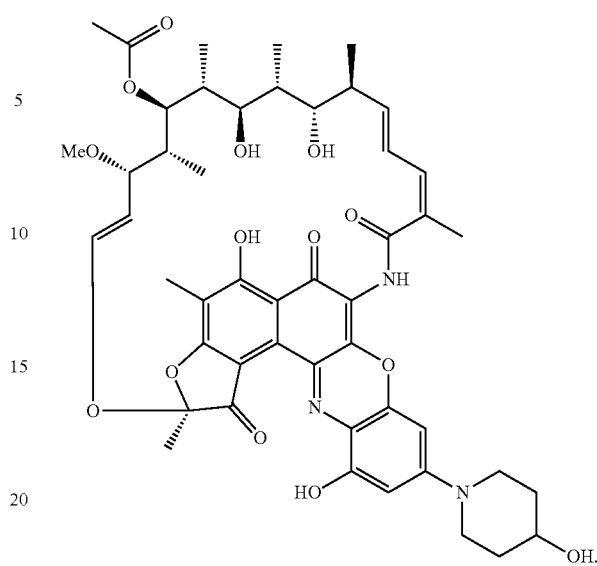

8. The compound of claim 1, wherein said Rifamycin A is Rifampicin or an antimicrobial derivative thereof.

9. The compound of claim 1, wherein said Rifamycin A is Rifapentin or an antimicrobial derivative thereof.

10. The compound of claim 1, wherein said Rifamycin A is Rifabutin or an antimicrobial derivative thereof.

11. The compound of claim 1, wherein said Rifamycin A is Rifalazil or an antimicrobial derivative thereof.

12. The compound of claim 1, wherein said Rifamycin A is Rifaximin or an antimicrobial derivative thereof.

13. The compound of claim 1, wherein said Rifamycin A is Rifandin or an antimicrobial derivative thereof.

14. A compound represented by a formula selected from the group consisting of:

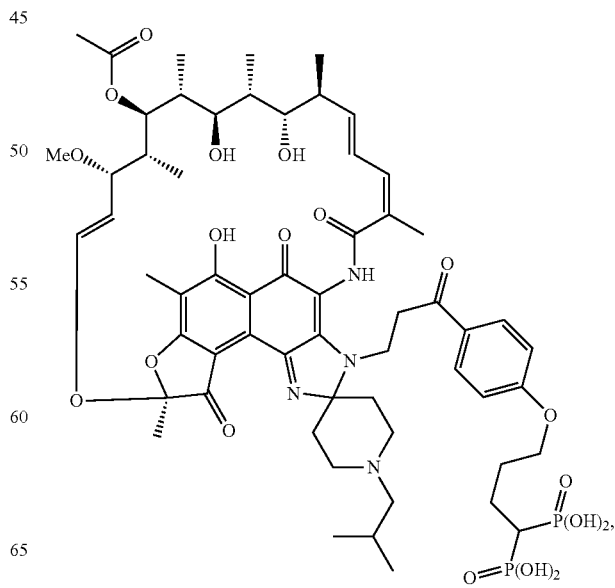

-continued

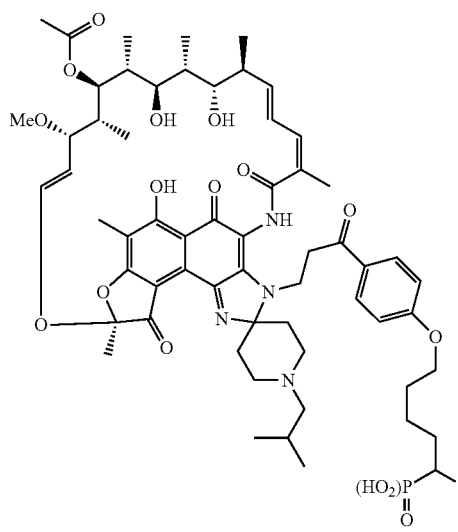
and

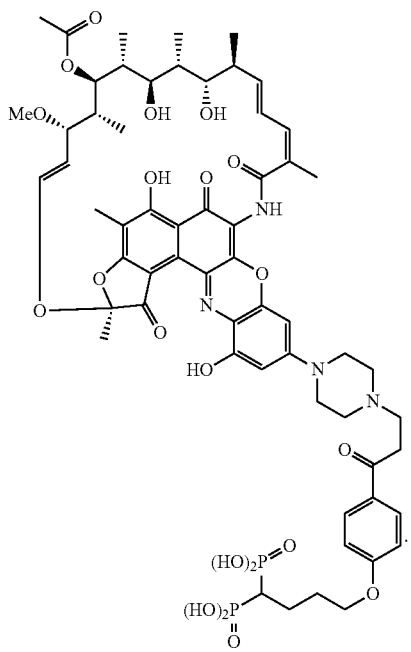

15. A compound represented by Formula (II) or a pharmaceutically acceptable salt thereof:

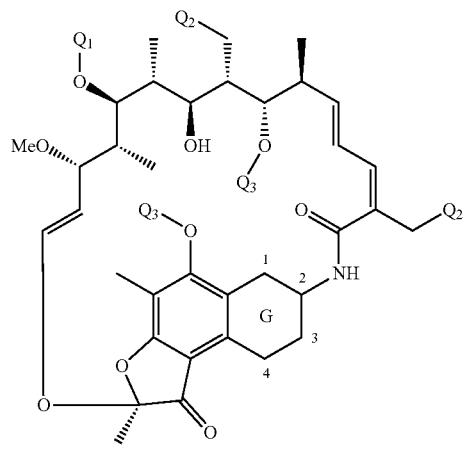

(II)

wherein:

$Q_1$ is H— or $R_1CO$—, wherein $R_1$ is a substituted or unsubstituted alkyl chain of 1-6 carbons;

each $Q_2$ is independently selected from the group consisting of H— and RO—, wherein R is H—, $R_1$— or $R_1CO$—, with $R_1$ defined as above;

each $Q_3$ is independently selected from the group consisting of H—;

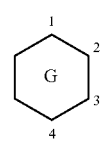

is selected from the group consisting of formulae A2-A10:

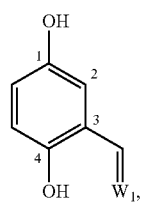
A2

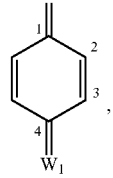
A3

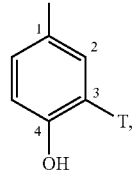
A4

-continued

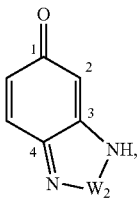
A5

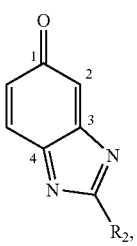
A6

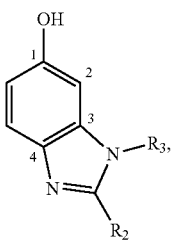
A7

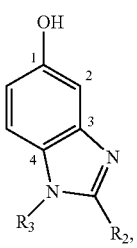
A8

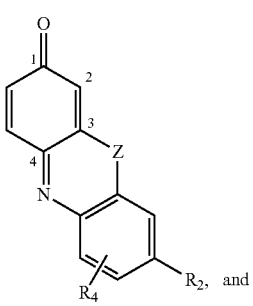
A9

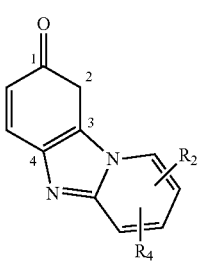
A10 wherein $R_2$ is H—, a substituted or unsubstituted alkyl chain of 1-10 carbons or a dialkyl amino group, wherein when $R_2$ is a substituted alkyl chain of 1-10 carbons the substituent is $L_6NR_7$—, wherein $R_7$ is a substituted or unsubstituted alkyl chain of 1-7 carbons;

$R_3$ is H—, a substituted or unsubstituted alkyl chain of 1-7 carbons or $L_7$-;

$R_4$ is a hydroxyl group, a sulfhydryl group or a substituted or unsubstituted alkyl chain of 1-3 carbons;

$W_1$ is oxygen or —$NR_2$, with $R_2$ defined as above;

$W_2$ is a substituted or unsubstituted methylene, comprising

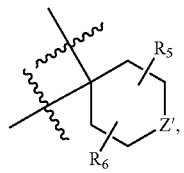

wherein $R_5$ and $R_6$ are independently H— or a substituted or unsubstituted alkyl chain of 1-5 carbons, and Z' is an oxygen atom, a sulfur atom, a substituted methylene, a carbonyl, —$NR_1$ or —$N(O)R_1$ where $R_1$ is defined as above;

T is a halogen or $R_2$, where $R_2$ is defined as above;

Z is O, S or $NR_3$, where $R_3$ is defined as above;

each $L_6$ and $L_7$ is a cleavable linker independently selected from the group consisting of:

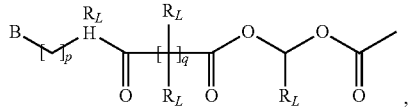

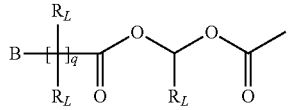

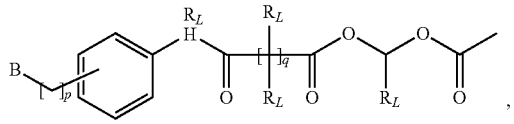

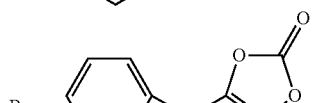

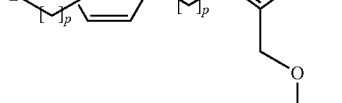

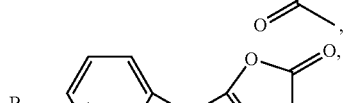

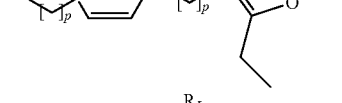

-continued

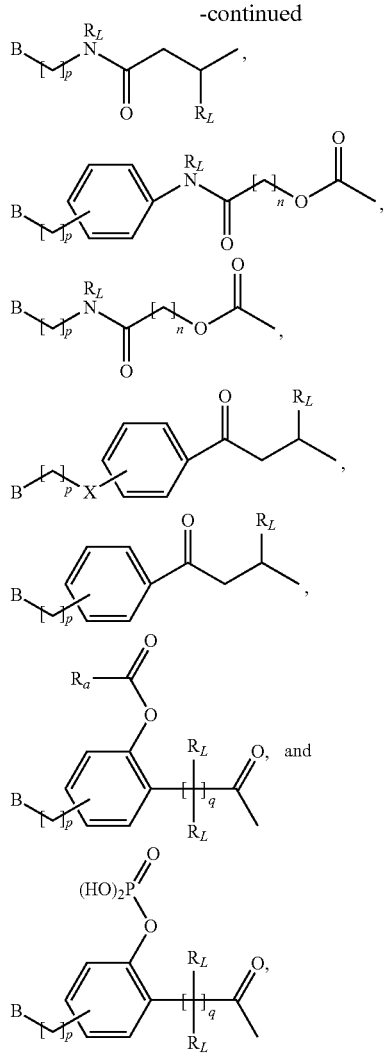

wherein:
n is an integer ≦10;
each p is independently 0 or an integer ≦10;
q is 2 or 3;
each $R_L$ is independently selected from the group consisting of H, ethyl and methyl;
$R_a$ is $C_xH_y$ where x is an integer of 0 to 20 and y is an integer of 1 to 2x+1; and
X is O, —$CONR_L$—, —CO—O—$CH_2$—, or —CO—O—;
B is a phosphonated group selected from the group consisting of:

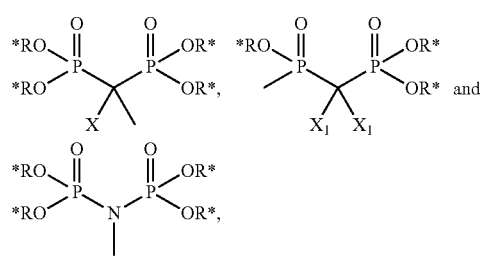

wherein:
each R* is independently selected from the group consisting of H, lower alkyl, cycloalkyl, aryl and heteroaryl, with the proviso that at least two R* are H;
X is H, OH, $NH_2$, or a halo group;
each $X_1$ is independently selected from the group consisting of H, OH, $NH_2$, and a halo group; with the proviso that at least one of $L_6$ and $L_7$ is present.

16. The compound of claim 15, wherein $R_2$ is a dialkyl amino group selected from the group consisting of a substituted piperidine, a substituted morpholine or a substituted piperazine, and wherein the substituent $L_6NR_7$—, wherein $R_7$ is a substituted or unsubstituted alkyl chain of 1-7 carbons.

17. A compound represented by the formula:

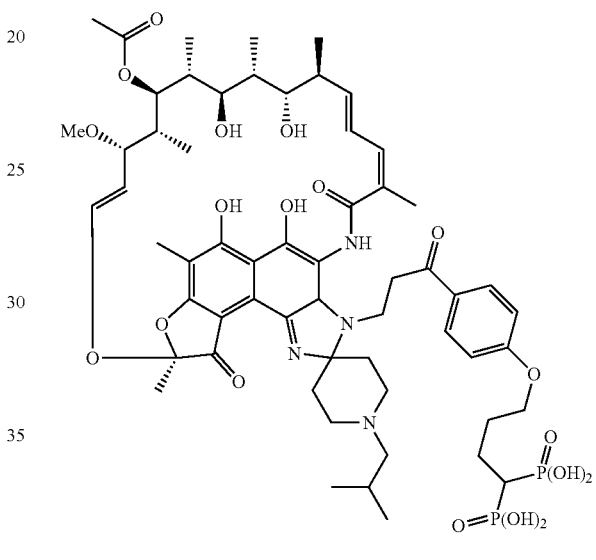

or a pharmaceutically acceptable salt thereof.

18. A compound represented by the formula:

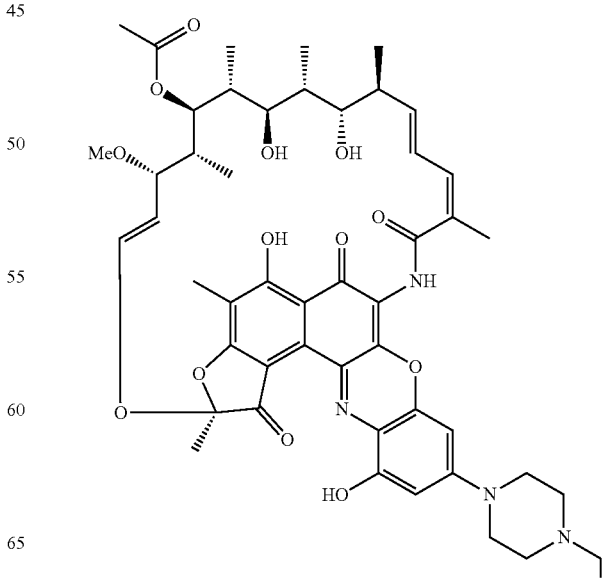

-continued

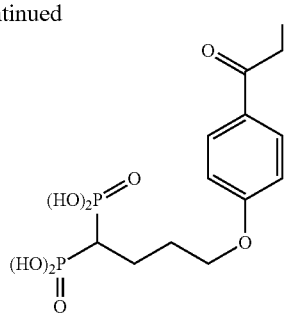

or a pharmaceutically acceptable salt thereof.

19. A pharmaceutical composition comprising a compound as defined in any one of claims 1, 14-17 and 18, and a pharmaceutically acceptable carrier or excipient.

20. A method for treating a bacterial infection in a bone or a joint of a subject, comprising administering to a subject in need of such treating a pharmaceutically effective amount of a pharmaceutical composition according to claim 19.

21. A method of prophylaxis for a bacterial infection in a subject, comprising administering to a subject in need of such prophylaxis a prophylactically effective amount of a pharmaceutical composition according to claim 19.

22. The method of claim 21, wherein said pharmaceutical composition is administered to said subject prior to, during, or after an invasive medical treatment.

23. The method of claim 20 wherein said subject is a human.

24. The method of claim 21 wherein said subject is a human.

25. The method of claim 20, further comprising administering an antibiotic concurrent with administration of said pharmaceutical composition.

26. The method of claim 25, wherein said antibiotic is selected from the group consisting of tetracycline, a tetracycline derived antibacterial agent, glycylcycline, a glycylcycline derived antibacterial agent, minocycline, a minocycline derived antibacterial agent, an oxazolidinone antibacterial agent, an aminoglycoside antibacterial agent, a quinolone antibacterial agent, vancomycin, a vancomycin derived antibacterial agent, a teicoplanin, a teicoplanin derived antibacterial agent, eremomycin, an eremomycin derived antibacterial agent, chloroeremomycin, a chloroeremomycin derived antibacterial agent, daptomycin, and a daptomycin derived antibacterial agent.

27. A method for accumulating a Rifamycin in a bone of a subject, comprising administering to a subject a pharmaceutical composition according to claim 19.

28. A compound of claim 1, wherein m is 1, 2 or 3.

* * * * *

UNITED STATES PATENT AND TRADEMARK OFFICE
CERTIFICATE OF CORRECTION

PATENT NO. : 8,404,664 B2  Page 1 of 1
APPLICATION NO. : 12/063300
DATED : March 26, 2013
INVENTOR(S) : Rose et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1446 days.

Signed and Sealed this
First Day of September, 2015

Michelle K. Lee
*Director of the United States Patent and Trademark Office*